United States Patent [19]
Suzuki

[11] Patent Number: 5,708,143
[45] Date of Patent: Jan. 13, 1998

[54] PROTOCADHERIN MATERIALS AND METHODS

[75] Inventor: Shintaro Suzuki, Torrance, Calif.

[73] Assignee: Doheny Eye Institute, Los Angeles, Calif.

[21] Appl. No.: 453,695

[22] Filed: May 30, 1995

Related U.S. Application Data

[60] Division of Ser. No. 268,161, Jun. 27, 1994, which is a continuation-in-part of Ser. No. 998,003, Dec. 29, 1992.

[51] Int. Cl.$^6$ .................... C07K 14/435; C12N 15/12
[52] U.S. Cl. .................... 530/350; 435/69.1; 530/395
[58] Field of Search .................... 530/350, 395; 435/69.1

[56] References Cited

FOREIGN PATENT DOCUMENTS

WO91/04745  4/1991  WIPO.
WO92/08731  5/1992  WIPO.

OTHER PUBLICATIONS

Sago et al., Genomics, 29, 631–640, 1995.

Amagai et al., "Autoantibodies against a Novel Epithelial Cadherin in Pemphigus Vulgaris, a Disease of Cell Adhesion", *Cell*, 67: 869–877 (Nov. 29, 1991).

Angerer et al., "Demonstration of Tissue–Specific Gene Expression of in Situ Hybridization", *Methods of Enzymology*, 152: 649–660, (1987).

Ausubel et al., Eds., *Current Protocols in Molecular Biology*, Sections 6.1.1 to 6.1.4 and 6.2.1 to 6.2.3, John Wiley & Sons, New York (1987).

Burt, "Morphologic Abnormalities in the Postnatal Differentiation of CA1 Pyramidal Cells and Granule Cells in the Hippocampal Formation of the Ataxic Mouse", *Anat. Rec.* 196: 61–69 (1980).

Chen et al., "Cell–Cell Contacts Mediated by E–Cadherin (Uvomorulin) Restrict Invasive Behavior of L–Cells:," *J. Cell. Biol.*, 114(2): 319–327 (Jul. 1991).

Civitelli et al., "Connexin43 Mediates Direct Intercellular Communication in Human Osteoblastic Cell Networks", *J. Clin. Invest.*, 91: 1888–1896 (1993).

Detrick et al., "The Effect of N–Cadherin Misexpression on Morphogenesis in Xenopus Embryos", *Neuron,* 4: 493–506 (Apr. 1990).

Donalies et al., "Expression of M–cadherin, a Member of the Cadherin Multigene Family, Correlates with Differentiation of Skeletal Muscle Cells", *Proc. Natl. Acad. Sci. USA,* 88: 8024–8028 (Sep. 1991).

Frixen et al., "E–Cadherin–Mediated Cell–Cell Adhesion Prevents Invasiveness of Human Carcinoma Cells" *J. Cell. Biol.*, 113(1): 173–185 (Apr. 1991).

Fujimori et al., "Ectopic Expression of N–cadherin Perturbs Histogenesis in *Xenopus* Embryos", *Development,* 110: 97–104 (1990).

Gallin et al., "Sequence Analysis of a cDNA Clone Encoding the Liver Cell Adhesion Molecule, L–CAM", *Proc. Natl. Acad. Sci. USA,* 84: 2808–2812 (May 1987).

Goodwin et al., "Desmoglein Shows Extensive Homology to the Cadherin Family of Cell Adhesion Molecules", *Biochem. Biophsy. Res. Commun.*, 173(3): 1224–1230 (Dec. 31, 1990).

Hatta et al., "Cloning and Expression of cDNA Encoding a Neural Calcium–dependent Cell Adhesion Molecule: Its Identity in the Cadherin Gene Family", *J. Cell. Biol.*, 106: 873–881 (Mar. 1988).

Holton et al., "Desmosomal Glycoproteins 2 and 3 (desmocollins) Show N–terminal Similarity to Calcium–Dependent Cell–Cell Adhesion Molecules", *J. Cell. Science,* 97: 239–246 (1990).

Hynes et al., "Contact and Adhesive Specificities in the Associations, Migrations, and Targeting of Cells and Axons", *Cell,* 68: 303–322, (Jan. 24, 1992).

Inuzuka et al., "R–Cadherin: A Novel $Ca^{2+}$–Dependent Cell–Cell Adhesion Molecule Expressed in the Retina", *Neruron,* 7: 69–79 (1991).

Kennett, "Cell Fusion", *Methods in Enzymol.,* 58: 345–359 (1979).

Kikuchi et al., "The Defective Organ of Corti in Shaker–1 Mice", *Acta Oto–Laryng.,* 60: 287–303 (1965).

Kintner, "Regulation of Embryonic Cell Adhesion by the Cadherin Cytoplasmic Domain", *Cell,* 69: 225–236 (Apr. 17, 1992).

Koch et al., "Identification of Desmoglein, a Constitutive Desmosomal Glycoprotein, as a Member of the Cadherin Family of Cell Adhesion Molecules", *Eur. J. Cell Biol.,* 53: 1–12 (1990).

Liaw et al., "Identification and Cloning of Two Species of Cadherins in Bovine Endothelial Cells", *EMBO J.,* 9(9): 2701–2708 (1990).

Lord et al., "Shaker, A New Mutation of the House Mouse" (*Mus Musculus*) *Am. Nat.,* 63: 453–442 (1929).

Lyon, M., "Twirler: A Mutant Affecting the Inner Ear of the House Mouse", *J. Embryol. Exp. Morphol.,* 6: 105–116 (1958).

Lyon, M., "Ataxia—A New Recessive Mutant of the House Mouse", *J. Hered.,* 46: 77–80 (1955).

Mahoney et al., "The *fat* Tumor Suppressor Gene in Drosophila Encodes a Novel Member of the Cadherin Gene Superfamily", *Cell,* 67: 853–868 (Nov. 29, 1991).

Maniatis et al., p. 196 in *Molecular Cloning: A Laboratory Manual,* Cold Spring Harbor, New York: Cold Spring Harbor Laboratory (1982).

(List continued on next page.)

*Primary Examiner*—Stephen Walsh
*Assistant Examiner*—Sally P. Teng
*Attorney, Agent, or Firm*—Marshall, O'Toole, Gerstein, Murray & Borun

[57] ABSTRACT

Polynucleotide sequences encoding novel cadherin-like polypeptides, designated protocadherins, and variants thereof are provided by the invention as well as methods and materials for the recombinant production of the same. Antibody substances specific for protocadherins are also disclosed as useful for modulating the natural binding and/or regulatory activities of the protocadherins.

2 Claims, 3 Drawing Sheets

OTHER PUBLICATIONS

Maruyama et al., "Detection of Calcium Binding Proteins by [45]Ca Autoradiography on Nitrocellulose Membrane after Sodium Dodecyl Sulfate Gel Electrophoresis[1]", J. Biochem., 95: 511–519 (1984).

Matsunaga et al., "Guidance of Optic Nerve Fibers by N–cadherin Adhesion Molecules", *Nature*, 334: 62–64 (Jul. 1988).

Miyatani et al., "Neural Cadherin: Role in Selective Cell–Cell Adhesion", *Science*, 245: 631–635 (Aug. 1989).

Nagafuchi et al., "Transformation of Cell Adhesion Properties by Exogenously Introduced E–cadherin cDNA", *Nature*, 329: 341–343 (Sep. 1987).

Napolitano, et al., "Molecular Cloning and Characterization of B–Cadherin, a Novel Chick Cadherin", *Cell Biol.*, 113(4): 893–905 (May 1991).

Nose et al., "Isolation of Placental Cadherin cDNA: Identification of a Novel gene Family of Cell–Cell Adhesion Molecules", *EMBO J.*, 6(12): 3655–3661 (1987).

Porter et al., "Dystrophin Colocalizes with β–Spectrin in Distinct Subsarcolemmal Domains in Mammalian Skeletal Muscle", *J. Cell. Biol.*, 117(5): 997–1005 (Jun. 1992).

Pytela et al., "Polymerase Chain Reaction Cloning with Degenerate Primers: Homology–Based Identification of Adhesion Molecules", *Methods in Enzymology*, Erkki Ruoslahti and Eva Engvall, Eds., 245:420–451, Academic Press, (1994).

Ranscht et al., "T–Cadherin, a Novel Caherin Cell Adhesion Mol. in the Nervous System Lacks the Conserved Cytoplasmic Region", *Neuron*, 7: 391–402 (Sep. 1991).

Ringwald te al., "The Structure of Cell Adhesion Molecular Uvomorulin. Insights into the Molecular Mechanism of $Ca^{2+}$–Dependent Cell Adhesion", *EMBO J.*, 6(12): 3647–3653 (1987).

Sano et al., "Protocadherins: A Large Family of Cadherin–Related Molecules in Central Nervous System", *The EMBO Journal*, 12(6): 2249–2256 (1993).

Seldon et al., "Genetic Analysis of Autoimmune gld Mice", *J. Exp. Med.*, 167: 688–693 (1988).

Shimoyama et al., "Molecular Cloning of a Human $Ca^{2+}$–Dependent Cell–Cell Adhesion Molecule Homologous to Mouse Placental Cadherin: Its Low Expression in Human Placental Tissues", *J. Cell. Biol.*, 109: 1787–1794 (Oct. 1989).

Suzuki et al., "Diversity of the Cadherin Family: Evidence for Eight New Cadherin in Nervous Tissue", *Cell Regulation*, 2: 261–270 (Apr. 1991).

Suzuki et al., "Evidence for Cadherin Superfamily" *Cell Struc. Func.*, 16: 605 (Nov. 23, 1991).

Suzuki et al., "Evidence of Cadherin Superfamily" *J. Cell. Biol.*, 115: 72(a) (Abstract 416) (Dec. 9, 1991).

Takeichi, "Cadherin Cell Adhesion Receptors as a Morphogenetic Regulator.", *Science*, 251: 1451–1455 (Mar. 1991).

Takeichi, "Cadherins: A Molecular Family Important in Selective Cell–Cell Adhesion:", *Annu. Rev. Biochem.*, 59: 237–252 (1990)

Thomas, "Hybridization of Denatured RNA and Small DNA Fragments Transferred to Nitrocellulose", *Proc. Natl. Acad. Sci. USA*, 77(9): 5201–5205 (Sep. 1980).

Towbin et al., "Electrophoretic Transfer of Proteins from Polyacrylamide Gels to Nitrocellulose Sheets: Procedure and Some Applications", *PNAS* 76: 4350–4354, (Sep. 1979).

Urushihara et al., "Immunological Detection of Cell Surface Components Related with Aggregation of Chinese Hamster and Chick Embryonic Cells", *Dev. Biol.*, 70: 206–216 (1979).

Vandenbark et al., "Experimental Allergic Encephalomyelitis and Cellular Immunity in the Lewis Rat", *Cell. Immunol.*, 12: 85–93 (1974).

Vleminckx et al., "Genetic Manipulation of E–Cadherin Expression by Epithelial Tumor Cells Reveals an Invasion Suppressor Role", *Cell*, 66: 107–119 (Jul. 12, 1991).

FIGURE 1A

| | | | | | |
|---|---|---|---|---|---|
| PC43 | EC 1 | (29) | ASTVIHYEIPEEREK------GFAVGNVVANL---GLDLGSLSA-- | (63) |
| | EC 2 | (136) | PTQEMKLEISEAVAP------GTRFPLESAH---DPDLGSNSL-- | (169) |
| | EC 3 | (245) | NQSLYRARVPGGCTS------GTRVVQVLAT---DLDEGPNGE-- | (278) |
| | EC 4 | (353) | TVTSVYSPVPEDAS-------GTVIALLSVT---DLDAGENGL-- | (385) |
| | EC 5 | (457) | SQSSYDVYIEENNLP------GAPILNLSVW---DPDAPQNAR-- | (490) |
| | EC 6 | (567) | LYPRPGGSSVEMLPRGTSA-GHLVSRVVGW---DADAGHNAW-- | (604) |
| PC42 | EC 1 | (42) | VPEEQPPNTLI----------GSL----------AADYGFPDVG- | (65) |
| | EC 2 | (147) | ASPVITLAIPENTNI------GSLFPIPLAS---DRDAGPNGV-- | (180) |
| | EC 3 | (247) | ERPSYEAELSENSPI------GHSVIQVKAN---DSDQGANAE-- | (280) |
| | EC 4 | (354) | EIRGIGLVTHQDGMANISEDVAEETAVALVQVSDRDEGENAA-- | (395) |
| | EC 5 | (473) | TQSVTEVAFPENNKP------GEVIAEITAS---DADSGSNAE-- | (506) |
| | EC 6 | (579) | MLSGYNFSVMENMPA------LSPVGMVTVI---DGDKGENAQ-- | (612) |
| | EC 7 | (682) | TAPSNTSHKLLTPQTRL----GETVSQVAAE---DFDSGVNAE-- | (717) |
| FAT | EC18 | (1) | EDTVYSFDIPENAQR-------GYQVGQIVAR---DADLGQNAQ-- | (34) |
| N-CAD | EC 1 | (1) | DWVIPPINLPENSRG------PFPQELVRIRS--DRDKNILSLRYT | (37) |
| | EC 2 | (109) | LHQVWNGSVPEGSKP------GTYVMTVTAI---DADDPNALNGM | (144) |
| | EC 3 | (224) | TAMTFYGEVPENRVD------IIVANLTVT----DKDQPHTPAWN | (258) |
| | EC 4 | (339) | APNPKIIRQEEGLHA------GTMLTTFFAG---DPDRYMQQN-- | (372) |
| | EC 5 | (447) | LPQEAETCETPDPNSINITTAL------------DYDIDPNAGP- | (478) |
| MOTIF | | | **o**v*En*****----Gt*v**v*A*---D*D*g*n**-- | |

| | | | |
|---|---|---|---|
| PC43 | EC 1 (64) | RRFPVVSGASRR------FFEVNRET-----GEMFVNDR--- | (91) |
| | EC 2 (170) | QTYELSRNEY------FALRVQTREDSTKYAELVLERA--- | (201) |
| | EC 3 (279) | IIYSFGSHNRAGVRQL---FALDLVT------GMLTIKGR--- | (309) |
| | EC 4 (386) | VTCEVPPGLP------FSLTSSLKNYFTLKTSAD--- | (413) |
| | EC 5 (491) | LSFFLLEQGAETGLVGRYFTINRDN-----GIVSSLVP--- | (523) |
| | EC 6 (605) | LSYSLFGSPNQSL------FAIGLHT------GQISTARPV--- | (633) |
| PC42 | EC 1 (66) | HLYKLEVGAP------YLRVDGKT----GDIFTTETS--- | (92) |
| | EC 2 (181) | ASYELQVAED------QEEKQPQLIVMGN------ | (203) |
| | EC 3 (281) | IEYTFHQAPEVVRRL---LRLDRNT------GLITVQGP--- | (310) |
| | EC 4 (396) | VTCVVAGDVP------FQLRQASETGSDSKKKYFLQTTTP | (429) |
| | EC 5 (507) | LVYSLEPEPAAKGL----FTISPET------GEIQVKTS--- | (535) |
| | EC 6 (613) | VQLSVEQDNGD------FVIQNGT------GTILSSLS--- | (638) |
| | EC 7 (718) | LIYSIAGGNPYGL------FQIGSHS------GAITLEKE--- | (745) |
| FAT | EC18 (35) | LSYGVVSDWANDV------FSLNPQT------GMLTLTAR--- | (62) |
| N-CAD | EC 1 (38) | VTGPGADQPPTGI------FIINPIS------GQLSVTKP--- | (65) |
| | EC 2 (145) | LRYRILSQAPSTPSPNM-FTINNET-----GDIITVAAG--- | (177) |
| | EC 3 (259) | AVTRISGGDPTGR------FAIQTDPNSND-GLVTVVKP--- | (290) |
| | EC 4 (373) | IRYTKLSDPAN------WLKIDPVN------GQITTIAV--- | (399) |
| | EC 5 (479) | FAYDLPLSPVTIKRN---WTITRLN------GDFAQLNLK--- | (509) |
| MOTIF | | I*O*I*********O*I***T------G*I*T***--- | |

FIGURE 1B

```
PC43  EC 1  (92)   LDREELCGTLPSCTVTLELVVENP----------LELFSVEVVIQDINDNNPAF  (135)
      EC 2  (202)  LDREREPSLQLVLTALDGGTPAL-----------SASLPIHIKVLDANDNAPVF  (244)
      EC 3  (310)  LDFEDTKLHEIYIQAKDKGANPE-----------GAHCKVLVEVVDVNDNAPEI  (352)
      EC 4  (414)  LDRETVPEYNLSITARDAGTPSL-----------SALTIVRVQVSDINDNPPQS  (456)
      EC 5  (524)  LDYEDRREFELTAHISDGGTPVL-----------ATNISVNIFVTDRNDNAPQV  (566)
      EC 6  (634)  QDTDSPRQTLTVL-IKDNGEPSLSTTATLTVSVTEDSPEARAEFPSGSAPREQKKN (688)

PC42  EC 1  (93)   IDREGLRECONQLPGDPCILEFEVSITDLVQNAS--PRLLEGQIEVQDINDNTPNF  (146)
      EC 2  (204)  LDRERWDSYDLTIKVQDGGSPPR-----------ATSALLRVTVLDTNDNAPKF  (246)
      EC 3  (311)  VDREDLSTLRFSVLAKDRGTNPK-----------SARAQVVVTVKDMNDNAPTI  (353)
      EC 4  (430)  LDYEKVKDYTIEIVAVDSGNPPL-----------SSTNSLKVQVQVDVNDNAPVF  (472)
      EC 5  (536)  LDREQRESYELKVVAADRGSPSL-----------QGTATVLVNVLDCNDNDPKF  (578)
      EC 6  (639)  FDREQQSTYTFQLKAVDGGVPPR-----------SAYVGVTINVLDENDNAPYI  (681)
      EC 7  (746)  IERRHHGLHRLVVKVSDRGKPPRYGTALVHLYVNETLANRTLLETLLGHSLDTPLD  (801)
                   (802) IDIAGDPEYERSKQRGN  (818)

FAT   EC18 (63)    LDYEEVQHYILIVQAQDNGQPSL-----------STTITVYCNVLDLNDNAPIF  (105)

N-CAD EC 1  (66)   LDREQIARFHLRAHAVDINGNQV-----------ENPIDIVINVIDMNDNRPEF  (108)
      EC 2  (178)  LDREKVQQYTLIIQATDMEGNPTYGL--------SNTATAVITVTDVNDNPPEF  (223)
      EC 3  (291)  IDFETNRMFVLTVAAENQVPLAKGIQHPP-----QSTATVSVTVIDVNE-NPYF  (338)
      EC 4  (400)  LDRESPNVKNNIYNATFLASDNGIPPM-------SGTGTLQIYLLDINDNAPQV  (446)
      EC 5  (510)  IKFLEAGIYEVPIIITDSGNPPKSNKS-------ILRVRVCQCDFNGDCTDVDR  (557)

MOTIF              LDRE*****o*L*v*A*D*G*P**----------**t*Tv*v*D*NDNAP*F
```

FIGURE 1C

SEQUENCE LISTING ( 1 ) GENERAL INFORMATION:

( i i i ) NUMBER OF SEQUENCES: 115

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

AARSSNNTNG AYTRYGA        17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TTRCTRTTRC GNGGNNN                                                                                          17

( 2 ) INFORMATION FOR SEQ ID NO:3:

( i ) SEQUENCE CHARACTERISTICS:
      ( A ) LENGTH: 131 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:3:

AAGGGAGTGG ACTTTGAGGA GCAGCCTGAG CTTAGTCTCA TCCTCACGGC TTTGGATGGA            60

GGGACTCCAT CCAGGTCTGG GACTGCATTG GTTCAAGTGG AAGTCATAGA TGCCAATGAC            120

AACGCACCGT A                                                                131

( 2 ) INFORMATION FOR SEQ ID NO:4:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:4:

Lys  Gly  Val  Asp  Phe  Glu  Glu  Gln  Pro  Glu  Leu  Ser  Leu  Ile  Leu  Thr
 1              5                        10                        15

Ala  Leu  Asp  Gly  Gly  Thr  Pro  Ser  Arg  Ser  Gly  Thr  Ala  Leu  Val  Gln
               20                        25                        30

Val  Glu  Val  Ile  Asp  Ala  Asn  Asp  Asn  Ala  Pro
               35                        40

( 2 ) INFORMATION FOR SEQ ID NO:5:

( i ) SEQUENCE CHARACTERISTICS:
      ( A ) LENGTH: 131 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:5:

AAACGCATGG ATTTCGAGGA GTCTTCCTCC TACCAGATCT ATGTGCAAGC TACTGACCGG            60

GGACCAGTAC CCATGGCGGG TCATTGCAAG GTGTTGGTGG ACATTATAGA TGTGAACGAC            120

AACGCACCTA A                                                                131

( 2 ) INFORMATION FOR SEQ ID NO:6:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:6:

Lys  Ala  Met  Asp  Phe  Glu  Glu  Ser  Ser  Ser  Tyr  Gln  Ile  Tyr  Val  Gln
 1              5                        10                        15

Ala Thr Asp Arg Gly Pro Val Pro Met Ala Gly His Cys Lys Val Leu
            20                  25                  30

Val Asp Ile Ile Asp Val Asn Asp Asn Ala Pro
            35                  40

( 2 ) INFORMATION FOR SEQ ID NO:7:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
AAGCGACTGG ACTTTGAGAC CCTGCAGACC TTCGAGTTCA GCGTGGGTGC CACAGACCAT      60
GGCTCCCCCT CGCTCCGCAG TCAGGCTCTG GTGCGCGTGG TGGTGCTGGA CCACAATGAC     120
AATGCCCCCA A                                                          131
```

( 2 ) INFORMATION FOR SEQ ID NO:8:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

Lys Arg Leu Asp Phe Glu Thr Leu Gln Thr Phe Glu Phe Ser Val Gly
1               5                   10                  15

Ala Thr Asp His Gly Ser Pro Ser Leu Arg Ser Gln Ala Leu Val Arg
            20                  25                  30

Val Val Val Leu Asp His Asn Asp Asn Ala Pro
            35                  40

( 2 ) INFORMATION FOR SEQ ID NO:9:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
AAGGGCCTGG ATTACGAGGC ACTGCAGTCC TTCGAGTTCT ACGTGGGCGC TACAGATGGA      60
GGCTCACCCG CGCTCAGCAG CCAGACTCTG GTGCGGATGG TGGTGCTGGA TGACAACGAC     120
AACGCCCCTA A                                                          131
```

( 2 ) INFORMATION FOR SEQ ID NO:10:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Lys Gly Leu Asp Tyr Glu Ala Leu Gln Ser Phe Glu Phe Tyr Val Gly
1               5                   10                  15

Ala Thr Asp Gly Gly Ser Pro Ala Leu Ser Ser Gln Thr Leu Val Arg
            20              25                  30

Met Val Val Leu Asp Asp Asn Asp Asn Ala Pro
            35              40
```

(2) INFORMATION FOR SEQ ID NO:11:

(i) SEQUENCE CHARACTERISTICS:
       (A) LENGTH: 131 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:11:

```
AAGGCGTTTG ATTTGAGGA TCAGAGAGAG TTCCAGCTAA CCGCTCATAT AAACGACGGA    60
GGTACCCCGG TTTTGGCCAC CAACATCAGC GTGAACATAT TTGTTACTGA CCGCAATGAC   120
AACGCCCCGC A                                                        131
```

(2) INFORMATION FOR SEQ ID NO:12:

(i) SEQUENCE CHARACTERISTICS:
       (A) LENGTH: 43 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:12:

```
Lys Ala Phe Asp Phe Glu Asp Gln Arg Glu Phe Gln Leu Thr Ala His
1               5                   10                  15

Ile Asn Asp Gly Gly Thr Pro Val Leu Ala Thr Asn Ile Ser Val Asn
            20              25                  30

Ile Phe Val Thr Asp Arg Asn Asp Asn Ala Pro
            35              40
```

(2) INFORMATION FOR SEQ ID NO:13:

(i) SEQUENCE CHARACTERISTICS:
       (A) LENGTH: 131 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:13:

```
AAGGCGGTGG ATTACGAAAT CACCAAGTCC TATGAGATAG ATGTTCAAGC CCAAGATCTG    60
GGTCCCAATT CTATTCCTGC TCATTGCAAA ATTATAATTA AGGTCGTGGA TGTCAACGAC   120
AACGCTCCCA A                                                        131
```

(2) INFORMATION FOR SEQ ID NO:14:

(i) SEQUENCE CHARACTERISTICS:
       (A) LENGTH: 43 amino acids
       (B) TYPE: amino acid
       (C) STRANDEDNESS: single
       (D) TOPOLOGY: linear (ii) MOLECULE TYPE: protein ( x i ) SEQUENCE DESCRIPTION: SEQ ID NO:14:

```
Lys Ala Val Asp Tyr Glu Ile Thr Lys Ser Tyr Glu Ile Asp Val Gln
 1               5                  10                  15

Ala Gln Asp Leu Gly Pro Asn Ser Ile Pro Ala His Cys Lys Ile Ile
            20                  25                  30

Ile Lys Val Val Asp Val Asn Asp Asn Ala Pro
            35              40
```

( 2 ) INFORMATION FOR SEQ ID NO:15:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

```
TATGACCATG ATTACGAGAC AACCAAAGAA TATACACTGC GGATCCGGGC CCAGGATGGT      60

GGCCGGACTC CACTTTCCAA CGTCTCCGGT CTAGTAACCG TGCAGGTCCT AGACATCAAC     120

GACAATGCCC CCCCA                                                     135
```

( 2 ) INFORMATION FOR SEQ ID NO:16:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

```
Tyr Asp His Asp Tyr Glu Thr Thr Lys Glu Tyr Thr Leu Arg Ile Arg
 1               5                  10                  15

Ala Gln Asp Gly Gly Arg Thr Pro Leu Ser Asn Val Ser Gly Leu Val
            20                  25                  30

Thr Val Gln Val Leu Asp Ile Asn Asp Asn Ala Pro
            35              40
```

( 2 ) INFORMATION FOR SEQ ID NO:17:

( i ) SEQUENCE CHARACTERISTICS:
        ( A ) LENGTH: 129 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

```
GGGGGGTCGA TTACGAGGAG AACGGCATGT TAGAGATCGA CGTGCAGGCC AGAGACCTAG      60

GACCTAACCC AATTCCAGCC CATTGCAAGG TCACAGTCAA GCTCATCGAC CGCAATGATA     120

ACGCCCCCA                                                             129
```

( 2 ) INFORMATION FOR SEQ ID NO:18:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

```
Arg Gly Val Asp Tyr Glu Glu Asn Gly Met Leu Glu Ile Asp Val Gln
 1               5                  10                  15
Ala Arg Asp Leu Gly Pro Asn Pro Ile Pro Ala His Cys Lys Val Thr
            20                  25                  30
Val Lys Leu Ile Asp Arg Asn Asp Asn Ala Pro
            35                  40
```

( 2 ) INFORMATION FOR SEQ ID NO:19:

( i ) SEQUENCE CHARACTERISTICS:
  ( A ) LENGTH: 131 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:19:

```
AAGGGGTTGG ACTACGAAGA CACCAAACTC CATGAGATTT ACATCCAGGC CAAAGACAAA      60
GGTGCCAATC CGGAAGGAGC GCATTGCAAA GTACTGGTAG AGGTTGTGGA CGTTAACGAC     120
AATGCCCCTC A                                                          131
```

( 2 ) INFORMATION FOR SEQ ID NO:20:

( i ) SEQUENCE CHARACTERISTICS:
  ( A ) LENGTH: 43 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:20:

```
Lys Gly Leu Asp Tyr Glu Asp Thr Lys Leu His Glu Ile Tyr Ile Gln
 1               5                  10                  15
Ala Lys Asp Lys Gly Ala Asn Pro Glu Gly Ala His Cys Lys Val Leu
            20                  25                  30
Val Glu Val Val Asp Val Asn Asp Asn Ala Pro
            35                  40
```

( 2 ) INFORMATION FOR SEQ ID NO:21:

( i ) SEQUENCE CHARACTERISTICS:
  ( A ) LENGTH: 131 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:21:

```
AAGGGTTTGG ACTTTGAGCA AGTAGATGTC TACAAAATCC GCGTTGACGC GACGGACAAA      60
GGACACCCTC CGATGGCAGG CCATTGCACT GTTTTAGTGA GGGTATTGGA TGAAAACGAC     120
AATGCGCCTC T                                                          131
```

( 2 ) INFORMATION FOR SEQ ID NO:22:

( i ) SEQUENCE CHARACTERISTICS:
  ( A ) LENGTH: 43 amino acids
  ( B ) TYPE: amino acid
  ( C ) STRANDEDNESS: single (D) TOPOLOGY: linear (ii) MOLECULE TYPE: protein (xi) SEQUENCE DESCRIPTION: SEQ ID NO:22:

```
Lys Gly Leu Asp Phe Glu Gln Val Asp Val Tyr Lys Ile Arg Val Asp
1               5                   10                  15
Ala Thr Asp Lys Gly His Pro Pro Met Ala Gly His Cys Thr Val Leu
                20                  25                  30
Val Arg Val Leu Asp Glu Asn Asp Asn Ala Pro
                35                  40
```

(2) INFORMATION FOR SEQ ID NO:23:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
AAGGGTATAG ACTTCGAGCA GATCAAGGAC TTCAGCTTTC AAGTGGAAGC CCGGGACGCC      60
GGCAGTCCCC AGGCGCTGTC CGGCAACTGC ACTGTCAACA TCTTGATAGT GGATCAGAAC     120
GACAACGCCC CTAA                                                       134
```

(2) INFORMATION FOR SEQ ID NO:24:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

```
Lys Gly Ile Asp Phe Glu Gln Ile Lys Asp Phe Ser Phe Gln Val Glu
1               5                   10                  15
Ala Arg Asp Ala Gly Ser Pro Gln Ala Leu Ala Gly Asn Thr Thr Val
                20                  25                  30
Asn Ile Leu Ile Val Asp Gln Asn Asp Asn Ala Pro
                35                  40
```

(2) INFORMATION FOR SEQ ID NO:25:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
AAGCCGTTCG ACTATGAGCA AACCGCCAAC ACGCTGGCAC AGATTGACGC CGTGCTGGAA      60
AAACAGGGCA GCAATAAATC GAGCATTCTG GATGCCACCA TTTTCCTGGC CGATAAAAAC     120
GACAATGCGC CAGA                                                       134
```

(2) INFORMATION FOR SEQ ID NO:26:

(i) SEQUENCE CHARACTERISTICS:
        (A) LENGTH: 44 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:26:

| Lys | Pro | Phe | Asp | Tyr | Glu | Gln | Thr | Ala | Asn | Thr | Leu | Ala | Gln | Ile | Asp |
|---|---|---|---|---|---|---|---|---|---|---|---|---|---|---|---|
| 1 | | | | 5 | | | | | 10 | | | | | 15 | |

| Ala | Val | Leu | Glu | Lys | Gln | Gly | Ser | Asn | Lys | Ser | Ser | Ile | Leu | Asp | Ala |
|---|---|---|---|---|---|---|---|---|---|---|---|---|---|---|---|
| | | | 20 | | | | | 25 | | | | | 30 | | |

| Thr | Ile | Phe | Leu | Ala | Asp | Lys | Asn | Asp | Asn | Ala | Pro |
|---|---|---|---|---|---|---|---|---|---|---|---|
| | | 35 | | | | | 40 | | | | |

( 2 ) INFORMATION FOR SEQ ID NO:27:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:27:

```
AAGCGGCTGG ATTTCGAACA GTTCCAGCAG CACAAGCTGC TCGTAAGGGC TGTTGATGGA        60
GGAATGCCGC CACTGAGCAG CGATGTGGTC GTCACTGTGG ATGTCACCGA CCTCAACGAT       120
AACGCGCCCT A                                                            131
```

( 2 ) INFORMATION FOR SEQ ID NO:28:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:28:

| Lys | Arg | Leu | Asp | Phe | Glu | Gln | Phe | Gln | Gln | His | Lys | Leu | Leu | Val | Arg |
|---|---|---|---|---|---|---|---|---|---|---|---|---|---|---|---|
| 1 | | | | 5 | | | | | 10 | | | | | 15 | |

| Ala | Val | Asp | Gly | Gly | Met | Pro | Pro | Leu | Ser | Ser | Asp | Val | Val | Val | Thr |
|---|---|---|---|---|---|---|---|---|---|---|---|---|---|---|---|
| | | | 20 | | | | | 25 | | | | | 30 | | |

| Val | Asp | Val | Thr | Asp | Leu | Asn | Asp | Asn | Ala | Pro |
|---|---|---|---|---|---|---|---|---|---|---|
| | | 35 | | | | | 40 | | | |

( 2 ) INFORMATION FOR SEQ ID NO:29:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:29:

```
AAGGGGATAG ACTTTGAGAG TGAGAATTAC TATGAATTTG ATGTGCGGGC TCGCGATGGG        60
GGTTCTCCAG CCATGGAGCA ACATTGCAGC CTTCGAGTGG ATCTGCTGGA CGTAAATGAC       120
AACGCCCCAC T                                                            131
```

( 2 ) INFORMATION FOR SEQ ID NO:30:

( i ) SEQUENCE CHARACTERISTICS:
    ( A ) LENGTH: 43 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:30:

```
Lys Gly Ile Asp Phe Glu Ser Glu Asn Tyr Tyr Glu Phe Asp Val Arg
1               5                   10                  15

Ala Arg Asp Gly Gly Ser Pro Ala Met Glu Gln His Cys Ser Leu Arg
            20                  25                  30

Val Asp Leu Leu Asp Val Asn Asp Asn Ala Pro
            35                  40
```

( 2 ) INFORMATION FOR SEQ ID NO:31:

( i ) SEQUENCE CHARACTERISTICS:
    ( A ) LENGTH: 131 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:31:

```
AAGGCATTGG ACTTTGAGGC CCGGCGACTG TATTCGCTGA CAGTTCAGGC CACGGACCGA      60

GGCGTGCCCT CGCTCACCGG GCGTGCCGAA GCGCTTATCC AGCTGCTAGA TGTCAACGAC     120

AACGCACCCA T                                                          131
```

( 2 ) INFORMATION FOR SEQ ID NO:32:

( i ) SEQUENCE CHARACTERISTICS:
    ( A ) LENGTH: 43 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:32:

```
Lys Ala Leu Asp Phe Glu Ala Arg Arg Leu Tyr Ser Leu Thr Val Gln
1               5                   10                  15

Ala Thr Asp Arg Gly Val Pro Ser Leu Thr Gly Arg Ala Glu Ala Leu
            20                  25                  30

Ile Gln Leu Leu Asp Val Asn Asp Asn Ala Pro
            35                  40
```

( 2 ) INFORMATION FOR SEQ ID NO:33:

( i ) SEQUENCE CHARACTERISTICS:
    ( A ) LENGTH: 125 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:33:

```
AAGCCAATTG ATTACGAGGC AACTCCATAC TATAACATGG AAATTGTAGC CACAGACAGC      60

GGAGGTCTTT CGGGAAAATG CACTGTGTCT ATACAGGTGG TGGATGTGAA CGACAACGCC     120

CCCAA                                                                 125
```

( 2 ) INFORMATION FOR SEQ ID NO:34:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:34:

```
Lys Pro Ile Asp Tyr Glu Ala Thr Pro Tyr Tyr Asn Met Glu Ile Val
 1               5                  10                  15
Ala Thr Asp Ser Gly Gly Leu Ser Gly Lys Cys Thr Val Ser Ile Gln
            20                  25                  30
Val Val Asp Val Asn Asp Asn Ala Pro
            35                  40
```

( 2 ) INFORMATION FOR SEQ ID NO:35:

( i ) SEQUENCE CHARACTERISTICS:
        ( A ) LENGTH: 446 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

```
AAGCGGGTAG ACTTCGAAAT GTGCAAAAGA TTTTACCTTG TGGTGGAAGC TAAAGACGGA      60
GGCACCCCAG CCCTCAGCAC GGCAGCCACT GTCAGCATCG ACCTCACAGA TGTGAATGAT     120
AACCCTCCTC GGTTCAGCCA AGATGTCTAC AGTGCTGTCA TCAGTGAGGA TGCCTTAGAG     180
GGGGACTCTG TCATTCTGCT GATAGCAGAA GATGTGGATA GCAAGCCTAA TGGACAGATT     240
CGGTTTTCCA TCGTGGGTGG AGATAGGGAC AATGAATTTG CTGTCGATCC AATCTTGGGA     300
CTTGTGAAAG TTAAGAAGAA ACTGGACCGG GAGCGGGTGT CAGGATACTC CCTGCTCATC     360
CAGGCAGTAG ATAGTGGCAT TCCTGCAATG TCCTCAACGA CAACTGTCAA CATTGATATT     420
TCTGATGTGA ACGACAACGC CCCCCT                                          446
```

( 2 ) INFORMATION FOR SEQ ID NO:36:

( i ) SEQUENCE CHARACTERISTICS:
        ( A ) LENGTH: 148 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:36:

```
Lys Arg Val Asp Phe Glu Met Cys Lys Arg Phe Tyr Leu Val Val Glu
 1               5                  10                  15
Ala Lys Asp Gly Gly Thr Pro Ala Leu Ser Thr Ala Ala Thr Val Ser
            20                  25                  30
Ile Asp Leu Thr Asp Val Asn Asp Asn Pro Pro Arg Phe Ser Gln Asp
            35                  40                  45
Val Tyr Asp Ala Val Ile Ser Glu Asp Ala Leu Glu Gly Asp Ser Val
    50                  55                  60
Ile Leu Leu Ile Ala Glu Asp Val Asp Ser Lys Pro Asn Gly Gln Ile
 65                  70                  75                  80
Arg Phe Ser Ile Val Gly Gly Asp Arg Asp Asn Glu Phe Ala Val Asp
                85                  90                  95
```

```
Pro  Ile  Leu  Gly  Leu  Val  Lys  Val  Lys  Lys  Leu  Asp  Arg  Glu  Arg
               100                 105                 110

Val  Ser  Gly  Tyr  Ser  Leu  Leu  Ile  Gln  Ala  Val  Asp  Ser  Gly  Ile  Pro
          115                      120                      125

Ala  Met  Ser  Ser  Thr  Thr  Thr  Val  Asn  Ile  Asp  Ile  Ser  Asp  Val  Asn
          130                      135                      140

Asp  Asn  Ala  Pro
145
```

( 2 ) INFORMATION FOR SEQ ID NO:37:

( i ) SEQUENCE CHARACTERISTICS:
        ( A ) LENGTH: 440 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

```
AAGGGGGTTG ATTATGAGAC AAACCCACGG CTACGACTGG TGCTACAGGC AGAGAGTGGA      60
GGAGCCTTTG CTTTCTCGGT GCTGACCCTG ACCCTTCAAG ATGCCAATGA CAATGCTCCC     120
CGTTTCCTGC AGCCTCACTA CGTGGCTTTC CTGCCAGAGT CCCGACCCTT GGAAGGGCCC     180
CTGCTGCAGG TGGAAGCAGA CGACCTGGAT CAAGGCTCTG GAGGACAGAT CTCCTACAGT     240
CTGGCTGCAT CCCAGCCAGC ACGGGGCTTG TTCCATGTAG ACCCAGCCAC AGGCACTATC     300
ACTACCACAG CCATCCTGGA CCGGGAAATC TGGGCTGAAA CACGGCTGGT ACTGATGGCC     360
ACAGACAGAG GAAGCCCAGC ATTGGTGGGC TCAGCTACCC TGACAGTGAT GGTCATCGAT     420
ACCAACGACA ATGCTCCCCT                                                 440
```

( 2 ) INFORMATION FOR SEQ ID NO:38:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:38:

```
Lys  Gly  Val  Asp  Tyr  Glu  Thr  Asn  Pro  Arg  Leu  Arg  Leu  Val  Leu  Gln
1                        5                        10                       15

Ala  Glu  Ser  Gly  Gly  Ala  Phe  Ala  Phe  Ser  Val  Leu  Thr  Leu  Thr  Leu
               20                      25                      30

Gln  Asp  Ala  Asn  Asp  Asn  Ala  Pro  Arg  Phe  Leu  Gln  Pro  His  Tyr  Val
          35                      40                      45

Ala  Phe  Leu  Pro  Glu  Ser  Arg  Pro  Leu  Glu  Gly  Pro  Leu  Leu  Gln  Val
     50                      55                      60

Glu  Ala  Asn  Asp  Leu  Asp  Gln  Gly  Ser  Gly  Gly  Gln  Ile  Ser  Tyr  Ser
65                       70                      75                       80

Leu  Ala  Ala  Ser  Gln  Pro  Ala  Arg  Gly  Leu  Phe  His  Val  Asp  Pro  Ala
               85                      90                      95

Thr  Gly  Thr  Ile  Thr  Thr  Thr  Ala  Ile  Leu  Asp  Arg  Glu  Ile  Trp  Ala
               100                     105                     110

Glu  Thr  Arg  Leu  Val  Leu  Met  Ala  Thr  Asp  Arg  Gly  Ser  Pro  Ala  Leu
          115                     120                     125

Val  Gly  Ser  Ala  Thr  Leu  Thr  Val  Met  Val  Ile  Asp  Thr  Asn  Asp  Asn
```

Ala Pro
145

(2) INFORMATION FOR SEQ ID NO:39:

(i) SEQUENCE CHARACTERISTICS:
      (A) LENGTH: 124 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:39:

```
AAGGTCTCGA TTATGAGGCA ACTCCATATT ATAACGTGGA AATTGTAGCC ACAGATGGTG    60
GGGGCCTTTC AGGAAAATGC ACTGTGGCTA TAGAAGTGGT GGATGTGAAC GACGGCGCTC   120
CAAT                                                                124
```

(2) INFORMATION FOR SEQ ID NO:40:

(i) SEQUENCE CHARACTERISTICS:
      (A) LENGTH: 41 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:40:

```
Lys Gly Leu Asp Tyr Glu Ala Thr Pro Tyr Tyr Asn Val Glu Ile Val
 1               5                  10                  15

Ala Thr Asp Gly Gly Ala Phe Asp Glu Asn Cys Thr Val Ala Ile Glu
                20                  25                  30

Val Val Asp Val Asn Asp Asn Ala Pro
                35                  40
```

(2) INFORMATION FOR SEQ ID NO:41:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: DNA (xi) SEQUENCE DESCRIPTION: SEQ ID NO:41:

```
Asp Xaa Asn Glu Xaa Pro Xaa Phe
 1               5
```

(2) INFORMATION FOR SEQ ID NO:42:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: DNA (xi) SEQUENCE DESCRIPTION: SEQ ID NO:42:

```
Asp Xaa Asp Glu Xaa Pro Xaa Phe
 1               5
```

(2) INFORMATION FOR SEQ ID NO:43:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: DNA ( x i ) SEQUENCE DESCRIPTION: SEQ ID NO:43:

Asp Xaa Asn Asp Asn Xaa Pro Xaa Phe
1               5

( 2 ) INFORMATION FOR SEQ ID NO:44:

( i ) SEQUENCE CHARACTERISTICS:
    ( A ) LENGTH: 131 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:44:

AAGCGGATGG ATTTGAAGA CACCAAACTC CATGAGATTT ACATCCAGGC CAAAGACAAA      60
GGTGCCAATC CGAAGGAGC GCATTGCAAA GTACTTGTAG AGGTTGTAGA CGTAAACGAC     120
AACGCCCCAG T                                                         131

( 2 ) INFORMATION FOR SEQ ID NO:45:

( i ) SEQUENCE CHARACTERISTICS:
    ( A ) LENGTH: 43 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:45:

Leu Arg Met Asp Phe Glu Asp Thr Lys Leu His Glu Ile Tyr Ile Gln
1               5                   10                  15

Ala Lys Asp Lys Gly Ala Asn Pro Glu Gly Ala His Cys Lys Val Leu
            20                  25                  30

Val Glu Val Val Asp Val Asn Asp Asn Ala Pro
        35                  40

( 2 ) INFORMATION FOR SEQ ID NO:46:

( i ) SEQUENCE CHARACTERISTICS:
    ( A ) LENGTH: 131 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:46:

AAGGCTTTGG ATTACGAGGA TCAGAGAGAG TTCCAACTAA CAGCTCATAT AAACGACGGA      60
GGTACCCCAG TCTTAGCCAC CAACATCAGC GTGAACGTAT TTGTTACTGA CCGCAATGAT    120
AACGCCCCCT A                                                          131

( 2 ) INFORMATION FOR SEQ ID NO:47:

( i ) SEQUENCE CHARACTERISTICS:
    ( A ) LENGTH: 43 amino acids
    ( B ) TYPE: amino acid (C) STRANDEDNESS: single
(D) TOPOLOGY: linear (ii) MOLECULE TYPE: protein (xi) SEQUENCE DESCRIPTION: SEQ ID NO:47:

```
Lys Ala Leu Asp Tyr Glu Asp Gln Arg Glu Phe Gln Leu Thr Ala His
1               5                   10                  15
Ile Asn Asp Gly Gly Thr Pro Val Leu Ala Thr Asn Ile Ser Val Asn
            20                  25                  30
Val Phe Val Thr Asp Arg Asn Asp Asn Ala Pro
            35                  40
```

(2) INFORMATION FOR SEQ ID NO:48:

(i) SEQUENCE CHARACTERISTICS:
(A) LENGTH: 131 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:48:

```
AAGCGCTTGG ACTACGAGGA GAGTAACAAT TATGAAATTC ACGTGGATGC TACAGATAAA      60
GGATACCCAC CTATGGTTGC TCACTGCACC GTACTCGTGG GAATCTTGGA TGAAAATGAC     120
AACGCACCCA T                                                         131
```

(2) INFORMATION FOR SEQ ID NO:49:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:49:

```
Lys Arg Leu Asp Tyr Glu Glu Ser Asn Asn Tyr Glu Ile His Val Asp
1               5                   10                  15
Ala Thr Asp Lys Gly Tyr Pro Pro Met Val Ala His Cys Thr Val Leu
            20                  25                  30
Val Gly Ile Leu Asp Glu Asn Asp Asn Ala Pro
            35                  40
```

(2) INFORMATION FOR SEQ ID NO:50:

(i) SEQUENCE CHARACTERISTICS:
(A) LENGTH: 131 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:50:

```
AAACCGGTGG ACTACGAGAA AGTCAAAGAC TATACCATCG AGATCGTGGC TGTGGATTCC      60
GGCAACCCTC CACTCTCTAG CACCAACTCC CTCAAGGTGC AGGTGGTAGA CGTCAACGAT     120
AACGCCCCTC T                                                         131
```

(2) INFORMATION FOR SEQ ID NO:51:

(i) SEQUENCE CHARACTERISTICS:

(A) LENGTH: 43 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:51:

| Lys | Pro | Val | Asp | Tyr | Glu | Lys | Val | Lys | Asp | Tyr | Thr | Ile | Glu | Ile | Val |
|---|---|---|---|---|---|---|---|---|---|---|---|---|---|---|---|
| 1 | | | | 5 | | | | | 10 | | | | | 15 | |

| Ala | Val | Asp | Ser | Gly | Asn | Pro | Pro | Leu | Ser | Ser | Thr | Asn | Ser | Leu | Lys |
|---|---|---|---|---|---|---|---|---|---|---|---|---|---|---|---|
| | | | 20 | | | | | 25 | | | | 30 | | | |

| Val | Gln | Val | Val | Asp | Val | Asn | Asp | Asn | Ala | Pro |
|---|---|---|---|---|---|---|---|---|---|---|
| | | 35 | | | | | 40 | | | |

(2) INFORMATION FOR SEQ ID NO:52:

(i) SEQUENCE CHARACTERISTICS:
(A) LENGTH: 131 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:52:

```
AAGCCTTTTG ATTTCGAGGA CACCAAACTC CATGAGATTT ACATCCAGGC CAAAGACAAG      60
GGCGCCAATC CCGAAGGAGC ACATTGCAAA GTGTTGGTGG AGGTTGTGGA TGTGAACGAC     120
AATGCCCCTC A                                                           131
```

(2) INFORMATION FOR SEQ ID NO:53:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:53:

| Lys | Pro | Phe | Asp | Phe | Glu | Asp | Thr | Lys | Leu | His | Glu | Ile | Tyr | Ile | Gln |
|---|---|---|---|---|---|---|---|---|---|---|---|---|---|---|---|
| 1 | | | | 5 | | | | | 10 | | | | | 15 | |

| Ala | Lys | Asp | Lys | Gly | Ala | Asn | Pro | Glu | Gly | Ala | His | Cys | Lys | Val | Leu |
|---|---|---|---|---|---|---|---|---|---|---|---|---|---|---|---|
| | | | 20 | | | | | 25 | | | | 30 | | | |

| Val | Glu | Val | Val | Asp | Val | Asn | Asp | Asn | Ala | Pro |
|---|---|---|---|---|---|---|---|---|---|---|
| | | 35 | | | | | 40 | | | |

(2) INFORMATION FOR SEQ ID NO:54:

(i) SEQUENCE CHARACTERISTICS:
(A) LENGTH: 122 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:54:

```
AAAGGTGTCG ATTACGAGGT GAGTCCACGG CTGCGACTGG TGCTGCAGGC AGAGAGTCGA      60
GGAGCCTTTG CCTTCACTGT GCTGACCCTG ACCCTGCAAG ATGCCAACGA CAACGCCCCG     120
AG                                                                     122
```

(2) INFORMATION FOR SEQ ID NO:55:

( i ) SEQUENCE CHARACTERISTICS:
   ( A ) LENGTH: 40 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:55:

```
Lys Gly Val Asp Tyr Glu Val Ser Pro Arg Leu Arg Leu Val Leu Gln
1               5                   10                  15
Ala Glu Ser Arg Gly Ala Phe Ala Phe Thr Val Leu Thr Leu Thr Leu
            20                  25                  30
Gln Asp Ala Asn Asp Asn Ala Pro
            35                  40
```

( 2 ) INFORMATION FOR SEQ ID NO:56:

( i ) SEQUENCE CHARACTERISTICS:
      ( A ) LENGTH: 131 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:56:

```
AAAGGGATTG ATTACGAGCA GTTGAGAGAC CTACAGCTGT GGGTGACAGC CAGCGACAGC     60
GGGGACCCGC CTCTTAGCAG CAACGTGTCA CTGAGCCTGT TTGTGCTGGA CCAGAACGAC    120
AACGCCCCCC T                                                         131
```

( 2 ) INFORMATION FOR SEQ ID NO:57:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:57:

```
Lys Gly Ile Asp Tyr Glu Gln Leu Arg Asp Leu Gln Leu Trp Val Thr
1               5                   10                  15
Ala Ser Asp Ser Gly Asp Pro Pro Leu Ser Ser Asn Val Ser Leu Ser
            20                  25                  30
Leu Phe Val Leu Asp Gln Asn Asp Asn Ala Pro
            35                  40
```

( 2 ) INFORMATION FOR SEQ ID NO:58:

( i ) SEQUENCE CHARACTERISTICS:
      ( A ) LENGTH: 125 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:58:

```
AAGGCGGTCG ATTTTGAGCG CACATCCTCT TATCAACTCA TCATTCAGGC CACCAATATG     60
GCAGGAATGG CTTCCAATGC TACAGTCAAT ATTCAGATTG TTGATGAAAA CGACAACGCC    120
CCCCA                                                                125
```

(2) INFORMATION FOR SEQ ID NO:59:

(i) SEQUENCE CHARACTERISTICS:
(A) LENGTH: 41 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:59:

```
Lys Ala Val Asp Phe Glu Arg Thr Ser Ser Tyr Gln Leu Ile Ile Gln
 1               5                  10                  15
Ala Thr Asn Met Ala Gly Met Ala Ser Asn Ala Thr Val Asn Ile Gln
             20                  25                  30
Ile Val Asp Glu Asn Asp Asn Ala Pro
             35              40
```

(2) INFORMATION FOR SEQ ID NO:60:

(i) SEQUENCE CHARACTERISTICS:
(A) LENGTH: 131 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:60:

```
AAACGGCTAG ACTTTGAAAA GATACAAAAA TATGTTGTAT GGATAGAGGC CAGAGATGGT      60
GGTTTCCCTC CTTTCTCCTC TTACGAGAAA CTTGATATAA CAGTATTAGA TGTCAACGAT     120
AACGCGCCTA A                                                          131
```

(2) INFORMATION FOR SEQ ID NO:61:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:61:

```
Lys Arg Leu Asp Phe Glu Lys Ile Gln Lys Tyr Val Val Trp Ile Glu
 1               5                  10                  15
Ala Arg Asp Gly Gly Phe Pro Pro Phe Ser Ser Tyr Glu Lys Leu Asp
             20                  25                  30
Ile Thr Val Leu Asp Val Asn Asp Asn Ala Pro
             35              40
```

(2) INFORMATION FOR SEQ ID NO:62:

(i) SEQUENCE CHARACTERISTICS:
(A) LENGTH: 131 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:62:

```
AAGGGGATCG ATTATGAGAA GGTCAAAGAC TACACCATTG AGATTGTGGC TGTGGACTCT      60
GGCAACCCCC CACTCTCCAG CACTAACTCC CTCAAGGTGC AGGTGGTGGA CGTCAATGAC     120
```

```
AACGCACCGT G                                                                                131
```

(2) INFORMATION FOR SEQ ID NO:63:

(i) SEQUENCE CHARACTERISTICS:
       (A) LENGTH: 43 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:63:

```
Lys Gly Ile Asp Tyr Glu Lys Val Lys Asp Tyr Thr Ile Glu Ile Val
 1               5                  10                  15

Ala Val Asp Ser Gly Asn Pro Pro Leu Ser Ser Thr Asn Ser Leu Lys
            20                  25                  30

Val Gln Val Val Asp Val Asn Asp Asn Ala Pro
         35                  40
```

(2) INFORMATION FOR SEQ ID NO:64:

(i) SEQUENCE CHARACTERISTICS:
       (A) LENGTH: 131 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:64:

```
AAGGGACTCG ACTACGAGGA TCGGCGGGAA TTTGAATTAA CAGCTCATAT CAGCGATGGG       60
GGCACCCCGG TCCTAGCCAC CAACATCAGC GTGAACATAT TTGTCACTGA TCGCAACGAT      120
AATGCCCCCG T                                                          131
```

(2) INFORMATION FOR SEQ ID NO:65:

(i) SEQUENCE CHARACTERISTICS:
       (A) LENGTH: 43 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:65:

```
Lys Gly Leu Asp Tyr Glu Asp Arg Arg Glu Phe Glu Leu Thr Ala His
 1               5                  10                  15

Ile Ser Asp Gly Gly Thr Pro Val Leu Ala Thr Asn Ile Ser Val Asn
            20                  25                  30

Ile Phe Val Thr Asp Arg Asn Asp Asn Ala Pro
         35                  40
```

(2) INFORMATION FOR SEQ ID NO:66:

(i) SEQUENCE CHARACTERISTICS:
       (A) LENGTH: 470 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:66:

```
AAGGGTTTGG ACTACGAGAC CACACAGGCC TACCAGCTCA CGGTCAACGC CACAGATCAA       60
```

-continued

```
GACAACACCA GGCCTCTGTC CACCCTGGCC AACTTGGCCA TCATCATCAC AGATGTCCAG    120
GACATGGACC CCATCTTCAT CAACCTGCCT TACAGCACCA ACATCTACGA GCATTCTCCT    180
CCGGGCACGA CGGTGCGCAT CATCACCGCC ATAGACCAGG ATCAAGGACG TCCCCGGGGC    240
ATTGGCTACA CCATCGTTTC AGGGAATACC AACAGCATCT TTGCCCTGGA CTACATCAGC    300
GGAGTGCTGA CCTTGAATGG CCTGCTGGAC CGGGAGAACC CCTGTACAG CCATGGCTTC     360
ATCCTGACTG TGAAGGGCAC GGAGCTGAAC GATGACCGCA CCCCATCTGA CGCTACAGTC    420
ACCACGACCT TCAATATCCT GGTTATTGAC ATCAACGACA ACGCCCCACT               470
```

( 2 ) INFORMATION FOR SEQ ID NO:67:

( i ) SEQUENCE CHARACTERISTICS:
       ( A ) LENGTH: 156 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:67:

```
Lys Gly Leu Asp Tyr Glu Thr Thr Gln Ala Tyr Gln Leu Thr Val Asn
1               5                   10                  15

Ala Thr Asp Gln Asp Asn Thr Arg Pro Leu Ser Thr Leu Ala Asn Leu
            20                  25                  30

Ala Ile Ile Ile Thr Asp Val Gln Asp Met Asp Pro Ile Phe Ile Asn
        35                  40                  45

Leu Pro Tyr Ser Thr Asn Ile Tyr Glu His Ser Pro Gly Thr Thr
    50                  55                  60

Val Arg Ile Ile Thr Ala Ile Asp Gln Asp Gln Gly Arg Pro Arg Gly
65                  70                  75                  80

Ile Gly Tyr Thr Ile Val Ser Gly Asn Thr Asn Ser Ile Phe Ala Leu
                85                  90                  95

Asp Tyr Ile Ser Gly Val Leu Thr Leu Asn Gly Leu Leu Asp Arg Glu
            100                 105                 110

Asn Pro Leu Tyr Ser Gly Gly Phe Ile Leu Thr Val Lys Gly Thr Glu
        115                 120                 125

Leu Asn Asp Asp Arg Thr Pro Ser Asp Ala Thr Val Thr Thr Thr Phe
    130                 135                 140

Asn Ile Leu Val Ile Asp Ile Asn Asp Asn Ala Pro
145                 150                 155
```

( 2 ) INFORMATION FOR SEQ ID NO:68:

( i ) SEQUENCE CHARACTERISTICS:
       ( A ) LENGTH: 131 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:68:

```
AAGGGGGTCG ATTACGAGGT ACTACAGGCC TTTGAGTTCC ACGTGAGCGC CACAGACCGA    60
GGCTCACCGG GGCTCAGCAG CCAGGCTCTG GTGCGCGTGG TGGTGCTGGA CGACAATGAC    120
AACGCTCCCG T                                                          131
```

( 2 ) INFORMATION FOR SEQ ID NO:69:

( i ) SEQUENCE CHARACTERISTICS:

( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:69:

| Lys | Gly | Val | Asp | Tyr | Glu | Val | Leu | Gln | Ala | Phe | Glu | Phe | His | Val | Ser |
|---|---|---|---|---|---|---|---|---|---|---|---|---|---|---|---|
| 1 | | | | 5 | | | | | 10 | | | | | 15 | |

| Ala | Thr | Asp | Arg | Gly | Ser | Pro | Gly | Leu | Ser | Ser | Gln | Ala | Leu | Val | Arg |
|---|---|---|---|---|---|---|---|---|---|---|---|---|---|---|---|
| | | | 20 | | | | | 25 | | | | | 30 | | |

| Val | Val | Val | Leu | Asp | Asp | Asn | Asp | Asn | Ala | Pro |
|---|---|---|---|---|---|---|---|---|---|---|
| | | 35 | | | | 40 | | | | |

( 2 ) INFORMATION FOR SEQ ID NO:70:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:70:

```
AAGGGGCTGG ATTATGAGCA GTTCCAGACC CTACAACTGG GAGTGACCGC TAGTGACAGT     60
GGAAACCCAC CATTAAGAAG CAATATTTCA CTGACCCTTT TCGTGCTGGA CCAGAATGAT    120
AACGCCCCAA A                                                          131
```

( 2 ) INFORMATION FOR SEQ ID NO:71:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:71:

| Lys | Gly | Leu | Asp | Tyr | Glu | Gln | Phe | Gln | Thr | Leu | Gln | Leu | Gly | Val | Thr |
|---|---|---|---|---|---|---|---|---|---|---|---|---|---|---|---|
| 1 | | | | 5 | | | | | 10 | | | | | 15 | |

| Ala | Ser | Asp | Ser | Gly | Asn | Pro | Pro | Leu | Arg | Ser | Asn | Ile | Ser | Leu | Thr |
|---|---|---|---|---|---|---|---|---|---|---|---|---|---|---|---|
| | | | 20 | | | | | 25 | | | | | 30 | | |

| Leu | Phe | Val | Leu | Asp | Gln | Asn | Asp | Asn | Ala | Pro |
|---|---|---|---|---|---|---|---|---|---|---|
| | | 35 | | | | 40 | | | | |

( 2 ) INFORMATION FOR SEQ ID NO:72:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:72:

```
AAGCGGGTTG ATTACGAGGA TGTCCAGAAA TACTCGCTGA GCATTAAGGC CAGGATGGG     60
CGGCCCCCGC TCATCAATTC TTCAGGGGTG GTGTCTGTGC AGGTGCTGGA TGTCAACGAC   120
AATGCCCCGG A                                                          131
```

( 2 ) INFORMATION FOR SEQ ID NO:73:

( i ) SEQUENCE CHARACTERISTICS:
    ( A ) LENGTH: 43 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:73:

| Lys | Arg | Val | Asp | Tyr | Glu | Asp | Val | Gln | Lys | Tyr | Ser | Leu | Ser | Ile | Lys |
|---|---|---|---|---|---|---|---|---|---|---|---|---|---|---|---|
| 1 | | | | 5 | | | | | 10 | | | | | 15 | |

| Ala | Gln | Asp | Gly | Arg | Pro | Pro | Leu | Ile | Asn | Ser | Ser | Gly | Val | Val | Ser |
|---|---|---|---|---|---|---|---|---|---|---|---|---|---|---|---|
| | | | 20 | | | | | 25 | | | | | 30 | | |

| Val | Gln | Val | Leu | Asp | Val | Asn | Asp | Asn | Ala | Pro |
|---|---|---|---|---|---|---|---|---|---|---|
| | | | 35 | | | | 40 | | | |

( 2 ) INFORMATION FOR SEQ ID NO:74:

( i ) SEQUENCE CHARACTERISTICS:
    ( A ) LENGTH: 125 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:74:

```
AAACCGGTAG ACTTTGAGCT ACAGCAGTTC TATGAAGTAG CTGTGGTGGC TTGGAACTCT      60
GAGGGATTTC ATGTCAAAAG GGTCATTAAA GTGCAACTTT TAGATGACAA CGACAATGCC     120
CCGAT                                                                  125
```

( 2 ) INFORMATION FOR SEQ ID NO:75:

( i ) SEQUENCE CHARACTERISTICS:
    ( A ) LENGTH: 41 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:75:

| Lys | Pro | Val | Asp | Phe | Glu | Leu | Gln | Gln | Phe | Tyr | Glu | Val | Ala | Val | Val |
|---|---|---|---|---|---|---|---|---|---|---|---|---|---|---|---|
| 1 | | | | 5 | | | | | 10 | | | | | 15 | |

| Ala | Trp | Asn | Ser | Glu | Gly | Phe | His | Val | Lys | Arg | Val | Ile | Lys | Val | Gln |
|---|---|---|---|---|---|---|---|---|---|---|---|---|---|---|---|
| | | | 20 | | | | | 25 | | | | | 30 | | |

| Leu | Leu | Asp | Asp | Asn | Asp | Asn | Ala | Pro |
|---|---|---|---|---|---|---|---|---|
| | | | 35 | | | | 40 | |

( 2 ) INFORMATION FOR SEQ ID NO:76:

( i ) SEQUENCE CHARACTERISTICS:
    ( A ) LENGTH: 125 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:76:

```
AAGGGATTAG ATTTTGAAAC TTTGCCCATT TACACATTGA TAATACAAGG AACTAACATG      60
GCTGGTTTGT CCACTAATAC AACGGTTCTA GTTCACTTGC AGGATGAGAA TGATAACGCC     120
CCAAA                                                                  125
```

( 2 ) INFORMATION FOR SEQ ID NO:77:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:77:

```
Lys Gly Leu Asp Phe Glu Thr Leu Pro Ile Tyr Thr Leu Ile Ile Gln
 1               5                  10                  15
Gly Thr Asn Met Ala Gly Leu Ser Thr Asn Thr Thr Val Leu Val His
            20                  25                  30
Leu Gln Asp Glu Asn Asp Asn Ala Pro
            35                  40
```

( 2 ) INFORMATION FOR SEQ ID NO:78:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:78:

```
AAGCGGGCGG ATTTCGAGGC GATCCGGGAG TACAGTCTGA GGATCAAAGC GCAGGACGGG      60
GGGCGGCCTC CCCTCAGCAA CACCACGGGC ATGGTCACAG TGCAGGTCGT GGACGTCAAT     120
GACAACGCAC CCCT                                                       134
```

( 2 ) INFORMATION FOR SEQ ID NO:79:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:79:

```
Lys Arg Ala Asp Phe Glu Ala Ile Arg Glu Tyr Ser Leu Arg Ile Lys
 1               5                  10                  15
Ala Gln Asp Gly Gly Arg Pro Pro Leu Ser Asn Thr Thr Gly Met Val
            20                  25                  30
Thr Val Gln Val Val Asp Val Asn Asp Asn Ala Pro
            35                  40
```

( 2 ) INFORMATION FOR SEQ ID NO:80:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:80:

```
AAGCGGTTGG ATTACGAAAA GGCATCGGAA TATGAAATCT ATGTTCAAGC CGCTGACAAA      60
GGCGCTGTCC CTATGGCTGG CCATTGCAAA GTGTTGCTGG AGATCGTGGA TGTCAACGAC     120
```

AACGCCCCCT T        131

( 2 ) INFORMATION FOR SEQ ID NO:81:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:81:

```
Lys Arg Leu Asp Tyr Glu Lys Ala Ser Glu Tyr Glu Ile Tyr Val Gln
 1               5                   10                  15

Ala Ala Asp Lys Gly Ala Val Pro Met Ala Gly His Cys Lys Val Leu
            20                  25                  30

Leu Glu Ile Val Asp Val Asn Asp Asn Ala Pro
            35                  40
```

( 2 ) INFORMATION FOR SEQ ID NO:82:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:82:

AAGGGGATCG ATTATGAGGA TCAGGTCTCT TACACATTAG CAGTAACAGC ACATGACTAT        60

GGCATCCCTC AAAAATCAGA CACTACCTAT TTGGAAATCT TAGTAATTGA TGTTAACGAC        120

AACGCGCCCC A        131

( 2 ) INFORMATION FOR SEQ ID NO:83:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:83:

```
Lys Gly Ile Asp Tyr Glu Asp Gln Val Ser Tyr Thr Leu Ala Val Thr
 1               5                   10                  15

Ala His Asp Tyr Gly Ile Pro Gln Lys Ser Asp Thr Thr Tyr Leu Glu
            20                  25                  30

Ile Leu Val Ile Asp Val Asn Asp Asn Ala Pro
            35                  40
```

( 2 ) INFORMATION FOR SEQ ID NO:84:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:84:

AAAGGGTTAG ATTTCGAGGG CACTAAAGAT TCAGCGTTTA AAATAGTGGC AGCTGACACA        60

```
GGGAAGCCCA GCCTCAACCA GACAGCCCTG GTGAGAGTAG AGCTGGAGGA TGAGAACGAC        120

AACGCCCCAA T                                                              131
```

(2) INFORMATION FOR SEQ ID NO:85:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:85:

```
Lys Gly Leu Asp Phe Glu Gly Thr Lys Asp Ser Ala Phe Lys Ile Val
 1               5                  10                  15

Ala Ala Asp Thr Gly Lys Pro Ser Leu Asn Gln Thr Ala Leu Val Arg
            20                  25                  30

Val Glu Leu Glu Asp Glu Asn Asp Asn Ala Pro
            35                  40
```

(2) INFORMATION FOR SEQ ID NO:86:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:86:

```
AAGGGTGTGG ATTTTGAAAG TGTGCGTAGC TACAGGCTGG TTATTCGTGC TCAAGATGGA        60

GGCAGCCCCT CCAGAAGTAA CACCACCCAG CTCTTGGTCA ACGTCATCGA TCGAATGACA       120

ATGCGCCGCT                                                              130
```

(2) INFORMATION FOR SEQ ID NO:87:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:87:

```
Lys Gly Val Asp Phe Glu Ser Val Arg Ser Tyr Arg Leu Val Ile Arg
 1               5                  10                  15

Ala Gln Asp Gly Gly Ser Pro Ser Arg Ser Asn Thr Thr Gln Leu Leu
            20                  25                  30

Val Asn Val Ile Asp Val Asn Asp Asn Ala Pro
            35                  40
```

(2) INFORMATION FOR SEQ ID NO:88:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:88:

| | | | | |
|---|---|---|---|---|
| AAGGGTGTGG | ACTTCGAGCT | GACACATCTG | TATGAGATTT | GGATTGAGGC TGCCGATGGA | 60 |
| GACACGCCAA | GTCTGCGTAG | TGTAACTCTT | ATAACGCTCA | ACGTAACGGA TGCCAATGAC | 120 |
| AATGCTCCCA A | | | | | 131 |

( 2 ) INFORMATION FOR SEQ ID NO:89:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:89:

```
Lys Gly Val Asp Phe Glu Leu Thr His Leu Tyr Glu Ile Trp Ile Glu
 1               5                  10                  15
Ala Ala Asp Gly Asp Thr Pro Ser Leu Arg Ser Val Thr Leu Ile Thr
            20                  25                  30
Leu Asn Val Thr Asp Ala Asn Asp Asn Ala Pro
            35                  40
```

( 2 ) INFORMATION FOR SEQ ID NO:90:

( i ) SEQUENCE CHARACTERISTICS:
        ( A ) LENGTH: 441 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:90:

| | | | | | |
|---|---|---|---|---|---|
| CAAGGCGTTT | GATTTGAAG | AGACAAGTAG | ATATGTGTTG | AGTGTGGAAG CTAAGGATGG | 60 |
| AGGAGTACAC | ACAGCTCACT | GTAATGTTCA | AATAGAAATT | GTTGACGAGA ATGACAATGC | 120 |
| CCCAGAGGTG | ACATTCATGT | CCTTCTCTAA | CCAGATTCCA | GAGGATTCAG ACCTTGGAAC | 180 |
| TGTAATAGCC | CTCATAAAAG | TGCGAGACAA | GGATTCTGGG | CAAAATGGCA TGGTGACATG | 240 |
| CTATACTCAG | GAAGAAGTTC | CTTTCAAATT | AGAATCCACC | TCGAAGAATT ATTACAAGCT | 300 |
| GGTGATTGCT | GGAGCCCTAA | ACCGGGAGCA | GACAGCAGAC | TACAACGTCA CAATCATAGC | 360 |
| CACCGACAAG | GGCAAACCAG | CCCTTTCCTC | CAGGACAAGC | ATCACCCTGC ACATCTCCGA | 420 |
| CATCAACGAT | AATGCCCCCG T | | | | 441 |

( 2 ) INFORMATION FOR SEQ ID NO:91:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:91:

```
Lys Ala Phe Asp Phe Glu Glu Thr Ser Arg Tyr Val Leu Ser Val Glu
 1               5                  10                  15
Ala Lys Asp Gly Gly Val His Thr Ala His Cys Asn Val Gln Ile Glu
            20                  25                  30
Ile Val Asp Glu Asn Asp Asn Ala Pro Glu Val Thr Phe Met Ser Phe
            35                  40                  45
Ser Asn Gln Ile Pro Glu Asp Ser Asp Leu Gly Thr Val Ile Ala Leu
```

```
              50                      55                       60
         Ile Lys Val Arg Asp Lys Asp Ser Gly Gln Asn Gly Met Val Thr Cys
         65                  70                  75                  80

Tyr Thr Gln Glu Glu Val Pro Phe Lys Leu Glu Ser Thr Ser Lys Asn
                         85                  90                  95

Tyr Tyr Lys Leu Val Ile Ala Gly Ala Leu Asn Arg Glu Gln Thr Ala
                         100                 105                 110

Asp Tyr Asn Val Thr Ile Ile Ala Thr Asp Lys Gly Lys Pro Ala Leu
                     115                 120                 125

Ser Ser Arg Thr Ser Ile Thr Leu His Ile Ser Asp Ile Asn Asp Asn
                 130                 135                 140

Ala Pro
         145
```

( 2 ) INFORMATION FOR SEQ ID NO:92:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:92:

```
AAGCGAGTGG ATTACGAGGC CACTCGGAAT TATAAGCTGA GAGTTAAGGC TACTGATCTT       60
GGGATTCCAC CGAGATCTTC TAACATGACA CTGTTCATTC ATGTCCTTGA TGTTAACGAC      120
AACGCTCCCT T                                                            131
```

( 2 ) INFORMATION FOR SEQ ID NO:93:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:93:

```
         Lys Arg Val Asp Tyr Glu Ala Thr Arg Asn Tyr Lys Leu Arg Val Lys
         1               5                   10                  15

Ala Thr Asp Leu Gly Ile Pro Pro Arg Ser Ser Asn Met Thr Leu Phe
                         20                  25                  30

Ile His Val Leu Asp Val Asn Asp Asn Ala Pro
                     35                  40
```

( 2 ) INFORMATION FOR SEQ ID NO:94:

( i ) SEQUENCE CHARACTERISTICS:
        ( A ) LENGTH: 4104 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 495..3572

( x i ) SEQUENCE DESCRIPTION: SEQ ID NO:94:

```
CCTCTATTCG ACATTCTCTT TGGATTGTTT TGCTATAACT TGAAATTTGG GATGTCACAA       60
```

| | |
|---|---|
| ACGAAACTGT CATCTGTTTC CGCCAAACTG TGGTTCTGCT AATCTCCCAG GCTGGCAGCA | 120 |
| TTGGAGACTT GCTGACTTCT TTCATCCCCC ACTCTTTTCA CCTGAAATTC CTTTCCTTGG | 180 |
| TTTTGCTCTA AGTCCTATGC TTCAGTCAGG GGCCAACCAA ATCTCACTGC CTCCTTTTTA | 240 |
| TCATGAAGCC TTTGATCACT GATAGTTCTT TTTATATCTT GAAAATCAC CCTTCCCAGT | 300 |
| ACAGTTAATA TTTAGTATCT CTACTCATCT TGGCACTTAC TCACAGCTCC ATAATTCAGT | 360 |
| CGTTTTCGTA CCTCTTCATG GTGATGGGGA GCCCTTTGGA GGTGGTGACT GTGCTTTATA | 420 |
| CTCCTCATGA TGCTTCACAT GTGGCAGGCG TGGAGTGCCC GGAGGCGGCC CTCCTGATTC | 480 |

```
TGGGGCCTCC CAGG ATG GAG CCC CTG AGG CAC AGC CCA GGC CCT GGG GGG      530
              Met Glu Pro Leu Arg His Ser Pro Gly Pro Gly Gly
              1             5                  10

CAA CGG CTA CTG CTG CCC TCC ATG CTG CTA GCA CTG CTC CTG CTG          578
Gln Arg Leu Leu Leu Pro Ser Met Leu Leu Ala Leu Leu Leu Leu
      15                  20                  25

GCT CCA TCC CCA GGC CAC GCC ACT CGG GTA GTG TAC AAG GTG CCG GAG      626
Ala Pro Ser Pro Gly His Ala Thr Arg Val Val Tyr Lys Val Pro Glu
      30                  35                      40

GAA CAG CCA CCC AAC ACC CTC ATT GGG AGC CTC GCA GCC GAC TAT GGT      674
Glu Gln Pro Pro Asn Thr Leu Ile Gly Ser Leu Ala Ala Asp Tyr Gly
45                  50                  55                  60

TTT CCA GAT GTG GGG CAC CTG TAC AAG CTA GAG GTG GGT GCC CCG TAC      722
Phe Pro Asp Val Gly His Leu Tyr Lys Leu Glu Val Gly Ala Pro Tyr
                  65                  70                  75

CTT CGC GTG GAT GGC AAG ACA GGT GAC ATT TTC ACC ACC GAG ACC TCC      770
Leu Arg Val Asp Gly Lys Thr Gly Asp Ile Phe Thr Thr Glu Thr Ser
              80                  85                      90

ATC GAC CGT GAG GGG CTC CGT GAA TGC CAG AAC CAG CTC CCT GGT GAT      818
Ile Asp Arg Glu Gly Leu Arg Glu Cys Gln Asn Gln Leu Pro Gly Asp
              95                  100                 105

CCC TGC ATC CTG GAG TTT GAG GTA TCT ATC ACA GAC CTC GTG CAG AAT      866
Pro Cys Ile Leu Glu Phe Glu Val Ser Ile Thr Asp Leu Val Gln Asn
      110                 115                 120

GCG AGC CCC CGG CTG CTA GAG GGC CAG ATA GAA GTA CAA GAC ATC AAT      914
Ala Ser Pro Arg Leu Leu Glu Gly Gln Ile Glu Val Gln Asp Ile Asn
125                 130                 135                 140

GAC AAC ACA CCC AAC TTC GCC TCA CCA GTC ATC ACT CTG GCC ATC CCT      962
Asp Asn Thr Pro Asn Phe Ala Ser Pro Val Ile Thr Leu Ala Ile Pro
                  145                 150                 155

GAG AAC ACC AAC ATC GGC TCA CTC TTC CCC ATC CCG CTG GCT TCA GAC      1010
Glu Asn Thr Asn Ile Gly Ser Leu Phe Pro Ile Pro Leu Ala Ser Asp
              160                 165                 170

CGT GAT GCT GGT CCC AAC GGT GTG GCA TCC TAT GAG CTG CAG GTG GCA      1058
Arg Asp Ala Gly Pro Asn Gly Val Ala Ser Tyr Glu Leu Gln Val Ala
      175                 180                 185

GAG GAC CAG GAG GAG AAG CAA CCA CAG CTC ATT GTG ATG GGC AAC CTG      1106
Glu Asp Gln Glu Glu Lys Gln Pro Gln Leu Ile Val Met Gly Asn Leu
190                 195                 200

GAC CGT GAG CGC TGG GAC TCC TAT GAC CTC ACC ATC AAG GTG CAG GAT      1154
Asp Arg Glu Arg Trp Asp Ser Tyr Asp Leu Thr Ile Lys Val Gln Asp
205                 210                 215                 220

GGC GGC AGC CCC CCA CGC GCC ACG AGT GCC CTG CTG CGT GTC ACC GTG      1202
Gly Gly Ser Pro Pro Arg Ala Thr Ser Ala Leu Leu Arg Val Thr Val
              225                 230                 235

CTT GAC ACC AAT GAC AAC GCC CCC AAG TTT GAG CGG CCC TCC TAT GAG      1250
Leu Asp Thr Asn Asp Asn Ala Pro Lys Phe Glu Arg Pro Ser Tyr Glu
              240                 245                 250

GCC GAA CTA TCT GAG AAT AGC CCC ATA GGC CAC TCG GTC ATC CAG GTG      1298
Ala Glu Leu Ser Glu Asn Ser Pro Ile Gly His Ser Val Ile Gln Val
```

-continued

| | | | 255 | | | | 260 | | | | 265 | | | | |
|---|---|---|---|---|---|---|---|---|---|---|---|---|---|---|---|
| AAG | GCC | AAT | GAC | TCA | GAC | CAA | GGT | GCC | AAT | GCA | GAA | ATC | GAA | TAC | ACA | 1346
| Lys | Ala | Asn | Asp | Ser | Asp | Gln | Gly | Ala | Asn | Ala | Glu | Ile | Glu | Tyr | Thr |
| 270 | | | | | 275 | | | | | 280 | | | | | | |
| TTC | CAC | CAG | GCG | CCC | GAA | GTT | GTG | AGG | CGT | CTT | CTT | CGA | CTG | GAC | AGG | 1394
| Phe | His | Gln | Ala | Pro | Glu | Val | Val | Arg | Arg | Leu | Leu | Arg | Leu | Asp | Arg |
| 285 | | | | | 290 | | | | | 295 | | | | | 300 | |
| AAC | ACT | GGA | CTT | ATC | ACT | GTT | CAG | GGC | CCG | GTG | GAC | CGT | GAG | GAC | CTA | 1442
| Asn | Thr | Gly | Leu | Ile | Thr | Val | Gln | Gly | Pro | Val | Asp | Arg | Glu | Asp | Leu |
| | | | | 305 | | | | | 310 | | | | | 315 | | |
| AGC | ACC | CTG | CGC | TTC | TCA | GTG | CTT | GCT | AAG | GAC | CGA | GGC | ACC | AAC | CCC | 1490
| Ser | Thr | Leu | Arg | Phe | Ser | Val | Leu | Ala | Lys | Asp | Arg | Gly | Thr | Asn | Pro |
| | | 320 | | | | | 325 | | | | | 330 | | | | |
| AAG | AGT | GCC | CGT | GCC | CAG | GTG | GTT | GTG | ACC | GTG | AAG | GAC | ATG | AAT | GAC | 1538
| Lys | Ser | Ala | Arg | Ala | Gln | Val | Val | Val | Thr | Val | Lys | Asp | Met | Asn | Asp |
| | | 335 | | | | | 340 | | | | | 345 | | | | |
| AAT | GCC | CCC | ACC | ATT | GAG | ATC | CGG | GGC | ATA | GGG | CTA | GTG | ACT | CAT | CAA | 1586
| Asn | Ala | Pro | Thr | Ile | Glu | Ile | Arg | Gly | Ile | Gly | Leu | Val | Thr | His | Gln |
| | | 350 | | | | | 355 | | | | | 360 | | | | |
| GAT | GGG | ATG | GCT | AAC | ATC | TCA | GAG | GAT | GTG | GCA | GAG | GAG | ACA | GCT | GTG | 1634
| Asp | Gly | Met | Ala | Asn | Ile | Ser | Glu | Asp | Val | Ala | Glu | Glu | Thr | Ala | Val |
| 365 | | | | | 370 | | | | | 375 | | | | | 380 | |
| GCC | CTG | GTG | CAG | GTG | TCT | GAC | CGA | GAT | GAG | GGA | GAG | AAT | GCA | GCT | GTC | 1682
| Ala | Leu | Val | Gln | Val | Ser | Asp | Arg | Asp | Glu | Gly | Glu | Asn | Ala | Ala | Val |
| | | | | 385 | | | | | 390 | | | | | 395 | | |
| ACC | TGT | GTG | GTG | GCA | GGT | GAT | GTG | CCC | TTC | CAG | CTG | CGC | CAG | GCC | AGT | 1730
| Thr | Cys | Val | Val | Ala | Gly | Asp | Val | Pro | Phe | Gln | Leu | Arg | Gln | Ala | Ser |
| | | | 400 | | | | | 405 | | | | | 410 | | | |
| GAG | ACA | GGC | AGT | GAC | AGC | AAG | AAG | AAG | TAT | TTC | CTG | CAG | ACT | ACC | ACC | 1778
| Glu | Thr | Gly | Ser | Asp | Ser | Lys | Lys | Lys | Tyr | Phe | Leu | Gln | Thr | Thr | Thr |
| | | 415 | | | | | 420 | | | | | 425 | | | | |
| CCG | CTA | GAC | TAC | GAG | AAG | GTC | AAA | GAC | TAC | ACC | ATT | GAG | ATT | GTG | GCT | 1826
| Pro | Leu | Asp | Tyr | Glu | Lys | Val | Lys | Asp | Tyr | Thr | Ile | Glu | Ile | Val | Ala |
| | 430 | | | | | 435 | | | | | 440 | | | | | |
| GTG | GAC | TCT | GGC | AAC | CCC | CCA | CTC | TCC | AGC | ACT | AAC | TCC | CTC | AAG | GTG | 1874
| Val | Asp | Ser | Gly | Asn | Pro | Pro | Leu | Ser | Ser | Thr | Asn | Ser | Leu | Lys | Val |
| 445 | | | | | 450 | | | | | 455 | | | | | 460 | |
| CAG | GTG | GTG | GAC | GTC | AAT | GAC | AAC | GCA | CCT | GTC | TTC | ACT | CAG | AGT | GTC | 1922
| Gln | Val | Val | Asp | Val | Asn | Asp | Asn | Ala | Pro | Val | Phe | Thr | Gln | Ser | Val |
| | | | | 465 | | | | | 470 | | | | | 475 | | |
| ACT | GAG | GTC | GCC | TTC | CCG | GAA | AAC | AAC | AAG | CCT | GGT | GAA | GTG | ATT | GCT | 1970
| Thr | Glu | Val | Ala | Phe | Pro | Glu | Asn | Asn | Lys | Pro | Gly | Glu | Val | Ile | Ala |
| | | | 480 | | | | | 485 | | | | | 490 | | | |
| GAG | ATC | ACT | GCC | AGT | GAT | GCT | GAC | TCT | GGC | TCT | AAT | GCT | GAG | CTG | GTT | 2018
| Glu | Ile | Thr | Ala | Ser | Asp | Ala | Asp | Ser | Gly | Ser | Asn | Ala | Glu | Leu | Val |
| | | 495 | | | | | 500 | | | | | 505 | | | | |
| TAC | TCT | CTG | GAG | CCT | GAG | CCG | GCT | GCT | AAG | GGC | CTC | TTC | ACC | ATC | TCA | 2066
| Tyr | Ser | Leu | Glu | Pro | Glu | Pro | Ala | Ala | Lys | Gly | Leu | Phe | Thr | Ile | Ser |
| 510 | | | | | 515 | | | | | 520 | | | | | | |
| CCC | GAG | ACT | GGA | GAG | ATC | CAG | GTG | AAG | ACA | TCT | CTG | GAT | CGG | GAA | CAG | 2114
| Pro | Glu | Thr | Gly | Glu | Ile | Gln | Val | Lys | Thr | Ser | Leu | Asp | Arg | Glu | Gln |
| 525 | | | | | 530 | | | | | 535 | | | | | 540 | |
| CGG | GAG | AGC | TAT | GAG | TTG | AAG | GTG | GTG | GCA | GCT | GAC | CGG | GGC | AGT | CCT | 2162
| Arg | Glu | Ser | Tyr | Glu | Leu | Lys | Val | Val | Ala | Ala | Asp | Arg | Gly | Ser | Pro |
| | | | | 545 | | | | | 550 | | | | | 555 | | |
| AGC | CTC | CAG | GGC | ACA | GCC | ACT | GTC | CTT | GTC | AAT | GTG | CTG | GAC | TGC | AAT | 2210
| Ser | Leu | Gln | Gly | Thr | Ala | Thr | Val | Leu | Val | Asn | Val | Leu | Asp | Cys | Asn |
| | | | | 560 | | | | | 565 | | | | | 570 | | |
| GAC | AAT | GAC | CCC | AAA | TTT | ATG | CTG | AGT | GGC | TAC | AAC | TTC | TCA | GTG | ATG | 2258
| Asp | Asn | Asp | Pro | Lys | Phe | Met | Leu | Ser | Gly | Tyr | Asn | Phe | Ser | Val | Met |

-continued

| | | | | | | | | | | | | | | | | |
|---|---|---|---|---|---|---|---|---|---|---|---|---|---|---|---|---|
| | 575 | | | | | 580 | | | | | 585 | | | | | |
| GAG | AAC | ATG | CCA | GCA | CTG | AGT | CCA | GTG | GGC | ATG | GTG | ACT | GTC | ATT | GAT | 2306 |
| Glu | Asn | Met | Pro | Ala | Leu | Ser | Pro | Val | Gly | Met | Val | Thr | Val | Ile | Asp | |
| 590 | | | | | 595 | | | | | 600 | | | | | | |
| GGA | GAC | AAG | GGG | GAG | AAT | GCC | CAG | GTG | CAG | CTC | TCA | GTG | GAG | CAG | GAC | 2354 |
| Gly | Asp | Lys | Gly | Glu | Asn | Ala | Gln | Val | Gln | Leu | Ser | Val | Glu | Gln | Asp | |
| 605 | | | | | 610 | | | | | 615 | | | | | 620 | |
| AAC | GGT | GAC | TTT | GTT | ATC | CAG | AAT | GGC | ACA | GGC | ACC | ATC | CTA | TCC | AGC | 2402 |
| Asn | Gly | Asp | Phe | Val | Ile | Gln | Asn | Gly | Thr | Gly | Thr | Ile | Leu | Ser | Ser | |
| | | | | 625 | | | | | 630 | | | | | 635 | | |
| CTG | AGC | TTT | GAT | CGA | GAG | CAA | CAA | AGC | ACC | TAC | ACC | TTC | CAG | CTG | AAG | 2450 |
| Leu | Ser | Phe | Asp | Arg | Glu | Gln | Gln | Ser | Thr | Tyr | Thr | Phe | Gln | Leu | Lys | |
| | | | 640 | | | | | 645 | | | | | 650 | | | |
| GCA | GTG | GAT | GGT | GGC | GTC | CCA | CCT | CGC | TCA | GCT | TAC | GTT | GGT | GTC | ACC | 2498 |
| Ala | Val | Asp | Gly | Gly | Val | Pro | Pro | Arg | Ser | Ala | Tyr | Val | Gly | Val | Thr | |
| | | 655 | | | | | 660 | | | | | 665 | | | | |
| ATC | AAT | GTG | CTG | GAC | GAG | AAT | GAC | AAC | GCA | CCC | TAT | ATC | ACT | GCC | CCT | 2546 |
| Ile | Asn | Val | Leu | Asp | Glu | Asn | Asp | Asn | Ala | Pro | Tyr | Ile | Thr | Ala | Pro | |
| | 670 | | | | | 675 | | | | | 680 | | | | | |
| TCT | AAC | ACC | TCT | CAC | AAG | CTG | CTG | ACC | CCC | CAG | ACA | CGT | CTT | GGT | GAG | 2594 |
| Ser | Asn | Thr | Ser | His | Lys | Leu | Leu | Thr | Pro | Gln | Thr | Arg | Leu | Gly | Glu | |
| 685 | | | | | 690 | | | | | 695 | | | | | 700 | |
| ACG | GTC | AGC | CAG | GTG | GCA | GCC | GAG | GAC | TTT | GAC | TCT | GGT | GTC | AAT | GCC | 2642 |
| Thr | Val | Ser | Gln | Val | Ala | Ala | Glu | Asp | Phe | Asp | Ser | Gly | Val | Asn | Ala | |
| | | | | 705 | | | | | 710 | | | | | 715 | | |
| GAG | CTG | ATC | TAC | AGC | ATT | GCA | GGT | GGC | AAC | CCT | TAT | GGA | CTC | TTC | CAG | 2690 |
| Glu | Leu | Ile | Tyr | Ser | Ile | Ala | Gly | Gly | Asn | Pro | Tyr | Gly | Leu | Phe | Gln | |
| | | | 720 | | | | | 725 | | | | | 730 | | | |
| ATT | GGG | TCA | CAT | TCA | GGT | GCC | ATC | ACC | CTG | GAG | AAG | GAG | ATT | GAG | CGG | 2738 |
| Ile | Gly | Ser | His | Ser | Gly | Ala | Ile | Thr | Leu | Glu | Lys | Glu | Ile | Glu | Arg | |
| | | 735 | | | | | 740 | | | | | 745 | | | | |
| CGC | CAC | CAT | GGG | CTA | CAC | CGC | CTG | GTG | GTG | AAG | GTC | AGT | GAC | CGC | GGC | 2786 |
| Arg | His | His | Gly | Leu | His | Arg | Leu | Val | Val | Lys | Val | Ser | Asp | Arg | Gly | |
| | 750 | | | | | 755 | | | | | 760 | | | | | |
| AAG | CCC | CCA | CGC | TAT | GGC | ACA | GCC | TTG | GTC | CAT | CTT | TAT | GTC | AAT | GAG | 2834 |
| Lys | Pro | Pro | Arg | Tyr | Gly | Thr | Ala | Leu | Val | His | Leu | Tyr | Val | Asn | Glu | |
| 765 | | | | | 770 | | | | | 775 | | | | | 780 | |
| ACT | CTG | GCC | AAC | CGC | ACG | CTG | CTG | GAG | ACC | CTC | CTG | GGC | CAC | AGC | CTG | 2882 |
| Thr | Leu | Ala | Asn | Arg | Thr | Leu | Leu | Glu | Thr | Leu | Leu | Gly | His | Ser | Leu | |
| | | | | 785 | | | | | 790 | | | | | 795 | | |
| GAC | ACG | CCG | CTG | GAT | ATT | GAC | ATT | GCT | GGG | GAT | CCA | GAA | TAT | GAG | CGC | 2930 |
| Asp | Thr | Pro | Leu | Asp | Ile | Asp | Ile | Ala | Gly | Asp | Pro | Glu | Tyr | Glu | Arg | |
| | | | 800 | | | | | 805 | | | | | 810 | | | |
| TCC | AAG | CAG | CGT | GGC | AAC | ATT | CTC | TTT | GGT | GTG | GTG | GCT | GGT | GTG | GTG | 2978 |
| Ser | Lys | Gln | Arg | Gly | Asn | Ile | Leu | Phe | Gly | Val | Val | Ala | Gly | Val | Val | |
| | | 815 | | | | | 820 | | | | | 825 | | | | |
| GCC | GTG | GCC | TTG | CTC | ATC | GCC | CTG | GCG | GTT | CTT | GTG | CGC | TAC | TGC | AGA | 3026 |
| Ala | Val | Ala | Leu | Leu | Ile | Ala | Leu | Ala | Val | Leu | Val | Arg | Tyr | Cys | Arg | |
| | 830 | | | | | 835 | | | | | 840 | | | | | |
| CAG | CGG | GAG | GCC | AAA | AGT | GGT | TAC | CAG | GCT | GGT | AAG | AAG | GAG | ACC | AAG | 3074 |
| Gln | Arg | Glu | Ala | Lys | Ser | Gly | Tyr | Gln | Ala | Gly | Lys | Lys | Glu | Thr | Lys | |
| 845 | | | | | 850 | | | | | 855 | | | | | 860 | |
| GAC | CTG | TAT | GCC | CCC | AAG | CCC | AGT | GGC | AAG | GCC | TCC | AAG | GGA | AAC | AAA | 3122 |
| Asp | Leu | Tyr | Ala | Pro | Lys | Pro | Ser | Gly | Lys | Ala | Ser | Lys | Gly | Asn | Lys | |
| | | | | 865 | | | | | 870 | | | | | 875 | | |
| AGC | AAA | GGC | AAG | AAG | AGC | AAG | TCC | CCA | AAG | CCC | GTG | AAG | CCA | GTG | GAG | 3170 |
| Ser | Lys | Gly | Lys | Lys | Ser | Lys | Ser | Pro | Lys | Pro | Val | Lys | Pro | Val | Glu | |
| | | | 880 | | | | | 885 | | | | | 890 | | | |
| GAC | GAG | GAT | GAG | GCC | GGG | CTG | CAG | AAG | TCC | CTC | AAG | TTC | AAC | CTG | ATG | 3218 |
| Asp | Glu | Asp | Glu | Ala | Gly | Leu | Gln | Lys | Ser | Leu | Lys | Phe | Asn | Leu | Met | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 895 |     |     |     |     | 900 |     |     |     |     | 905 |     |     |     |     |      |
| AGC | GAT | GCC | CCT | GGG | GAC | AGT | CCC | CGC | ATC | CAC | CTG | CCC | CTC | AAC | TAC | 3266 |
| Ser | Asp | Ala | Pro | Gly | Asp | Ser | Pro | Arg | Ile | His | Leu | Pro | Leu | Asn | Tyr |      |
|     | 910 |     |     |     |     | 915 |     |     |     |     | 920 |     |     |     |     |      |
| CCA | CCA | GGC | AGC | CCT | GAC | CTG | GGC | CGC | CAC | TAT | CGC | TCT | AAC | TCC | CCA | 3314 |
| Pro | Pro | Gly | Ser | Pro | Asp | Leu | Gly | Arg | His | Tyr | Arg | Ser | Asn | Ser | Pro |      |
| 925 |     |     |     |     |     | 930 |     |     |     |     | 935 |     |     |     | 940 |      |
| CTG | CCT | TCC | ATC | CAG | CTG | CAG | CCC | CAG | TCA | CCC | TCA | GCC | TCC | AAG | AAG | 3362 |
| Leu | Pro | Ser | Ile | Gln | Leu | Gln | Pro | Gln | Ser | Pro | Ser | Ala | Ser | Lys | Lys |      |
|     |     |     |     | 945 |     |     |     |     | 950 |     |     |     |     | 955 |     |      |
| CAC | CAG | GTG | GTA | CAG | GAC | CTG | CCA | CCT | GCA | AAC | ACA | TTC | GTG | GGC | ACC | 3410 |
| His | Gln | Val | Val | Gln | Asp | Leu | Pro | Pro | Ala | Asn | Thr | Phe | Val | Gly | Thr |      |
|     |     |     | 960 |     |     |     |     | 965 |     |     |     |     | 970 |     |     |      |
| GGG | GAC | ACC | ACG | TCC | ACG | GGC | TCT | GAG | CAG | TAC | TCC | GAC | TAC | AGC | TAC | 3458 |
| Gly | Asp | Thr | Thr | Ser | Thr | Gly | Ser | Glu | Gln | Tyr | Ser | Asp | Tyr | Ser | Tyr |      |
|     |     | 975 |     |     |     |     | 980 |     |     |     |     | 985 |     |     |     |      |
| CGC | ACC | AAC | CCC | CCC | AAA | TAC | CCC | AGC | AAG | CAG | GTA | GGC | CAG | CCC | TTT | 3506 |
| Arg | Thr | Asn | Pro | Pro | Lys | Tyr | Pro | Ser | Lys | Gln | Val | Gly | Gln | Pro | Phe |      |
|     | 990 |     |     |     |     | 995 |     |     |     |     | 1000|     |     |     |     |      |
| CAG | CTC | AGC | ACA | CCC | CAG | CCC | CTA | CCC | CAC | CCC | TAC | CAC | GGA | GCC | ATC | 3554 |
| Gln | Leu | Ser | Thr | Pro | Gln | Pro | Leu | Pro | His | Pro | Tyr | His | Gly | Ala | Ile |      |
| 1005|     |     |     |     | 1010|     |     |     |     | 1015|     |     |     |     | 1020|      |
| TGG | ACC | GAG | GTG | TGG | GAG | TGATGGAGCA | GGTTACTGT | GCCTGCCCGT |  |  |  |  |  |  |  | 3602 |
| Trp | Thr | Glu | Val | Trp | Glu |     |     |     |     |     |     |     |     |     |     |      |
|     |     |     |     | 1025|     |     |     |     |     |     |     |     |     |     |     |      |

| | | | | |
|---|---|---|---|---|
| GTTGGGGGCC | AGCCTGAGCC | AGCAGTGGGA | GGTGGGGCCT | TAGTGCCTCA | CCGGGCACAC | 3662 |
| GGATTAGGCT | GAGTGAAGAT | TAAGGGAGGG | TGTGCTCTGT | GGTCTCCTCC | CTGCCCTCTC | 3722 |
| CCCACTGGGG | AGAGACCTGT | GATTTGCCAA | GTCCCTGGAC | CCTGGACCAG | CTACTGGGCC | 3782 |
| TTATGGGTTG | GGGGTGGTAG | GCAGGTGAGC | GTAAGTGGGG | AGGGAAATGG | GTAAGAAGTC | 3842 |
| TACTCCAAAC | CTAGGTCTCT | ATGTCAGACC | AGACCTAGGT | GCTTCTCTAG | GAGGGAAACA | 3902 |
| GGGAGACCTG | GGGTCCTGTG | GATAACTGAG | TGGGGAGTCT | GCCAGGGGAG | GGCACCTTCC | 3962 |
| CATTGTGCCT | TCTGTGTGTA | TTGTGCATTA | ACCTCTTCCT | CACCACTAGG | CTTCTGGGGC | 4022 |
| TGGGTCCCAC | ATGCCCTTGA | CCCTGACAAT | AAAGTTCTCT | ATTTTTGGAA | AAAAAAAAA | 4082 |
| AAAAAAAAAA | AAAAAAAAAA | AA | | | | 4104 |

( 2 ) INFORMATION FOR SEQ ID NO:95:

( i ) SEQUENCE CHARACTERISTICS:
        ( A ) LENGTH: 1026 amino acids
        ( B ) TYPE: amino acid
        ( D ) TOPOLOGY: linear ( i i ) MOLECULE TYPE: protein ( x i ) SEQUENCE DESCRIPTION: SEQ ID NO:95:

| | | | | | | | | | | | | | | |
|---|---|---|---|---|---|---|---|---|---|---|---|---|---|---|
| Met | Glu | Pro | Leu | Arg | His | Ser | Pro | Gly | Pro | Gly | Gly | Gln | Arg | Leu | Leu |
| 1 |  |  |  | 5 |  |  |  |  | 10 |  |  |  |  | 15 |  |
| Leu | Pro | Ser | Met | Leu | Leu | Ala | Leu | Leu | Leu | Leu | Ala | Pro | Ser | Pro |
|  |  |  | 20 |  |  |  | 25 |  |  |  |  | 30 |  |  |
| Gly | His | Ala | Thr | Arg | Val | Val | Tyr | Lys | Val | Pro | Glu | Glu | Gln | Pro | Pro |
|  |  | 35 |  |  |  | 40 |  |  |  |  | 45 |  |  |  |  |
| Asn | Thr | Leu | Ile | Gly | Ser | Leu | Ala | Ala | Asp | Tyr | Gly | Phe | Pro | Asp | Val |
|  | 50 |  |  |  |  | 55 |  |  |  |  | 60 |  |  |  |  |
| Gly | His | Leu | Tyr | Lys | Leu | Glu | Val | Gly | Ala | Pro | Tyr | Leu | Arg | Val | Asp |
| 65 |  |  |  |  | 70 |  |  |  |  | 75 |  |  |  |  | 80 |
| Gly | Lys | Thr | Gly | Asp | Ile | Phe | Thr | Thr | Glu | Thr | Ser | Ile | Asp | Arg | Glu |

-continued

```
                        85                         90                          95
Gly  Leu  Arg  Glu  Cys  Gln  Asn  Gln  Leu  Pro  Gly  Asp  Pro  Cys  Ile  Leu
               100                      105                      110

Glu  Phe  Glu  Val  Ser  Ile  Thr  Asp  Leu  Val  Gln  Asn  Ala  Ser  Pro  Arg
               115                      120                      125

Leu  Leu  Glu  Gly  Gln  Ile  Glu  Val  Gln  Asp  Ile  Asn  Asp  Asn  Thr  Pro
     130                      135                      140

Asn  Phe  Ala  Ser  Pro  Val  Ile  Thr  Leu  Ala  Ile  Pro  Glu  Asn  Thr  Asn
145                      150                      155                      160

Ile  Gly  Ser  Leu  Phe  Pro  Ile  Pro  Leu  Ala  Ser  Asp  Arg  Asp  Ala  Gly
               165                      170                      175

Pro  Asn  Gly  Val  Ala  Ser  Tyr  Glu  Leu  Gln  Val  Ala  Glu  Asp  Gln  Glu
               180                      185                      190

Glu  Lys  Gln  Pro  Gln  Leu  Ile  Val  Met  Gly  Asn  Leu  Asp  Arg  Glu  Arg
          195                      200                      205

Trp  Asp  Ser  Tyr  Asp  Leu  Thr  Ile  Lys  Val  Gln  Asp  Gly  Gly  Ser  Pro
     210                      215                      220

Pro  Arg  Ala  Thr  Ser  Ala  Leu  Leu  Arg  Val  Thr  Val  Leu  Asp  Thr  Asn
225                      230                      235                      240

Asp  Asn  Ala  Pro  Lys  Phe  Glu  Arg  Pro  Ser  Tyr  Glu  Ala  Glu  Leu  Ser
               245                      250                      255

Glu  Asn  Ser  Pro  Ile  Gly  His  Ser  Val  Ile  Gln  Val  Lys  Ala  Asn  Asp
               260                      265                      270

Ser  Asp  Gln  Gly  Ala  Asn  Ala  Glu  Ile  Glu  Tyr  Thr  Phe  His  Gln  Ala
          275                      280                      285

Pro  Glu  Val  Val  Arg  Arg  Leu  Leu  Arg  Leu  Asp  Arg  Asn  Thr  Gly  Leu
     290                      295                      300

Ile  Thr  Val  Gln  Gly  Pro  Val  Asp  Arg  Glu  Asp  Leu  Ser  Thr  Leu  Arg
305                      310                      315                      320

Phe  Ser  Val  Leu  Ala  Lys  Asp  Arg  Gly  Thr  Asn  Pro  Lys  Ser  Ala  Arg
               325                      330                      335

Ala  Gln  Val  Val  Val  Thr  Val  Lys  Asp  Met  Asn  Asp  Asn  Ala  Pro  Thr
               340                      345                      350

Ile  Glu  Ile  Arg  Gly  Ile  Gly  Leu  Val  Thr  His  Gln  Asp  Gly  Met  Ala
          355                      360                      365

Asn  Ile  Ser  Glu  Asp  Val  Ala  Glu  Glu  Thr  Ala  Val  Ala  Leu  Val  Gln
     370                      375                      380

Val  Ser  Asp  Arg  Asp  Glu  Gly  Glu  Asn  Ala  Ala  Val  Thr  Cys  Val  Val
385                      390                      395                      400

Ala  Gly  Asp  Val  Pro  Phe  Gln  Leu  Arg  Gln  Ala  Ser  Glu  Thr  Gly  Ser
               405                      410                      415

Asp  Ser  Lys  Lys  Lys  Tyr  Phe  Leu  Gln  Thr  Thr  Thr  Pro  Leu  Asp  Tyr
               420                      425                      430

Glu  Lys  Val  Lys  Asp  Tyr  Thr  Ile  Glu  Ile  Val  Ala  Val  Asp  Ser  Gly
          435                      440                      445

Asn  Pro  Pro  Leu  Ser  Ser  Thr  Asn  Ser  Leu  Lys  Val  Gln  Val  Val  Asp
     450                      455                      460

Val  Asn  Asp  Asn  Ala  Pro  Val  Phe  Thr  Gln  Ser  Val  Thr  Glu  Val  Ala
465                      470                      475                      480

Phe  Pro  Glu  Asn  Asn  Lys  Pro  Gly  Glu  Val  Ile  Ala  Glu  Ile  Thr  Ala
               485                      490                      495

Ser  Asp  Ala  Asp  Ser  Gly  Ser  Asn  Ala  Glu  Leu  Val  Tyr  Ser  Leu  Glu
               500                      505                      510
```

| | | | | | | | | | | | | | | |
|---|---|---|---|---|---|---|---|---|---|---|---|---|---|---|
| Pro | Glu | Pro<br>515 | Ala | Ala | Lys | Gly | Leu<br>520 | Phe | Thr | Ile | Ser | Pro<br>525 | Glu | Thr | Gly |
| Glu | Ile<br>530 | Gln | Val | Lys | Thr | Ser<br>535 | Leu | Asp | Arg | Glu | Gln<br>540 | Arg | Glu | Ser | Tyr |
| Glu<br>545 | Leu | Lys | Val | Val | Ala<br>550 | Ala | Asp | Arg | Gly | Ser<br>555 | Pro | Ser | Leu | Gln | Gly<br>560 |
| Thr | Ala | Thr | Val | Leu<br>565 | Val | Asn | Val | Leu | Asp<br>570 | Cys | Asn | Asp | Asn<br>575 | Asp | Pro |
| Lys | Phe | Met | Leu<br>580 | Ser | Gly | Tyr | Asn | Phe<br>585 | Ser | Val | Met | Glu | Asn<br>590 | Met | Pro |
| Ala | Leu | Ser<br>595 | Pro | Val | Gly | Met<br>600 | Val | Thr | Val | Ile | Asp<br>605 | Gly | Asp | Lys | Gly |
| Glu | Asn<br>610 | Ala | Gln | Val | Gln | Leu<br>615 | Ser | Val | Glu | Gln | Asp<br>620 | Asn | Gly | Asp | Phe |
| Val<br>625 | Ile | Gln | Asn | Gly | Thr<br>630 | Gly | Thr | Ile | Leu | Ser<br>635 | Ser | Leu | Ser | Phe | Asp<br>640 |
| Arg | Glu | Gln | Gln | Ser<br>645 | Thr | Tyr | Thr | Phe | Gln<br>650 | Leu | Lys | Ala | Val | Asp<br>655 | Gly |
| Gly | Val | Pro | Arg<br>660 | Ser | Ala | Tyr | Val | Gly<br>665 | Val | Thr | Ile | Asn | Val<br>670 | Leu |
| Asp | Glu | Asn | Asp | Asn<br>675 | Ala | Pro | Tyr | Ile | Thr<br>680 | Ala | Pro | Ser | Asn<br>685 | Thr | Ser |
| His | Lys<br>690 | Leu | Leu | Thr | Pro | Gln<br>695 | Thr | Arg | Leu | Gly | Glu<br>700 | Thr | Val | Ser | Gln |
| Val<br>705 | Ala | Ala | Glu | Asp | Phe<br>710 | Asp | Ser | Gly | Val | Asn<br>715 | Ala | Glu | Leu | Ile | Tyr<br>720 |
| Ser | Ile | Ala | Gly | Gly<br>725 | Asn | Pro | Tyr | Gly | Leu<br>730 | Phe | Gln | Ile | Gly | Ser<br>735 | His |
| Ser | Gly | Ala | Ile<br>740 | Thr | Leu | Glu | Lys | Glu<br>745 | Ile | Glu | Arg | Arg | His<br>750 | His | Gly |
| Leu | His | Arg<br>755 | Leu | Val | Val | Lys | Val<br>760 | Ser | Asp | Arg | Gly | Lys<br>765 | Pro | Pro | Arg |
| Tyr | Gly<br>770 | Thr | Ala | Leu | Val | His<br>775 | Leu | Tyr | Val | Asn | Glu<br>780 | Thr | Leu | Ala | Asn |
| Arg<br>785 | Thr | Leu | Leu | Glu | Thr<br>790 | Leu | Leu | Gly | His | Ser<br>795 | Leu | Asp | Thr | Pro | Leu<br>800 |
| Asp | Ile | Asp | Ile | Ala<br>805 | Gly | Asp | Pro | Glu | Tyr<br>810 | Glu | Arg | Ser | Lys | Gln<br>815 | Arg |
| Gly | Asn | Ile | Leu<br>820 | Phe | Gly | Val | Val | Ala<br>825 | Gly | Val | Val | Ala | Val<br>830 | Ala | Leu |
| Leu | Ile | Ala<br>835 | Leu | Ala | Val | Leu | Val<br>840 | Arg | Tyr | Cys | Arg | Gln<br>845 | Arg | Glu | Ala |
| Lys | Ser<br>850 | Gly | Tyr | Gln | Ala | Gly<br>855 | Lys | Lys | Glu | Thr | Lys<br>860 | Asp | Leu | Tyr | Ala |
| Pro<br>865 | Lys | Pro | Ser | Gly | Lys<br>870 | Ala | Ser | Lys | Gly | Asn<br>875 | Lys | Ser | Lys | Gly | Lys<br>880 |
| Lys | Ser | Lys | Ser | Pro<br>885 | Lys | Pro | Val | Lys | Pro<br>890 | Val | Glu | Asp | Glu | Asp<br>895 | Glu |
| Ala | Gly | Leu | Gln<br>900 | Lys | Ser | Leu | Lys | Phe<br>905 | Asn | Leu | Met | Ser | Asp<br>910 | Ala | Pro |
| Gly | Asp | Ser<br>915 | Pro | Arg | Ile | His | Leu<br>920 | Pro | Leu | Asn | Tyr | Pro<br>925 | Pro | Gly | Ser |
| Pro | Asp<br>930 | Leu | Gly | Arg | His | Tyr<br>935 | Arg | Ser | Asn | Ser | Pro<br>940 | Leu | Pro | Ser | Ile |

```
Gln Leu Gln Pro Gln Ser Pro Ser Ala Ser Lys Lys His Gln Val Val
945                 950                 955                 960

Gln Asp Leu Pro Pro Ala Asn Thr Phe Val Gly Thr Gly Asp Thr Thr
                965                 970                 975

Ser Thr Gly Ser Glu Gln Tyr Ser Asp Tyr Ser Tyr Arg Thr Asn Pro
            980                 985                 990

Pro Lys Tyr Pro Ser Lys Gln Val Gly Gln Pro Phe Gln Leu Ser Thr
        995                 1000                1005

Pro Gln Pro Leu Pro His Pro Tyr His Gly Ala Ile Trp Thr Glu Val
        1010                1015                1020

Trp Glu
1025
```

(2) INFORMATION FOR SEQ ID NO:96:

(i) SEQUENCE CHARACTERISTICS:
        (A) LENGTH: 4705 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 115..2827

(xi) SEQUENCE DESCRIPTION: SEQ ID NO:96:

```
CGAAAGCCAT GTCGGACTCG TCGCCCAGCG CCCAAGCGCT AACCCGCTGA AAGTTTCTCA        60

GCGAAATCTC AGGGACGATC TGGACCCCGC TGAGAGGAAC TGCTTTTGAG TGAG ATG         117
                                                            Met
                                                             1

GTC CCA GAG GCC TGG AGG AGC GGA CTG GTA AGC ACC GGG AGG GTA GTG         165
Val Pro Glu Ala Trp Arg Ser Gly Leu Val Ser Thr Gly Arg Val Val
             5               10                  15

GGA GTT TTG CTT CTG CTT GGT GCC TTG AAC AAG GCT TCC ACG GTC ATT         213
Gly Val Leu Leu Leu Leu Gly Ala Leu Asn Lys Ala Ser Thr Val Ile
         20                  25                  30

CAC TAT GAG ATC CCG GAG GAA AGA GAG AAG GGT TTC GCT GTG GGC AAC         261
His Tyr Glu Ile Pro Glu Glu Arg Glu Lys Gly Phe Ala Val Gly Asn
     35                  40                  45

GTG GTC GCG AAC CTT GGT TTG GAT CTC GGT AGC CTC TCA GCC CGC AGG         309
Val Val Ala Asn Leu Gly Leu Asp Leu Gly Ser Leu Ser Ala Arg Arg
 50              55                  60                      65

TTC CCG GTG GTG TCT GGA GCT AGC CGA AGA TTC TTT GAG GTG AAC CGG         357
Phe Pro Val Val Ser Gly Ala Ser Arg Arg Phe Phe Glu Val Asn Arg
             70                  75                  80

GAG ACC GGA GAG ATG TTT GTG AAC GAC CGT CTG GAT CGA GAG GAG CTG         405
Glu Thr Gly Glu Met Phe Val Asn Asp Arg Leu Asp Arg Glu Glu Leu
             85                  90                  95

TGT GGG ACA CTG CCC TCT TGC ACT GTA ACT CTG GAG TTG GTA GTG GAG         453
Cys Gly Thr Leu Pro Ser Cys Thr Val Thr Leu Glu Leu Val Val Glu
             100                 105                 110

AAC CCG CTG GAG CTG TTC AGC GTG GAA GTG GTG ATC CAG GAC ATC AAC         501
Asn Pro Leu Glu Leu Phe Ser Val Glu Val Val Ile Gln Asp Ile Asn
 115                 120                 125

GAC AAC AAT CCT GCT TTC CCT ACC CAG GAA ATG AAA TTG GAG ATT AGC         549
Asp Asn Asn Pro Ala Phe Pro Thr Gln Glu Met Lys Leu Glu Ile Ser
 130                 135                 140             145

GAG GCC GTG GCT CCG GGG ACG CGC TTT CCG CTC GAG AGC GCG CAC GAT         597
Glu Ala Val Ala Pro Gly Thr Arg Phe Pro Leu Glu Ser Ala His Asp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 150 |     |     |     |     | 155 |     |     |     |     | 160 |     |     |      |
| CCC | GAT | CTG | GGA | AGC | AAC | TCT | TTA | CAA | ACC | TAT | GAG | CTG | AGC | CGA | AAT | 645  |
| Pro | Asp | Leu | Gly | Ser | Asn | Ser | Leu | Gln | Thr | Tyr | Glu | Leu | Ser | Arg | Asn |      |
|     |     |     | 165 |     |     |     |     | 170 |     |     |     |     | 175 |     |     |      |
| GAA | TAC | TTT | GCG | CTT | CGC | GTG | CAG | ACG | CGG | GAG | GAC | AGC | ACC | AAG | TAC | 693  |
| Glu | Tyr | Phe | Ala | Leu | Arg | Val | Gln | Thr | Arg | Glu | Asp | Ser | Thr | Lys | Tyr |      |
|     |     | 180 |     |     |     |     | 185 |     |     |     |     | 190 |     |     |     |      |
| GCG | GAG | CTG | GTG | TTG | GAG | CGC | GCC | CTG | GAC | CGA | GAA | CGG | GAG | CCT | AGT | 741  |
| Ala | Glu | Leu | Val | Leu | Glu | Arg | Ala | Leu | Asp | Arg | Glu | Arg | Glu | Pro | Ser |      |
|     | 195 |     |     |     |     | 200 |     |     |     |     | 205 |     |     |     |     |      |
| CTC | CAG | TTA | GTG | CTG | ACG | GCG | TTG | GAC | GGA | GGG | ACC | CCA | GCT | CTC | TCC | 789  |
| Leu | Gln | Leu | Val | Leu | Thr | Ala | Leu | Asp | Gly | Gly | Thr | Pro | Ala | Leu | Ser |      |
| 210 |     |     |     |     | 215 |     |     |     |     | 220 |     |     |     |     | 225 |      |
| GCC | AGC | CTG | CCT | ATT | CAC | ATC | AAG | GTG | CTG | GAC | GCG | AAT | GAC | AAT | GCG | 837  |
| Ala | Ser | Leu | Pro | Ile | His | Ile | Lys | Val | Leu | Asp | Ala | Asn | Asp | Asn | Ala |      |
|     |     |     |     | 230 |     |     |     |     | 235 |     |     |     |     | 240 |     |      |
| CCT | GTC | TTC | AAC | CAG | TCC | TTG | TAC | CGG | GCG | CGC | GTT | CCT | GGA | GGA | TGC | 885  |
| Pro | Val | Phe | Asn | Gln | Ser | Leu | Tyr | Arg | Ala | Arg | Val | Pro | Gly | Gly | Cys |      |
|     |     |     | 245 |     |     |     |     | 250 |     |     |     |     | 255 |     |     |      |
| ACC | TCC | GGC | ACG | CGC | GTG | GTA | CAA | GTC | CTT | GCA | ACG | GAT | CTG | GAT | GAA | 933  |
| Thr | Ser | Gly | Thr | Arg | Val | Val | Gln | Val | Leu | Ala | Thr | Asp | Leu | Asp | Glu |      |
|     |     | 260 |     |     |     |     | 265 |     |     |     |     | 270 |     |     |     |      |
| GGC | CCC | AAC | GGT | GAA | ATT | ATT | TAC | TCC | TTC | GGC | AGC | CAC | AAC | CGC | GCC | 981  |
| Gly | Pro | Asn | Gly | Glu | Ile | Ile | Tyr | Ser | Phe | Gly | Ser | His | Asn | Arg | Ala |      |
|     | 275 |     |     |     |     | 280 |     |     |     |     | 285 |     |     |     |     |      |
| GGC | GTG | CGG | CAA | CTA | TTC | GCC | TTA | GAC | CTT | GTA | ACC | GGG | ATG | CTG | ACA | 1029 |
| Gly | Val | Arg | Gln | Leu | Phe | Ala | Leu | Asp | Leu | Val | Thr | Gly | Met | Leu | Thr |      |
| 290 |     |     |     |     | 295 |     |     |     |     | 300 |     |     |     |     | 305 |      |
| ATC | AAG | GGT | CGG | CTG | GAC | TTC | GAG | GAC | ACC | AAA | CTC | CAT | GAG | ATT | TAC | 1077 |
| Ile | Lys | Gly | Arg | Leu | Asp | Phe | Glu | Asp | Thr | Lys | Leu | His | Glu | Ile | Tyr |      |
|     |     |     |     | 310 |     |     |     |     | 315 |     |     |     |     | 320 |     |      |
| ATC | CAG | GCC | AAA | GAC | AAG | GGC | GCC | AAT | CCC | GAA | GGA | GCA | CAT | TGC | AAA | 1125 |
| Ile | Gln | Ala | Lys | Asp | Lys | Gly | Ala | Asn | Pro | Glu | Gly | Ala | His | Cys | Lys |      |
|     |     |     | 325 |     |     |     |     | 330 |     |     |     |     | 335 |     |     |      |
| GTG | TTG | GTG | GAG | GTT | GTG | GAT | GTG | AAT | GAC | AAC | GCC | CCG | GAG | ATC | ACA | 1173 |
| Val | Leu | Val | Glu | Val | Val | Asp | Val | Asn | Asp | Asn | Ala | Pro | Glu | Ile | Thr |      |
|     |     | 340 |     |     |     |     | 345 |     |     |     |     | 350 |     |     |     |      |
| GTC | ACC | TCC | GTG | TAC | AGC | CCA | GTA | CCC | GAG | GAT | GCC | TCT | GGG | ACT | GTC | 1221 |
| Val | Thr | Ser | Val | Tyr | Ser | Pro | Val | Pro | Glu | Asp | Ala | Ser | Gly | Thr | Val |      |
|     | 355 |     |     |     |     | 360 |     |     |     |     | 365 |     |     |     |     |      |
| ATC | GCT | TTG | CTC | AGT | GTG | ACT | GAC | CTG | GAT | GCT | GGC | GAG | AAC | GGG | CTG | 1269 |
| Ile | Ala | Leu | Leu | Ser | Val | Thr | Asp | Leu | Asp | Ala | Gly | Glu | Asn | Gly | Leu |      |
| 370 |     |     |     |     | 375 |     |     |     |     | 380 |     |     |     |     | 385 |      |
| GTG | ACC | TGC | GAA | GTT | CCA | CCG | GGT | CTC | CCT | TTC | AGC | CTT | ACT | TCT | TCC | 1317 |
| Val | Thr | Cys | Glu | Val | Pro | Pro | Gly | Leu | Pro | Phe | Ser | Leu | Thr | Ser | Ser |      |
|     |     |     |     | 390 |     |     |     |     | 395 |     |     |     |     | 400 |     |      |
| CTC | AAG | AAT | TAC | TTC | ACT | TTG | AAA | ACC | AGT | GCA | GAC | CTG | GAT | CGG | GAG | 1365 |
| Leu | Lys | Asn | Tyr | Phe | Thr | Leu | Lys | Thr | Ser | Ala | Asp | Leu | Asp | Arg | Glu |      |
|     |     |     | 405 |     |     |     |     | 410 |     |     |     |     | 415 |     |     |      |
| ACT | GTG | CCA | GAA | TAC | AAC | CTC | AGC | ATC | ACC | GCC | CGA | GAC | GCC | GGA | ACC | 1413 |
| Thr | Val | Pro | Glu | Tyr | Asn | Leu | Ser | Ile | Thr | Ala | Arg | Asp | Ala | Gly | Thr |      |
|     |     | 420 |     |     |     |     | 425 |     |     |     |     | 430 |     |     |     |      |
| CCT | TCC | CTC | TCA | GCC | CTT | ACA | ATA | GTG | CGT | GTT | CAA | GTG | TCC | GAC | ATC | 1461 |
| Pro | Ser | Leu | Ser | Ala | Leu | Thr | Ile | Val | Arg | Val | Gln | Val | Ser | Asp | Ile |      |
|     | 435 |     |     |     |     | 440 |     |     |     |     | 445 |     |     |     |     |      |
| AAT | GAC | AAC | CCT | CCA | CAA | TCT | TCT | CAA | TCT | TCC | TAC | GAC | GTT | TAC | ATT | 1509 |
| Asn | Asp | Asn | Pro | Pro | Gln | Ser | Ser | Gln | Ser | Ser | Tyr | Asp | Val | Tyr | Ile |      |
| 450 |     |     |     |     | 455 |     |     |     |     | 460 |     |     |     |     | 465 |      |
| GAA | GAA | AAC | AAC | CTC | CCC | GGG | GCT | CCA | ATA | CTA | AAC | CTA | AGT | GTC | TGG | 1557 |
| Glu | Glu | Asn | Asn | Leu | Pro | Gly | Ala | Pro | Ile | Leu | Asn | Leu | Ser | Val | Trp |      |

-continued

```
                        470                              475                              480
GAC  CCC  GAC  GCC  CCG  CAG  AAT  GCT  CGG  CTT  TCT  TTC  TTT  CTC  TTG  GAG     1605
Asp  Pro  Asp  Ala  Pro  Gln  Asn  Ala  Arg  Leu  Ser  Phe  Phe  Leu  Leu  Glu
               485                    490                         495

CAA  GGA  GCT  GAA  ACC  GGG  CTA  GTG  GGT  CGC  TAT  TTC  ACA  ATA  AAT  CGT     1653
Gln  Gly  Ala  Glu  Thr  Gly  Leu  Val  Gly  Arg  Tyr  Phe  Thr  Ile  Asn  Arg
               500                    505                         510

GAC  AAT  GGC  ATA  GTG  TCA  TCC  TTA  GTG  CCC  CTA  GAC  TAT  GAG  GAT  CGG     1701
Asp  Asn  Gly  Ile  Val  Ser  Ser  Leu  Val  Pro  Leu  Asp  Tyr  Glu  Asp  Arg
          515                    520                         525

CGG  GAA  TTT  GAA  TTA  ACA  GCT  CAT  ATC  AGC  GAT  GGG  GGC  ACC  CCG  GTC     1749
Arg  Glu  Phe  Glu  Leu  Thr  Ala  His  Ile  Ser  Asp  Gly  Gly  Thr  Pro  Val
530                         535                    540                         545

CTA  GCC  ACC  AAC  ATC  AGC  GTG  AAC  ATA  TTT  GTC  ACT  GAT  CGC  AAT  GAC     1797
Leu  Ala  Thr  Asn  Ile  Ser  Val  Asn  Ile  Phe  Val  Thr  Asp  Arg  Asn  Asp
                    550                    555                         560

AAT  GCC  CCC  CAG  GTC  CTA  TAT  CCT  CGG  CCA  GGT  GGG  AGC  TCG  GTG  GAG     1845
Asn  Ala  Pro  Gln  Val  Leu  Tyr  Pro  Arg  Pro  Gly  Gly  Ser  Ser  Val  Glu
               565                    570                         575

ATG  CTG  CCT  CGA  GGT  ACC  TCA  GCT  GGC  CAC  CTA  GTG  TCA  CGG  GTG  GTA     1893
Met  Leu  Pro  Arg  Gly  Thr  Ser  Ala  Gly  His  Leu  Val  Ser  Arg  Val  Val
               580                    585                         590

GGC  TGG  GAC  GCG  GAT  GCA  GGG  CAC  AAT  GCC  TGG  CTC  TCC  TAC  AGT  CTC     1941
Gly  Trp  Asp  Ala  Asp  Ala  Gly  His  Asn  Ala  Trp  Leu  Ser  Tyr  Ser  Leu
     595                    600                         605

TTT  GGA  TCC  CCT  AAC  CAG  AGC  CTT  TTT  GCC  ATA  GGG  CTG  CAC  ACT  GGT     1989
Phe  Gly  Ser  Pro  Asn  Gln  Ser  Leu  Phe  Ala  Ile  Gly  Leu  His  Thr  Gly
610                         615                    620                         625

CAA  ATC  AGT  ACT  GCC  CGT  CCA  GTC  CAA  GAC  ACA  GAT  TCA  CCC  AGG  CAG     2037
Gln  Ile  Ser  Thr  Ala  Arg  Pro  Val  Gln  Asp  Thr  Asp  Ser  Pro  Arg  Gln
                    630                    635                         640

ACT  CTC  ACT  GTC  TTG  ATC  AAA  GAC  AAT  GGG  GAG  CCT  TCG  CTC  TCC  ACC     2085
Thr  Leu  Thr  Val  Leu  Ile  Lys  Asp  Asn  Gly  Glu  Pro  Ser  Leu  Ser  Thr
               645                    650                         655

ACT  GCT  ACC  CTC  ACT  GTG  TCA  GTA  ACC  GAG  GAC  TCT  CCT  GAA  GCC  CGA     2133
Thr  Ala  Thr  Leu  Thr  Val  Ser  Val  Thr  Glu  Asp  Ser  Pro  Glu  Ala  Arg
               660                    665                         670

GCC  GAG  TTC  CCC  TCT  GGC  TCT  GCC  CCC  CGG  GAG  CAG  AAA  AAA  AAT  CTC     2181
Ala  Glu  Phe  Pro  Ser  Gly  Ser  Ala  Pro  Arg  Glu  Gln  Lys  Lys  Asn  Leu
675                         680                    685

ACC  TTT  TAT  CTA  CTT  CTT  TCT  CTA  ATC  CTG  GTT  TCT  GTG  GGC  TTC  GTG     2229
Thr  Phe  Tyr  Leu  Leu  Leu  Ser  Leu  Ile  Leu  Val  Ser  Val  Gly  Phe  Val
690                         695                    700                         705

GTC  ACA  GTG  TTC  GGA  GTA  ATC  ATA  TTC  AAA  GTT  TAC  AAG  TGG  AAG  CAG     2277
Val  Thr  Val  Phe  Gly  Val  Ile  Ile  Phe  Lys  Val  Tyr  Lys  Trp  Lys  Gln
                    710                    715                         720

TCT  AGA  GAC  CTA  TAC  CGA  GCC  CCG  GTG  AGC  TCA  CTG  TAC  CGA  ACA  CCA     2325
Ser  Arg  Asp  Leu  Tyr  Arg  Ala  Pro  Val  Ser  Ser  Leu  Tyr  Arg  Thr  Pro
               725                    730                         735

GGG  CCC  TCC  TTG  CAC  GCG  GAC  GCC  GTG  CGG  GGA  GGC  CTG  ATG  TCG  CCG     2373
Gly  Pro  Ser  Leu  His  Ala  Asp  Ala  Val  Arg  Gly  Gly  Leu  Met  Ser  Pro
               740                    745                         750

CAC  CTT  TAC  CAT  CAG  GTG  TAT  CTC  ACC  ACG  GAC  TCC  CGC  CGC  AGC  GAC     2421
His  Leu  Tyr  His  Gln  Val  Tyr  Leu  Thr  Thr  Asp  Ser  Arg  Arg  Ser  Asp
755                         760                    765

CCG  CTG  CTG  AAG  AAA  CCT  GGT  GCA  GCC  AGT  CCA  CTG  GCC  AGC  CGC  CAG     2469
Pro  Leu  Leu  Lys  Lys  Pro  Gly  Ala  Ala  Ser  Pro  Leu  Ala  Ser  Arg  Gln
770                         775                    780                         785

AAC  ACG  CTG  CGG  AGC  TGT  GAT  CCG  GTG  TTC  TAT  AGG  CAG  GTG  TTG  GGT     2517
Asn  Thr  Leu  Arg  Ser  Cys  Asp  Pro  Val  Phe  Tyr  Arg  Gln  Val  Leu  Gly
```

-continued

|     |     |     |     |     |     | 790 |     |     |     | 795 |     |     |     | 800 |     |      |
|-----|-----|-----|-----|-----|-----|-----|-----|-----|-----|-----|-----|-----|-----|-----|-----|------|
| GCA | GAG | AGC | GCC | CCT | CCC | GGA | CAG | CAA | GCC | CCG | CCC | AAC | ACG | GAC | TGG | 2565 |
| Ala | Glu | Ser | Ala | Pro | Pro | Gly | Gln | Gln | Ala | Pro | Pro | Asn | Thr | Asp | Trp |      |
|     |     | 805 |     |     |     |     | 810 |     |     |     |     | 815 |     |     |     |      |

```
CGT TTC TCT CAG GCC CAG AGA CCC GGC ACC AGC GGC TCC CAA AAT GGC      2613
Arg Phe Ser Gln Ala Gln Arg Pro Gly Thr Ser Gly Ser Gln Asn Gly
        820                 825                 830

GAT GAC ACC GGC ACC TGG CCC AAC AAC CAG TTT GAC ACA GAG ATG CTG      2661
Asp Asp Thr Gly Thr Trp Pro Asn Asn Gln Phe Asp Thr Glu Met Leu
        835                 840                 845

CAA GCC ATG ATC TTG GCG TCC GCC AGT GAA GCT GCT GAT GGG AGC TCC      2709
Gln Ala Met Ile Leu Ala Ser Ala Ser Glu Ala Ala Asp Gly Ser Ser
850                 855                 860                 865

ACC CTG GGA GGG GGT GCC GGC ACC ATG GGA TTG AGC GCC CGC TAC GGA      2757
Thr Leu Gly Gly Gly Ala Gly Thr Met Gly Leu Ser Ala Arg Tyr Gly
                870                 875                 880

CCC CAG TTC ACC CTG CAG CAC GTG CCC GAC TAC CGC CAG AAT GTC TAC      2805
Pro Gln Phe Thr Leu Gln His Val Pro Asp Tyr Arg Gln Asn Val Tyr
        885                 890                 895

ATC CCA GGC AGC AAT GCA CAC T GACCAACGCA GCTGGCAAGC GGATGGCAAG       2857
Ile Pro Gly Ser Asn Ala His
        900
```

| GCCCAGCAGG | TGGCAATGGC | AACAAGAAGA | AGTCGGCAAG | AAGGAGAAGA | AGTAACATGG | 2917 |
|---|---|---|---|---|---|---|
| AGGCCAGGCC | AAGAGCCACA | GGGCAGCCTC | TCCCCGAACC | AGCCCAGCTT | CTCCTTACCT | 2977 |
| GCACCCAGGC | CTCAGAGTTT | CAGGGCTAAC | CCCCAGAATA | CTGGTAGGGG | CCAAGGCATC | 3037 |
| TCCCTTGGAA | ACAGAAACAA | GTGCCATCAC | ACCATCCCTT | CCCCAGGTGT | AATATCCAAA | 3097 |
| GCAGTTCCGC | TGGGAACCCC | ATCCAATCAG | TGGCTGTACC | CATTTGGGTA | GTGGGGTTCA | 3157 |
| TGTAGACACC | AAGAACCATT | TGCCACACCC | CGTTTAGTTA | CAGCTGAACC | CTCCATCTTC | 3217 |
| CAAATCAATC | AGGCCCATCC | ATCCATGCC  | TCCCTCCTCC | CCACCCCACT | CCAACAGTTC | 3277 |
| CTCTTTCCCG | AGTAAGGTGG | TTGGGGTGTT | GAAGTACCAA | GTAACCTACA | AGCCTCCTAG | 3337 |
| TTCTGAAAAG | TTGGAAGGGC | ATCATGACCT | CTTGGCCTCT | CCTTTGATTC | TCAATCTTCC | 3397 |
| CCCAAAGCAT | GGTTTGGTGC | CAGCCCCTTC | ACCTCCTTCC | AGAGCCCAAG | ATCAATGCTC | 3457 |
| AAGTTTTGGA | GGACATGATC | ACCATCCCCA | TGGTACTGAT | GCTTGCTGGA | TTTAGGGAGG | 3517 |
| GCATTTTGCT | ACCAAGCCTC | TTCCCAACGC | CCTGGGACCA | GTCTTCTGTT | TTGTTTTTCA | 3577 |
| TTGTTGAGC  | TTTCCACTGC | ATGCCTTGAC | TTCCCCCACC | TCCTCCTCAA | ACAAGAGACT | 3637 |
| CCACTGCATG | TTCCAAGACA | GTATGGGGTG | GTAAGATAAG | GAAGGGAAGT | GTGTGGATGT | 3697 |
| GGATGGTGGG | GGCATGGACA | AAGCTTGACA | CATCAAGTTA | TCAAGGCCTT | GGAGGAGGCT | 3757 |
| CTGTATGTCC | TCAGGGGACT | GACAACATCC | TCCAGATTCC | AGCCATAAAC | CAATAACTAG | 3817 |
| GCTGGACCCT | TCCCACTACA | TAATAGGGCT | CAGCCAGGCA | GCCAGCTTTG | GGCTGAGCTA | 3877 |
| ACAGGACCAA | TGGATTAACT | GGCATTTCAG | TCCAAGGAAG | CTCGAAGCAG | GTTTAGGACC | 3937 |
| AGGTCCCCTT | GAGAGGTCAG | AGGGGCCTCT | GTGGGTGCTG | GGTACTCCAG | AGGTGCCACT | 3997 |
| GGTGGAAGGG | TCAGCGGAGC | CCCAGCAGGA | AGGGTGGGCC | AGCCAGGCCA | TTCTTAGTCC | 4057 |
| CTGGGTTGGG | GAGGCAGGGA | GCTAGGGCAG | GGACCAAATG | AACAGAAAGT | CTCAGCCCAG | 4117 |
| GATGGGGCTT | CTTCAACAGG | CCCCTGCCCT | CCTGAAGCCT | CAGTCCTTCA | CCTTGCCAGG | 4177 |
| TGCCGTTTCT | CTTCCGTGAA | GGCCACTGCC | CAGGTCCCCA | GTGCGCCCCC | TAGTGGCCAT | 4237 |
| AGCCTGGTTA | AAGTTCCCCA | GTGCCTCCTT | GTGATAGACC | TTCTTCTCCC | ACCCCCTTCT | 4297 |
| GCCCCTGGGT | CCCCGGCCAT | CCAGCGGGGC | TGCCAGAGAA | CCCCAGACCT | GCCCTTACAG | 4357 |

5,708,143

-continued

```
TAGTGTAGCG CCCCCTCCCT CTTTCGGCTG GTGTAGAATA GCCAGTAGTG TAGTGCGGTG    4417
TGCTTTTACG TGATGGCGGG TGGGCAGCGG GCGGCGGCGT CCGCGCAGCC GTCTGTCCTT    4477
GATCTGCCCG CGGCGGCCCG TGTTGTGTTT TGTGCTGTGT CCAGCGCTAA GGCGACCCCC    4537
TCCCCCGTAC TGACTTCTCC TATAAGCGCT TCTCTTCGCA TAGTCACGTA GCTCCACCC    4597
CACCCTCTTC CTGTGTCTCA CGCAAGTTTT ATACTCTAAT ATTTATATGG CTTTTTTTCT    4657
TCGACAAAAA AATAATAAAA CGTTCTTCT GAAAAAAAAA AAAAAAA                   4705
```

( 2 ) INFORMATION FOR SEQ ID NO:97:

( i ) SEQUENCE CHARACTERISTICS:
        ( A ) LENGTH: 904 amino acids
        ( B ) TYPE: amino acid
        ( D ) TOPOLOGY: linear ( i i ) MOLECULE TYPE: protein ( x i ) SEQUENCE DESCRIPTION: SEQ ID NO:97:

```
Met Val Pro Glu Ala Trp Arg Ser Gly Leu Val Ser Thr Gly Arg Val
 1               5                  10                  15

Val Gly Val Leu Leu Leu Gly Ala Leu Asn Lys Ala Ser Thr Val
            20                  25                  30

Ile His Tyr Glu Ile Pro Glu Glu Arg Glu Lys Gly Phe Ala Val Gly
            35                  40                  45

Asn Val Val Ala Asn Leu Gly Leu Asp Leu Gly Ser Leu Ser Ala Arg
 50                  55                  60

Arg Phe Pro Val Val Ser Gly Ala Ser Arg Arg Phe Phe Glu Val Asn
 65                  70                  75                  80

Arg Glu Thr Gly Glu Met Phe Val Asn Asp Arg Leu Asp Arg Glu Glu
                    85                  90                  95

Leu Cys Gly Thr Leu Pro Ser Cys Thr Val Thr Leu Glu Leu Val Val
                100                 105                 110

Glu Asn Pro Leu Glu Leu Phe Ser Val Glu Val Val Ile Gln Asp Ile
            115                 120                 125

Asn Asp Asn Asn Pro Ala Phe Pro Thr Gln Glu Met Lys Leu Glu Ile
130                 135                 140

Ser Glu Ala Val Ala Pro Gly Thr Arg Phe Pro Leu Glu Ser Ala His
145                 150                 155                 160

Asp Pro Asp Leu Gly Ser Asn Ser Leu Gln Thr Tyr Glu Leu Ser Arg
                165                 170                 175

Asn Glu Tyr Phe Ala Leu Arg Val Gln Thr Arg Glu Asp Ser Thr Lys
            180                 185                 190

Tyr Ala Glu Leu Val Leu Glu Arg Ala Leu Asp Arg Glu Arg Glu Pro
        195                 200                 205

Ser Leu Gln Leu Val Leu Thr Ala Leu Asp Gly Gly Thr Pro Ala Leu
210                 215                 220

Ser Ala Ser Leu Pro Ile His Ile Lys Val Leu Asp Ala Asn Asp Asn
225                 230                 235                 240

Ala Pro Val Phe Asn Gln Ser Leu Tyr Arg Ala Arg Val Pro Gly Gly
                245                 250                 255

Cys Thr Ser Gly Thr Arg Val Val Gln Val Leu Ala Thr Asp Leu Asp
            260                 265                 270

Glu Gly Pro Asn Gly Glu Ile Ile Tyr Ser Phe Gly Ser His Asn Arg
        275                 280                 285

Ala Gly Val Arg Gln Leu Phe Ala Leu Asp Leu Val Thr Gly Met Leu
290                 295                 300
```

-continued

| | | | | | | | | | | | | | | | |
|---|---|---|---|---|---|---|---|---|---|---|---|---|---|---|---|
| Thr | Ile | Lys | Gly | Arg | Leu | Asp | Phe | Glu | Asp | Thr | Lys | Leu | His | Glu | Ile |
| 305 | | | | 310 | | | | | 315 | | | | | | 320 |
| Tyr | Ile | Gln | Ala | Lys | Asp | Lys | Gly | Ala | Asn | Pro | Glu | Gly | Ala | His | Cys |
| | | | | 325 | | | | | 330 | | | | | 335 | |
| Lys | Val | Leu | Val | Glu | Val | Val | Asp | Val | Asn | Asp | Asn | Ala | Pro | Glu | Ile |
| | | | | 340 | | | | 345 | | | | | 350 | | |
| Thr | Val | Thr | Ser | Val | Tyr | Ser | Pro | Val | Pro | Glu | Asp | Ala | Ser | Gly | Thr |
| | | | 355 | | | | | 360 | | | | 365 | | | |
| Val | Ile | Ala | Leu | Leu | Ser | Val | Thr | Asp | Leu | Asp | Ala | Gly | Glu | Asn | Gly |
| | | 370 | | | | 375 | | | | | 380 | | | | |
| Leu | Val | Thr | Cys | Glu | Val | Pro | Pro | Gly | Leu | Pro | Phe | Ser | Leu | Thr | Ser |
| 385 | | | | | 390 | | | | | 395 | | | | | 400 |
| Ser | Leu | Lys | Asn | Tyr | Phe | Thr | Leu | Lys | Thr | Ser | Ala | Asp | Leu | Asp | Arg |
| | | | | 405 | | | | | 410 | | | | | 415 | |
| Glu | Thr | Val | Pro | Glu | Tyr | Asn | Leu | Ser | Ile | Thr | Ala | Arg | Asp | Ala | Gly |
| | | | 420 | | | | | 425 | | | | | 430 | | |
| Thr | Pro | Ser | Leu | Ser | Ala | Leu | Thr | Ile | Val | Arg | Val | Gln | Val | Ser | Asp |
| | | 435 | | | | | 440 | | | | | 445 | | | |
| Ile | Asn | Asp | Asn | Pro | Pro | Gln | Ser | Ser | Gln | Ser | Ser | Tyr | Asp | Val | Tyr |
| | 450 | | | | | 455 | | | | | 460 | | | | |
| Ile | Glu | Glu | Asn | Asn | Leu | Pro | Gly | Ala | Pro | Ile | Leu | Asn | Leu | Ser | Val |
| 465 | | | | | 470 | | | | | 475 | | | | | 480 |
| Trp | Asp | Pro | Asp | Ala | Pro | Gln | Asn | Ala | Arg | Leu | Ser | Phe | Phe | Leu | Leu |
| | | | | 485 | | | | | 490 | | | | | 495 | |
| Glu | Gln | Gly | Ala | Glu | Thr | Gly | Leu | Val | Gly | Arg | Tyr | Phe | Thr | Ile | Asn |
| | | | 500 | | | | | 505 | | | | | 510 | | |
| Arg | Asp | Asn | Gly | Ile | Val | Ser | Ser | Leu | Val | Pro | Leu | Asp | Tyr | Glu | Asp |
| | | | 515 | | | | 520 | | | | | 525 | | | |
| Arg | Arg | Glu | Phe | Glu | Leu | Thr | Ala | His | Ile | Ser | Asp | Gly | Gly | Thr | Pro |
| | | 530 | | | | | 535 | | | | | 540 | | | |
| Val | Leu | Ala | Thr | Asn | Ile | Ser | Val | Asn | Ile | Phe | Val | Thr | Asp | Arg | Asn |
| 545 | | | | | 550 | | | | | 555 | | | | | 560 |
| Asp | Asn | Ala | Pro | Gln | Val | Leu | Tyr | Pro | Arg | Pro | Gly | Gly | Ser | Ser | Val |
| | | | | 565 | | | | | 570 | | | | | 575 | |
| Glu | Met | Leu | Pro | Arg | Gly | Thr | Ser | Ala | Gly | His | Leu | Val | Ser | Arg | Val |
| | | | 580 | | | | | 585 | | | | | 590 | | |
| Val | Gly | Trp | Asp | Ala | Asp | Ala | Gly | His | Asn | Ala | Trp | Leu | Ser | Tyr | Ser |
| | | | 595 | | | | 600 | | | | | 605 | | | |
| Leu | Phe | Gly | Ser | Pro | Asn | Gln | Ser | Leu | Phe | Ala | Ile | Gly | Leu | His | Thr |
| | | 610 | | | | | 615 | | | | | 620 | | | |
| Gly | Gln | Ile | Ser | Thr | Ala | Arg | Pro | Val | Gln | Asp | Thr | Asp | Ser | Pro | Arg |
| 625 | | | | | 630 | | | | | 635 | | | | | 640 |
| Gln | Thr | Leu | Thr | Val | Leu | Ile | Lys | Asp | Asn | Gly | Glu | Pro | Ser | Leu | Ser |
| | | | | 645 | | | | | 650 | | | | | 655 | |
| Thr | Thr | Ala | Thr | Leu | Thr | Val | Ser | Val | Thr | Glu | Asp | Ser | Pro | Glu | Ala |
| | | | 660 | | | | | 665 | | | | | 670 | | |
| Arg | Ala | Glu | Phe | Pro | Ser | Gly | Ser | Ala | Pro | Arg | Glu | Gln | Lys | Lys | Asn |
| | | 675 | | | | | 680 | | | | | 685 | | | |
| Leu | Thr | Phe | Tyr | Leu | Leu | Leu | Ser | Leu | Ile | Leu | Val | Ser | Val | Gly | Phe |
| | | 690 | | | | 695 | | | | | 700 | | | | |
| Val | Val | Thr | Val | Phe | Gly | Val | Ile | Ile | Phe | Lys | Val | Tyr | Lys | Trp | Lys |
| 705 | | | | | 710 | | | | | 715 | | | | | 720 |
| Gln | Ser | Arg | Asp | Leu | Tyr | Arg | Ala | Pro | Val | Ser | Ser | Leu | Tyr | Arg | Thr |

725                          730                          735

Pro  Gly  Pro  Ser  Leu  His  Ala  Asp  Ala  Val  Arg  Gly  Gly  Leu  Met  Ser
                    740                     745                     750

Pro  His  Leu  Tyr  His  Gln  Val  Tyr  Leu  Thr  Thr  Asp  Ser  Arg  Arg  Ser
          755                     760                     765

Asp  Pro  Leu  Leu  Lys  Lys  Pro  Gly  Ala  Ala  Ser  Pro  Leu  Ala  Ser  Arg
     770                     775                          780

Gln  Asn  Thr  Leu  Arg  Ser  Cys  Asp  Pro  Val  Phe  Tyr  Arg  Gln  Val  Leu
785                      790                     795                          800

Gly  Ala  Glu  Ser  Ala  Pro  Pro  Gly  Gln  Gln  Ala  Pro  Pro  Asn  Thr  Asp
               805                          810                     815

Trp  Arg  Phe  Ser  Gln  Ala  Gln  Arg  Pro  Gly  Thr  Ser  Gly  Ser  Gln  Asn
               820                     825                     830

Gly  Asp  Asp  Thr  Gly  Thr  Trp  Pro  Asn  Asn  Gln  Phe  Asp  Thr  Glu  Met
          835                     840                     845

Leu  Gln  Ala  Met  Ile  Leu  Ala  Ser  Ala  Ser  Glu  Ala  Ala  Asp  Gly  Ser
     850                          855                     860

Ser  Thr  Leu  Gly  Gly  Gly  Ala  Gly  Thr  Met  Gly  Leu  Ser  Ala  Arg  Tyr
865                      870                     875                          880

Gly  Pro  Gln  Phe  Thr  Leu  Gln  His  Val  Pro  Asp  Tyr  Arg  Gln  Asn  Val
               885                     890                     895

Tyr  Ile  Pro  Gly  Ser  Asn  Ala  His
               900

( 2 ) INFORMATION FOR SEQ ID NO:98:

( i ) SEQUENCE CHARACTERISTICS:
      ( A ) LENGTH: 556 amino acids
      ( B ) TYPE: amino acid
      ( D ) TOPOLOGY: linear ( i i ) MOLECULE TYPE: protein ( x i ) SEQUENCE DESCRIPTION: SEQ ID NO:98:

Asp  Trp  Val  Ile  Pro  Pro  Ile  Asn  Leu  Pro  Glu  Asn  Ser  Arg  Gly  Pro
1                   5                    10                       15

Phe  Pro  Gln  Glu  Leu  Val  Arg  Ile  Arg  Ser  Asp  Arg  Asp  Lys  Asn  Leu
               20                     25                      30

Ser  Leu  Arg  Tyr  Thr  Val  Thr  Gly  Pro  Gly  Ala  Asp  Gln  Pro  Pro  Thr
          35                     40                     45

Gly  Ile  Phe  Ile  Ile  Asn  Pro  Ile  Ser  Gly  Gln  Leu  Ser  Val  Thr  Lys
     50                     55                     60

Pro  Leu  Asp  Arg  Glu  Gln  Ile  Ala  Arg  Phe  His  Leu  Arg  Ala  His  Ala
65                    70                      75                           80

Val  Asp  Ile  Asn  Gly  Asn  Gln  Val  Glu  Asn  Pro  Ile  Asp  Ile  Val  Ile
                    85                     90                      95

Asn  Val  Ile  Asp  Met  Asn  Asp  Asn  Arg  Pro  Glu  Phe  Leu  His  Gln  Val
                    100                    105                     110

Trp  Asn  Gly  Ser  Val  Pro  Glu  Gly  Ser  Lys  Pro  Gly  Thr  Tyr  Val  Met
               115                    120                     125

Thr  Val  Thr  Ala  Ile  Asp  Ala  Asp  Asp  Pro  Asn  Ala  Leu  Asn  Gly  Met
     130                    135                     140

Leu  Arg  Tyr  Arg  Ile  Leu  Ser  Gln  Ala  Pro  Ser  Thr  Pro  Ser  Pro  Asn
145                      150                    155                         160

Met  Phe  Thr  Ile  Asn  Asn  Glu  Thr  Gly  Asp  Ile  Ile  Thr  Val  Ala  Ala
                    165                    170                         175

-continued

```
Gly Leu Asp Arg Glu Lys Val Gln Gln Tyr Thr Leu Ile Ile Gln Ala
            180             185                 190

Thr Asp Met Glu Gly Asn Pro Thr Tyr Gly Leu Ser Asn Thr Ala Thr
        195             200                 205

Ala Val Ile Thr Val Thr Asp Val Asn Asp Asn Pro Pro Glu Phe Thr
    210             215             220

Ala Met Thr Phe Tyr Gly Glu Val Pro Glu Asn Arg Val Asp Ile Ile
225             230             235                         240

Val Ala Asn Leu Thr Val Thr Asp Lys Asp Gln Pro His Thr Pro Ala
            245             250                     255

Trp Asn Ala Val Thr Arg Ile Ser Gly Gly Asp Pro Thr Gly Arg Phe
            260             265             270

Ala Ile Gln Thr Asp Pro Asn Ser Asn Asp Gly Leu Val Thr Val Val
        275             280             285

Lys Pro Ile Asp Phe Glu Thr Asn Arg Met Phe Val Leu Thr Val Ala
    290             295             300

Ala Glu Asn Gln Val Pro Leu Ala Lys Gly Ile Gln His Pro Pro Gln
305             310             315                         320

Ser Thr Ala Thr Val Ser Val Thr Val Ile Asp Val Asn Glu Asn Pro
            325             330                     335

Tyr Phe Ala Pro Asn Pro Lys Ile Ile Arg Gln Glu Glu Gly Leu His
            340             345             350

Ala Gly Thr Met Leu Thr Thr Phe Thr Ala Gly Asp Pro Asp Arg Tyr
        355             360             365

Met Gln Gln Asn Ile Arg Tyr Thr Lys Leu Ser Asp Pro Ala Asn Trp
        370             375             380

Leu Lys Ile Asp Pro Val Asn Gly Gln Ile Thr Thr Ile Ala Val Leu
385             390             395                         400

Asp Arg Glu Ser Pro Asn Val Lys Asn Asn Ile Tyr Asn Ala Thr Phe
            405             410                     415

Leu Ala Ser Asp Asn Gly Ile Pro Pro Met Ser Gly Thr Gly Thr Leu
            420             425             430

Gln Ile Tyr Leu Leu Asp Ile Asn Asp Asn Ala Pro Gln Val Leu Pro
        435             440             445

Gln Glu Ala Glu Thr Cys Glu Thr Pro Asp Pro Asn Ser Ile Asn Ile
    450             455             460

Thr Thr Ala Leu Asp Tyr Asp Ile Asp Pro Asn Ala Gly Pro Phe Ala
465             470             475                         480

Tyr Asp Leu Pro Leu Ser Pro Val Thr Ile Lys Arg Asn Trp Thr Ile
            485             490                     495

Thr Arg Leu Asn Gly Asp Phe Ala Gln Leu Asn Leu Lys Ile Lys Phe
            500             505             510

Leu Glu Ala Gly Ile Tyr Glu Val Pro Ile Ile Ile Thr Asp Ser Gly
        515             520             525

Asn Pro Pro Lys Ser Asn Lys Ser Ile Leu Arg Val Arg Val Cys Gln
    530             535             540

Cys Asp Phe Asn Gly Asp Cys Thr Asp Val Asp Arg
545             550             555
```

(2) INFORMATION FOR SEQ ID NO:99:

(i) SEQUENCE CHARACTERISTICS:
(A) LENGTH: 105 amino acids
(B) TYPE: amino acid
(C) STRANDEDNESS: single
(D) TOPOLOGY: linear ( i i ) MOLECULE TYPE: protein ( x i ) SEQUENCE DESCRIPTION: SEQ ID NO:99:

| Glu | Asp | Thr | Val | Ser | Phe | Asp | Ile | Pro | Glu | Asn | Ala | Gln | Arg | Gly |
|---|---|---|---|---|---|---|---|---|---|---|---|---|---|---|
| 1 | | | | 5 | | | | | 10 | | | | | 15 |
| Tyr | Gln | Val | Gly | Gln | Ile | Val | Ala | Arg | Asp | Ala | Asp | Leu | Gly | Gln | Asn |
| | | | 20 | | | | | 25 | | | | | 30 | | |
| Ala | Gln | Leu | Ser | Tyr | Gly | Val | Val | Ser | Asp | Trp | Ala | Asn | Asp | Val | Phe |
| | | | 35 | | | | 40 | | | | | 45 | | | |
| Ser | Leu | Asn | Pro | Gln | Thr | Gly | Met | Leu | Thr | Leu | Thr | Ala | Arg | Leu | Asp |
| | 50 | | | | | 55 | | | | | 60 | | | | |
| Tyr | Glu | Glu | Val | Gln | His | Tyr | Ile | Leu | Ile | Val | Gln | Ala | Gln | Asp | Asn |
| 65 | | | | | 70 | | | | | 75 | | | | | 80 |
| Gly | Gln | Pro | Ser | Leu | Ser | Thr | Thr | Ile | Thr | Val | Tyr | Cys | Asn | Val | Leu |
| | | | | 85 | | | | 90 | | | | | | 95 | |
| Asp | Leu | Asn | Asp | Asn | Ala | Pro | Ile | Phe | | | | | | | |
| | | | 100 | | | | | 105 | | | | | | | |

( 2 ) INFORMATION FOR SEQ ID NO:100:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:100:

| Asp | Xaa | Asp | Xaa | Gly | Xaa | Asn |
|---|---|---|---|---|---|---|
| 1 | | | | 5 | | |

( 2 ) INFORMATION FOR SEQ ID NO:101:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:101:

| Ala | Xaa | Asp | Xaa | Gly | Xaa | Pro |
|---|---|---|---|---|---|---|
| 1 | | | | 5 | | |

( 2 ) INFORMATION FOR SEQ ID NO:102:

( i ) SEQUENCE CHARACTERISTICS:
  ( A ) LENGTH: 4650 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 495..4103

( x i ) SEQUENCE DESCRIPTION: SEQ ID NO:102:

```
CCTCTATTCG ACATTCTCTT TGGATTGTTT TGCTATAACT TGAAATTTGG GATGTCACAA      60
ACGAAACTGT CATCTGTTTC CGCCAAACTG TGGTTCTGCT AATCTCCCAG GCTGGCAGCA     120
TTGGAGACTT GCTGACTTCT TTCATCCCCC ACTCTTTTCA CCTGAAATTC CTTTCCTTGG     180
```

-continued

```
TTTTGCTCTA AGTCCTATGC TTCAGTCAGG GGCCAACCAA ATCTCACTGC CTCCTTTTTA        240

TCATGAAGCC TTTGATCACT GATAGTTCTT TTTATATCTT GAAAAATCAC CCTTCCCAGT        300

ACAGTTAATA TTTAGTATCT CTACTCATCT TGGCACTTAC TCACAGCTCC ATAATTCAGT        360

CGTTTTCGTA CCTCTTCATG GTGATGGGGA GCCCTTTGGA GGTGGTGACT GTGCTTTATA        420

CTCCTCATGA TGCTTCACAT GTGGCAGGCG TGGAGTGCCC GGAGGCGGCC CTCCTGATTC        480

TGGGGCCTCC CAGG ATG GAG CCC CTG AGG CAC AGC CCA GGC CCT GGG GGG          530
              Met Glu Pro Leu Arg His Ser Pro Gly Pro Gly Gly
               1               5                    10

CAA CGG CTA CTG CTG CCC TCC ATG CTG CTA GCA CTG CTC CTG CTG              578
Gln Arg Leu Leu Leu Pro Ser Met Leu Leu Ala Leu Leu Leu Leu
         15                  20                  25

GCT CCA TCC CCA GGC CAC GCC ACT CGG GTA GTG TAC AAG GTG CCG GAG          626
Ala Pro Ser Pro Gly His Ala Thr Arg Val Val Tyr Lys Val Pro Glu
         30                  35                  40

GAA CAG CCA CCC AAC ACC CTC ATT GGG AGC CTC GCA GCC GAC TAT GGT          674
Glu Gln Pro Pro Asn Thr Leu Ile Gly Ser Leu Ala Ala Asp Tyr Gly
 45                  50                  55                  60

TTT CCA GAT GTG GGG CAC CTG TAC AAG CTA GAG GTG GGT GCC CCG TAC          722
Phe Pro Asp Val Gly His Leu Tyr Lys Leu Glu Val Gly Ala Pro Tyr
                     65                  70                  75

CTT CGC GTG GAT GGC AAG ACA GGT GAC ATT TTC ACC ACC GAG ACC TCC          770
Leu Arg Val Asp Gly Lys Thr Gly Asp Ile Phe Thr Thr Glu Thr Ser
             80                  85                  90

ATC GAC CGT GAG GGG CTC CGT GAA TGC CAG AAC CAG CTC CCT GGT GAT          818
Ile Asp Arg Glu Gly Leu Arg Glu Cys Gln Asn Gln Leu Pro Gly Asp
             95                  100                 105

CCC TGC ATC CTG GAG TTT GAG GTA TCT ATC ACA GAC CTC GTG CAG AAT          866
Pro Cys Ile Leu Glu Phe Glu Val Ser Ile Thr Asp Leu Val Gln Asn
    110                 115                 120

GCG AGC CCC CGG CTG CTA GAG GGC CAG ATA GAA GTA CAA GAC ATC AAT          914
Ala Ser Pro Arg Leu Leu Glu Gly Gln Ile Glu Val Gln Asp Ile Asn
125                 130                 135                 140

GAC AAC ACA CCC AAC TTC GCC TCA CCA GTC ATC ACT CTG GCC ATC CCT          962
Asp Asn Thr Pro Asn Phe Ala Ser Pro Val Ile Thr Leu Ala Ile Pro
                145                 150                 155

GAG AAC ACC AAC ATC GGC TCA CTC TTC CCC ATC CCG CTG GCT TCA GAC          1010
Glu Asn Thr Asn Ile Gly Ser Leu Phe Pro Ile Pro Leu Ala Ser Asp
             160                 165                 170

CGT GAT GCT GGT CCC AAC GGT GTG GCA TCC TAT GAG CTG CAG GTG GCA          1058
Arg Asp Ala Gly Pro Asn Gly Val Ala Ser Tyr Glu Leu Gln Val Ala
        175                 180                 185

GAG GAC CAG GAG GAG AAG CAA CCA CAG CTC ATT GTG ATG GGC AAC CTG          1106
Glu Asp Gln Glu Glu Lys Gln Pro Gln Leu Ile Val Met Gly Asn Leu
190                 195                 200

GAC CGT GAG CGC TGG GAC TCC TAT GAC CTC ACC ATC AAG GTG CAG GAT          1154
Asp Arg Glu Arg Trp Asp Ser Tyr Asp Leu Thr Ile Lys Val Gln Asp
205                 210                 215                 220

GGC GGC AGC CCC CCA CGC GCC ACG AGT GCC CTG CTG CGT GTC ACC GTG          1202
Gly Gly Ser Pro Pro Arg Ala Thr Ser Ala Leu Leu Arg Val Thr Val
                225                 230                 235

CTT GAC ACC AAT GAC AAC GCC CCC AAG TTT GAG CGG CCC TCC TAT GAG          1250
Leu Asp Thr Asn Asp Asn Ala Pro Lys Phe Glu Arg Pro Ser Tyr Glu
            240                 245                 250

GCC GAA CTA TCT GAG AAT AGC CCC ATA GGC CAC TCG GTC ATC CAG GTG          1298
Ala Glu Leu Ser Glu Asn Ser Pro Ile Gly His Ser Val Ile Gln Val
        255                 260                 265

AAG GCC AAT GAC TCA GAC CAA GGT GCC AAT GCA GAA ATC GAA TAC ACA          1346
```

-continued

| | | | | | | | | | | | | | | | |
|---|---|---|---|---|---|---|---|---|---|---|---|---|---|---|---|
| Lys | Ala | Asn | Asp | Ser | Asp | Gln | Gly | Ala | Asn | Ala | Glu | Ile | Glu | Tyr | Thr |
| | | 270 | | | 275 | | | | | 280 | | | | | |

| TTC | CAC | CAG | GCG | CCC | GAA | GTT | GTG | AGG | CGT | CTT | CTT | CGA | CTG | GAC | AGG | 1394 |
|---|---|---|---|---|---|---|---|---|---|---|---|---|---|---|---|---|
| Phe | His | Gln | Ala | Pro | Glu | Val | Val | Arg | Arg | Leu | Leu | Arg | Leu | Asp | Arg | |
| 285 | | | | | 290 | | | | | 295 | | | | | 300 | |

| AAC | ACT | GGA | CTT | ATC | ACT | GTT | CAG | GGC | CCG | GTG | GAC | CGT | GAG | GAC | CTA | 1442 |
|---|---|---|---|---|---|---|---|---|---|---|---|---|---|---|---|---|
| Asn | Thr | Gly | Leu | Ile | Thr | Val | Gln | Gly | Pro | Val | Asp | Arg | Glu | Asp | Leu | |
| | | | | 305 | | | | | 310 | | | | | 315 | | |

| AGC | ACC | CTG | CGC | TTC | TCA | GTG | CTT | GCT | AAG | GAC | CGA | GGC | ACC | AAC | CCC | 1490 |
|---|---|---|---|---|---|---|---|---|---|---|---|---|---|---|---|---|
| Ser | Thr | Leu | Arg | Phe | Ser | Val | Leu | Ala | Lys | Asp | Arg | Gly | Thr | Asn | Pro | |
| | | | 320 | | | | | 325 | | | | | 330 | | | |

| AAG | AGT | GCC | CGT | GCC | CAG | GTG | GTT | GTG | ACC | GTG | AAG | GAC | ATG | AAT | GAC | 1538 |
|---|---|---|---|---|---|---|---|---|---|---|---|---|---|---|---|---|
| Lys | Ser | Ala | Arg | Ala | Gln | Val | Val | Val | Thr | Val | Lys | Asp | Met | Asn | Asp | |
| | | 335 | | | | | 340 | | | | | 345 | | | | |

| AAT | GCC | CCC | ACC | ATT | GAG | ATC | CGG | GGC | ATA | GGG | CTA | GTG | ACT | CAT | CAA | 1586 |
|---|---|---|---|---|---|---|---|---|---|---|---|---|---|---|---|---|
| Asn | Ala | Pro | Thr | Ile | Glu | Ile | Arg | Gly | Ile | Gly | Leu | Val | Thr | His | Gln | |
| | 350 | | | | | 355 | | | | | 360 | | | | | |

| GAT | GGG | ATG | GCT | AAC | ATC | TCA | GAG | GAT | GTG | GCA | GAG | GAG | ACA | GCT | GTG | 1634 |
|---|---|---|---|---|---|---|---|---|---|---|---|---|---|---|---|---|
| Asp | Gly | Met | Ala | Asn | Ile | Ser | Glu | Asp | Val | Ala | Glu | Glu | Thr | Ala | Val | |
| 365 | | | | | 370 | | | | | 375 | | | | | 380 | |

| GCC | CTG | GTG | CAG | GTG | TCT | GAC | CGA | GAT | GAG | GGA | GAG | AAT | GCA | GCT | GTC | 1682 |
|---|---|---|---|---|---|---|---|---|---|---|---|---|---|---|---|---|
| Ala | Leu | Val | Gln | Val | Ser | Asp | Arg | Asp | Glu | Gly | Glu | Asn | Ala | Ala | Val | |
| | | | | 385 | | | | | 390 | | | | | 395 | | |

| ACC | TGT | GTG | GTG | GCA | GGT | GAT | GTG | CCC | TTC | CAG | CTG | CGC | CAG | GCC | AGT | 1730 |
|---|---|---|---|---|---|---|---|---|---|---|---|---|---|---|---|---|
| Thr | Cys | Val | Val | Ala | Gly | Asp | Val | Pro | Phe | Gln | Leu | Arg | Gln | Ala | Ser | |
| | | | 400 | | | | | 405 | | | | | 410 | | | |

| GAG | ACA | GGC | AGT | GAC | AGC | AAG | AAG | AAG | TAT | TTC | CTG | CAG | ACT | ACC | ACC | 1778 |
|---|---|---|---|---|---|---|---|---|---|---|---|---|---|---|---|---|
| Glu | Thr | Gly | Ser | Asp | Ser | Lys | Lys | Lys | Tyr | Phe | Leu | Gln | Thr | Thr | Thr | |
| | | 415 | | | | | 420 | | | | | 425 | | | | |

| CCG | CTA | GAC | TAC | GAG | AAG | GTC | AAA | GAC | TAC | ACC | ATT | GAG | ATT | GTG | GCT | 1826 |
|---|---|---|---|---|---|---|---|---|---|---|---|---|---|---|---|---|
| Pro | Leu | Asp | Tyr | Glu | Lys | Val | Lys | Asp | Tyr | Thr | Ile | Glu | Ile | Val | Ala | |
| | 430 | | | | | 435 | | | | | 440 | | | | | |

| GTG | GAC | TCT | GGC | AAC | CCC | CCA | CTC | TCC | AGC | ACT | AAC | TCC | CTC | AAG | GTG | 1874 |
|---|---|---|---|---|---|---|---|---|---|---|---|---|---|---|---|---|
| Val | Asp | Ser | Gly | Asn | Pro | Pro | Leu | Ser | Ser | Thr | Asn | Ser | Leu | Lys | Val | |
| 445 | | | | | 450 | | | | | 455 | | | | | 460 | |

| CAG | GTG | GTG | GAC | GTC | AAT | GAC | AAC | GCA | CCT | GTC | TTC | ACT | CAG | AGT | GTC | 1922 |
|---|---|---|---|---|---|---|---|---|---|---|---|---|---|---|---|---|
| Gln | Val | Val | Asp | Val | Asn | Asp | Asn | Ala | Pro | Val | Phe | Thr | Gln | Ser | Val | |
| | | | | 465 | | | | | 470 | | | | | 475 | | |

| ACT | GAG | GTC | GCC | TTC | CCG | GAA | AAC | AAC | AAG | CCT | GGT | GAA | GTG | ATT | GCT | 1970 |
|---|---|---|---|---|---|---|---|---|---|---|---|---|---|---|---|---|
| Thr | Glu | Val | Ala | Phe | Pro | Glu | Asn | Asn | Lys | Pro | Gly | Glu | Val | Ile | Ala | |
| | | | 480 | | | | | 485 | | | | | 490 | | | |

| GAG | ATC | ACT | GCC | AGT | GAT | GCT | GAC | TCT | GGC | TCT | AAT | GCT | GAG | CTG | GTT | 2018 |
|---|---|---|---|---|---|---|---|---|---|---|---|---|---|---|---|---|
| Glu | Ile | Thr | Ala | Ser | Asp | Ala | Asp | Ser | Gly | Ser | Asn | Ala | Glu | Leu | Val | |
| | | 495 | | | | | 500 | | | | | 505 | | | | |

| TAC | TCT | CTG | GAG | CCT | GAG | CCG | GCT | GCT | AAG | GGC | CTC | TTC | ACC | ATC | TCA | 2066 |
|---|---|---|---|---|---|---|---|---|---|---|---|---|---|---|---|---|
| Tyr | Ser | Leu | Glu | Pro | Glu | Pro | Ala | Ala | Lys | Gly | Leu | Phe | Thr | Ile | Ser | |
| | 510 | | | | | 515 | | | | | 520 | | | | | |

| CCC | GAG | ACT | GGA | GAG | ATC | CAG | GTG | AAG | ACA | TCT | CTG | GAT | CGG | GAA | CAG | 2114 |
|---|---|---|---|---|---|---|---|---|---|---|---|---|---|---|---|---|
| Pro | Glu | Thr | Gly | Glu | Ile | Gln | Val | Lys | Thr | Ser | Leu | Asp | Arg | Glu | Gln | |
| 525 | | | | | 530 | | | | | 535 | | | | | 540 | |

| CGG | GAG | AGC | TAT | GAG | TTG | AAG | GTG | GTG | GCA | GCT | GAC | CGG | GGC | AGT | CCT | 2162 |
|---|---|---|---|---|---|---|---|---|---|---|---|---|---|---|---|---|
| Arg | Glu | Ser | Tyr | Glu | Leu | Lys | Val | Val | Ala | Ala | Asp | Arg | Gly | Ser | Pro | |
| | | | | 545 | | | | | 550 | | | | | 555 | | |

| AGC | CTC | CAG | GGC | ACA | GCC | ACT | GTC | CTT | GTC | AAT | GTG | CTG | GAC | TGC | AAT | 2210 |
|---|---|---|---|---|---|---|---|---|---|---|---|---|---|---|---|---|
| Ser | Leu | Gln | Gly | Thr | Ala | Thr | Val | Leu | Val | Asn | Val | Leu | Asp | Cys | Asn | |
| | | | 560 | | | | | 565 | | | | | 570 | | | |

| GAC | AAT | GAC | CCC | AAA | TTT | ATG | CTG | AGT | GGC | TAC | AAC | TTC | TCA | GTG | ATG | 2258 |
|---|---|---|---|---|---|---|---|---|---|---|---|---|---|---|---|---|
| Asp | Asn | Asp | Pro | Lys | Phe | Met | Leu | Ser | Gly | Tyr | Asn | Phe | Ser | Val | Met | |
| | | 575 | | | | | 580 | | | | | 585 | | | | |

| GAG | AAC | ATG | CCA | GCA | CTG | AGT | CCA | GTG | GGC | ATG | GTG | ACT | GTC | ATT | GAT | 2306 |

```
Glu Asn Met Pro Ala Leu Ser Pro Val Gly Met Val Thr Val Ile Asp
    590             595                 600

GGA GAC AAG GGG GAG AAT GCC CAG GTG CAG CTC TCA GTG GAG CAG GAC        2354
Gly Asp Lys Gly Glu Asn Ala Gln Val Gln Leu Ser Val Glu Gln Asp
605             610                 615                 620

AAC GGT GAC TTT GTT ATC CAG AAT GGC ACA GGC ACC ATC CTA TCC AGC        2402
Asn Gly Asp Phe Val Ile Gln Asn Gly Thr Gly Thr Ile Leu Ser Ser
                625                 630                 635

CTG AGC TTT GAT CGA GAG CAA CAA AGC ACC TAC ACC TTC CAG CTG AAG        2450
Leu Ser Phe Asp Arg Glu Gln Gln Ser Thr Tyr Thr Phe Gln Leu Lys
            640                 645                 650

GCA GTG GAT GGT GGC GTC CCA CCT CGC TCA GCT TAC GTT GGT GTC ACC        2498
Ala Val Asp Gly Gly Val Pro Pro Arg Ser Ala Tyr Val Gly Val Thr
        655                 660                 665

ATC AAT GTG CTG GAC GAG AAT GAC AAC GCA CCC TAT ATC ACT GCC CCT        2546
Ile Asn Val Leu Asp Glu Asn Asp Asn Ala Pro Tyr Ile Thr Ala Pro
    670                 675                 680

TCT AAC ACC TCT CAC AAG CTG CTG ACC CCC CAG ACA CGT CTT GGT GAG        2594
Ser Asn Thr Ser His Lys Leu Leu Thr Pro Gln Thr Arg Leu Gly Glu
685                 690                 695                 700

ACG GTC AGC CAG GTG GCA GCC GAG GAC TTT GAC TCT GGT GTC AAT GCC        2642
Thr Val Ser Gln Val Ala Ala Glu Asp Phe Asp Ser Gly Val Asn Ala
                705                 710                 715

GAG CTG ATC TAC AGC ATT GCA GGT GGC AAC CCT TAT GGA CTC TTC CAG        2690
Glu Leu Ile Tyr Ser Ile Ala Gly Gly Asn Pro Tyr Gly Leu Phe Gln
            720                 725                 730

ATT GGG TCA CAT TCA GGT GCC ATC ACC CTG GAG AAG GAG ATT GAG CGG        2738
Ile Gly Ser His Ser Gly Ala Ile Thr Leu Glu Lys Glu Ile Glu Arg
        735                 740                 745

CGC CAC CAT GGG CTA CAC CGC CTG GTG GTG AAG GTC AGT GAC CGC GGC        2786
Arg His His Gly Leu His Arg Leu Val Val Lys Val Ser Asp Arg Gly
    750                 755                 760

AAG CCC CCA CGC TAT GGC ACA GCC TTG GTC CAT CTT TAT GTC AAT GAG        2834
Lys Pro Pro Arg Tyr Gly Thr Ala Leu Val His Leu Tyr Val Asn Glu
765                 770                 775                 780

ACT CTG GCC AAC CGC ACG CTG CTG GAG ACC CTC CTG GGC CAC AGC CTG        2882
Thr Leu Ala Asn Arg Thr Leu Leu Glu Thr Leu Leu Gly His Ser Leu
                785                 790                 795

GAC ACG CCG CTG GAT ATT GAC ATT GCT GGG GAT CCA GAA TAT GAG CGC        2930
Asp Thr Pro Leu Asp Ile Asp Ile Ala Gly Asp Pro Glu Tyr Glu Arg
            800                 805                 810

TCC AAG CAG CGT GGC AAC ATT CTC TTT GGT GTG GTG GCT GGT GTG GTG        2978
Ser Lys Gln Arg Gly Asn Ile Leu Phe Gly Val Val Ala Gly Val Val
        815                 820                 825

GCC GTG GCC TTG CTC ATC GCC CTG GCG GTT CTT GTG CGC TAC TGC AGA        3026
Ala Val Ala Leu Leu Ile Ala Leu Ala Val Leu Val Arg Tyr Cys Arg
    830                 835                 840

CAG CGG GAG GCC AAA AGT GGT TAC CAG GCT GGT AAG AAG GAG ACC AAG        3074
Gln Arg Glu Ala Lys Ser Gly Tyr Gln Ala Gly Lys Lys Glu Thr Lys
845                 850                 855                 860

GAC CTG TAT GCC CCC AAG CCC AGT GGC AAG GCC TCC AAG GGA AAC AAA        3122
Asp Leu Tyr Ala Pro Lys Pro Ser Gly Lys Ala Ser Lys Gly Asn Lys
                865                 870                 875

AGC AAA GGC AAG AAG AGC AAG TCC CCA AAG CCC GTG AAG CCA GTG GAG        3170
Ser Lys Gly Lys Lys Ser Lys Ser Pro Lys Pro Val Lys Pro Val Glu
            880                 885                 890

GAC GAG GAT GAG GCC GGG CTG CAG AAG TCC CTC AAG TTC AAC CTG ATG        3218
Asp Glu Asp Glu Ala Gly Leu Gln Lys Ser Leu Lys Phe Asn Leu Met
        895                 900                 905

AGC GAT GCC CCT GGG GAC AGT CCC CGC ATC CAC CTG CCC CTC AAC TAC        3266
```

```
                Ser Asp Ala Pro Gly Asp Ser Pro Arg Ile His Leu Pro Leu Asn Tyr
                    910                 915                 920
CCA CCA GGC AGC CCT GAC CTG GGC CGC CAC TAT CGC TCT AAC TCC CCA              3314
Pro Pro Gly Ser Pro Asp Leu Gly Arg His Tyr Arg Ser Asn Ser Pro
925             930                 935                 940
CTG CCT TCC ATC CAG CTG CAG CCC CAG TCA CCC TCA GCC TCC AAG AAG              3362
Leu Pro Ser Ile Gln Leu Gln Pro Gln Ser Pro Ser Ala Ser Lys Lys
                945                 950                 955
CAC CAG GTG GTA CAG GAC CTG CCA CCT GCA AAC ACA TTC GTG GGC ACC              3410
His Gln Val Val Gln Asp Leu Pro Pro Ala Asn Thr Phe Val Gly Thr
            960                 965                 970
GGG GAC ACC ACG TCC ACG GGC TCT GAG CAG TAC TCC GAC TAC AGC TAC              3458
Gly Asp Thr Thr Ser Thr Gly Ser Glu Gln Tyr Ser Asp Tyr Ser Tyr
        975                 980                 985
CGC ACC AAC CCC CCC AAA TAC CCC AGC AAG CAG TTA CCT CAC CGC CGC              3506
Arg Thr Asn Pro Pro Lys Tyr Pro Ser Lys Gln Leu Pro His Arg Arg
    990                 995                 1000
GTC ACC TTC TCG GCC ACC AGC CAG GCC CAG GAG CTG CAG GAC CCA TCC              3554
Val Thr Phe Ser Ala Thr Ser Gln Ala Gln Glu Leu Gln Asp Pro Ser
1005                1010                1015                1020
CAG CAC AGT TAC TAT GAC AGT GGC CTG GAG GAG TCT GAG ACG CCG TCC              3602
Gln His Ser Tyr Tyr Asp Ser Gly Leu Glu Glu Ser Glu Thr Pro Ser
            1025                1030                1035
AGC AAG TCA TCC TCA GGG CCT CGA CTC GGT CCC CTG GCC CTG CCT GAG              3650
Ser Lys Ser Ser Ser Gly Pro Arg Leu Gly Pro Leu Ala Leu Pro Glu
        1040                1045                1050
GAT CAC TAT GAG CGC ACC ACC CCT GAT GGC AGC ATA GGA GAG ATG GAG              3698
Asp His Tyr Glu Arg Thr Thr Pro Asp Gly Ser Ile Gly Glu Met Glu
    1055                1060                1065
CAC CCC GAG AAT GAC CTT CGC CCT TTG CCT GAT GTC GCC ATG ACA GGC              3746
His Pro Glu Asn Asp Leu Arg Pro Leu Pro Asp Val Ala Met Thr Gly
1070                1075                1080
ACA TGT ACC CGG GAG TGC AGT GAG TTT GGC CAC TCT GAC ACA TGC TGG              3794
Thr Cys Thr Arg Glu Cys Ser Glu Phe Gly His Ser Asp Thr Cys Trp
            1085                1090                1095                1100
ATG CCT GGC CAG TCA TCT CCC AGC CGC CGG ACC AAG AGC AGC GCC CTC              3842
Met Pro Gly Gln Ser Ser Pro Ser Arg Arg Thr Lys Ser Ser Ala Leu
                    1105                1110                1115
AAA CTC TCC ACC TTC ATG CCT TAC CAG GAC CGA GGA GGG CAG GAG CCT              3890
Lys Leu Ser Thr Phe Met Pro Tyr Gln Asp Arg Gly Gly Gln Glu Pro
                1120                1125                1130
GCG GGC GCC GGC AGC CCC AGC CCC CCG GAA GAC CGG AAC ACC AAA ACG              3938
Ala Gly Ala Gly Ser Pro Ser Pro Pro Glu Asp Arg Asn Thr Lys Thr
                1135                1140                1145
GCC CCC GTG CGC CTC CTG CCC TCC TAC AGT GCC TTC TCC CAC AGT AGC              3986
Ala Pro Val Arg Leu Leu Pro Ser Tyr Ser Ala Phe Ser His Ser Ser
    1150                1155                1160
CAT GAT TCC TGC AAG GAC TCG GCC ACC TTG GAG GAA ATC CCC CTG ACC              4034
His Asp Ser Cys Lys Asp Ser Ala Thr Leu Glu Glu Ile Pro Leu Thr
1165                1170                1175                1180
CAG ACC TCG GAC TTC CCA CCC GCA GCC ACA CCG GCA TCT GCC CAG ACG              4082
Gln Thr Ser Asp Phe Pro Pro Ala Ala Thr Pro Ala Ser Ala Gln Thr
                1185                1190                1195
GCC AAG CGC GAG ATC TAC CTG TGAGCCCCT ACTGGCCGGC CCCCCTCCCC                  4133
Ala Lys Arg Glu Ile Tyr Leu
                1200
CAGCGCCGGC CAGCTCCCAA ATGCCCATTC CAGGGCCTCA CTCTCCACCC CTTCAGCGTG            4193

GACTTCCTGC CAGGGCCCAA GTGGGGGTAT CACTGACCTC ATGACCACGC TGGCCCTTCT            4253

CCCATGCAGG GTCCAGGTCC TCTCCCCTCA TTTCCATCTC CCAGCCCAGG GGCCCCTTCC            4313
```

```
CCTTTATGGG GCTTCCCCCA GCTGATGCCC AAGAGGGCTC CTCTGCAATG ACTGGGCTCC    4373

TTCCCTTGAC TTCCAGGGAG CACCCCCTCG ATTTGGGCAG ATGGTGGAGT CAAGGGTGGG    4433

CAGCGTACTT CTAACTCATT GTTTCCCTCA TGGCCGACCA GGGCGGGGAT AGCATGCCCA    4493

ATTTTAGCCC TGAAGCAGGG CTGAACTGGG GAGCCCCTTT CCCTGGGAGC TCCCAGAGGA    4553

AACTCTTGAC CACCAGTGGC TCCCTGAAGG GCTTTTGTTA CCAAAGGTGG GGTAGGGACG    4613

GGGGTGGGAG TGGAGCGGAG GCCTTGTTTT CCCGTGG                             4650
```

(2) INFORMATION FOR SEQ ID NO:103:

(i) SEQUENCE CHARACTERISTICS:
        (A) LENGTH: 1203 amino acids
        (B) TYPE: amino acid
        (D) TOPOLOGY: linear (ii) MOLECULE TYPE: protein (xi) SEQUENCE DESCRIPTION: SEQ ID NO:103:

```
Met Glu Pro Leu Arg His Ser Pro Gly Pro Gly Gly Gln Arg Leu Leu
 1               5                  10                  15

Leu Pro Ser Met Leu Leu Ala Leu Leu Leu Leu Ala Pro Ser Pro
            20                  25                  30

Gly His Ala Thr Arg Val Val Tyr Lys Val Pro Glu Glu Gln Pro Pro
        35                  40                      45

Asn Thr Leu Ile Gly Ser Leu Ala Ala Asp Tyr Gly Phe Pro Asp Val
    50                  55                  60

Gly His Leu Tyr Lys Leu Glu Val Gly Ala Pro Tyr Leu Arg Val Asp
65                  70                  75                      80

Gly Lys Thr Gly Asp Ile Phe Thr Thr Glu Thr Ser Ile Asp Arg Glu
                85                  90                  95

Gly Leu Arg Glu Cys Gln Asn Gln Leu Pro Gly Asp Pro Cys Ile Leu
            100                 105                 110

Glu Phe Glu Val Ser Ile Thr Asp Leu Val Gln Asn Ala Ser Pro Arg
        115                 120                 125

Leu Leu Glu Gly Gln Ile Glu Val Gln Asp Ile Asn Asp Asn Thr Pro
    130                 135                 140

Asn Phe Ala Ser Pro Val Ile Thr Leu Ala Ile Pro Glu Asn Thr Asn
145                 150                 155                     160

Ile Gly Ser Leu Phe Pro Ile Pro Leu Ala Ser Asp Arg Asp Ala Gly
                165                 170                 175

Pro Asn Gly Val Ala Ser Tyr Glu Leu Gln Val Ala Glu Asp Gln Glu
            180                 185                 190

Glu Lys Gln Pro Gln Leu Ile Val Met Gly Asn Leu Asp Arg Glu Arg
        195                 200                 205

Trp Asp Ser Tyr Asp Leu Thr Ile Lys Val Gln Asp Gly Gly Ser Pro
    210                 215                 220

Pro Arg Ala Thr Ser Ala Leu Leu Arg Val Thr Val Leu Asp Thr Asn
225                 230                 235                     240

Asp Asn Ala Pro Lys Phe Glu Arg Pro Ser Tyr Glu Ala Glu Leu Ser
                245                 250                 255

Glu Asn Ser Pro Ile Gly His Ser Val Ile Gln Val Lys Ala Asn Asp
            260                 265                 270

Ser Asp Gln Gly Ala Asn Ala Glu Ile Glu Tyr Thr Phe His Gln Ala
        275                 280                 285

Pro Glu Val Val Arg Arg Leu Leu Arg Leu Asp Arg Asn Thr Gly Leu
```

|     |     |     | 290 |     |     |     | 295 |     |     |     | 300 |     |     |     |
|-----|-----|-----|-----|-----|-----|-----|-----|-----|-----|-----|-----|-----|-----|-----|

Ile Thr Val Gln Gly Pro Val Asp Arg Glu Asp Leu Ser Thr Leu Arg
305                 310                 315                 320

Phe Ser Val Leu Ala Lys Asp Arg Gly Thr Asn Pro Lys Ser Ala Arg
                325                 330                 335

Ala Gln Val Val Val Thr Val Lys Asp Met Asn Asp Asn Ala Pro Thr
            340                 345                 350

Ile Glu Ile Arg Gly Ile Gly Leu Val Thr His Gln Asp Gly Met Ala
        355                 360                 365

Asn Ile Ser Glu Asp Val Ala Glu Thr Ala Val Ala Leu Val Gln
    370                 375                 380

Val Ser Asp Arg Asp Glu Gly Glu Asn Ala Ala Val Thr Cys Val Val
385                 390                 395                 400

Ala Gly Asp Val Pro Phe Gln Leu Arg Gln Ala Ser Glu Thr Gly Ser
                405                 410                 415

Asp Ser Lys Lys Lys Tyr Phe Leu Gln Thr Thr Thr Pro Leu Asp Tyr
            420                 425                 430

Glu Lys Val Lys Asp Tyr Thr Ile Glu Ile Val Ala Val Asp Ser Gly
        435                 440                 445

Asn Pro Pro Leu Ser Ser Thr Asn Ser Leu Lys Val Gln Val Val Asp
    450                 455                 460

Val Asn Asp Asn Ala Pro Val Phe Thr Gln Ser Val Thr Glu Val Ala
465                 470                 475                 480

Phe Pro Glu Asn Asn Lys Pro Gly Glu Val Ile Ala Glu Ile Thr Ala
                485                 490                 495

Ser Asp Ala Asp Ser Gly Ser Asn Ala Glu Leu Val Tyr Ser Leu Glu
            500                 505                 510

Pro Glu Pro Ala Ala Lys Gly Leu Phe Thr Ile Ser Pro Glu Thr Gly
        515                 520                 525

Glu Ile Gln Val Lys Thr Ser Leu Asp Arg Glu Gln Arg Glu Ser Tyr
    530                 535                 540

Glu Leu Lys Val Val Ala Ala Asp Arg Gly Ser Pro Ser Leu Gln Gly
545                 550                 555                 560

Thr Ala Thr Val Leu Val Asn Val Leu Asp Cys Asn Asp Asn Asp Pro
                565                 570                 575

Lys Phe Met Leu Ser Gly Tyr Asn Phe Ser Val Met Glu Asn Met Pro
            580                 585                 590

Ala Leu Ser Pro Val Gly Met Val Thr Val Ile Asp Gly Asp Lys Gly
        595                 600                 605

Glu Asn Ala Gln Val Gln Leu Ser Val Glu Gln Asp Asn Gly Asp Phe
    610                 615                 620

Val Ile Gln Asn Gly Thr Gly Thr Ile Leu Ser Ser Leu Ser Phe Asp
625                 630                 635                 640

Arg Glu Gln Gln Ser Thr Tyr Thr Phe Gln Leu Lys Ala Val Asp Gly
                645                 650                 655

Gly Val Pro Pro Arg Ser Ala Tyr Val Gly Val Thr Ile Asn Val Leu
            660                 665                 670

Asp Glu Asn Asp Asn Ala Pro Tyr Ile Thr Ala Pro Ser Asn Thr Ser
        675                 680                 685

His Lys Leu Leu Thr Pro Gln Thr Arg Leu Gly Glu Thr Val Ser Gln
    690                 695                 700

Val Ala Ala Glu Asp Phe Asp Ser Gly Val Asn Ala Glu Leu Ile Tyr
705                 710                 715                 720

| | | | | | | | | | | | | | | |
|---|---|---|---|---|---|---|---|---|---|---|---|---|---|---|
| Ser | Ile | Ala | Gly | Gly | Asn | Pro | Tyr | Gly | Leu | Phe | Gln | Ile | Gly | Ser | His |
| | | | | 725 | | | | 730 | | | | | | 735 | |
| Ser | Gly | Ala | Ile | Thr | Leu | Glu | Lys | Glu | Ile | Glu | Arg | Arg | His | His | Gly |
| | | | | 740 | | | | 745 | | | | | 750 | | |
| Leu | His | Arg | Leu | Val | Val | Lys | Val | Ser | Asp | Arg | Gly | Lys | Pro | Pro | Arg |
| | | | 755 | | | | 760 | | | | 765 | | | | |
| Tyr | Gly | Thr | Ala | Leu | Val | His | Leu | Tyr | Val | Asn | Glu | Thr | Leu | Ala | Asn |
| | 770 | | | | | 775 | | | | | 780 | | | | |
| Arg | Thr | Leu | Leu | Glu | Thr | Leu | Leu | Gly | His | Ser | Leu | Asp | Thr | Pro | Leu |
| 785 | | | | | 790 | | | | 795 | | | | | | 800 |
| Asp | Ile | Asp | Ile | Ala | Gly | Asp | Pro | Glu | Tyr | Glu | Arg | Ser | Lys | Gln | Arg |
| | | | | 805 | | | | 810 | | | | | | 815 | |
| Gly | Asn | Ile | Leu | Phe | Gly | Val | Val | Ala | Gly | Val | Val | Ala | Val | Ala | Leu |
| | | | 820 | | | | | 825 | | | | | 830 | | |
| Leu | Ile | Ala | Leu | Ala | Val | Leu | Val | Arg | Tyr | Cys | Arg | Gln | Arg | Glu | Ala |
| | | 835 | | | | | 840 | | | | | 845 | | | |
| Lys | Ser | Gly | Tyr | Gln | Ala | Gly | Lys | Lys | Glu | Thr | Lys | Asp | Leu | Tyr | Ala |
| | 850 | | | | | 855 | | | | | 860 | | | | |
| Pro | Lys | Pro | Ser | Gly | Lys | Ala | Ser | Lys | Gly | Asn | Lys | Ser | Lys | Gly | Lys |
| 865 | | | | | 870 | | | | | 875 | | | | | 880 |
| Lys | Ser | Lys | Ser | Pro | Lys | Pro | Val | Lys | Pro | Val | Glu | Asp | Glu | Asp | Glu |
| | | | | 885 | | | | 890 | | | | | | 895 | |
| Ala | Gly | Leu | Gln | Lys | Ser | Leu | Lys | Phe | Asn | Leu | Met | Ser | Asp | Ala | Pro |
| | | | 900 | | | | | 905 | | | | | 910 | | |
| Gly | Asp | Ser | Pro | Arg | Ile | His | Leu | Pro | Leu | Asn | Tyr | Pro | Gly | Ser | |
| | | | 915 | | | | | 920 | | | | | 925 | | |
| Pro | Asp | Leu | Gly | Arg | His | Tyr | Arg | Ser | Asn | Ser | Pro | Leu | Pro | Ser | Ile |
| | 930 | | | | | 935 | | | | | 940 | | | | |
| Gln | Leu | Gln | Pro | Gln | Ser | Pro | Ser | Ala | Ser | Lys | Lys | His | Gln | Val | Val |
| 945 | | | | | 950 | | | | | 955 | | | | | 960 |
| Gln | Asp | Leu | Pro | Pro | Ala | Asn | Thr | Phe | Val | Gly | Thr | Gly | Asp | Thr | Thr |
| | | | | 965 | | | | 970 | | | | | 975 | | |
| Ser | Thr | Gly | Ser | Glu | Gln | Tyr | Ser | Asp | Tyr | Ser | Tyr | Arg | Thr | Asn | Pro |
| | | | 980 | | | | | 985 | | | | | 990 | | |
| Pro | Lys | Tyr | Pro | Ser | Lys | Gln | Leu | Pro | His | Arg | Arg | Val | Thr | Phe | Ser |
| | | 995 | | | | 1000 | | | | | 1005 | | | | |
| Ala | Thr | Ser | Gln | Ala | Gln | Glu | Leu | Gln | Asp | Pro | Ser | Gln | His | Ser | Tyr |
| | 1010 | | | | | 1015 | | | | | 1020 | | | | |
| Tyr | Asp | Ser | Gly | Leu | Glu | Glu | Ser | Glu | Thr | Pro | Ser | Ser | Lys | Ser | Ser |
| 1025 | | | | | 1030 | | | | | 1035 | | | | | 1040 |
| Ser | Gly | Pro | Arg | Leu | Gly | Pro | Leu | Ala | Leu | Pro | Glu | Asp | His | Tyr | Glu |
| | | | | 1045 | | | | 1050 | | | | | 1055 | | |
| Arg | Thr | Thr | Pro | Asp | Gly | Ser | Ile | Gly | Glu | Met | Glu | His | Pro | Glu | Asn |
| | | | 1060 | | | | | 1065 | | | | | 1070 | | |
| Asp | Leu | Arg | Pro | Leu | Pro | Asp | Val | Ala | Met | Thr | Gly | Thr | Cys | Thr | Arg |
| | | | 1075 | | | | 1080 | | | | | 1085 | | | |
| Glu | Cys | Ser | Glu | Phe | Gly | His | Ser | Asp | Thr | Cys | Trp | Met | Pro | Gly | Gln |
| | | 1090 | | | | | 1095 | | | | | 1100 | | | |
| Ser | Ser | Pro | Ser | Arg | Arg | Thr | Lys | Ser | Ser | Ala | Leu | Lys | Leu | Ser | Thr |
| 1105 | | | | | 1110 | | | | | 1115 | | | | | 1120 |
| Phe | Met | Pro | Tyr | Gln | Asp | Arg | Gly | Gly | Gln | Glu | Pro | Ala | Gly | Ala | Gly |
| | | | | 1125 | | | | | 1130 | | | | | 1135 | |
| Ser | Pro | Ser | Pro | Pro | Glu | Asp | Arg | Asn | Thr | Lys | Thr | Ala | Pro | Val | Arg |
| | | | 1140 | | | | | 1145 | | | | | 1150 | | |

| | | | | | | | | | | | | | | |
|---|---|---|---|---|---|---|---|---|---|---|---|---|---|---|
|Leu|Leu|Pro|Ser|Tyr|Ser|Ala|Phe|Ser|His|Ser|Ser|His|Asp|Ser|Cys|
| | |1155| | |1160| | | |1165| | | | | |

Lys Asp Ser Ala Thr Leu Glu Glu Ile Pro Leu Thr Gln Thr Ser Asp
1170              1175              1180

Phe Pro Pro Ala Ala Thr Pro Ala Ser Ala Gln Thr Ala Lys Arg Glu
1185              1190              1195              1200

Ile Tyr Leu ( 2 ) INFORMATION FOR SEQ ID NO:104:

( i ) SEQUENCE CHARACTERISTICS:
        ( A ) LENGTH: 2789 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 115..2622

( x i ) SEQUENCE DESCRIPTION: SEQ ID NO:104:

```
CGAAAGCCAT GTCGGACTCG TCGCCCAGCG CCCAAGCGCT AACCCGCTGA AAGTTTCTCA        60

GCGAAATCTC AGGGACGATC TGGACCCCGC TGAGAGGAAC TGCTTTTGAG TGAG ATG        117
                                                              Met
                                                              1

GTC CCA GAG GCC TGG AGG AGC GGA CTG GTA AGC ACC GGG AGG GTA GTG        165
Val Pro Glu Ala Trp Arg Ser Gly Leu Val Ser Thr Gly Arg Val Val
            5                   10                  15

GGA GTT TTG CTT CTG CTT GGT GCC TTG AAC AAG GCT TCC ACG GTC ATT        213
Gly Val Leu Leu Leu Leu Gly Ala Leu Asn Lys Ala Ser Thr Val Ile
        20                  25                  30

CAC TAT GAG ATC CCG GAG GAA AGA GAG AAG GGT TTC GCT GTG GGC AAC        261
His Tyr Glu Ile Pro Glu Glu Arg Glu Lys Gly Phe Ala Val Gly Asn
    35                  40                  45

GTG GTC GCG AAC CTT GGT TTG GAT CTC GGT AGC CTC TCA GCC CGC AGG        309
Val Val Ala Asn Leu Gly Leu Asp Leu Gly Ser Leu Ser Ala Arg Arg
50                  55                  60                       65

TTC CCG GTG GTG TCT GGA GCT AGC CGA AGA TTC TTT GAG GTG AAC CGG        357
Phe Pro Val Val Ser Gly Ala Ser Arg Arg Phe Phe Glu Val Asn Arg
                70                  75                  80

GAG ACC GGA GAG ATG TTT GTG AAC GAC CGT CTG GAT CGA GAG GAG CTG        405
Glu Thr Gly Glu Met Phe Val Asn Asp Arg Leu Asp Arg Glu Glu Leu
            85                  90                  95

TGT GGG ACA CTG CCC TCT TGC ACT GTA ACT CTG GAG TTG GTA GTG GAG        453
Cys Gly Thr Leu Pro Ser Cys Thr Val Thr Leu Glu Leu Val Val Glu
        100                 105                 110

AAC CCG CTG GAG CTG TTC AGC GTG GAA GTG GTG ATC CAG GAC ATC AAC        501
Asn Pro Leu Glu Leu Phe Ser Val Glu Val Val Ile Gln Asp Ile Asn
    115                 120                 125

GAC AAC AAT CCT GCT TTC CCT ACC CAG GAA ATG AAA TTG GAG ATT AGC        549
Asp Asn Asn Pro Ala Phe Pro Thr Gln Glu Met Lys Leu Glu Ile Ser
130                 135                 140                 145

GAG GCC GTG GCT CCG GGG ACG CGC TTT CCG CTC GAG AGC GCG CAC GAT        597
Glu Ala Val Ala Pro Gly Thr Arg Phe Pro Leu Glu Ser Ala His Asp
                150                 155                 160

CCC GAT CTG GGA AGC AAC TCT TTA CAA ACC TAT GAG CTG AGC CGA AAT        645
Pro Asp Leu Gly Ser Asn Ser Leu Gln Thr Tyr Glu Leu Ser Arg Asn
            165                 170                 175

GAA TAC TTT GCG CTT CGC GTG CAG ACG CGG GAG GAC AGC ACC AAG TAC        693
```

-continued

| | | | | | | | | | | | | | | | |
|---|---|---|---|---|---|---|---|---|---|---|---|---|---|---|---|
| Glu | Tyr | Phe<br>180 | Ala | Leu | Arg | Val | Gln<br>185 | Thr | Arg | Glu | Asp | Ser<br>190 | Thr | Lys | Tyr |

| GCG | GAG | CTG | GTG | TTG | GAG | CGC | GCC | CTG | GAC | CGA | GAA | CGG | GAG | CCT | AGT | 741 |
|---|---|---|---|---|---|---|---|---|---|---|---|---|---|---|---|---|
| Ala | Glu<br>195 | Leu | Val | Leu | Glu | Arg<br>200 | Ala | Leu | Asp | Arg | Glu<br>205 | Arg | Glu | Pro | Ser | |

| CTC | CAG | TTA | GTG | CTG | ACG | GCG | TTG | GAC | GGA | GGG | ACC | CCA | GCT | CTC | TCC | 789 |
|---|---|---|---|---|---|---|---|---|---|---|---|---|---|---|---|---|
| Leu<br>210 | Gln | Leu | Val | Leu | Thr<br>215 | Ala | Leu | Asp | Gly | Gly<br>220 | Thr | Pro | Ala | Leu | Ser<br>225 | |

| GCC | AGC | CTG | CCT | ATT | CAC | ATC | AAG | GTG | CTG | GAC | GCG | AAT | GAC | AAT | GCG | 837 |
|---|---|---|---|---|---|---|---|---|---|---|---|---|---|---|---|---|
| Ala | Ser | Leu | Pro | Ile<br>230 | His | Ile | Lys | Val | Leu<br>235 | Asp | Ala | Asn | Asp | Asn<br>240 | Ala | |

| CCT | GTC | TTC | AAC | CAG | TCC | TTG | TAC | CGG | GCG | CGC | GTT | CCT | GGA | GGA | TGC | 885 |
|---|---|---|---|---|---|---|---|---|---|---|---|---|---|---|---|---|
| Pro | Val | Phe | Asn<br>245 | Gln | Ser | Leu | Tyr | Arg<br>250 | Ala | Arg | Val | Pro | Gly<br>255 | Gly | Cys | |

| ACC | TCC | GGC | ACG | CGC | GTG | GTA | CAA | GTC | CTT | GCA | ACG | GAT | CTG | GAT | GAA | 933 |
|---|---|---|---|---|---|---|---|---|---|---|---|---|---|---|---|---|
| Thr | Ser | Gly | Thr<br>260 | Arg | Val | Val | Gln | Val<br>265 | Leu | Ala | Thr | Asp | Leu<br>270 | Asp | Glu | |

| GGC | CCC | AAC | GGT | GAA | ATT | ATT | TAC | TCC | TTC | GGC | AGC | CAC | AAC | CGC | GCC | 981 |
|---|---|---|---|---|---|---|---|---|---|---|---|---|---|---|---|---|
| Gly | Pro | Asn<br>275 | Gly | Glu | Ile | Ile<br>280 | Tyr | Ser | Phe | Gly | Ser<br>285 | His | Asn | Arg | Ala | |

| GGC | GTG | CGG | CAA | CTA | TTC | GCC | TTA | GAC | CTT | GTA | ACC | GGG | ATG | CTG | ACA | 1029 |
|---|---|---|---|---|---|---|---|---|---|---|---|---|---|---|---|---|
| Gly | Val<br>290 | Arg | Gln | Leu | Phe<br>295 | Ala | Leu | Asp | Leu | Val<br>300 | Thr | Gly | Met | Leu | Thr<br>305 | |

| ATC | AAG | GGT | CGG | CTG | GAC | TTC | GAG | GAC | ACC | AAA | CTC | CAT | GAG | ATT | TAC | 1077 |
|---|---|---|---|---|---|---|---|---|---|---|---|---|---|---|---|---|
| Ile | Lys | Gly | Arg | Leu<br>310 | Asp | Phe | Glu | Asp | Thr<br>315 | Lys | Leu | His | Glu | Ile<br>320 | Tyr | |

| ATC | CAG | GCC | AAA | GAC | AAG | GGC | GCC | AAT | CCC | GAA | GGA | GCA | CAT | TGC | AAA | 1125 |
|---|---|---|---|---|---|---|---|---|---|---|---|---|---|---|---|---|
| Ile | Gln | Ala | Lys<br>325 | Asp | Lys | Gly | Ala | Asn<br>330 | Pro | Glu | Gly | Ala | His<br>335 | Cys | Lys | |

| GTG | TTG | GTG | GAG | GTT | GTG | GAT | GTG | AAT | GAC | AAC | GCC | CCG | GAG | ATC | ACA | 1173 |
|---|---|---|---|---|---|---|---|---|---|---|---|---|---|---|---|---|
| Val | Leu | Val<br>340 | Glu | Val | Val | Asp | Val<br>345 | Asn | Asp | Asn | Ala | Pro<br>350 | Glu | Ile | Thr | |

| GTC | ACC | TCC | GTG | TAC | AGC | CCA | GTA | CCC | GAG | GAT | GCC | TCT | GGG | ACT | GTC | 1221 |
|---|---|---|---|---|---|---|---|---|---|---|---|---|---|---|---|---|
| Val | Thr<br>355 | Ser | Val | Tyr | Ser<br>360 | Pro | Val | Pro | Glu | Asp<br>365 | Ala | Ser | Gly | Thr | Val | |

| ATC | GCT | TTG | CTC | AGT | GTG | ACT | GAC | CTG | GAT | GCT | GGC | GAG | AAC | GGG | CTG | 1269 |
|---|---|---|---|---|---|---|---|---|---|---|---|---|---|---|---|---|
| Ile | Ala | Leu<br>370 | Leu | Ser | Val | Thr<br>375 | Asp | Leu | Asp | Ala | Gly<br>380 | Glu | Asn | Gly | Leu<br>385 | |

| GTG | ACC | TGC | GAA | GTT | CCA | CCG | GGT | CTC | CCT | TTC | AGC | CTT | ACT | TCT | TCC | 1317 |
|---|---|---|---|---|---|---|---|---|---|---|---|---|---|---|---|---|
| Val | Thr | Cys | Glu | Val<br>390 | Pro | Pro | Gly | Leu | Pro<br>395 | Phe | Ser | Leu | Thr | Ser<br>400 | Ser | |

| CTC | AAG | AAT | TAC | TTC | ACT | TTG | AAA | ACC | AGT | GCA | GAC | CTG | GAT | CGG | GAG | 1365 |
|---|---|---|---|---|---|---|---|---|---|---|---|---|---|---|---|---|
| Leu | Lys | Asn | Tyr<br>405 | Phe | Thr | Leu | Lys | Thr<br>410 | Ser | Ala | Asp | Leu | Asp<br>415 | Arg | Glu | |

| ACT | GTG | CCA | GAA | TAC | AAC | CTC | AGC | ATC | ACC | GCC | CGA | GAC | GCC | GGA | ACC | 1413 |
|---|---|---|---|---|---|---|---|---|---|---|---|---|---|---|---|---|
| Thr | Val | Pro | Glu<br>420 | Tyr | Asn | Leu | Ser | Ile<br>425 | Thr | Ala | Arg | Asp | Ala<br>430 | Gly | Thr | |

| CCT | TCC | CTC | TCA | GCC | CTT | ACA | ATA | GTG | CGT | GTT | CAA | GTG | TCC | GAC | ATC | 1461 |
|---|---|---|---|---|---|---|---|---|---|---|---|---|---|---|---|---|
| Pro | Ser | Leu<br>435 | Ser | Ala | Leu | Thr<br>440 | Ile | Val | Arg | Val | Gln<br>445 | Val | Ser | Asp | Ile | |

| AAT | GAC | AAC | CCT | CCA | CAA | TCT | TCT | CAA | TCT | TCC | TAC | GAC | GTT | TAC | ATT | 1509 |
|---|---|---|---|---|---|---|---|---|---|---|---|---|---|---|---|---|
| Asn<br>450 | Asp | Asn | Pro | Pro | Gln<br>455 | Ser | Ser | Gln | Ser | Ser<br>460 | Tyr | Asp | Val | Tyr | Ile<br>465 | |

| GAA | GAA | AAC | AAC | CTC | CCC | GGG | GCT | CCA | ATA | CTA | AAC | CTA | AGT | GTC | TGG | 1557 |
|---|---|---|---|---|---|---|---|---|---|---|---|---|---|---|---|---|
| Glu | Glu | Asn | Asn | Leu<br>470 | Pro | Gly | Ala | Pro | Ile<br>475 | Leu | Asn | Leu | Ser | Val<br>480 | Trp | |

| GAC | CCC | GAC | GCC | CCG | CAG | AAT | GCT | CGG | CTT | TCT | TTC | TTT | CTC | TTG | GAG | 1605 |
|---|---|---|---|---|---|---|---|---|---|---|---|---|---|---|---|---|
| Asp | Pro | Asp | Ala<br>485 | Pro | Gln | Asn | Ala | Arg<br>490 | Leu | Ser | Phe | Phe | Leu<br>495 | Leu | Glu | |

| CAA | GGA | GCT | GAA | ACC | GGG | CTA | GTG | GGT | CGC | TAT | TTC | ACA | ATA | AAT | CGT | 1653 |
|---|---|---|---|---|---|---|---|---|---|---|---|---|---|---|---|---|

```
Gln Gly Ala Glu Thr Gly Leu Val Gly Arg Tyr Phe Thr Ile Asn Arg
    500             505                 510

GAC AAT GGC ATA GTG TCA TCC TTA GTG CCC CTA GAC TAT GAG GAT CGG     1701
Asp Asn Gly Ile Val Ser Ser Leu Val Pro Leu Asp Tyr Glu Asp Arg
    515             520                 525

CGG GAA TTT GAA TTA ACA GCT CAT ATC AGC GAT GGG GGC ACC CCG GTC     1749
Arg Glu Phe Glu Leu Thr Ala His Ile Ser Asp Gly Gly Thr Pro Val
530             535                 540                 545

CTA GCC ACC AAC ATC AGC GTG AAC ATA TTT GTC ACT GAT CGC AAT GAC     1797
Leu Ala Thr Asn Ile Ser Val Asn Ile Phe Val Thr Asp Arg Asn Asp
            550                 555                 560

AAT GCC CCC CAG GTC CTA TAT CCT CGG CCA GGT GGG AGC TCG GTG GAG     1845
Asn Ala Pro Gln Val Leu Tyr Pro Arg Pro Gly Gly Ser Ser Val Glu
        565                 570                 575

ATG CTG CCT CGA GGT ACC TCA GCT GGC CAC CTA GTG TCA CGG GTG GTA     1893
Met Leu Pro Arg Gly Thr Ser Ala Gly His Leu Val Ser Arg Val Val
            580                 585                 590

GGC TGG GAC GCG GAT GCA GGG CAC AAT GCC TGG CTC TCC TAC AGT CTC     1941
Gly Trp Asp Ala Asp Ala Gly His Asn Ala Trp Leu Ser Tyr Ser Leu
        595                 600                 605

TTT GGA TCC CCT AAC CAG AGC CTT TTT GCC ATA GGG CTG CAC ACT GGT     1989
Phe Gly Ser Pro Asn Gln Ser Leu Phe Ala Ile Gly Leu His Thr Gly
610             615                 620                 625

CAA ATC AGT ACT GCC CGT CCA GTC CAA GAC ACA GAT TCA CCC AGG CAG     2037
Gln Ile Ser Thr Ala Arg Pro Val Gln Asp Thr Asp Ser Pro Arg Gln
            630                 635                 640

ACT CTC ACT GTC TTG ATC AAA GAC AAT GGG GAG CCT TCG CTC TCC ACC     2085
Thr Leu Thr Val Leu Ile Lys Asp Asn Gly Glu Pro Ser Leu Ser Thr
        645                 650                 655

ACT GCT ACC CTC ACT GTG TCA GTA ACC GAG GAC TCT CCT GAA GCC CGA     2133
Thr Ala Thr Leu Thr Val Ser Val Thr Glu Asp Ser Pro Glu Ala Arg
            660                 665                 670

GCC GAG TTC CCC TCT GGC TCT GCC CCC CGG GAG CAG AAA AAA AAT CTC     2181
Ala Glu Phe Pro Ser Gly Ser Ala Pro Arg Glu Gln Lys Lys Asn Leu
675             680                 685

ACC TTT TAT CTA CTT CTT TCT CTA ATC CTG GTT TCT GTG GGC TTC GTG     2229
Thr Phe Tyr Leu Leu Leu Ser Leu Ile Leu Val Ser Val Gly Phe Val
690             695                 700                 705

GTC ACA GTG TTC GGA GTA ATC ATA TTC AAA GTT TAC AAG TGG AAG CAG     2277
Val Thr Val Phe Gly Val Ile Ile Phe Lys Val Tyr Lys Trp Lys Gln
            710                 715                 720

TCT AGA GAC CTA TAC CGA GCC CCG GTG AGC TCA CTG TAC CGA ACA CCA     2325
Ser Arg Asp Leu Tyr Arg Ala Pro Val Ser Ser Leu Tyr Arg Thr Pro
        725                 730                 735

GGG CCC TCC TTG CAC GCG GAC GCC GTG CGG GGA GGC CTG ATG TCG CCG     2373
Gly Pro Ser Leu His Ala Asp Ala Val Arg Gly Gly Leu Met Ser Pro
            740                 745                 750

CAC CTT TAC CAT CAG GTG TAT CTC ACC ACG GAC TCC CGC CGC AGC GAC     2421
His Leu Tyr His Gln Val Tyr Leu Thr Thr Asp Ser Arg Arg Ser Asp
        755                 760                 765

CCG CTG CTG AAG AAA CCT GGT GCA GCC AGT CCA CTG GCC AGC CGC CAG     2469
Pro Leu Leu Lys Lys Pro Gly Ala Ala Ser Pro Leu Ala Ser Arg Gln
770             775                 780                 785

AAC ACG CTG CGG AGC TGT GAT CCG GTG TTC TAT AGG CAG GTG TTG GGT     2517
Asn Thr Leu Arg Ser Cys Asp Pro Val Phe Tyr Arg Gln Val Leu Gly
            790                 795                 800

GCA GAG AGC GCC CCT CCC GGA CAG GTA AGG TTT AGC AAG TCA TGC TTG     2565
Ala Glu Ser Ala Pro Pro Gly Gln Val Arg Phe Ser Lys Ser Cys Leu
        805                 810                 815

ACC CTG TTA GTG CCT TTT TAT TCC TAC ATC ATA TTG AGA AGG CTG GAG     2613
```

```
Thr  Leu  Leu  Val  Pro  Phe  Tyr  Ser  Tyr  Ile  Ile  Leu  Arg  Arg  Leu  Glu
     820                     825                    830

CTG  TTT  TTT  TAGTGATGAA  GATGTTTTCC  TGGTGATGCA  TTCACACTTT                    2662
Leu  Phe  Phe
     835

CAACTGGCTC  TTCCTAGATC  AAAGTTAGTG  CCTTTGTGAG  ATGGTGGCCT  GCCAGAGTGT           2722

GGTTTGTGGT  CCCATTTCAG  GGGGAAGATA  CTTGACTCAT  CTGTGGACCT  AATTCACATC           2782

CTCAGCG                                                                         2789
```

(2) INFORMATION FOR SEQ ID NO:105:

(i) SEQUENCE CHARACTERISTICS:
        (A) LENGTH: 836 amino acids
        (B) TYPE: amino acid
        (D) TOPOLOGY: linear (ii) MOLECULE TYPE: protein (xi) SEQUENCE DESCRIPTION: SEQ ID NO:105:

```
Met  Val  Pro  Glu  Ala  Trp  Arg  Ser  Gly  Leu  Val  Ser  Thr  Gly  Arg  Val
 1                    5                    10                   15

Val  Gly  Val  Leu  Leu  Leu  Leu  Gly  Ala  Leu  Asn  Lys  Ala  Ser  Thr  Val
               20                   25                   30

Ile  His  Tyr  Glu  Ile  Pro  Glu  Glu  Arg  Glu  Lys  Gly  Phe  Ala  Val  Gly
               35                   40                   45

Asn  Val  Val  Ala  Asn  Leu  Gly  Leu  Asp  Leu  Gly  Ser  Leu  Ser  Ala  Arg
     50                   55                   60

Arg  Phe  Pro  Val  Val  Ser  Gly  Ala  Ser  Arg  Arg  Phe  Phe  Glu  Val  Asn
65                   70                   75                        80

Arg  Glu  Thr  Gly  Glu  Met  Phe  Val  Asn  Asp  Arg  Leu  Asp  Arg  Glu  Glu
                    85                   90                   95

Leu  Cys  Gly  Thr  Leu  Pro  Ser  Cys  Thr  Val  Thr  Leu  Glu  Leu  Val  Val
               100                  105                  110

Glu  Asn  Pro  Leu  Glu  Leu  Phe  Ser  Val  Glu  Val  Val  Ile  Gln  Asp  Ile
               115                  120                  125

Asn  Asp  Asn  Asn  Pro  Ala  Phe  Pro  Thr  Gln  Glu  Met  Lys  Leu  Glu  Ile
     130                  135                  140

Ser  Glu  Ala  Val  Ala  Pro  Gly  Thr  Arg  Phe  Pro  Leu  Glu  Ser  Ala  His
145                  150                  155                       160

Asp  Pro  Asp  Leu  Gly  Ser  Asn  Ser  Leu  Gln  Thr  Tyr  Glu  Leu  Ser  Arg
               165                  170                  175

Asn  Glu  Tyr  Phe  Ala  Leu  Arg  Val  Gln  Thr  Arg  Glu  Asp  Ser  Thr  Lys
               180                  185                  190

Tyr  Ala  Glu  Leu  Val  Leu  Glu  Arg  Ala  Leu  Asp  Arg  Glu  Arg  Glu  Pro
          195                  200                  205

Ser  Leu  Gln  Leu  Val  Leu  Thr  Ala  Leu  Asp  Gly  Gly  Thr  Pro  Ala  Leu
     210                  215                  220

Ser  Ala  Ser  Leu  Pro  Ile  His  Ile  Lys  Val  Leu  Asp  Ala  Asn  Asp  Asn
225                  230                  235                       240

Ala  Pro  Val  Phe  Asn  Gln  Ser  Leu  Tyr  Arg  Ala  Arg  Val  Pro  Gly  Gly
               245                  250                  255

Cys  Thr  Ser  Gly  Thr  Arg  Val  Val  Gln  Val  Leu  Ala  Thr  Asp  Leu  Asp
               260                  265                  270

Glu  Gly  Pro  Asn  Gly  Glu  Ile  Ile  Tyr  Ser  Phe  Gly  Ser  His  Asn  Arg
               275                  280                  285

Ala  Gly  Val  Arg  Gln  Leu  Phe  Ala  Leu  Asp  Leu  Val  Thr  Gly  Met  Leu
```

```
              290                    295                   300
Thr  Ile  Lys  Gly  Arg  Leu  Asp  Phe  Glu  Asp  Thr  Lys  Leu  His  Glu  Ile
305                       310                  315                       320

Tyr  Ile  Gln  Ala  Lys  Asp  Lys  Gly  Ala  Asn  Pro  Glu  Gly  Ala  His  Cys
               325                  330                       335

Lys  Val  Leu  Val  Glu  Val  Val  Asp  Val  Asn  Asp  Asn  Ala  Pro  Glu  Ile
                340                      345                  350

Thr  Val  Thr  Ser  Val  Tyr  Ser  Pro  Val  Pro  Glu  Asp  Ala  Ser  Gly  Thr
          355                      360                  365

Val  Ile  Ala  Leu  Leu  Ser  Val  Thr  Asp  Leu  Asp  Ala  Gly  Glu  Asn  Gly
     370                 375                      380

Leu  Val  Thr  Cys  Glu  Val  Pro  Pro  Gly  Leu  Pro  Phe  Ser  Leu  Thr  Ser
385                      390                  395                       400

Ser  Leu  Lys  Asn  Tyr  Phe  Thr  Leu  Lys  Thr  Ser  Ala  Asp  Leu  Asp  Arg
                    405                 410                       415

Glu  Thr  Val  Pro  Glu  Tyr  Asn  Leu  Ser  Ile  Thr  Ala  Arg  Asp  Ala  Gly
                420                      425                 430

Thr  Pro  Ser  Leu  Ser  Ala  Leu  Thr  Ile  Val  Arg  Val  Gln  Val  Ser  Asp
               435                 440                  445

Ile  Asn  Asp  Asn  Pro  Pro  Gln  Ser  Ser  Gln  Ser  Ser  Tyr  Asp  Val  Tyr
450                       455                      460

Ile  Glu  Glu  Asn  Asn  Leu  Pro  Gly  Ala  Pro  Ile  Leu  Asn  Leu  Ser  Val
465                      470                  475                       480

Trp  Asp  Pro  Asp  Ala  Pro  Gln  Asn  Ala  Arg  Leu  Ser  Phe  Phe  Leu  Leu
               485                      490                       495

Glu  Gln  Gly  Ala  Glu  Thr  Gly  Leu  Val  Gly  Arg  Tyr  Phe  Thr  Ile  Asn
               500                 505                      510

Arg  Asp  Asn  Gly  Ile  Val  Ser  Ser  Leu  Val  Pro  Leu  Asp  Tyr  Glu  Asp
          515                 520                  525

Arg  Arg  Glu  Phe  Glu  Leu  Thr  Ala  His  Ile  Ser  Asp  Gly  Gly  Thr  Pro
     530                 535                      540

Val  Leu  Ala  Thr  Asn  Ile  Ser  Val  Asn  Ile  Phe  Val  Thr  Asp  Arg  Asn
545                      550                  555                       560

Asp  Asn  Ala  Pro  Gln  Val  Leu  Tyr  Pro  Arg  Pro  Gly  Gly  Ser  Ser  Val
               565                      570                       575

Glu  Met  Leu  Pro  Arg  Gly  Thr  Ser  Ala  Gly  His  Leu  Val  Ser  Arg  Val
               580                 585                      590

Val  Gly  Trp  Asp  Ala  Asp  Ala  Gly  His  Asn  Ala  Trp  Leu  Ser  Tyr  Ser
          595                 600                       605

Leu  Phe  Gly  Ser  Pro  Asn  Gln  Ser  Leu  Phe  Ala  Ile  Gly  Leu  His  Thr
     610                      615                 620

Gly  Gln  Ile  Ser  Thr  Ala  Arg  Pro  Val  Gln  Asp  Thr  Asp  Ser  Pro  Arg
625                      630                  635                       640

Gln  Thr  Leu  Thr  Val  Leu  Ile  Lys  Asp  Asn  Gly  Glu  Pro  Ser  Leu  Ser
                645                      650                       655

Thr  Thr  Ala  Thr  Leu  Thr  Val  Ser  Val  Thr  Glu  Asp  Ser  Pro  Glu  Ala
               660                      665                  670

Arg  Ala  Glu  Phe  Pro  Ser  Gly  Ser  Ala  Pro  Arg  Glu  Gln  Lys  Lys  Asn
          675                      680                  685

Leu  Thr  Phe  Tyr  Leu  Leu  Leu  Ser  Leu  Ile  Leu  Val  Ser  Val  Gly  Phe
          690                 695                 700

Val  Val  Thr  Val  Phe  Gly  Val  Ile  Ile  Phe  Lys  Val  Tyr  Lys  Trp  Lys
705                      710                  715                       720
```

| | | | | | | | | | | | | | | |
|---|---|---|---|---|---|---|---|---|---|---|---|---|---|---|
|Gln|Ser|Arg|Asp|Leu|Tyr|Arg|Ala|Pro|Val|Ser|Ser|Leu|Tyr|Arg|Thr|
| | | | |725| | | |730| | | | |735| |

Pro Gly Pro Ser Leu His Ala Asp Ala Val Arg Gly Gly Leu Met Ser
           740                745                     750

Pro His Leu Tyr His Gln Val Tyr Leu Thr Thr Asp Ser Arg Arg Ser
         755                 760                765

Asp Pro Leu Leu Lys Lys Pro Gly Ala Ala Ser Pro Leu Ala Ser Arg
     770             775                 780

Gln Asn Thr Leu Arg Ser Cys Asp Pro Val Phe Tyr Arg Gln Val Leu
785             790                 795                     800

Gly Ala Glu Ser Ala Pro Pro Gly Gln Val Arg Phe Ser Lys Ser Cys
             805                 810                 815

Leu Thr Leu Leu Val Pro Phe Tyr Ser Tyr Ile Ile Leu Arg Arg Leu
             820             825                 830

Glu Leu Phe Phe
         835

(2) INFORMATION FOR SEQ ID NO:106:

(i) SEQUENCE CHARACTERISTICS:
      (A) LENGTH: 2751 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 115..2160

(xi) SEQUENCE DESCRIPTION: SEQ ID NO:106:

```
CGAAAGCCAT GTCGGACTCG TCGCCCAGCG CCCAAGCGCT AACCCGCTGA AAGTTTCTCA     60

GCGAAATCTC AGGGACGATC TGGACCCCGC TGAGAGGAAC TGCTTTTGAG TGAG ATG      117
                                                              Met
                                                               1

GTC CCA GAG GCC TGG AGG AGC GGA CTG GTA AGC ACC GGG AGG GTA GTG      165
Val Pro Glu Ala Trp Arg Ser Gly Leu Val Ser Thr Gly Arg Val Val
              5                  10                  15

GGA GTT TTG CTT CTG CTT GGT GCC TTG AAC AAG GCT TCC ACG GTC ATT      213
Gly Val Leu Leu Leu Leu Gly Ala Leu Asn Lys Ala Ser Thr Val Ile
         20                  25                  30

CAC TAT GAG ATC CCG GAG GAA AGA GAG AAG GGT TTC GCT GTG GGC AAC      261
His Tyr Glu Ile Pro Glu Glu Arg Glu Lys Gly Phe Ala Val Gly Asn
     35                  40                  45

GTG GTC GCG AAC CTT GGT TTG GAT CTC GGT AGC CTC TCA GCC CGC AGG      309
Val Val Ala Asn Leu Gly Leu Asp Leu Gly Ser Leu Ser Ala Arg Arg
 50                  55                  60                  65

TTC CCG GTG GTG TCT GGA GCT AGC CGA AGA TTC TTT GAG GTG AAC CGG      357
Phe Pro Val Val Ser Gly Ala Ser Arg Arg Phe Phe Glu Val Asn Arg
                 70                  75                  80

GAG ACC GGA GAG ATG TTT GTG AAC GAC CGT CTG GAT CGA GAG GAG CTG      405
Glu Thr Gly Glu Met Phe Val Asn Asp Arg Leu Asp Arg Glu Glu Leu
             85                  90                  95

TGT GGG ACA CTG CCC TCT TGC ACT GTA ACT CTG GAG TTG GTA GTG GAG      453
Cys Gly Thr Leu Pro Ser Cys Thr Val Thr Leu Glu Leu Val Val Glu
            100                 105                 110

AAC CCG CTG GAG CTG TTC AGC GTG GAA GTG GTG ATC CAG GAC ATC AAC      501
Asn Pro Leu Glu Leu Phe Ser Val Glu Val Val Ile Gln Asp Ile Asn
        115                 120                 125

GAC AAC AAT CCT GCT TTC CCT ACC CAG GAA ATG AAA TTG GAG ATT AGC      549
```

| | | | | | | | | | | | | | | | | |
|---|---|---|---|---|---|---|---|---|---|---|---|---|---|---|---|---|
| Asp | Asn | Asn | Pro | Ala | Phe | Pro | Thr | Gln | Glu | Met | Lys | Leu | Glu | Ile | Ser | |
| 130 | | | | | 135 | | | | 140 | | | | | | 145 | |

| | | | | | | | | | | | | | | | | |
|---|---|---|---|---|---|---|---|---|---|---|---|---|---|---|---|---|
| GAG | GCC | GTG | GCT | CCG | GGG | ACG | CGC | TTT | CCG | CTC | GAG | AGC | GCG | CAC | GAT | 597 |
| Glu | Ala | Val | Ala | Pro | Gly | Thr | Arg | Phe | Pro | Leu | Glu | Ser | Ala | His | Asp | |
| | | | | 150 | | | | 155 | | | | | | 160 | | |

| | | | | | | | | | | | | | | | | |
|---|---|---|---|---|---|---|---|---|---|---|---|---|---|---|---|---|
| CCC | GAT | CTG | GGA | AGC | AAC | TCT | TTA | CAA | ACC | TAT | GAG | CTG | AGC | CGA | AAT | 645 |
| Pro | Asp | Leu | Gly | Ser | Asn | Ser | Leu | Gln | Thr | Tyr | Glu | Leu | Ser | Arg | Asn | |
| | | | 165 | | | | | 170 | | | | | 175 | | | |

| | | | | | | | | | | | | | | | | |
|---|---|---|---|---|---|---|---|---|---|---|---|---|---|---|---|---|
| GAA | TAC | TTT | GCG | CTT | CGC | GTG | CAG | ACG | CGG | GAG | GAC | AGC | ACC | AAG | TAC | 693 |
| Glu | Tyr | Phe | Ala | Leu | Arg | Val | Gln | Thr | Arg | Glu | Asp | Ser | Thr | Lys | Tyr | |
| | | 180 | | | | | 185 | | | | | 190 | | | | |

| | | | | | | | | | | | | | | | | |
|---|---|---|---|---|---|---|---|---|---|---|---|---|---|---|---|---|
| GCG | GAG | CTG | GTG | TTG | GAG | CGC | GCC | CTG | GAC | CGA | GAA | CGG | GAG | CCT | AGT | 741 |
| Ala | Glu | Leu | Val | Leu | Glu | Arg | Ala | Leu | Asp | Arg | Glu | Arg | Glu | Pro | Ser | |
| 195 | | | | | 200 | | | | | 205 | | | | | | |

| | | | | | | | | | | | | | | | | |
|---|---|---|---|---|---|---|---|---|---|---|---|---|---|---|---|---|
| CTC | CAG | TTA | GTG | CTG | ACG | GCG | TTG | GAC | GGA | GGG | ACC | CCA | GCT | CTC | TCC | 789 |
| Leu | Gln | Leu | Val | Leu | Thr | Ala | Leu | Asp | Gly | Gly | Thr | Pro | Ala | Leu | Ser | |
| 210 | | | | | 215 | | | | | 220 | | | | | 225 | |

| | | | | | | | | | | | | | | | | |
|---|---|---|---|---|---|---|---|---|---|---|---|---|---|---|---|---|
| GCC | AGC | CTG | CCT | ATT | CAC | ATC | AAG | GTG | CTG | GAC | GCG | AAT | GAC | AAT | GCG | 837 |
| Ala | Ser | Leu | Pro | Ile | His | Ile | Lys | Val | Leu | Asp | Ala | Asn | Asp | Asn | Ala | |
| | | | | 230 | | | | 235 | | | | | 240 | | | |

| | | | | | | | | | | | | | | | | |
|---|---|---|---|---|---|---|---|---|---|---|---|---|---|---|---|---|
| CCT | GTC | TTC | AAC | CAG | TCC | TTG | TAC | CGG | GCG | CGC | GTT | CCT | GGA | GGA | TGC | 885 |
| Pro | Val | Phe | Asn | Gln | Ser | Leu | Tyr | Arg | Ala | Arg | Val | Pro | Gly | Gly | Cys | |
| | | | 245 | | | | | 250 | | | | | 255 | | | |

| | | | | | | | | | | | | | | | | |
|---|---|---|---|---|---|---|---|---|---|---|---|---|---|---|---|---|
| ACC | TCC | GGC | ACG | CGC | GTG | GTA | CAA | GTC | CTT | GCA | ACG | GAT | CTG | GAT | GAA | 933 |
| Thr | Ser | Gly | Thr | Arg | Val | Val | Gln | Val | Leu | Ala | Thr | Asp | Leu | Asp | Glu | |
| | | 260 | | | | | 265 | | | | | 270 | | | | |

| | | | | | | | | | | | | | | | | |
|---|---|---|---|---|---|---|---|---|---|---|---|---|---|---|---|---|
| GGC | CCC | AAC | GGT | GAA | ATT | ATT | TAC | TCC | TTC | GGC | AGC | CAC | AAC | CGC | GCC | 981 |
| Gly | Pro | Asn | Gly | Glu | Ile | Ile | Tyr | Ser | Phe | Gly | Ser | His | Asn | Arg | Ala | |
| | 275 | | | | | 280 | | | | | 285 | | | | | |

| | | | | | | | | | | | | | | | | |
|---|---|---|---|---|---|---|---|---|---|---|---|---|---|---|---|---|
| GGC | GTG | CGG | CAA | CTA | TTC | GCC | TTA | GAC | CTT | GTA | ACC | GGG | ATG | CTG | ACA | 1029 |
| Gly | Val | Arg | Gln | Leu | Phe | Ala | Leu | Asp | Leu | Val | Thr | Gly | Met | Leu | Thr | |
| 290 | | | | | 295 | | | | | 300 | | | | | 305 | |

| | | | | | | | | | | | | | | | | |
|---|---|---|---|---|---|---|---|---|---|---|---|---|---|---|---|---|
| ATC | AAG | GGT | CGG | CTG | GAC | TTC | GAG | GAC | ACC | AAA | CTC | CAT | GAG | ATT | TAC | 1077 |
| Ile | Lys | Gly | Arg | Leu | Asp | Phe | Glu | Asp | Thr | Lys | Leu | His | Glu | Ile | Tyr | |
| | | | | 310 | | | | | 315 | | | | | | 320 | |

| | | | | | | | | | | | | | | | | |
|---|---|---|---|---|---|---|---|---|---|---|---|---|---|---|---|---|
| ATC | CAG | GCC | AAA | GAC | AAG | GGC | GCC | AAT | CCC | GAA | GGA | GCA | CAT | TGC | AAA | 1125 |
| Ile | Gln | Ala | Lys | Asp | Lys | Gly | Ala | Asn | Pro | Glu | Gly | Ala | His | Cys | Lys | |
| | | | 325 | | | | | 330 | | | | | 335 | | | |

| | | | | | | | | | | | | | | | | |
|---|---|---|---|---|---|---|---|---|---|---|---|---|---|---|---|---|
| GTG | TTG | GTG | GAG | GTT | GTG | GAT | GTG | AAT | GAC | AAC | GCC | CCG | GAG | ATC | ACA | 1173 |
| Val | Leu | Val | Glu | Val | Val | Asp | Val | Asn | Asp | Asn | Ala | Pro | Glu | Ile | Thr | |
| | | | 340 | | | | | 345 | | | | | 350 | | | |

| | | | | | | | | | | | | | | | | |
|---|---|---|---|---|---|---|---|---|---|---|---|---|---|---|---|---|
| GTC | ACC | TCC | GTG | TAC | AGC | CCA | GTA | CCC | GAG | GAT | GCC | TCT | GGG | ACT | GTC | 1221 |
| Val | Thr | Ser | Val | Tyr | Ser | Pro | Val | Pro | Glu | Asp | Ala | Ser | Gly | Thr | Val | |
| | 355 | | | | | 360 | | | | | 365 | | | | | |

| | | | | | | | | | | | | | | | | |
|---|---|---|---|---|---|---|---|---|---|---|---|---|---|---|---|---|
| ATC | GCT | TTG | CTC | AGT | GTG | ACT | GAC | CTG | GAT | GCT | GGC | GAG | AAC | GGG | CTG | 1269 |
| Ile | Ala | Leu | Leu | Ser | Val | Thr | Asp | Leu | Asp | Ala | Gly | Glu | Asn | Gly | Leu | |
| 370 | | | | | 375 | | | | | 380 | | | | | 385 | |

| | | | | | | | | | | | | | | | | |
|---|---|---|---|---|---|---|---|---|---|---|---|---|---|---|---|---|
| GTG | ACC | TGC | GAA | GTT | CCA | CCG | GGT | CTC | CCT | TTC | AGC | CTT | ACT | TCT | TCC | 1317 |
| Val | Thr | Cys | Glu | Val | Pro | Pro | Gly | Leu | Pro | Phe | Ser | Leu | Thr | Ser | Ser | |
| | | | | 390 | | | | | 395 | | | | | 400 | | |

| | | | | | | | | | | | | | | | | |
|---|---|---|---|---|---|---|---|---|---|---|---|---|---|---|---|---|
| CTC | AAG | AAT | TAC | TTC | ACT | TTG | AAA | ACC | AGT | GCA | GAC | CTG | GAT | CGG | GAG | 1365 |
| Leu | Lys | Asn | Tyr | Phe | Thr | Leu | Lys | Thr | Ser | Ala | Asp | Leu | Asp | Arg | Glu | |
| | | | | 405 | | | | | 410 | | | | | 415 | | |

| | | | | | | | | | | | | | | | | |
|---|---|---|---|---|---|---|---|---|---|---|---|---|---|---|---|---|
| ACT | GTG | CCA | GAA | TAC | AAC | CTC | AGC | ATC | ACC | GCC | CGA | GAC | GCC | GGA | ACC | 1413 |
| Thr | Val | Pro | Glu | Tyr | Asn | Leu | Ser | Ile | Thr | Ala | Arg | Asp | Ala | Gly | Thr | |
| | | | 420 | | | | | 425 | | | | | 430 | | | |

| | | | | | | | | | | | | | | | | |
|---|---|---|---|---|---|---|---|---|---|---|---|---|---|---|---|---|
| CCT | TCC | CTC | TCA | GCC | CTT | ACA | ATA | GTG | CGT | GTT | CAA | GTG | TCC | GAC | ATC | 1461 |
| Pro | Ser | Leu | Ser | Ala | Leu | Thr | Ile | Val | Arg | Val | Gln | Val | Ser | Asp | Ile | |
| | | 435 | | | | | 440 | | | | | 445 | | | | |

| | | | | | | | | | | | | | | | | |
|---|---|---|---|---|---|---|---|---|---|---|---|---|---|---|---|---|
| AAT | GAC | AAC | CCT | CCA | CAA | TCT | TCT | CAA | TCT | TCC | TAC | GAC | GTT | TAC | ATT | 1509 |

-continued

```
Asn Asp Asn Pro Pro Gln Ser Ser Gln Ser Ser Tyr Asp Val Tyr Ile
450             455                 460             465

GAA GAA AAC AAC CTC CCC GGG GCT CCA ATA CTA AAC CTA AGT GTC TGG        1557
Glu Glu Asn Asn Leu Pro Gly Ala Pro Ile Leu Asn Leu Ser Val Trp
                470                 475             480

GAC CCC GAC GCC CCG CAG AAT GCT CGG CTT TCT TTC TTT CTC TTG GAG        1605
Asp Pro Asp Ala Pro Gln Asn Ala Arg Leu Ser Phe Phe Leu Leu Glu
            485                 490             495

CAA GGA GCT GAA ACC GGG CTA GTG GGT CGC TAT TTC ACA ATA AAT CGT        1653
Gln Gly Ala Glu Thr Gly Leu Val Gly Arg Tyr Phe Thr Ile Asn Arg
        500                 505             510

GAC AAT GGC ATA GTG TCA TCC TTA GTG CCC CTA GAC TAT GAG GAT CGG        1701
Asp Asn Gly Ile Val Ser Ser Leu Val Pro Leu Asp Tyr Glu Asp Arg
    515                 520             525

CGG GAA TTT GAA TTA ACA GCT CAT ATC AGC GAT GGG GGC ACC CCG GTC        1749
Arg Glu Phe Glu Leu Thr Ala His Ile Ser Asp Gly Gly Thr Pro Val
530             535             540             545

CTA GCC ACC AAC ATC AGC GTG AAC ATA TTT GTC ACT GAT CGC AAT GAC        1797
Leu Ala Thr Asn Ile Ser Val Asn Ile Phe Val Thr Asp Arg Asn Asp
                550                 555             560

AAT GCC CCC CAG GTC CTA TAT CCT CGG CCA GGT GGG AGC TCG GTG GAG        1845
Asn Ala Pro Gln Val Leu Tyr Pro Arg Pro Gly Gly Ser Ser Val Glu
            565                 570             575

ATG CTG CCT CGA GGT ACC TCA GCT GGC CAC CTA GTG TCA CGG GTG GTA        1893
Met Leu Pro Arg Gly Thr Ser Ala Gly His Leu Val Ser Arg Val Val
        580                 585             590

GGC TGG GAC GCG GAT GCA GGG CAC AAT GCC TGG CTC TCC TAC AGT CTC        1941
Gly Trp Asp Ala Asp Ala Gly His Asn Ala Trp Leu Ser Tyr Ser Leu
    595                 600             605

TTT GGA TCC CCT AAC CAG AGC CTT TTT GCC ATA GGG CTG CAC ACT GGT        1989
Phe Gly Ser Pro Asn Gln Ser Leu Phe Ala Ile Gly Leu His Thr Gly
610             615             620             625

CAA ATC AGT ACT GCC CGT CCA GTC CAA GAC ACA GAT TCA CCC AGG CAG        2037
Gln Ile Ser Thr Ala Arg Pro Val Gln Asp Thr Asp Ser Pro Arg Gln
                630                 635             640

ACT CTC ACT GTC TTG ATC AAA GAC AAT GGG GAG CCT TCG CTC TCC ACC        2085
Thr Leu Thr Val Leu Ile Lys Asp Asn Gly Glu Pro Ser Leu Ser Thr
            645                 650             655

ACT GCT ACC CTC ACT GTG TCA GTA ACC GAG GAC TCT CCT GAA GCC CGA        2133
Thr Ala Thr Leu Thr Val Ser Val Thr Glu Asp Ser Pro Glu Ala Arg
        660                 665             670

GCC GAG TTC CCC TCT GGC TCT GCC AGT TAAACCTTCT TTAATTATGG              2180
Ala Glu Phe Pro Ser Gly Ser Ala Ser
675                 680

ATTAGCCATT AACATTTTTG AAACGTGGAC CATTTAACCT CGGCCTACCC CCTCCAACTG      2240
TCCTGGTGAT GAGTTCATTA GCTAAGTTAA ATTAATTGAA CTTTGATCTA AACCAAAACA      2300
AATCAGGAAA ATAAAGCTGT AAAGGAACTT ATCAAGCATT CCAAAACCAA CTAGAAATTA      2360
CTTGAAGTTT CGAGTGAGCA TTGCCTGTGC CAGTATTCTT CATTATAGGA TTATAAACTC      2420
GTTTTTTTCC CAAAGCGCAT GTCTACGCCA GGCAGAGGAG TAATTATTCA GCCAATTTCA      2480
TGGATGTAAC GATGGATATA AATAATTGAT AGCACCTAGA GGCTTCCAGT TTGGGTGGAA      2540
GGCTAAAAGT AGAGGGGAAC TCACTCACTT GAGAAATGAT ATTTAAGTGA ATAAATAGTT      2600
CTCTTCTATG AAACTATTAC TATTTAGTTC TCTGGAAAAC TTAAGTGTAT TAATGATTAG      2660
AACATCAAAT CCTAAGTAAA GAATGACAT TTTAAATATA AAAAGCCAAA CTTTAAATAA       2720
ATCATAGAGA CCTCAGACAT AATATAGGAA A                                     2751
```

( 2 ) INFORMATION FOR SEQ ID NO:107:

( i ) SEQUENCE CHARACTERISTICS:
    ( A ) LENGTH: 682 amino acids
    ( B ) TYPE: amino acid
    ( D ) TOPOLOGY: linear ( i i ) MOLECULE TYPE: protein ( x i ) SEQUENCE DESCRIPTION: SEQ ID NO:107:

```
Met Val Pro Glu Ala Trp Arg Ser Gly Leu Val Ser Thr Gly Arg Val
 1               5                   10                  15

Val Gly Val Leu Leu Leu Leu Gly Ala Leu Asn Lys Ala Ser Thr Val
            20                  25                  30

Ile His Tyr Glu Ile Pro Glu Glu Arg Glu Lys Gly Phe Ala Val Gly
        35                  40                  45

Asn Val Val Ala Asn Leu Gly Leu Asp Leu Gly Ser Leu Ser Ala Arg
    50                  55                  60

Arg Phe Pro Val Val Ser Gly Ala Ser Arg Arg Phe Phe Glu Val Asn
65                  70                  75                  80

Arg Glu Thr Gly Glu Met Phe Val Asn Asp Arg Leu Asp Arg Glu Glu
                85                  90                  95

Leu Cys Gly Thr Leu Pro Ser Cys Thr Val Thr Leu Glu Leu Val Val
                100                 105                 110

Glu Asn Pro Leu Glu Leu Phe Ser Val Glu Val Val Ile Gln Asp Ile
            115                 120                 125

Asn Asp Asn Asn Pro Ala Phe Pro Thr Gln Glu Met Lys Leu Glu Ile
    130                 135                 140

Ser Glu Ala Val Ala Pro Gly Thr Arg Phe Pro Leu Glu Ser Ala His
145                 150                 155                 160

Asp Pro Asp Leu Gly Ser Asn Ser Leu Gln Thr Tyr Glu Leu Ser Arg
                165                 170                 175

Asn Glu Tyr Phe Ala Leu Arg Val Gln Thr Arg Glu Asp Ser Thr Lys
                180                 185                 190

Tyr Ala Glu Leu Val Leu Glu Arg Ala Leu Asp Arg Glu Arg Glu Pro
            195                 200                 205

Ser Leu Gln Leu Val Leu Thr Ala Leu Asp Gly Gly Thr Pro Ala Leu
    210                 215                 220

Ser Ala Ser Leu Pro Ile His Ile Lys Val Leu Asp Ala Asn Asp Asn
225                 230                 235                 240

Ala Pro Val Phe Asn Gln Ser Leu Tyr Arg Ala Arg Val Pro Gly Gly
                245                 250                 255

Cys Thr Ser Gly Thr Arg Val Val Gln Val Leu Ala Thr Asp Leu Asp
            260                 265                 270

Glu Gly Pro Asn Gly Glu Ile Ile Tyr Ser Phe Gly Ser His Asn Arg
    275                 280                 285

Ala Gly Val Arg Gln Leu Phe Ala Leu Asp Leu Val Thr Gly Met Leu
290                 295                 300

Thr Ile Lys Gly Arg Leu Asp Phe Glu Asp Thr Lys Leu His Glu Ile
305                 310                 315                 320

Tyr Ile Gln Ala Lys Asp Lys Gly Ala Asn Pro Glu Gly Ala His Cys
                325                 330                 335

Lys Val Leu Val Glu Val Val Asp Val Asn Asp Asn Ala Pro Glu Ile
            340                 345                 350

Thr Val Thr Ser Val Tyr Ser Pro Val Pro Glu Asp Ala Ser Gly Thr
        355                 360                 365
```

```
Val  Ile  Ala  Leu  Leu  Ser  Val  Thr  Asp  Leu  Asp  Ala  Gly  Glu  Asn  Gly
     370                 375                 380

Leu  Val  Thr  Cys  Glu  Val  Pro  Pro  Gly  Leu  Pro  Phe  Ser  Leu  Thr  Ser
385                      390                 395                           400

Ser  Leu  Lys  Asn  Tyr  Phe  Thr  Leu  Lys  Thr  Ser  Ala  Asp  Leu  Asp  Arg
                    405                 410                      415

Glu  Thr  Val  Pro  Glu  Tyr  Asn  Leu  Ser  Ile  Thr  Ala  Arg  Asp  Ala  Gly
                    420                 425                      430

Thr  Pro  Ser  Leu  Ser  Ala  Leu  Thr  Ile  Val  Arg  Val  Gln  Val  Ser  Asp
               435                 440                 445

Ile  Asn  Asp  Asn  Pro  Pro  Gln  Ser  Ser  Gln  Ser  Ser  Tyr  Asp  Val  Tyr
     450                      455                 460

Ile  Glu  Glu  Asn  Asn  Leu  Pro  Gly  Ala  Pro  Ile  Leu  Asn  Leu  Ser  Val
465                      470                 475                           480

Trp  Asp  Pro  Asp  Ala  Pro  Gln  Asn  Ala  Arg  Leu  Ser  Phe  Phe  Leu  Leu
                    485                 490                           495

Glu  Gln  Gly  Ala  Glu  Thr  Gly  Leu  Val  Gly  Arg  Tyr  Phe  Thr  Ile  Asn
               500                 505                      510

Arg  Asp  Asn  Gly  Ile  Val  Ser  Ser  Leu  Val  Pro  Leu  Asp  Tyr  Glu  Asp
          515                      520                 525

Arg  Arg  Glu  Phe  Glu  Leu  Thr  Ala  His  Ile  Ser  Asp  Gly  Gly  Thr  Pro
     530                 535                      540

Val  Leu  Ala  Thr  Asn  Ile  Ser  Val  Asn  Ile  Phe  Val  Thr  Asp  Arg  Asn
545                      550                 555                           560

Asp  Asn  Ala  Pro  Gln  Val  Leu  Tyr  Pro  Arg  Pro  Gly  Gly  Ser  Ser  Val
                    565                 570                      575

Glu  Met  Leu  Pro  Arg  Gly  Thr  Ser  Ala  Gly  His  Leu  Val  Ser  Arg  Val
               580                 585                      590

Val  Gly  Trp  Asp  Ala  Asp  Ala  Gly  His  Asn  Ala  Trp  Leu  Ser  Tyr  Ser
          595                      600                 605

Leu  Phe  Gly  Ser  Pro  Asn  Gln  Ser  Leu  Phe  Ala  Ile  Gly  Leu  His  Thr
     610                      615                 620

Gly  Gln  Ile  Ser  Thr  Ala  Arg  Pro  Val  Gln  Asp  Thr  Asp  Ser  Pro  Arg
625                      630                 635                           640

Gln  Thr  Leu  Thr  Val  Leu  Ile  Lys  Asp  Asn  Gly  Glu  Pro  Ser  Leu  Ser
               645                 650                      655

Thr  Thr  Ala  Thr  Leu  Thr  Val  Ser  Val  Thr  Glu  Asp  Ser  Pro  Glu  Ala
               660                 665                      670

Arg  Ala  Glu  Phe  Pro  Ser  Gly  Ser  Ala  Ser
          675                 680
```

( 2 ) INFORMATION FOR SEQ ID NO:108:

( i ) SEQUENCE CHARACTERISTICS:
      ( A ) LENGTH: 2831 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:108:

```
GAATTCGGCA CGAGGCTGAA CTGAGGGTGA CGGACATAAA CGACTATTCT CCAGTGTTCA      60
GTGAAAGAGA AATGATACTG AGGATACCAG AAAACAGTGC TCGGGGAAAT ACATTCCCTT     120
TAAACAATGC TCTGGACTCA GACGTAGATA TCAACAATAT CCAGACCTAT AGGCTCAGCT     180
CAAACTCTCA TTTCCTGGTT GTAACCCGCA ACCGCAGTGA TGGCAGGAAG TACCCAGAGC     240
```

```
TGGTGCTGGA GAAAGAACTG GATCGAGAGG AGGAACCTGA GCTGAGGTTA ACGCTGACAG      300
CTTTGGATGG TGGCTCTCCT CCCCGGTCTG GGACGACACA GGTCCTCATT GAAGTAGTGG      360
ACACCAACGA TAATGCACCC GAGTTTCAGC AGCCAACATA CCAAGTGCAA ACTCCCGAGA      420
ACAGTCCCAC CGGCTCTCTG GTACTCACAG TCTCAGCCAA TGACTTAGAC AGTGGAGACT      480
ATGGGAAAGT CTTGTACGCA CTTTCGCAAC CCTCAGAAGA TATTAGCAAA ACATTCGAGG      540
TAAACCCTGT AACCGGGGAA ATTCGCCTAC GAAAAGAGGT GAATTTTGAA ACTATTCCTT      600
CGTATGAAGT GGTTATCAAG GGGACGGACG GGGAGGTCT CTCAGGAAAA TGCACTCTGT       660
TACTGCAGGT GGTGGACGTG AATGACAATG CCCCAGAAGT GATGCTATCT GCGCTAACCA      720
ACCCAGTCCC AGAAAATTCC CCGATGAGG TAGTGGCTGT TTTCAGTGTT AGAGATCCTG       780
ACTCTGGGAA CAACGGAAAA GTGATTGCAT CCATCGAGGA AGACCTGCCC TTTCTTCTAA      840
AATCTTCAGG AAAGAACTTT TACACTTTAG TAACCAAGGG AGCACTTGAC AGGGAAGAAA      900
GAGAGCAATT GAACATCACC ATCACAGTCA CTGACCTGGG CATACCCAGG CTCACCACCC      960
AACACACCAT AACAGTGCAG GTGGCAGACA TCAACGACAA TGCCCCCTCC TTCACCCAAA     1020
CCTCCTACAC CATGTTTGTC CGCGAGAACA ACAGCCCGC CCTGCACATA GGCACCATCA      1080
GCGCCACAGA CTCAGACTCA GGATCCAATG CCCACATCAC CTACTCGCTG CTACCGCCCC     1140
AAGACCCACA GCTGGCCCTC GACTCGCTCA TCTCCATCAA TGTAGACAAC GGGCAGCTGT     1200
TCGCGCTCAG GGCGCTAGAC TATGAGGCTC TGCAGGGCTT CGAGTTCCAT GTGGGCGCCA     1260
CAGACCAAGG CTCGCCCGCG CTCAGCAGCC AGGCTCTGGT GCACGTGGTG GTGTTGGACG     1320
ACAATGACAA TGCGCCCTTC GTGCTCTACC CGCTGCAAAA CGCCTCTGCA CCCTTCACTG     1380
AGCTGCTGCC CAGGGCGGCA GAGCCTGGAT ACCTGGTTAC CAAGGTGGTA GCTGTGGACC     1440
GCGACTCTGG CCAGAATGCC TGGCTGTCAT TCCAGCTGCT CAAGGCCACG GAGCCCGGGC     1500
TGTTCAACGT ATGGGCGCAC AATGGCGAGG TACGCACCTC CAGGCTGCTG AGCGAGCGCG     1560
ACGCACCCAA GCACAAGCTG CTGCTGTTGG TCAAGGACAA TGGAGATCCT CCACGCTCTG     1620
CCAGTGTTAC TCTGCACGTG CTAGTGGTGG ATGCCTTCTC TCAGCCCTAC CTGCCTCTGC     1680
CAGAGGTGGC GCACGACCCT GCACAAGAAG AAGATGCGCT AACACTCTAC CTGGTCATAG     1740
CTTTGGCATC TGTGTCTTCT CTCTTCCTCT TGTCTGTGCT GCTGTTCGTG GGGTGAGGC     1800
TCTGCAGGAG GGCCAGGGCA GCCTCTCTGA GTGCCTATTC TGTGCCTGAA GGCCACTTTC     1860
CTGGCCAGCT GGTGGATGTC AGAGGTATGG GGACCCTGTC CCAGAGCTAC CAGTATGATG     1920
TATGTCTGAT GGGGGATTCT TCTGGGACCA GCGAATTTAA CTTCTTAAAG CCAGTTCTGC     1980
CTAGCTCTCT GCACCAGTGC TCTGGGAAAG AAATAGAGGA AAATTCCACA CTCCAGAATA     2040
GTTTTGGGTT TCATCATTAA TAGAAAACTA CTTTACAGAT ATTTAATTCC AAATATCATC     2100
TTGTTGATTA ACTAAAGTCT GTTCACATGT AGCTAGCTAG CAACGATTTT AATGTTCACT     2160
TTACCCATCT TTTTTCAGGG TCATGTCTAA AGCTACAAGT TTGNCTTTAC TTATACTTGT     2220
CGCACAGAAT NNNNNNNNNN TGGTGTATAA GTCACAGTCA TGGGATACTG GCACAAGATG     2280
GCAGCTTGAT TGCTCAGTTA TGGCTGCAAA GGGGNGCTTG AGTTTAGGGA ATGTGTTAGA     2340
GCTGGAATAA GTTTTCTGAG AAATGTGTAA GACAAATTTC TTTTGCACAT TCCCTGTGTT     2400
CCTGTACCCC TGTTTCCAGA ACTACGAAAT GTGTCATCAG AAGGCATGCT CACATTTTCC     2460
CCTTTGTTTG CGTGACCCGG GTGCCAGAAA TTAAATAAAA TTAGCATGGA GTTCAATGCA     2520
GCATTAAAAC AAAGTTACTT CTACAAACCT TTTATTCGAC GGTTAAAATT GTAACTTCCC     2580
CACCCATGAG GCTGGCTGTA AGAACCAGTA TGAATGGGTG TCTATCGCAA CCTTATTTTC     2640
```

```
AAAAATCAAA  CAAAAGGAGA  AATGAGAGAC  CAAACAACAC  GCTACAGGAA  AGATTTCATA    2700

AGGATGTATG  TATGGACACA  AAAACTGGGA  TACAGACATT  TTAAATCTGT  TGGTACCACA    2760

TGGTGGCGCT  GCAGGCTAAA  GAAATGCAAG  GGAAATTAAA  AAGAGGCTGA  GCTAGAAGTC    2820

AAAAAAAAAA  A                                                             2831
```

(2) INFORMATION FOR SEQ ID NO:109:

(i) SEQUENCE CHARACTERISTICS:
        (A) LENGTH: 3353 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 763..3123

(xi) SEQUENCE DESCRIPTION: SEQ ID NO:109:

```
GTATTTTCC   ACAGTTAAAA  ATTTTCATAA  AATCATAACT  CTCTGACTTT  ATGTAGAAAG     60

GATACCACAC  TGGAATTAAC  GTGTAGCTTT  TTCTTGATGT  AATCCAACCA  ATGGGAGCAC    120

AATTCTGGTA  CATAGGCTGT  CTAGAATTTG  AAAGAAATTA  AAGAATTCAT  TTTGTTTTGC    180

TGATAAATTT  TTAAGAAATC  ACGTGGCTTT  ATGTTATTAT  TATTACAAGA  TGACTGATCA    240

CTATTATGTC  TTCTTTCACT  TCTCAATTTC  CCTCAGAACA  CTACACCCAG  ACTACAGGCT    300

CTGGAGGGTG  GGGACCATGT  CTGGGTTGTT  TACTGATGTA  TTTCATAATT  TGGCACATAG    360

AGACCAATAA  TACTCCTTTA  AATGAAGAAA  TTAATAATTA  CCATTGCGTG  ATATTGTGAT    420

TACATCATTT  CCTCCCAATT  TCCAAACTCC  TAATAGAATA  GAGAATAGAT  CAATTGTAGC    480

AATTCGTTTC  GAAGCAAAGA  CAACGCATGG  TGGCGCTGCA  GGCTAAGGCT  TCAAAAAAAG    540

GAAAAGGAAA  AAGCCCATGA  AATGCTACTA  GCTACTTCAG  ACCTCTTTCA  GCCTAAGAGG    600

AAAGCCTGTT  AGCAGAGCAC  GGACCAGTGT  CTCCGGAGAA  TGCTATTCTC  CTACATTTCC    660

GAACAGGTTA  TCAACGCACA  GATCGATCAC  TGCCTCTGTC  CCATCGCTCC  CTGAAGTAGC    720

TCTGACTCCG  GTTCCTTGAA  AGGGGCGTGT  ACAGAAGTAA  AG  ATG GAG  CCT GCA       774
                                                 Met Glu  Pro Ala
                                                  1
```

```
GGG GAG CGC TTT CCC GAA CAA AGG CAA GTC CTG ATT CTC CTT CTT TTA           822
Gly Glu Arg Phe Pro Glu Gln Arg Gln Val Leu Ile Leu Leu Leu Leu
 5              10              15              20

CTG GAA GTG ACT CTG GCA GGC TGG GAA CCC CGT CGC TAT TCT GTG ATG           870
Leu Glu Val Thr Leu Ala Gly Trp Glu Pro Arg Arg Tyr Ser Val Met
                25              30              35

GAG GAA ACA GAG AGA GGT TCT TTT GTA GCC AAC CTG GCC AAT GAC CTA           918
Glu Glu Thr Glu Arg Gly Ser Phe Val Ala Asn Leu Ala Asn Asp Leu
         40              45              50

GGG CTG GGA GTG GGG GAG CTA GCC GAG CGG GGA GCC CGG GTA GTT TCT           966
Gly Leu Gly Val Gly Glu Leu Ala Glu Arg Gly Ala Arg Val Val Ser
     55              60              65

GAG GAT AAC GAA CAA GGC TTG CAG CTT GAT CTG CAG ACC GGG CAG TTG          1014
Glu Asp Asn Glu Gln Gly Leu Gln Leu Asp Leu Gln Thr Gly Gln Leu
 70              75              80

ATA TTA AAT GAG AAG CTG GAC CGG GAG AAG CTG TGT GGC CCT ACT GAG          1062
Ile Leu Asn Glu Lys Leu Asp Arg Glu Lys Leu Cys Gly Pro Thr Glu
 85              90              95             100

CCC TGT ATA ATG CAT TTC CAA GTG TTA CTG AAA AAA CCT TTG GAA GTA          1110
Pro Cys Ile Met His Phe Gln Val Leu Leu Lys Lys Pro Leu Glu Val
```

-continued

| | 105 | | | | 110 | | | | | 115 | | | | |
|---|---|---|---|---|---|---|---|---|---|---|---|---|---|---|
| TTT | CGA | GCT | GAA | CTA | CTA | GTG | ACA | GAC | ATA | AAC | GAT | CAT | TCT | CCT | GAG | 1158 |
| Phe | Arg | Ala | Glu | Leu | Leu | Val | Thr | Asp | Ile | Asn | Asp | His | Ser | Pro | Glu | |
| | | | 120 | | | | | 125 | | | | 130 | | | | |
| TTT | CCT | GAA | AGA | GAA | ATG | ACC | CTG | AAA | ATC | CCA | GAA | ACT | AGC | TCC | CTT | 1206 |
| Phe | Pro | Glu | Arg | Glu | Met | Thr | Leu | Lys | Ile | Pro | Glu | Thr | Ser | Ser | Leu | |
| | | 135 | | | | | 140 | | | | | 145 | | | | |
| GGG | ACT | GTG | TTT | CCT | CTG | AAA | AAA | GCT | CGG | GAC | TTG | GAC | GTG | GGC | AGC | 1254 |
| Gly | Thr | Val | Phe | Pro | Leu | Lys | Lys | Ala | Arg | Asp | Leu | Asp | Val | Gly | Ser | |
| | 150 | | | | | 155 | | | | | 160 | | | | | |
| AAT | AAT | GTT | CAA | AAC | TAC | AAT | ATT | TCT | CCC | AAT | TCT | CAT | TTC | CAT | GTT | 1302 |
| Asn | Asn | Val | Gln | Asn | Tyr | Asn | Ile | Ser | Pro | Asn | Ser | His | Phe | His | Val | |
| 165 | | | | | 170 | | | | | 175 | | | | | 180 | |
| TCC | ACT | CGC | ACC | CGA | GGG | GAT | GGC | AGG | AAA | TAC | CCA | GAG | CTG | GTG | CTG | 1350 |
| Ser | Thr | Arg | Thr | Arg | Gly | Asp | Gly | Arg | Lys | Tyr | Pro | Glu | Leu | Val | Leu | |
| | | | | 185 | | | | | 190 | | | | | 195 | | |
| GAC | ACA | GAA | CTG | GAT | CGC | GAG | GAG | CAG | GCC | GAG | CTC | AGA | TTA | ACC | TTG | 1398 |
| Asp | Thr | Glu | Leu | Asp | Arg | Glu | Glu | Gln | Ala | Glu | Leu | Arg | Leu | Thr | Leu | |
| | | | 200 | | | | | 205 | | | | | 210 | | | |
| ACA | GCG | GTG | GAC | GGT | GGC | TCT | CCA | CCC | CGA | TCT | GGC | ACC | GTC | CAG | ATC | 1446 |
| Thr | Ala | Val | Asp | Gly | Gly | Ser | Pro | Pro | Arg | Ser | Gly | Thr | Val | Gln | Ile | |
| | | 215 | | | | | 220 | | | | | 225 | | | | |
| CTC | ATC | TTG | GTC | TTG | GAC | GCC | AAT | GAC | AAT | GCC | CCG | GAG | TTT | GTG | CAG | 1494 |
| Leu | Ile | Leu | Val | Leu | Asp | Ala | Asn | Asp | Asn | Ala | Pro | Glu | Phe | Val | Gln | |
| | 230 | | | | | 235 | | | | | 240 | | | | | |
| GCG | CTC | TAC | GAG | GTG | CAG | GTC | CCA | GAG | AAC | AGC | CCA | GTA | GGC | TCC | CTA | 1542 |
| Ala | Leu | Tyr | Glu | Val | Gln | Val | Pro | Glu | Asn | Ser | Pro | Val | Gly | Ser | Leu | |
| 245 | | | | | 250 | | | | | 255 | | | | | 260 | |
| GTT | GTC | AAG | GTC | TCT | GCT | AGG | GAT | TTA | GAC | ACT | GGG | ACA | AAT | GGA | GAG | 1590 |
| Val | Val | Lys | Val | Ser | Ala | Arg | Asp | Leu | Asp | Thr | Gly | Thr | Asn | Gly | Glu | |
| | | | | 265 | | | | | 270 | | | | | 275 | | |
| ATA | TCA | TAC | TCC | CTT | TAT | TAC | AGC | TCT | CAG | GAG | ATA | GAC | AAA | CCT | TTT | 1638 |
| Ile | Ser | Tyr | Ser | Leu | Tyr | Tyr | Ser | Ser | Gln | Glu | Ile | Asp | Lys | Pro | Phe | |
| | | | 280 | | | | | 285 | | | | | 290 | | | |
| GAG | CTA | AGC | AGC | CTT | TCA | GGA | GAA | ATT | CGA | CTA | ATT | AAA | AAA | CTA | GAT | 1686 |
| Glu | Leu | Ser | Ser | Leu | Ser | Gly | Glu | Ile | Arg | Leu | Ile | Lys | Lys | Leu | Asp | |
| | | 295 | | | | | 300 | | | | | 305 | | | | |
| TTT | GAG | ACA | ATG | TCT | TCA | TAT | GAT | CTA | GAT | ATA | GAG | GCA | TCT | GAT | GGC | 1734 |
| Phe | Glu | Thr | Met | Ser | Ser | Tyr | Asp | Leu | Asp | Ile | Glu | Ala | Ser | Asp | Gly | |
| | 310 | | | | | 315 | | | | | 320 | | | | | |
| GGG | GGA | CTT | TCT | GGA | AAA | TGC | TCT | GTC | TCT | GTT | AAG | GTG | CTG | GAT | GTT | 1782 |
| Gly | Gly | Leu | Ser | Gly | Lys | Cys | Ser | Val | Ser | Val | Lys | Val | Leu | Asp | Val | |
| 325 | | | | | 330 | | | | | 335 | | | | | 340 | |
| AAC | GAT | AAC | TTC | CCG | GAA | CTA | AGT | ATT | TCA | TCA | CTT | ACC | AGC | CCT | ATT | 1830 |
| Asn | Asp | Asn | Phe | Pro | Glu | Leu | Ser | Ile | Ser | Ser | Leu | Thr | Ser | Pro | Ile | |
| | | | | 345 | | | | | 350 | | | | | 355 | | |
| CCC | GAG | AAT | TCT | CCA | GAG | ACA | GAA | GTG | GCC | CTG | TTT | AGG | ATT | AGA | GAC | 1878 |
| Pro | Glu | Asn | Ser | Pro | Glu | Thr | Glu | Val | Ala | Leu | Phe | Arg | Ile | Arg | Asp | |
| | | | 360 | | | | | 365 | | | | | 370 | | | |
| CGA | GAC | TCT | GGA | GAA | AAT | GGA | AAA | ATG | ATT | TGC | TCA | ATT | CAG | GAT | GAT | 1926 |
| Arg | Asp | Ser | Gly | Glu | Asn | Gly | Lys | Met | Ile | Cys | Ser | Ile | Gln | Asp | Asp | |
| | | 375 | | | | | 380 | | | | | 385 | | | | |
| GTT | CCT | TTT | AAG | CTA | AAA | CCT | TCT | GTT | GAG | AAT | TTC | TAC | AGG | CTG | GTA | 1974 |
| Val | Pro | Phe | Lys | Leu | Lys | Pro | Ser | Val | Glu | Asn | Phe | Tyr | Arg | Leu | Val | |
| | 390 | | | | | 395 | | | | | 400 | | | | | |
| ACA | GAA | GGG | GCG | CTG | GAC | AGA | GAG | ACC | AGA | GCC | GAG | TAC | AAC | ATC | ACC | 2022 |
| Thr | Glu | Gly | Ala | Leu | Asp | Arg | Glu | Thr | Arg | Ala | Glu | Tyr | Asn | Ile | Thr | |
| 405 | | | | | 410 | | | | | 415 | | | | | 420 | |
| ATC | ACC | ATC | ACA | GAC | TTG | GGG | ACT | CCA | AGG | CTG | AAA | ACC | GAG | CAG | AGC | 2070 |
| Ile | Thr | Ile | Thr | Asp | Leu | Gly | Thr | Pro | Arg | Leu | Lys | Thr | Glu | Gln | Ser | |

```
                     425                              430                              435
ATA  ACC  GTG  CTG  GTG  TCG  GAC  GTC  AAT  GAC  AAC  GCC  CCC  GCC  TTC  ACC        2118
Ile  Thr  Val  Leu  Val  Ser  Asp  Val  Asn  Asp  Asn  Ala  Pro  Ala  Phe  Thr
               440                           445                           450

CAA  ACC  TCC  TAC  ACC  CTG  TTC  GTC  CGC  GAG  AAC  AAC  AGC  CCC  GCC  CTG        2166
Gln  Thr  Ser  Tyr  Thr  Leu  Phe  Val  Arg  Glu  Asn  Asn  Ser  Pro  Ala  Leu
               455                           460                           465

CAC  ATC  GGC  AGT  GTC  AGC  GCC  ACA  GAC  AGA  GAC  TCG  GGC  ACC  AAC  GCC        2214
His  Ile  Gly  Ser  Val  Ser  Ala  Thr  Asp  Arg  Asp  Ser  Gly  Thr  Asn  Ala
               470                           475                           480

CAG  GTC  ACC  TAC  TCG  CTG  CTG  CCG  CCC  CAG  GAC  CCG  CAC  CTG  CCC  CTA        2262
Gln  Val  Thr  Tyr  Ser  Leu  Leu  Pro  Pro  Gln  Asp  Pro  His  Leu  Pro  Leu
485                      490                           495                      500

ACC  TCC  CTG  GTC  TCC  ATT  AAC  ACG  GAC  AAC  GGC  CAC  CTG  TTC  GCT  CTC        2310
Thr  Ser  Leu  Val  Ser  Ile  Asn  Thr  Asp  Asn  Gly  His  Leu  Phe  Ala  Leu
                    505                           510                           515

CAG  TCG  CTG  GAC  TAC  GAG  GCC  CTG  CAG  GCT  TTC  GAG  TTC  CGC  GTG  GGC        2358
Gln  Ser  Leu  Asp  Tyr  Glu  Ala  Leu  Gln  Ala  Phe  Glu  Phe  Arg  Val  Gly
               520                           525                           530

GCC  ACA  GAC  CGC  GGC  TTC  CCG  GCG  CTG  AGC  AGC  GAG  GCG  CTG  GTG  CGA        2406
Ala  Thr  Asp  Arg  Gly  Phe  Pro  Ala  Leu  Ser  Ser  Glu  Ala  Leu  Val  Arg
          535                           540                           545

GTG  CTG  GTG  CTG  GAC  GCC  AAC  GAC  AAC  TCG  CCC  TTC  GTG  CTG  TAC  CCG        2454
Val  Leu  Val  Leu  Asp  Ala  Asn  Asp  Asn  Ser  Pro  Phe  Val  Leu  Tyr  Pro
550                      555                           560

CTG  CAG  AAC  GGC  TCC  GCG  CCC  TGC  ACC  GAG  CTG  GTG  CCC  CGG  GCG  GCC        2502
Leu  Gln  Asn  Gly  Ser  Ala  Pro  Cys  Thr  Glu  Leu  Val  Pro  Arg  Ala  Ala
565                      570                           575                      580

GAG  CCG  GGC  TAC  CTG  GTG  ACC  AAG  GTG  GTG  GCG  GTG  GAC  GGC  GAC  TCG        2550
Glu  Pro  Gly  Tyr  Leu  Val  Thr  Lys  Val  Val  Ala  Val  Asp  Gly  Asp  Ser
                    585                           590                           595

GGC  CAG  AAC  GCC  TGG  CTG  TCG  TAC  CAG  CTG  CTC  AAG  GCC  ACG  GAG  CCC        2598
Gly  Gln  Asn  Ala  Trp  Leu  Ser  Tyr  Gln  Leu  Leu  Lys  Ala  Thr  Glu  Pro
               600                           605                           610

GGG  CTG  TTC  GGC  GTG  TGG  GCG  CAC  AAT  GGC  GAG  GTG  CGC  ACC  GCC  AGG        2646
Gly  Leu  Phe  Gly  Val  Trp  Ala  His  Asn  Gly  Glu  Val  Arg  Thr  Ala  Arg
          615                           620                           625

CTG  CTG  AGC  GAG  CGC  GAC  GTG  GCC  AAG  CAC  AGG  CTA  GTG  GTG  CTG  GTC        2694
Leu  Leu  Ser  Glu  Arg  Asp  Val  Ala  Lys  His  Arg  Leu  Val  Val  Leu  Val
630                      635                           640

AAG  GAC  AAT  GGC  GAG  CCT  CCG  CGC  TCG  GCC  ACA  GCC  ACG  CTG  CAA  GTG        2742
Lys  Asp  Asn  Gly  Glu  Pro  Pro  Arg  Ser  Ala  Thr  Ala  Thr  Leu  Gln  Val
645                      650                           655                      660

CTC  CTG  GTG  GAC  GGC  TTC  TCT  CAG  CCC  TAC  CTG  CCG  CTC  CCA  GAG  GCG        2790
Leu  Leu  Val  Asp  Gly  Phe  Ser  Gln  Pro  Tyr  Leu  Pro  Leu  Pro  Glu  Ala
                    665                           670                           675

GCC  CCG  GCC  CAA  GCC  CAG  GCC  GAC  TCG  CTT  ACC  GTC  TAC  CTG  GTG  GTG        2838
Ala  Pro  Ala  Gln  Ala  Gln  Ala  Asp  Ser  Leu  Thr  Val  Tyr  Leu  Val  Val
               680                           685                           690

GCA  TTG  GCC  TCG  GTG  TCT  TCG  CTC  TTC  CTC  TTC  TCG  GTG  TTC  CTG  TTC        2886
Ala  Leu  Ala  Ser  Val  Ser  Ser  Leu  Phe  Leu  Phe  Ser  Val  Phe  Leu  Phe
          695                           700                           705

GTG  GCA  GTG  CGG  CTG  TGC  AGG  AGG  AGC  AGG  GCG  GCC  TCA  GTG  GGT  CGC        2934
Val  Ala  Val  Arg  Leu  Cys  Arg  Arg  Ser  Arg  Ala  Ala  Ser  Val  Gly  Arg
710                      715                           720

TGC  TCG  GTG  CCC  GAG  GGC  CCC  TTT  CCA  GGG  CAT  CTG  GTG  GAC  GTG  AGC        2982
Cys  Ser  Val  Pro  Glu  Gly  Pro  Phe  Pro  Gly  His  Leu  Val  Asp  Val  Ser
725                      730                           735                      740

GGC  ACC  GGG  ACC  CTT  TCC  CAG  AGC  TAC  CAG  TAC  GAG  GTG  TGT  CTG  ACG        3030
Gly  Thr  Gly  Thr  Leu  Ser  Gln  Ser  Tyr  Gln  Tyr  Glu  Val  Cys  Leu  Thr
```

-continued

```
              745                        750                        755
GGA  GGC  TCT  GAA  AGT  AAT  GAT  TTC  AAG  TTC  TTG  AAG  CCT  ATA  TTC  CCA        3078
Gly  Gly  Ser  Glu  Ser  Asn  Asp  Phe  Lys  Phe  Leu  Lys  Pro  Ile  Phe  Pro
               760                        765                        770

AAT  ATT  GTA  AGC  CAG  GAC  TCT  AGG  AGG  AAA  TCA  GAA  TTT  CTA  GAA             3123
Asn  Ile  Val  Ser  Gln  Asp  Ser  Arg  Arg  Lys  Ser  Glu  Phe  Leu  Glu
               775                        780                        785

TAATGTAGGT  ATCTGTAGCT  TTCCGACCGT  CTGTTAATTT  TGTCTTCCTC  ACTTTTCACC                3183
TTAGTTTTTT  TTAACCCTTT  AGTAATCTTG  AATTCTACTT  TTTTTAAAT   TTCTACTGTT                3243
GTCTTAGTA   ATGTTACTCA  TTTCCTTTGT  CTGATTGTTA  GTTTCAAAT   TATTGTATTA                3303
TTATAAATAT  TTTATATCAG  GAAAGTTCAT  ATTTCTGAAT  AAATTAATAG                            3353
```

( 2 ) INFORMATION FOR SEQ ID NO:110:

( i ) SEQUENCE CHARACTERISTICS:
        ( A ) LENGTH: 787 amino acids
        ( B ) TYPE: amino acid
        ( D ) TOPOLOGY: linear ( i i ) MOLECULE TYPE: protein ( x i ) SEQUENCE DESCRIPTION: SEQ ID NO:110:

```
Met  Glu  Pro  Ala  Gly  Glu  Arg  Phe  Pro  Glu  Gln  Arg  Gln  Val  Leu  Ile
 1                    5                        10                       15

Leu  Leu  Leu  Leu  Leu  Glu  Val  Thr  Leu  Ala  Gly  Trp  Glu  Pro  Arg  Arg
                20                        25                        30

Tyr  Ser  Val  Met  Glu  Glu  Thr  Glu  Arg  Gly  Ser  Phe  Val  Ala  Asn  Leu
           35                        40                        45

Ala  Asn  Asp  Leu  Gly  Leu  Gly  Val  Gly  Glu  Leu  Ala  Glu  Arg  Gly  Ala
      50                        55                        60

Arg  Val  Val  Ser  Glu  Asp  Asn  Glu  Gln  Gly  Leu  Gln  Leu  Asp  Leu  Gln
 65                        70                        75                       80

Thr  Gly  Gln  Leu  Ile  Leu  Asn  Glu  Lys  Leu  Asp  Arg  Glu  Lys  Leu  Cys
                85                        90                        95

Gly  Pro  Thr  Glu  Pro  Cys  Ile  Met  His  Phe  Gln  Val  Leu  Leu  Lys  Lys
          100                       105                       110

Pro  Leu  Glu  Val  Phe  Arg  Ala  Glu  Leu  Leu  Val  Thr  Asp  Ile  Asn  Asp
          115                       120                       125

His  Ser  Pro  Glu  Phe  Pro  Glu  Arg  Glu  Met  Thr  Leu  Lys  Ile  Pro  Glu
     130                       135                       140

Thr  Ser  Ser  Leu  Gly  Thr  Val  Phe  Pro  Leu  Lys  Lys  Ala  Arg  Asp  Leu
145                       150                       155                      160

Asp  Val  Gly  Ser  Asn  Asn  Val  Gln  Asn  Tyr  Asn  Ile  Ser  Pro  Asn  Ser
                165                       170                       175

His  Phe  His  Val  Ser  Thr  Arg  Thr  Arg  Gly  Asp  Gly  Arg  Lys  Tyr  Pro
          180                       185                       190

Glu  Leu  Val  Leu  Asp  Thr  Glu  Leu  Asp  Arg  Glu  Gln  Ala  Glu  Leu
          195                       200                       205

Arg  Leu  Thr  Leu  Thr  Ala  Val  Asp  Gly  Gly  Ser  Pro  Pro  Arg  Ser  Gly
     210                       215                       220

Thr  Val  Gln  Ile  Leu  Ile  Leu  Val  Leu  Asp  Ala  Asn  Asp  Asn  Ala  Pro
225                       230                       235                      240

Glu  Phe  Val  Gln  Ala  Leu  Tyr  Glu  Val  Gln  Val  Pro  Glu  Asn  Ser  Pro
                245                       250                       255

Val  Gly  Ser  Leu  Val  Val  Lys  Val  Ser  Ala  Arg  Asp  Leu  Asp  Thr  Gly
          260                       265                       270
```

| | | | | | | | | | | | | | | |
|---|---|---|---|---|---|---|---|---|---|---|---|---|---|---|
|Thr|Asn|Gly|Glu|Ile|Ser|Tyr|Ser|Leu|Tyr|Tyr|Ser|Ser|Gln|Glu|Ile|
| | |275| | | | |280| | | | |285| | | |
|Asp|Lys|Pro|Phe|Glu|Leu|Ser|Ser|Leu|Ser|Gly|Glu|Ile|Arg|Leu|Ile|
| |290| | | | |295| | | | |300| | | | |
|Lys|Lys|Leu|Asp|Phe|Glu|Thr|Met|Ser|Ser|Tyr|Asp|Leu|Asp|Ile|Glu|
|305| | | | |310| | | | |315| | | | |320|
|Ala|Ser|Asp|Gly|Gly|Gly|Leu|Ser|Gly|Lys|Cys|Ser|Val|Ser|Val|Lys|
| | | | |325| | | | |330| | | | |335| |
|Val|Leu|Asp|Val|Asn|Asp|Asn|Phe|Pro|Glu|Leu|Ser|Ile|Ser|Ser|Leu|
| | | |340| | | | |345| | | | |350| | |
|Thr|Ser|Pro|Ile|Pro|Glu|Asn|Ser|Pro|Glu|Thr|Glu|Val|Ala|Leu|Phe|
| | |355| | | | |360| | | | |365| | | |
|Arg|Ile|Arg|Asp|Arg|Asp|Ser|Gly|Glu|Asn|Gly|Lys|Met|Ile|Cys|Ser|
| |370| | | | |375| | | | |380| | | | |
|Ile|Gln|Asp|Asp|Val|Pro|Phe|Lys|Leu|Lys|Pro|Ser|Val|Glu|Asn|Phe|
|385| | | | |390| | | | |395| | | | |400|
|Tyr|Arg|Leu|Val|Thr|Glu|Gly|Ala|Leu|Asp|Arg|Glu|Thr|Arg|Ala|Glu|
| | | | |405| | | | |410| | | | |415| |
|Tyr|Asn|Ile|Thr|Ile|Thr|Ile|Thr|Asp|Leu|Gly|Thr|Pro|Arg|Leu|Lys|
| | | |420| | | | |425| | | | |430| | |
|Thr|Glu|Gln|Ser|Ile|Thr|Val|Leu|Val|Ser|Asp|Val|Asn|Asp|Asn|Ala|
| | |435| | | | |440| | | | |445| | | |
|Pro|Ala|Phe|Thr|Gln|Thr|Ser|Tyr|Thr|Leu|Phe|Val|Arg|Glu|Asn|Asn|
| |450| | | | |455| | | | |460| | | | |
|Ser|Pro|Ala|Leu|His|Ile|Gly|Ser|Val|Ser|Ala|Thr|Asp|Arg|Asp|Ser|
|465| | | | |470| | | | |475| | | | |480|
|Gly|Thr|Asn|Ala|Gln|Val|Thr|Tyr|Ser|Leu|Leu|Pro|Pro|Gln|Asp|Pro|
| | | | |485| | | | |490| | | | |495| |
|His|Leu|Pro|Leu|Thr|Ser|Leu|Val|Ser|Ile|Asn|Thr|Asp|Asn|Gly|His|
| | | |500| | | | |505| | | | |510| | |
|Leu|Phe|Ala|Leu|Gln|Ser|Leu|Asp|Tyr|Glu|Ala|Leu|Gln|Ala|Phe|Glu|
| | |515| | | | |520| | | | |525| | | |
|Phe|Arg|Val|Gly|Ala|Thr|Asp|Arg|Gly|Phe|Pro|Ala|Leu|Ser|Ser|Glu|
| |530| | | | |535| | | | |540| | | | |
|Ala|Leu|Val|Arg|Val|Leu|Val|Leu|Asp|Ala|Asn|Asp|Asn|Ser|Pro|Phe|
|545| | | | |550| | | | |555| | | | |560|
|Val|Leu|Tyr|Pro|Leu|Gln|Asn|Gly|Ser|Ala|Pro|Cys|Thr|Glu|Leu|Val|
| | | | |565| | | | |570| | | | |575| |
|Pro|Arg|Ala|Ala|Glu|Pro|Gly|Tyr|Leu|Val|Thr|Lys|Val|Val|Ala|Val|
| | | |580| | | | |585| | | | |590| | |
|Asp|Gly|Asp|Ser|Gly|Gln|Asn|Ala|Trp|Leu|Ser|Tyr|Gln|Leu|Leu|Lys|
| | |595| | | | |600| | | | |605| | | |
|Ala|Thr|Glu|Pro|Gly|Leu|Phe|Gly|Val|Trp|Ala|His|Asn|Gly|Glu|Val|
| |610| | | | |615| | | | |620| | | | |
|Arg|Thr|Ala|Arg|Leu|Leu|Ser|Glu|Arg|Asp|Val|Ala|Lys|His|Arg|Leu|
|625| | | | |630| | | | |635| | | | |640|
|Val|Val|Leu|Val|Lys|Asp|Asn|Gly|Glu|Pro|Pro|Arg|Ser|Ala|Thr|Ala|
| | | | |645| | | | |650| | | | |655| |
|Thr|Leu|Gln|Val|Leu|Leu|Val|Asp|Gly|Phe|Ser|Gln|Pro|Tyr|Leu|Pro|
| | | |660| | | | |665| | | | |670| | |
|Leu|Pro|Glu|Ala|Ala|Pro|Ala|Gln|Ala|Gln|Ala|Asp|Ser|Leu|Thr|Val|
| | |675| | | | |680| | | | |685| | | |
|Tyr|Leu|Val|Val|Ala|Leu|Ala|Ser|Val|Ser|Ser|Leu|Phe|Leu|Phe|Ser|

|     |     |     |     |     | 690 |     |     |     | 695 |     |     |     |     | 700 |     |
| --- | --- | --- | --- | --- | --- | --- | --- | --- | --- | --- | --- | --- | --- | --- | --- |
| Val | Phe | Leu | Phe | Val | Ala | Val | Arg | Leu | Cys | Arg | Arg | Ser | Arg | Ala | Ala |
| 705 |     |     |     |     | 710 |     |     |     | 715 |     |     |     |     | 720 |     |

| Ser | Val | Gly | Arg | Cys | Ser | Val | Pro | Glu | Gly | Pro | Phe | Pro | Gly | His | Leu |
|---|---|---|---|---|---|---|---|---|---|---|---|---|---|---|---|
|  |  |  |  | 725 |  |  |  | 730 |  |  |  |  | 735 |  |  |

| Val | Asp | Val | Ser | Gly | Thr | Gly | Thr | Leu | Ser | Gln | Ser | Tyr | Gln | Tyr | Glu |
|---|---|---|---|---|---|---|---|---|---|---|---|---|---|---|---|
|  |  |  | 740 |  |  |  |  | 745 |  |  |  |  | 750 |  |  |

| Val | Cys | Leu | Thr | Gly | Gly | Ser | Glu | Ser | Asn | Asp | Phe | Lys | Phe | Leu | Lys |
|---|---|---|---|---|---|---|---|---|---|---|---|---|---|---|---|
|  |  |  | 755 |  |  |  | 760 |  |  |  |  | 765 |  |  |  |

| Pro | Ile | Phe | Pro | Asn | Ile | Val | Ser | Gln | Asp | Ser | Arg | Arg | Lys | Ser | Glu |
|---|---|---|---|---|---|---|---|---|---|---|---|---|---|---|---|
|  | 770 |  |  |  |  | 775 |  |  |  |  | 780 |  |  |  |  |

Phe Leu Glu
785

( 2 ) INFORMATION FOR SEQ ID NO:111:

( i ) SEQUENCE CHARACTERISTICS:
        ( A ) LENGTH: 3033 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 138..2528

( x i ) SEQUENCE DESCRIPTION: SEQ ID NO:111:

| GTGATTGGAC | GTGTTTTTGT | GACTATTTGG | GAAGAAGACA | CCTTCCTAAT | CAGATTTACT | 60 |
|---|---|---|---|---|---|---|
| CCAATATCTT | CCCGGACCCT | CATGAGTGGA | TTGCAATTGA | CTTGAAGAAG | CAGCACCCTC | 120 |

| AGGACTGAAT | CTGAACA | ATG<br>Met<br>1 | GAG<br>Glu | ACA<br>Thr | GCA<br>Ala | CTA<br>Leu | GCA<br>Ala<br>5 | AAA<br>Lys | ATA<br>Ile | CCA<br>Pro | CAG<br>Gln | CAA<br>Gln<br>10 | 170 |
|---|---|---|---|---|---|---|---|---|---|---|---|---|---|
| AGG<br>Arg | CAA<br>Gln | GTC<br>Val | TTT<br>Phe<br>15 | TTT<br>Phe | CTT<br>Leu | ACT<br>Thr | ATA<br>Ile | TTG<br>Leu<br>20 | TCG<br>Ser | TTA<br>Leu | TTG<br>Leu | TGG<br>Trp | AAG<br>Lys<br>25 | TCT<br>Ser | AGC<br>Ser | 218 |
| TCT<br>Ser | GAG<br>Glu | GCC<br>Ala<br>30 | ATT<br>Ile | AGA<br>Arg | TAT<br>Tyr | TCC<br>Ser | ATG<br>Met<br>35 | CCA<br>Pro | GAA<br>Glu | GAA<br>Glu | ACA<br>Thr | GAG<br>Glu<br>40 | AGT<br>Ser | GGC<br>Gly | TAT<br>Tyr | 266 |
| ATG<br>Met | GTG<br>Val<br>45 | GCT<br>Ala | AAC<br>Asn | CTG<br>Leu | GCG<br>Ala | AAA<br>Lys<br>50 | GAT<br>Asp | CTG<br>Leu | GGG<br>Gly | ATC<br>Ile | AGG<br>Arg<br>55 | GTT<br>Val | GGA<br>Gly | GAA<br>Glu | CTG<br>Leu | 314 |
| TCC<br>Ser<br>60 | TCT<br>Ser | AGA<br>Arg | GGA<br>Gly | GCT<br>Ala | CAA<br>Gln<br>65 | ATC<br>Ile | CAT<br>His | TAC<br>Tyr | AAA<br>Lys | GGA<br>Gly<br>70 | AAC<br>Asn | AAA<br>Lys | GAA<br>Glu | CTT<br>Leu | TTG<br>Leu<br>75 | 362 |
| CAG<br>Gln | CTG<br>Leu | GAT<br>Asp | GCA<br>Ala | GAG<br>Glu<br>80 | ACT<br>Thr | GGG<br>Gly | AAT<br>Asn | TTG<br>Leu | TTC<br>Phe<br>85 | TTA<br>Leu | AAG<br>Lys | GAA<br>Glu | AAA<br>Lys | CTA<br>Leu<br>90 | GAC<br>Asp | 410 |
| AGA<br>Arg | GAA<br>Glu | CTG<br>Leu | CTG<br>Leu<br>95 | TGT<br>Cys | GGA<br>Gly | GAG<br>Glu | ACA<br>Thr | GAA<br>Glu<br>100 | CCC<br>Pro | TGT<br>Cys | GTG<br>Val | CTG<br>Leu | AAC<br>Asn<br>105 | TTC<br>Phe | CAG<br>Gln | 458 |
| ATC<br>Ile | ATA<br>Ile | CTG<br>Leu<br>110 | GAA<br>Glu | AAC<br>Asn | CCT<br>Pro | ATG<br>Met | CAG<br>Gln<br>115 | TTC<br>Phe | TTC<br>Phe | CAA<br>Gln | ACT<br>Thr | GAA<br>Glu<br>120 | CTG<br>Leu | CAG<br>Gln | CTC<br>Leu | 506 |
| ACA<br>Thr | GAT<br>Asp<br>125 | ATA<br>Ile | AAC<br>Asn | GAC<br>Asp | CAT<br>His | TCT<br>Ser<br>130 | CCA<br>Pro | GAG<br>Glu | TTC<br>Phe | CCC<br>Pro | AAC<br>Asn<br>135 | AAG<br>Lys | AAA<br>Lys | ATG<br>Met | CTT<br>Leu | 554 |
| CTA<br>Leu<br>140 | ACA<br>Thr | ATT<br>Ile | CCT<br>Pro | GAG<br>Glu | AGT<br>Ser<br>145 | GCC<br>Ala | CAT<br>His | CCA<br>Pro | GGG<br>Gly | ACT<br>Thr<br>150 | GTG<br>Val | TTT<br>Phe | CCT<br>Pro | CTG<br>Leu | AAG<br>Lys<br>155 | 602 |

```
GCA GCT CGG GAC TCT GAC ATA GGG AGC AAC GCT GTT CAG AAC TAC ACA           650
Ala Ala Arg Asp Ser Asp Ile Gly Ser Asn Ala Val Gln Asn Tyr Thr
            160             165                 170

GTC AAT CCC AAC CTC CAT TTC CAC GTC GTT ACT CAC AGT CGC ACA GAT           698
Val Asn Pro Asn Leu His Phe His Val Val Thr His Ser Arg Thr Asp
            175             180                 185

GGC AGG AAA TAC CCA GAG CTG GTG CTG GAC AGA GCC CTG GAT AGG GAG           746
Gly Arg Lys Tyr Pro Glu Leu Val Leu Asp Arg Ala Leu Asp Arg Glu
            190             195                 200

GAG CAG CCT GAG CTC ACT TTA ATC CTC ACT GCT CTG GAT GGT GGA GCT           794
Glu Gln Pro Glu Leu Thr Leu Ile Leu Thr Ala Leu Asp Gly Gly Ala
205             210             215

CCT TCC AGG TCA GGA ACC ACC ACA GTT CAC ATA GAA GTT GTG GAC ATC           842
Pro Ser Arg Ser Gly Thr Thr Thr Val His Ile Glu Val Val Asp Ile
220             225             230                 235

AAT GAT AAC TCC CCC CAG TTT GTA CAG TCA CTC TAT AAG GTG CAA GTT           890
Asn Asp Asn Ser Pro Gln Phe Val Gln Ser Leu Tyr Lys Val Gln Val
                240             245                 250

CCT GAG AAT AAT CCC CTC AAT GCC TTT GTT GTC ACG GTC TCT GCC ACG           938
Pro Glu Asn Asn Pro Leu Asn Ala Phe Val Val Thr Val Ser Ala Thr
                255             260                 265

GAT TTA GAT GCT GGG GTA TAT GGC AAT GTG ACC TAT TCT CTG TTT CAA           986
Asp Leu Asp Ala Gly Val Tyr Gly Asn Val Thr Tyr Ser Leu Phe Gln
            270             275                 280

GGG TAT GGG GTA TTT CAA CCA TTT GTA ATA GAC GAA ATC ACT GGA GAA          1034
Gly Tyr Gly Val Phe Gln Pro Phe Val Ile Asp Glu Ile Thr Gly Glu
285             290             295

ATC CAT CTG AGC AAA GAG CTG GAT TTT GAG GAA ATT AGC AAT CAT AAC          1082
Ile His Leu Ser Lys Glu Leu Asp Phe Glu Glu Ile Ser Asn His Asn
300             305             310                 315

ATA GAA ATC GCA GCC ACA GAT GGA GGA GGC CTT TCA GGA AAA TGC ACT          1130
Ile Glu Ile Ala Ala Thr Asp Gly Gly Gly Leu Ser Gly Lys Cys Thr
                320             325                 330

GTG GCT GTA CAG GTG TTG GAT GTG AAT GAC AAC GCC CCA GAG TTG ACA          1178
Val Ala Val Gln Val Leu Asp Val Asn Asp Asn Ala Pro Glu Leu Thr
            335             340                 345

ATT AGG AAG CTC ACA GTC CTG GTC CCA GAA AAT TCC GCA GAG ACT GTA          1226
Ile Arg Lys Leu Thr Val Leu Val Pro Glu Asn Ser Ala Glu Thr Val
            350             355                 360

GTT GCT GTT TTT AGT GTT TCT GAT TCT GAT TCG GGG GAC AAT GGA AGG          1274
Val Ala Val Phe Ser Val Ser Asp Ser Asp Ser Gly Asp Asn Gly Arg
            365             370                 375

ATG GTG TGT TCT ATT CCG AAC AAT ATC CCA TTT CTC CTG AAA CCC ACA          1322
Met Val Cys Ser Ile Pro Asn Asn Ile Pro Phe Leu Leu Lys Pro Thr
380             385             390                 395

TTT GAG AAT TAT TAC ACG TTA GTG ACT GAG GGG CCA CTT GAT AGA GAG          1370
Phe Glu Asn Tyr Tyr Thr Leu Val Thr Glu Gly Pro Leu Asp Arg Glu
            400             405                 410

AAC AGA GCT GAG TAC AAC ATC ACC ATC ACG GTC TCA GAT CTG GGC ACA          1418
Asn Arg Ala Glu Tyr Asn Ile Thr Ile Thr Val Ser Asp Leu Gly Thr
            415             420                 425

CCC AGG CTC ACA ACC CAG CAC ACC ATA ACA GTG CAA GTG TCC GAC ATC          1466
Pro Arg Leu Thr Thr Gln His Thr Ile Thr Val Gln Val Ser Asp Ile
            430             435                 440

AAC GAC AAC GCC CCT GCC TTC ACC CAA ACC TCC TAC ACC ATG TTT GTC          1514
Asn Asp Asn Ala Pro Ala Phe Thr Gln Thr Ser Tyr Thr Met Phe Val
            445             450                 455

CAC GAG AAC AAC AGC CCC GCC CTG CAC ATA GGC ACC ATC AGT GCC ACA          1562
His Glu Asn Asn Ser Pro Ala Leu His Ile Gly Thr Ile Ser Ala Thr
460             465             470                 475
```

```
GAC TCA GAC TCA GGC TCC AAT GCC CAC ATC ACC TAC TCG CTG CTG CCG      1610
Asp Ser Asp Ser Gly Ser Asn Ala His Ile Thr Tyr Ser Leu Leu Pro
            480                 485                 490

CCT GAT GAC CCG CAG CTG GCC CTC GAC TCA CTC ATC TCC ATC AAT GTT      1658
Pro Asp Asp Pro Gln Leu Ala Leu Asp Ser Leu Ile Ser Ile Asn Val
            495                 500                 505

GAC AAT GGG CAG CTG TTC GCG CTC AGA GCT CTA GAC TAT GAG GCA CTG      1706
Asp Asn Gly Gln Leu Phe Ala Leu Arg Ala Leu Asp Tyr Glu Ala Leu
            510                 515                 520

CAG TCC TTC GAG TTC TAC GTG GGC GCT ACA GAT GGA GGC TCA CCC GCG      1754
Gln Ser Phe Glu Phe Tyr Val Gly Ala Thr Asp Gly Gly Ser Pro Ala
            525                 530                 535

CTC AGC AGC CAG ACT CTG GTG CGG ATG GTG GTG CTG GAT GAC AAT GAC      1802
Leu Ser Ser Gln Thr Leu Val Arg Met Val Val Leu Asp Asp Asn Asp
540                 545                 550                 555

AAT GCC CCC TTC GTG CTC TAC CCA CTG CAG AAT GCC TCA GCA CCC TGT      1850
Asn Ala Pro Phe Val Leu Tyr Pro Leu Gln Asn Ala Ser Ala Pro Cys
            560                 565                 570

ACT GAG CTA CTG CCT AGG GCA GCA GAG CCC GGC TAC CTG ATC ACC AAA      1898
Thr Glu Leu Leu Pro Arg Ala Ala Glu Pro Gly Tyr Leu Ile Thr Lys
            575                 580                 585

GTG GTG GCT GTG GAT CGC GAC TCT GGA CAG AAT GCT TGG CTG TCG TTC      1946
Val Val Ala Val Asp Arg Asp Ser Gly Gln Asn Ala Trp Leu Ser Phe
            590                 595                 600

CAG CTA CTT AAA GCT ACA GAG CCA GGG CTG TTC AGT GTA TGG GCA CAC      1994
Gln Leu Leu Lys Ala Thr Glu Pro Gly Leu Phe Ser Val Trp Ala His
            605                 610                 615

AAT GGT GAA GTG CGC ACC ACT AGG CTG CTG AGT GAG CGA GAT GCT CAG      2042
Asn Gly Glu Val Arg Thr Thr Arg Leu Leu Ser Glu Arg Asp Ala Gln
620                 625                 630                 635

AAG CAC AAG CTA CTG CTG CTG GTC AAG GAC AAT GGC GAT CCT CTG CGC      2090
Lys His Lys Leu Leu Leu Leu Val Lys Asp Asn Gly Asp Pro Leu Arg
            640                 645                 650

TCT GCC AAT GTC ACT CTT CAC GTG CTA GTG GTG GAT GGC TTC TCG CAG      2138
Ser Ala Asn Val Thr Leu His Val Leu Val Val Asp Gly Phe Ser Gln
            655                 660                 665

CCT TAC CTA CCA TTG GCT GAG GTG GCA CAG GAT TCC ATG CAA GAT AAT      2186
Pro Tyr Leu Pro Leu Ala Glu Val Ala Gln Asp Ser Met Gln Asp Asn
            670                 675                 680

TAC GAC GTT CTC ACA CTG TAC CTA GTC ATT GCC TTG GCA TCT GTA TCT      2234
Tyr Asp Val Leu Thr Leu Tyr Leu Val Ile Ala Leu Ala Ser Val Ser
            685                 690                 695

TCT CTC TTC CTC TTG TCT GTA GTG CTG TTT GTG GGG GTG AGG CTG TGC      2282
Ser Leu Phe Leu Leu Ser Val Val Leu Phe Val Gly Val Arg Leu Cys
700                 705                 710                 715

AGG AGG GCC AGG GAG GCC TCC TTG GGT GAC TAC TCT GTG CCT GAG GGA      2330
Arg Arg Ala Arg Glu Ala Ser Leu Gly Asp Tyr Ser Val Pro Glu Gly
            720                 725                 730

CAC TTT CCT AGC CAC TTG GTG GAT GTC AGC GGT GCC GGG ACC CTG TCC      2378
His Phe Pro Ser His Leu Val Asp Val Ser Gly Ala Gly Thr Leu Ser
            735                 740                 745

CAG AGT TAT CAA TAT GAG GTG TGT CTT AAT GGA GGT ACT AGA ACA AAT      2426
Gln Ser Tyr Gln Tyr Glu Val Cys Leu Asn Gly Gly Thr Arg Thr Asn
            750                 755                 760

GAG TTT AAC TTT CTT AAA CCA TTG TTT CCT ATC CTT CCG ACC CAG GCT      2474
Glu Phe Asn Phe Leu Lys Pro Leu Phe Pro Ile Leu Pro Thr Gln Ala
765                 770                 775

GCT GCT GCT GAA GAA AGA GAA AAC GCT GTT GTG CAC AAT AGC GTT GGA      2522
Ala Ala Ala Glu Glu Arg Glu Asn Ala Val Val His Asn Ser Val Gly
            780                 785                 790                 795
```

```
TTC TAT TAGAGCACTG ATTTTGAAGT GGTGGTTACC TCATTTTTCC TTAACTATCC        2578
Phe Tyr
CTGATGTAGA ATGGTGTAGT GCCGTGAATC AACTCCTGAG ATATATGTTC ATTTTATCCT     2638

TTGTTTTGAA TCAAACTATT CAGATGTGAT CCTACTCTAG AGAATTTGGT TCTACTCCAT     2698

TGTGTTTGTT TAGATTTCTA CGCCATACCA GTGCATGCTG GGTTGTTTTT TTTTTTACAA     2758

TTATTATAAC TTTGCTTTGG AGGGGAACTC ATATTCGCTG TAACGAATTG GAACCACTTT     2818

CATTGTTAGA GATGCCTTGC TTTGTTGTGT TATTTCAGAC AGGGTCTTAA ATTGTAGCCC     2878

TGGGTGACCT GAAATGACTA TGTACAGACT GACTTGAAT TTGTGGCAGT CCATCTGCCT      2938

CTGTTGTCCT ATGTTGGGAT TGTGAGCATG CATGAGTAGG CTCAGCTGTG GTGAGCGACC    2998

TTAATAAAAA TCAAATACTA AAAAAAAAA AAAAA                                 3033
```

(2) INFORMATION FOR SEQ ID NO:112:

(i) SEQUENCE CHARACTERISTICS:
    (A) LENGTH: 797 amino acids
    (B) TYPE: amino acid
    (D) TOPOLOGY: linear (ii) MOLECULE TYPE: protein (xi) SEQUENCE DESCRIPTION: SEQ ID NO:112:

```
Met Glu Thr Ala Leu Ala Lys Ile Pro Gln Gln Arg Gln Val Phe Phe
  1               5                  10                  15

Leu Thr Ile Leu Ser Leu Leu Trp Lys Ser Ser Ser Glu Ala Ile Arg
             20                  25                  30

Tyr Ser Met Pro Glu Glu Thr Glu Ser Gly Tyr Met Val Ala Asn Leu
         35                  40                  45

Ala Lys Asp Leu Gly Ile Arg Val Gly Glu Leu Ser Ser Arg Gly Ala
     50                  55                  60

Gln Ile His Tyr Lys Gly Asn Lys Glu Leu Leu Gln Leu Asp Ala Glu
 65                  70                  75                  80

Thr Gly Asn Leu Phe Leu Lys Glu Lys Leu Asp Arg Glu Leu Leu Cys
                 85                  90                  95

Gly Glu Thr Glu Pro Cys Val Leu Asn Phe Gln Ile Ile Leu Glu Asn
            100                 105                 110

Pro Met Gln Phe Phe Gln Thr Glu Leu Gln Leu Thr Asp Ile Asn Asp
        115                 120                 125

His Ser Pro Glu Phe Pro Asn Lys Lys Met Leu Leu Thr Ile Pro Glu
    130                 135                 140

Ser Ala His Pro Gly Thr Val Phe Pro Leu Lys Ala Ala Arg Asp Ser
145                 150                 155                 160

Asp Ile Gly Ser Asn Ala Val Gln Asn Tyr Thr Val Asn Pro Asn Leu
                165                 170                 175

His Phe His Val Val Thr His Ser Arg Thr Asp Gly Arg Lys Tyr Pro
            180                 185                 190

Glu Leu Val Leu Asp Arg Ala Leu Asp Arg Glu Glu Gln Pro Glu Leu
        195                 200                 205

Thr Leu Ile Leu Thr Ala Leu Asp Gly Gly Ala Pro Ser Arg Ser Gly
    210                 215                 220

Thr Thr Thr Val His Ile Glu Val Val Asp Ile Asn Asp Asn Ser Pro
225                 230                 235                 240

Gln Phe Val Gln Ser Leu Tyr Lys Val Gln Val Pro Glu Asn Asn Pro
                245                 250                 255

Leu Asn Ala Phe Val Val Thr Val Ser Ala Thr Asp Leu Asp Ala Gly
```

```
                    260                         265                         270
Val  Tyr  Gly  Asn  Val  Thr  Tyr  Ser  Leu  Phe  Gln  Gly  Tyr  Gly  Val  Phe
               275                         280                    285

Gln  Pro  Phe  Val  Ile  Asp  Glu  Ile  Thr  Gly  Glu  Ile  His  Leu  Ser  Lys
     290                         295                         300

Glu  Leu  Asp  Phe  Glu  Glu  Ile  Ser  Asn  His  Asn  Ile  Glu  Ile  Ala  Ala
305                      310                         315                      320

Thr  Asp  Gly  Gly  Gly  Leu  Ser  Gly  Lys  Cys  Thr  Val  Ala  Val  Gln  Val
                    325                         330                    335

Leu  Asp  Val  Asn  Asp  Asn  Ala  Pro  Glu  Leu  Thr  Ile  Arg  Lys  Leu  Thr
               340                         345                    350

Val  Leu  Val  Pro  Glu  Asn  Ser  Ala  Glu  Thr  Val  Val  Ala  Val  Phe  Ser
          355                         360                    365

Val  Ser  Asp  Ser  Asp  Ser  Gly  Asp  Asn  Gly  Arg  Met  Val  Cys  Ser  Ile
     370                         375                    380

Pro  Asn  Asn  Ile  Pro  Phe  Leu  Leu  Lys  Pro  Thr  Phe  Glu  Asn  Tyr  Tyr
385                           390                        395                      400

Thr  Leu  Val  Thr  Glu  Gly  Pro  Leu  Asp  Arg  Glu  Asn  Arg  Ala  Glu  Tyr
                    405                        410                      415

Asn  Ile  Thr  Ile  Thr  Val  Ser  Asp  Leu  Gly  Thr  Pro  Arg  Leu  Thr  Thr
               420                        425                    430

Gln  His  Thr  Ile  Thr  Val  Gln  Val  Ser  Asp  Ile  Asn  Asp  Asn  Ala  Pro
          435                         440                    445

Ala  Phe  Thr  Gln  Thr  Ser  Tyr  Thr  Met  Phe  Val  His  Glu  Asn  Asn  Ser
     450                         455                    460

Pro  Ala  Leu  His  Ile  Gly  Thr  Ile  Ser  Ala  Thr  Asp  Ser  Asp  Ser  Gly
465                           470                        475                      480

Ser  Asn  Ala  His  Ile  Thr  Tyr  Ser  Leu  Leu  Pro  Pro  Asp  Asp  Pro  Gln
                    485                        490                      495

Leu  Ala  Leu  Asp  Ser  Leu  Ile  Ser  Ile  Asn  Val  Asp  Asn  Gly  Gln  Leu
               500                         505                    510

Phe  Ala  Leu  Arg  Ala  Leu  Asp  Tyr  Glu  Ala  Leu  Gln  Ser  Phe  Glu  Phe
          515                         520                    525

Tyr  Val  Gly  Ala  Thr  Asp  Gly  Gly  Ser  Pro  Ala  Leu  Ser  Ser  Gln  Thr
     530                         535                    540

Leu  Val  Arg  Met  Val  Val  Leu  Asp  Asp  Asn  Asp  Asn  Ala  Pro  Phe  Val
545                           550                        555                      560

Leu  Tyr  Pro  Leu  Gln  Asn  Ala  Ser  Ala  Pro  Cys  Thr  Glu  Leu  Leu  Pro
                    565                         570                    575

Arg  Ala  Ala  Glu  Pro  Gly  Tyr  Leu  Ile  Thr  Lys  Val  Val  Ala  Val  Asp
               580                         585                    590

Arg  Asp  Ser  Gly  Gln  Asn  Ala  Trp  Leu  Ser  Phe  Gln  Leu  Leu  Lys  Ala
          595                         600                    605

Thr  Glu  Pro  Gly  Leu  Phe  Ser  Val  Trp  Ala  His  Asn  Gly  Glu  Val  Arg
     610                         615                    620

Thr  Thr  Arg  Leu  Leu  Ser  Glu  Arg  Asp  Ala  Gln  Lys  His  Lys  Leu  Leu
625                           630                        635                      640

Leu  Leu  Val  Lys  Asp  Asn  Gly  Asp  Pro  Leu  Arg  Ser  Ala  Asn  Val  Thr
                    645                         650                    655

Leu  His  Val  Leu  Val  Asp  Gly  Phe  Ser  Gln  Pro  Tyr  Leu  Pro  Leu
               660                         665                    670

Ala  Glu  Val  Ala  Gln  Asp  Ser  Met  Gln  Asp  Asn  Tyr  Asp  Val  Leu  Thr
     675                         680                    685
```

```
Leu  Tyr  Leu  Val  Ile  Ala  Leu  Ala  Ser  Val  Ser  Ser  Leu  Phe  Leu  Leu
     690                 695                      700

Ser  Val  Val  Leu  Phe  Val  Gly  Val  Arg  Leu  Cys  Arg  Arg  Ala  Arg  Glu
705                      710                 715                           720

Ala  Ser  Leu  Gly  Asp  Tyr  Ser  Val  Pro  Glu  Gly  His  Phe  Pro  Ser  His
                    725                      730                           735

Leu  Val  Asp  Val  Ser  Gly  Ala  Gly  Thr  Leu  Ser  Gln  Ser  Tyr  Gln  Tyr
               740                      745                      750

Glu  Val  Cys  Leu  Asn  Gly  Gly  Thr  Arg  Thr  Asn  Glu  Phe  Asn  Phe  Leu
          755                      760                      765

Lys  Pro  Leu  Phe  Pro  Ile  Leu  Pro  Thr  Gln  Ala  Ala  Ala  Ala  Glu  Glu
     770                      775                      780

Arg  Glu  Asn  Ala  Val  Val  His  Asn  Ser  Val  Gly  Phe  Tyr
785                 790                      795
```

( 2 ) INFORMATION FOR SEQ ID NO:113:

( i ) SEQUENCE CHARACTERISTICS:
        ( A ) LENGTH: 2347 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:113:

```
AAAACACGGG GGAAATGACA GTAGCAAAGA ATCTGGACTA TGAAGAATGC TCATTGTATG      60
AAATGGAAAT ACAGGCTGAA GATGTGGGGG CGCTTCTGGG GAGGAGCAAA GTGGTAATTA     120
TGGTAGAAGA TGTAAATGAC AATCGGCCAG AAGTGACCAT TACATCCTTG TTTAACCCGG     180
TATTGGAAAA TTCTCTTCCC GGGACAGTAA TTGCCTTCTT GAATGTGCAT GACCGAGACT     240
CTGGAAAGAA CGGCCAAGTT GTCTGTTACA CGCATGATAA CTTACCTTTT AAATTAGAAA     300
AGTCAATAGA TAATTATTAT AGATTGGTGA CATGGAAATA TTTGGACCGA GAAAAAGTCT     360
CCATCTACAA TATCACAGTG ATAGCCTCAG ATCTAGGAGC CCACTCTGTC ACTGAAACTT     420
ACATTGCCCT GATTGTGGCA GACACTAATG ACAACCCTCC TCGTTTTCCT CACACCTCCT     480
ACACAGCCTA TATTCCAGAG AACAACCTGA GGGGCGCCTC CATCTTCTCA CTGACTGCAC     540
ATGATCCTGA CAGTCAGGAA AATGCACAGG TCACTTACTC TGTGTCTGAG GACACCATAC     600
AGGGAGTGCC TTTGTCCTCT TATATCTCCA TCAACTCAGA TACTGGTGTC CTGTATGCAC     660
TGCACTCTTT TGACTTCGAG AAGATACAAG ACTTGCAGCT ACTGGTTGTT GCCACTGACA     720
GTGGAAGCCC ACCTCTCAGC AGCAATGTGT CATTGAGCTT GTTTGTGTTG GACCAGAACG     780
ACAACGCACC TGAGATTCTA TATCCTAGCT TCCCCACAGA TGGCTCCACT GGTGTGGAAC     840
TAGCACCCCG CTCTGCAGAG CCTGGATACC TAGTGACCAA AGTGGTGGCA GTGGACAAAG     900
ACTCAGGACA GAATGCTTGG CTGTCCTACC GTCTGCTGAA GGCCAGCGAA CCTGGGCTCT     960
TCTCTGTAGG ACTTCACACG GGTGAGGTGC GTACAGCGAG GGCCCTGCTG ACAGAGATG     1020
CTCTCAAACA GAATCTGGTG ATGGCCGTGC AGGACCATGG CCAACCCCCT CTCTCGGCCA    1080
CTGTAACTCT CACTGTGGCA GTGGCTAACA GCATCCCTGA GGTGTTGGCT GACTTGAGCA    1140
GCATTAGGAC CCCTGGGGTA CCAGAGGATT CTGATATCAC GCTCCACCTG GTGGTGGCAG    1200
TGGCTGTGGT CTCCTGTGTC TTCCTTGTCT TTGTCATTGT CCTCCTAGCT CTCAGGCTTC    1260
AGCGCTGGCA GAAGTCTCGC CAGCTCCAGG GCTCCAAAGG TGGATTGGCT CCTGCACCTC    1320
CATCACATTT TGTGGGCATC GACGGGGTAC AGGCTTTTCT ACAAACCTAT TCTCATGAAG    1380
```

```
TCTCGCTCAC TTCAGGCTCC CAGACAAGCC ACATTATCTT TCCTCAGCCC AACTATGCAG    1440

ACATGCTCAT TAACCAAGAA GGCTGTGAGA AAAATGATTC CTTATTAACA TCCATAGATT    1500

TTCATGAGAG TAACCGTGAA GATGCTTGCG CCCCGCAAGC CCCGCCCAAC ACTGACTGGC    1560

GTTTCTCTCA AGCCCAGAGA CCCGGCACGA GCGGATCCCA AAATGGGGAT GAAACCGGCA    1620

CCTGGCCCAA CAACCAGTTC GATACAGAGA TGCTGCAAGC CATGATCTTG GCCTCTGCCA    1680

GTGAAGCCGC TGATGGGAGC TCCACTCTGG GAGGGGGCAC TGGCACTATG GGTTTGAGCG    1740

CTCGATATGG ACCCCAGTTT ACCCTGCAGC ACGTGCCTGA CTACCGCCAG AACGTGTACA    1800

TCCCTGGCAG CAATGCCACA CTGACCAACG CAGCTGGCAA ACGAGATGGC AAGGCTCCGG    1860

CAGGCGGCAA TGGCAACAAC AACAAGTCGG GCAAGAAAGA GAAGAAGTAA TATGGAGGCC    1920

AGGCCTTGAG CCACAGGGCA GCCTCCCTCC CCAGCCAGTC CAGCTTGTCC TTACTTGTAC    1980

CCAGGCCTCA GAATTTCAGG GCTCACCCCA GGATTCTGGT AGGAGCCACA GCCAGGCCAT    2040

GCTCCCCGTT GGGAAACAGA AACAAGTGCC CAAGCCAACA CCCCCTCTTT GTACCCTAGG    2100

GGGGTTGAAT ATGCAAAGAG AGTTCTGCTG GGACCCCCTA TCCAATCAGT GATTGTACCC    2160

ACATAGGTAG CAGGGTTAGT GTGGATACAC ACACACAC ACACACAC ACACACAA         2220

CCCTTGTCCT CCGCAGTGCC TGCCACTTTC TGGGACTTTC TCATCCCCCT ACGCCCTTCC    2280

TTTATCCTCT CCCACCCAGA CACAGCTGCT GGAGAATAAA TTTGGGGATG CTGATGCTAA    2340

AAAAAAA                                                              2347
```

(2) INFORMATION FOR SEQ ID NO:114:

(i) SEQUENCE CHARACTERISTICS:
      (A) LENGTH: 2972 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 2..1849

(xi) SEQUENCE DESCRIPTION: SEQ ID NO:114:

```
A GAG GCT GCT CAC CAC CTG GTC CTC ACG GCC TCG GAT GGC GGC AAG              46
  Glu Ala Ala His His Leu Val Leu Thr Ala Ser Asp Gly Gly Lys
  1               5                  10                  15

CCG CCT CGC TCT AGC ACA GTG CGC ATC CAC GTG ACA GTG TTG GAT ACA             94
Pro Pro Arg Ser Ser Thr Val Arg Ile His Val Thr Val Leu Asp Thr
                20                  25                  30

AAT GAC AAT GCC CCG GTT TTT CCT CAC CCG ATT TAC CGA GTG AAA GTC           142
Asn Asp Asn Ala Pro Val Phe Pro His Pro Ile Tyr Arg Val Lys Val
            35                  40                  45

CTT GAG AAC ATG CCC CCA GGC ACG CGG CTG CTT ACT GTA ACA GCC AGC           190
Leu Glu Asn Met Pro Pro Gly Thr Arg Leu Leu Thr Val Thr Ala Ser
        50                  55                  60

GAC CCG GAT GAG GGA ATC AAC GGA AAA GTG GCA TAC AAA TTC CGG AAA           238
Asp Pro Asp Glu Gly Ile Asn Gly Lys Val Ala Tyr Lys Phe Arg Lys
    65                  70                  75

ATT AAT GAA AAA CAA ACT CCG TTA TTC CAG CTT AAT GAA AAT ACT GGG           286
Ile Asn Glu Lys Gln Thr Pro Leu Phe Gln Leu Asn Glu Asn Thr Gly
80                  85                  90                  95

GAA ATA TCA ATA GCA AAA AGT CTA GAT TAT GAA GAA TGT TCA TTT TAT           334
Glu Ile Ser Ile Ala Lys Ser Leu Asp Tyr Glu Glu Cys Ser Phe Tyr
                100                 105                 110

GAA ATG GAA ATA CAA GCC GAA GAT GTG GGG GCA CTT CTG GGG AGG ACC           382
```

-continued

| | | | | | | | | | | | | | | | |
|---|---|---|---|---|---|---|---|---|---|---|---|---|---|---|---|
| Glu | Met | Glu | Ile | Gln | Ala | Glu | Asp | Val | Gly | Ala | Leu | Leu | Gly | Arg | Thr |
| | | | 115 | | | | 120 | | | | | | 125 | | |

| AAA | TTG | CTC | ATT | TCT | GTG | GAA | GAT | GTA | AAT | GAC | AAT | AGA | CCA | GAA | GTG | 430 |
|---|---|---|---|---|---|---|---|---|---|---|---|---|---|---|---|---|
| Lys | Leu | Leu | Ile | Ser | Val | Glu | Asp | Val | Asn | Asp | Asn | Arg | Pro | Glu | Val | |
| | | 130 | | | | 135 | | | | | 140 | | | | | |

| ATC | ATT | ACG | TCT | TTG | TTT | AGC | CCA | GTG | TTA | GAA | AAT | TCT | CTT | CCC | GGG | 478 |
|---|---|---|---|---|---|---|---|---|---|---|---|---|---|---|---|---|
| Ile | Ile | Thr | Ser | Leu | Phe | Ser | Pro | Val | Leu | Glu | Asn | Ser | Leu | Pro | Gly | |
| | 145 | | | | | 150 | | | | | 155 | | | | | |

| ACA | GTA | ATT | GCC | TTC | TTG | AGT | GTG | CAT | GAC | CAA | GAC | TCT | GGA | AAG | AAT | 526 |
|---|---|---|---|---|---|---|---|---|---|---|---|---|---|---|---|---|
| Thr | Val | Ile | Ala | Phe | Leu | Ser | Val | His | Asp | Gln | Asp | Ser | Gly | Lys | Asn | |
| 160 | | | | | 165 | | | | | 170 | | | | | 175 | |

| GGT | CAA | GTT | GTC | TGT | TAC | ACA | CGT | GAT | AAT | TTA | CCT | TTT | AAA | TTA | GAA | 574 |
|---|---|---|---|---|---|---|---|---|---|---|---|---|---|---|---|---|
| Gly | Gln | Val | Val | Cys | Tyr | Thr | Arg | Asp | Asn | Leu | Pro | Phe | Lys | Leu | Glu | |
| | | | | 180 | | | | | 185 | | | | | 190 | | |

| AAG | TCA | ATA | GGT | AAT | TAT | TAT | AGA | TTA | GTG | ACA | AGG | AAA | TAT | TTG | GAC | 622 |
|---|---|---|---|---|---|---|---|---|---|---|---|---|---|---|---|---|
| Lys | Ser | Ile | Gly | Asn | Tyr | Tyr | Arg | Leu | Val | Thr | Arg | Lys | Tyr | Leu | Asp | |
| | | | 195 | | | | | 200 | | | | | 205 | | | |

| CGA | GAA | AAT | GTC | TCT | ATC | TAC | AAT | ATC | ACA | GTG | ATG | GCC | TCA | GAT | CTA | 670 |
|---|---|---|---|---|---|---|---|---|---|---|---|---|---|---|---|---|
| Arg | Glu | Asn | Val | Ser | Ile | Tyr | Asn | Ile | Thr | Val | Met | Ala | Ser | Asp | Leu | |
| | | 210 | | | | | 215 | | | | | 220 | | | | |

| GGA | ACA | CCA | CCT | CTG | TCC | ACT | GAA | ACT | CAA | ATC | GCT | CTG | CAC | GTG | GCA | 718 |
|---|---|---|---|---|---|---|---|---|---|---|---|---|---|---|---|---|
| Gly | Thr | Pro | Pro | Leu | Ser | Thr | Glu | Thr | Gln | Ile | Ala | Leu | His | Val | Ala | |
| | 225 | | | | | 230 | | | | | 235 | | | | | |

| GAC | ATT | AAC | GAC | AAC | CCT | CCT | ACT | TTC | CCT | CAT | GCC | TCC | TAC | TCA | GCG | 766 |
|---|---|---|---|---|---|---|---|---|---|---|---|---|---|---|---|---|
| Asp | Ile | Asn | Asp | Asn | Pro | Pro | Thr | Phe | Pro | His | Ala | Ser | Tyr | Ser | Ala | |
| 240 | | | | | 245 | | | | | 250 | | | | | 255 | |

| TAT | ATC | CTA | GAG | AAC | AAC | CTG | AGA | GGA | GCC | TCC | ATC | TTT | TCC | TTG | ACT | 814 |
|---|---|---|---|---|---|---|---|---|---|---|---|---|---|---|---|---|
| Tyr | Ile | Leu | Glu | Asn | Asn | Leu | Arg | Gly | Ala | Ser | Ile | Phe | Ser | Leu | Thr | |
| | | | | 260 | | | | | 265 | | | | | 270 | | |

| GCA | CAC | GAC | CCC | GAC | AGC | CAG | GAG | AAT | GCC | CAG | GTC | ACT | TAC | TCT | GTG | 862 |
|---|---|---|---|---|---|---|---|---|---|---|---|---|---|---|---|---|
| Ala | His | Asp | Pro | Asp | Ser | Gln | Glu | Asn | Ala | Gln | Val | Thr | Tyr | Ser | Val | |
| | | 275 | | | | | 280 | | | | | 285 | | | | |

| ACC | GAG | GAC | ACG | CTG | CAG | GGG | GCG | CCC | CTG | TCC | TCG | TAT | ATC | TCC | ATC | 910 |
|---|---|---|---|---|---|---|---|---|---|---|---|---|---|---|---|---|
| Thr | Glu | Asp | Thr | Leu | Gln | Gly | Ala | Pro | Leu | Ser | Ser | Tyr | Ile | Ser | Ile | |
| | | 290 | | | | | 295 | | | | | 300 | | | | |

| AAC | TCT | GAC | ACC | GGT | GTC | CTG | TAT | GCG | CTG | CAA | TCT | TTC | GAC | TAT | GAG | 958 |
|---|---|---|---|---|---|---|---|---|---|---|---|---|---|---|---|---|
| Asn | Ser | Asp | Thr | Gly | Val | Leu | Tyr | Ala | Leu | Gln | Ser | Phe | Asp | Tyr | Glu | |
| | 305 | | | | | 310 | | | | | 315 | | | | | |

| CAG | ATC | CGA | GAC | CTG | CAG | CTA | CTG | GTA | ACA | GCC | AGC | GAC | AGC | GGG | GAC | 1006 |
|---|---|---|---|---|---|---|---|---|---|---|---|---|---|---|---|---|
| Gln | Ile | Arg | Asp | Leu | Gln | Leu | Leu | Val | Thr | Ala | Ser | Asp | Ser | Gly | Asp | |
| 320 | | | | | 325 | | | | | 330 | | | | | 335 | |

| CCG | CCC | CTC | AGC | AGC | AAC | ATG | TCA | CTG | AGC | CTG | TTC | GTG | CTG | GAC | CAG | 1054 |
|---|---|---|---|---|---|---|---|---|---|---|---|---|---|---|---|---|
| Pro | Pro | Leu | Ser | Ser | Asn | Met | Ser | Leu | Ser | Leu | Phe | Val | Leu | Asp | Gln | |
| | | | | 340 | | | | | 345 | | | | | 350 | | |

| AAT | GAC | AAC | GCG | CCC | GAG | ATC | CTG | TAC | CCC | GCC | CTC | CCC | ACA | GAC | GGT | 1102 |
|---|---|---|---|---|---|---|---|---|---|---|---|---|---|---|---|---|
| Asn | Asp | Asn | Ala | Pro | Glu | Ile | Leu | Tyr | Pro | Ala | Leu | Pro | Thr | Asp | Gly | |
| | | | 355 | | | | | 360 | | | | | 365 | | | |

| TCC | ACT | GGC | GTG | GAG | CTG | GCG | CCC | CGC | TCC | GCA | GAG | CGT | GGC | TAC | CTG | 1150 |
|---|---|---|---|---|---|---|---|---|---|---|---|---|---|---|---|---|
| Ser | Thr | Gly | Val | Glu | Leu | Ala | Pro | Arg | Ser | Ala | Glu | Arg | Gly | Tyr | Leu | |
| | | 370 | | | | | 375 | | | | | 380 | | | | |

| GTG | ACC | AAG | GTG | GTG | GCG | GTG | GAC | AGA | GAC | TCG | GGC | CAG | AAC | GCC | TGG | 1198 |
|---|---|---|---|---|---|---|---|---|---|---|---|---|---|---|---|---|
| Val | Thr | Lys | Val | Val | Ala | Val | Asp | Arg | Asp | Ser | Gly | Gln | Asn | Ala | Trp | |
| | 385 | | | | | 390 | | | | | 395 | | | | | |

| CTG | TCC | TAC | CGC | CTG | CTC | AAG | GCC | AGC | GAG | CCG | GGA | CTC | TTC | TCG | GTG | 1246 |
|---|---|---|---|---|---|---|---|---|---|---|---|---|---|---|---|---|
| Leu | Ser | Tyr | Arg | Leu | Leu | Lys | Ala | Ser | Glu | Pro | Gly | Leu | Phe | Ser | Val | |
| 400 | | | | | 405 | | | | | 410 | | | | | 415 | |

| GGT | CTG | CAC | ACG | GGC | GAG | GTG | CGC | ACG | GCG | CGA | GCC | CTG | CTG | GAC | AGA | 1294 |
|---|---|---|---|---|---|---|---|---|---|---|---|---|---|---|---|---|
| Gly | Leu | His | Thr | Gly | Glu | Val | Arg | Thr | Ala | Arg | Ala | Leu | Leu | Asp | Arg | |
| | | | 420 | | | | | 425 | | | | | 430 | | | |

| GAC | GCG | CTC | AAG | CAG | AGC | CTC | GTG | GTG | GCC | GTC | CAG | GAC | CAT | GGC | CAG | 1342 |

5,708,143

-continued

| | | | | | | | | | | | | | | | |
|---|---|---|---|---|---|---|---|---|---|---|---|---|---|---|---|
| Asp | Ala | Leu | Lys | Gln | Ser | Leu | Val | Val | Ala | Val | Gln | Asp | His | Gly | Gln |
| | | | 435 | | | | 440 | | | | | | 445 | | |

```
CCC CCT CTC TCC GCC ACT GTC ACG CTC ACC GTA GCC GTG GCT GAC AGC    1390
Pro Pro Leu Ser Ala Thr Val Thr Leu Thr Val Ala Val Ala Asp Ser
        450                 455                 460

ATC CCC GAA GTC CTG ACC GAG TTG GGC AGT CTG AAG CCT TCG GTC GAC    1438
Ile Pro Glu Val Leu Thr Glu Leu Gly Ser Leu Lys Pro Ser Val Asp
    465                 470                 475

CCG AAC GAT TCG AGC CTT ACA CTC TAT CTC GTG GTG GCA GTG GCT GCC    1486
Pro Asn Asp Ser Ser Leu Thr Leu Tyr Leu Val Val Ala Val Ala Ala
480                 485                 490                 495

ATC TCC TGT GTC TTC CTC GCC TTT GTC GCT GTG CTT CTG GGG CTC AGG    1534
Ile Ser Cys Val Phe Leu Ala Phe Val Ala Val Leu Leu Gly Leu Arg
                500                 505                 510

CTG AGG CGC TGG CAC AAG TCA CGC CTG CTC CAG GAT TCC GGT GGC AGA    1582
Leu Arg Arg Trp His Lys Ser Arg Leu Leu Gln Asp Ser Gly Gly Arg
            515                 520                 525

TTG GTA GGC GTG CCT GCC TCA CAT TTT GTG GGT GTT GAG GAG GTA CAG    1630
Leu Val Gly Val Pro Ala Ser His Phe Val Gly Val Glu Glu Val Gln
        530                 535                 540

GCT TTC CTG CAG ACC TAT TCC CAG GAA GTC TCC CTC ACC GCC GAC TCG    1678
Ala Phe Leu Gln Thr Tyr Ser Gln Glu Val Ser Leu Thr Ala Asp Ser
    545                 550                 555

CGG AAG AGT CAC CTG ATC TTT CCC CAG CCC AAC TAC GCA GAC ATG CTC    1726
Arg Lys Ser His Leu Ile Phe Pro Gln Pro Asn Tyr Ala Asp Met Leu
560                 565                 570                 575

ATC AGT CAG GAG GGC TGT GAG AAA AAT GAT TCT TTG TTA ACA TCC GTA    1774
Ile Ser Gln Glu Gly Cys Glu Lys Asn Asp Ser Leu Leu Thr Ser Val
                580                 585                 590

GAT TTT CAT GAA TAT AAG AAT GAA GCT GAT CAT GGT CAG GTG AGT TTA    1822
Asp Phe His Glu Tyr Lys Asn Glu Ala Asp His Gly Gln Val Ser Leu
            595                 600                 605

GTT CTT TGC TTG CTT TTA ATT TCC AGA TGAATTTTAT TTGGCATAAA          1869
Val Leu Cys Leu Leu Leu Ile Ser Arg
        610                 615
```

```
TTATGTTTTG AAAAACATTG TGAAGATAGT TGAAAATAAT TTTTAAGGTG TATCACAGAG    1929
TTTTGGGTTT ATTTTGGTGG TGTTACCAAA AAATTGAACT CTAATAGTCA TAGGTTATTG    1989
TTTCATTTGC TTTTAAACGA CTTGGAAAAG ATTGTTCCAC CATTTTAAAC CTTCCAGTAT    2049
TTTATTCCTA TTATCACTCA TTCACTTAAG AAGTAGCTAC CCGTCCATAC TGGTAATTTT    2109
GCTATTGTTT GTTTGTGTGT GTGTGTGTGT GTGTGTGTGT GTGTGTGTAT CCCAAACTAG    2169
AACTTCAGAA AATTATCAAG AAGTCTAAAG CCTTGTTATT AGCTTAGCAA AAGTAAAATA    2229
TATCTCAGAA TTTTAGGGT TATGTTTAGC ATTTGAACCT GTAACTAGGC TCTTGTATAT     2289
TTCTTCACTT TAAACCTCTT TTCTGAGCCC TGTTTCTGTA CCAGTGCCCT TCAAAACTTT    2349
AATACTTCTT ACCATCCTTC AAAACATGAA CAAACTTTAA AGATGGATCT TGGTGGGAGA    2409
TGAGACTGGT TACTAAATAT TAAGTATGTG AGTCAGTGGT CACCTGGGCT CCATCCCCAT    2469
GGAGACATGA AATCTAAAGC CTAGAATGTC CATTGCTCCC CCAAACAAAA AACAAAAGCA    2529
AAAACATTAG ATCTGAATTA AAATGTAATT TTAAACTGTT GAAAGTGACT TTTGTAAAAT    2589
ATGTAAGAAC ATATTTCAAT ACAATTCCAA TTAGCTGTTT CGGTTGTGCA TTGATGTGAA    2649
GTGGTGAGAA TGTTGATATT AAGAACCAAT GTTTCAGGTA CACAAGTTCT AAATAAGCTG    2709
ATCAATTCAA TTAAAGTTAT TCAGTCTTGG CTGGACACAG TGCCTCATGT CTGAAATCCC    2769
AGCACTTTGG GAGGCTGGGG CAGGAGGACC GCTTGAGCCC CGGGGGTTTG AAACTGCAGT    2829
GAGCTATGAT CATGCCACTG CACTCCAGCC TAGGTGGCAG AACTAGACCC TGTCTCTAAA    2889
```

```
AAAACTATTA TTAGGCCGCG TGCGGTGGCT CACGCCTGTA ATCCCAGCAC TTTGGGAGAC    2949

TGAGGTGGGT GGATCACCTG AGC                                            2972
```

( 2 ) INFORMATION FOR SEQ ID NO:115:

( i ) SEQUENCE CHARACTERISTICS:
        ( A ) LENGTH: 616 amino acids
        ( B ) TYPE: amino acid
        ( D ) TOPOLOGY: linear ( i i ) MOLECULE TYPE: protein ( x i ) SEQUENCE DESCRIPTION: SEQ ID NO:115:

```
Glu Ala Ala His His Leu Val Leu Thr Ala Ser Asp Gly Gly Lys Pro
 1               5                  10                  15

Pro Arg Ser Ser Thr Val Arg Ile His Val Thr Val Leu Asp Thr Asn
            20                  25                  30

Asp Asn Ala Pro Val Phe Pro His Pro Ile Tyr Arg Val Lys Val Leu
        35                  40                  45

Glu Asn Met Pro Pro Gly Thr Arg Leu Leu Thr Val Thr Ala Ser Asp
    50                  55                  60

Pro Asp Glu Gly Ile Asn Gly Lys Val Ala Tyr Lys Phe Arg Lys Ile
65                  70                  75                  80

Asn Glu Lys Gln Thr Pro Leu Phe Gln Leu Asn Glu Asn Thr Gly Glu
                85                  90                  95

Ile Ser Ile Ala Lys Ser Leu Asp Tyr Glu Glu Cys Ser Phe Tyr Glu
            100                 105                 110

Met Glu Ile Gln Ala Glu Asp Val Gly Ala Leu Leu Gly Arg Thr Lys
        115                 120                 125

Leu Leu Ile Ser Val Glu Asp Val Asn Asp Asn Arg Pro Glu Val Ile
    130                 135                 140

Ile Thr Ser Leu Phe Ser Pro Val Leu Glu Asn Ser Leu Pro Gly Thr
145                 150                 155                 160

Val Ile Ala Phe Leu Ser Val His Asp Gln Asp Ser Gly Lys Asn Gly
                165                 170                 175

Gln Val Val Cys Tyr Thr Arg Asp Asn Leu Pro Phe Lys Leu Glu Lys
            180                 185                 190

Ser Ile Gly Asn Tyr Tyr Arg Leu Val Thr Arg Lys Tyr Leu Asp Arg
        195                 200                 205

Glu Asn Val Ser Ile Tyr Asn Ile Thr Val Met Ala Ser Asp Leu Gly
    210                 215                 220

Thr Pro Pro Leu Ser Thr Glu Thr Gln Ile Ala Leu His Val Ala Asp
225                 230                 235                 240

Ile Asn Asp Asn Pro Pro Thr Phe Pro His Ala Ser Tyr Ser Ala Tyr
                245                 250                 255

Ile Leu Glu Asn Asn Leu Arg Gly Ala Ser Ile Phe Ser Leu Thr Ala
            260                 265                 270

His Asp Pro Asp Ser Gln Glu Asn Ala Gln Val Thr Tyr Ser Val Thr
        275                 280                 285

Glu Asp Thr Leu Gln Gly Ala Pro Leu Ser Ser Tyr Ile Ser Ile Asn
    290                 295                 300

Ser Asp Thr Gly Val Leu Tyr Ala Leu Gln Ser Phe Asp Tyr Glu Gln
305                 310                 315                 320

Ile Arg Asp Leu Gln Leu Leu Val Thr Ala Ser Asp Ser Gly Asp Pro
                325                 330                 335
```

-continued

| | | | | | | | | | | | | | | |
|---|---|---|---|---|---|---|---|---|---|---|---|---|---|---|
| Pro | Leu | Ser | Ser 340 | Asn | Met | Ser | Leu 345 | Ser | Leu | Phe | Val | Leu | Asp 350 | Gln | Asn |
| Asp | Asn | Ala 355 | Pro | Glu | Ile | Leu | Tyr 360 | Pro | Ala | Leu | Pro | Thr 365 | Asp | Gly | Ser |
| Thr | Gly 370 | Val | Glu | Leu | Ala | Pro 375 | Arg | Ser | Ala | Glu | Arg 380 | Gly | Tyr | Leu | Val |
| Thr 385 | Lys | Val | Val | Ala | Val 390 | Asp | Arg | Asp | Ser | Gly 395 | Gln | Asn | Ala | Trp | Leu 400 |
| Ser | Tyr | Arg | Leu | Leu 405 | Lys | Ala | Ser | Glu | Pro 410 | Gly | Leu | Phe | Ser | Val 415 | Gly |
| Leu | His | Thr | Gly 420 | Glu | Val | Arg | Thr | Ala 425 | Arg | Ala | Leu | Leu | Asp 430 | Arg | Asp |
| Ala | Leu | Lys 435 | Gln | Ser | Leu | Val | Val 440 | Ala | Val | Gln | Asp | His 445 | Gly | Gln | Pro |
| Pro | Leu 450 | Ser | Ala | Thr | Val | Thr 455 | Leu | Thr | Val | Ala | Val 460 | Ala | Asp | Ser | Ile |
| Pro 465 | Glu | Val | Leu | Thr | Glu 470 | Leu | Gly | Ser | Leu | Lys 475 | Pro | Ser | Val | Asp | Pro 480 |
| Asn | Asp | Ser | Ser | Leu 485 | Thr | Leu | Tyr | Leu | Val 490 | Val | Ala | Val | Ala | Ala 495 | Ile |
| Ser | Cys | Val | Phe 500 | Leu | Ala | Phe | Val | Ala 505 | Val | Leu | Leu | Gly | Leu 510 | Arg | Leu |
| Arg | Arg | Trp 515 | His | Lys | Ser | Arg | Leu 520 | Leu | Gln | Asp | Ser | Gly 525 | Gly | Arg | Leu |
| Val | Gly 530 | Val | Pro | Ala | Ser | His 535 | Phe | Val | Gly | Val | Glu 540 | Glu | Val | Gln | Ala |
| Phe 545 | Leu | Gln | Thr | Tyr | Ser 550 | Gln | Glu | Val | Ser | Leu 555 | Thr | Ala | Asp | Ser | Arg 560 |
| Lys | Ser | His | Leu | Ile 565 | Phe | Pro | Gln | Pro | Asn 570 | Tyr | Ala | Asp | Met | Leu 575 | Ile |
| Ser | Gln | Glu | Gly 580 | Cys | Glu | Lys | Asn | Asp 585 | Ser | Leu | Leu | Thr | Ser 590 | Val | Asp |
| Phe | His | Glu 595 | Tyr | Lys | Asn | Glu | Ala 600 | Asp | His | Gly | Gln | Val 605 | Ser | Leu | Val |
| Leu | Cys 610 | Leu | Leu | Leu | Ile | Ser 615 | Arg | | | | | | | | |

PROTOCADHERIN MATERIALS AND METHODS

This is a Rule 60 Divisional of U.S. application Ser. No. 08/268,161, filed Jun. 27, 1994, which in turn is a continuation-in-part of International Patent Application No. PCT/US93/12588, filed Dec. 23, 1993, which in turn is a continuation-in-part of U.S. patent application Ser. No. 07/998,003, filed Dec. 29, 1992.

FIELD OF THE INVENTION

The present invention relates, in general, to materials and methods relevant to cell-cell adhesion. More particularly, the invention relates to novel adhesion proteins, designated protocadherins, and to polynucleotide sequences encoding the protocadherins. The invention also relates to methods for inhibiting binding of the protocadherins to their natural ligands/antiligands.

BACKGROUND

In vivo, intercellular adhesion plays an important role in a wide range of events including morphogenesis and organ formation, leukocyte extravasion, tumor metastasis and invasion, and the formation of cell junctions. Additionally, cell-cell adhesion is crucial for the maintenance of tissue integrity.

Intercellular adhesion is mediated by specific cell surface adhesion molecules. Cell adhesion molecules have been classified into at least four families including the immunoglobulin superfamily, the integrin superfamily, the selectin family and the cadherin superfamily. All cell types that form solid tissues express some members of the cadherin superfamily suggesting that cadherins are involved in selective adhesion of most cell types.

Cadherins have been generally described as glycosylated integral membrane proteins that have an N-terminal extracellular domain (the N-terminal 113 amino acids of the domain appear to be directly involved in binding) consisting of five subdomains characterized by sequences unique to cadherins, a hydrophobic membrane-spanning domain and a C-terminal cytoplasmic domain that interacts with the cytoskeleton through carenins and other cytoskeleton-associated proteins. Some cadherins lack a cytoplasmic domain, however, and appear to function in cell-cell adhesion by a different mechanism than cadherins having a cytoplasmic domain. The cytoplasmic domain is required for the adhesive function of the extracellular domain in cadherins that do have an cytoplasmic domain. Binding between members of the cadherin family expressed on different cells is homophilic (i.e., a member of the cadherin family binds to cadherins of its own or a closely related subclass) and $Ca^{2+}$-dependent. For recent reviews on cadherins, see Takeichi, Annu. Rev. Biochem., 59: 237-252 (1990) and Takeichi, Science, 251: 1451-1455 (1991).

The first cadherins to be described (E-cadherin in mouse epithelial cells, L-CAM in arian liver, uvomorulin in the mouse blastocyst, and CAM 120/80 in human epithelial cells) were identified by their involvement in $Ca^{2+}$-dependent cell adhesion and their unique immunological characteristics and tissue localization. With the later immunological identification of N-cadherin, which was found to have a different tissue distribution than E-cadherin, it became apparent that a new family of $Ca^{2+}$-dependent cell-cell adhesion molecules had been discovered.

The molecular cloning of the genes encoding E-cadherin [see Nagafuchi et al., Nature, 329:341-343 (1987)], N-cadherin [Hatta et al., J. Cell. Biol., 106: 873-881 (1988)], and P-cadherin [Nose et al., EMBO J., 6: 3655-3661 (1987)] provided structural evidence that the cadherins comprised a family of cell adhesion molecules. Cloning of L-CAM [Gillin et al., Proc. Natl. Acad. Sci. USA, 84: 2808-2812 (1987)] and uvomorulin [Ringwald et al., EMBO J., 6: 3647-3653 (1986)] revealed that they were identical to E-cadherin. Comparisons of the amino acid sequences of E-, N-, and P-cadherins showed a level of amino acid similarity of about 45%-58% among the three subclasses. Liaw et al., EMBO J., 9: 2701-2708 (1990) describes the use of PCR with degenerate oligonucleotides based on conserved regions of the E-, N- and P-cadherins to amplify N- and P-cadherin from a bovine microvascular endothelial cell cDNA.

The isolation by PCR of eight additional cadherins was reported in Suzuki et al., Cell Regulation, 2: 261-270 (1991). Subsequently, several other cadherins were described including R-cadherin [Inuzuka et al., Neuron, 7: 69-79 (1991)], M-cadherin [Donalies, Proc. Natl. Acad. Sci. USA, 88: 8024-8028 (1991)], B-cadherin [Napolitano, J. Cell. Biol., 113: 893-905 (1991)] and T-cadherin [Ranscht, Neuron, 7: 391-402 (1991)].

Additionally, proteins distantly related to cadherins such as desmoglein [Goodwin et al., Biochem. Biophys. Res. Commun., 173: 1224-1230 (1990) and Koch et al., Eur. J. Cell Biol., 53: 1-12 (1990)] and the desmocollins [Holton et al., J. Cell Science, 97: 239-246 (1990)] have been described. The extracellular domains of these molecules are structurally related to the extracellular domains of typical cadherins, but each has a unique cytoplasmic domain. Mahoney et al., Cell, 67: 853-868 (1991) describes a tumor suppressor gene of Drosophila, called fat, that also encodes a cadherin-related protein. The fat tumor suppressor comprises 34 cadherin-like subdomains followed by four EGF-like repeats, a transmembrane domain, and a novel cytoplasmic domain. The identification of these cadherin-related proteins is evidence that a large superfamily characterized by a cadherin extracellular domain motif exists.

Studies of the tissue expression of the various cadherin-related proteins reveal that each subclass of molecule has a unique tissue distribution pattern. For example, E-cadherin is found in epithelial cells while N-cadherin is found in neural and muscle cells. Expression of cadherin-related proteins also appears to be spatially and temporally regulated during development because individual proteins appear to be expressed by specific cells and tissues at specific developmental stages [for review see Takeichi (1991), supra]. Both the ectopic expression of cadherin-related proteins and the inhibition of native expression of cadherin-related proteins hinders the formation of normal tissue structure [Detrick et al., Neuron, 4: 493-506 (1990); Fujimoil et al., Development, 110: 97-104 (1990); Kintner, Cell, 69: 225-236 (1992)].

The unique temporal and tissue expression pattern of the different cadherins and cadherin-related proteins is particularly significant when the role each subclass of proteins may play in vivo in normal events (e.g., the maintenance of the intestinal epithelial barrier) and in abnormal events (e.g., tumor metastasis or inflammation) is considered. Different subclasses or combinations of subclasses of cadherin-related proteins are likely to be responsible for different cell-cell adhesion events in which therapeutic detection and/or intervention may be desirable. For example, auto-antibodies from patients with pemphigus vulgaris, an autoimmune skin disease characterized by blister formation caused by loss of cell adhesion, react with a cadherin-related protein offering direct support for adhesion function of cadherins in vivo [Amagai et al., *Cell*, 67: 869–877 (1991)]. Studies have also suggested that cadherins and cadherin-related proteins may have regulatory functions in addition to adhesive activity. Matsunaga et al., *Nature*, 334: 62–64 (1988) reports that N-cadherin has neurite outgrowth promoting activity. The Drosophila fat tumor supressor gene appears to regulate cell growth and supress tumor invasion as does mammalian E-cadherin [see Mahoney et al., supra; Frixen et al., *J. Cell. Biol.*, 113:173–185 (1991); Chen et al., *J. Cell, Biol.*, 114:319–327 (1991); and Vleminckx et al., *Cell*, 66:107–119 (1991)]. Thus, therapeutic intervention in the regulatory activities of cadherin-related proteins expressed in specific tissues may be desirable.

There thus continues to exist a need in the art for the identification and characterization of additional cadherin-related proteins which participate in cell-cell adhesion and/or regulatory events. Moreover, to the extent that cadherin-related proteins might form the basis for the development of therapeutic and diagnostic agents, it is essential that the genes encoding the proteins be cloned. Information about the DNA sequences and amino acid sequences encoding the cadherin-related proteins would provide for the large scale production of the proteins by recombinant techniques and for the identification of the tissues/cells naturally producing the proteins. Such sequence information would also permit the preparation of antibody substances or other novel binding molecules specifically reactive with the cadherin-related proteins that may be useful in modulating the natural ligand/antiligand binding reactions in which the proteins are involved.

SUMMARY OF THE INVENTION

The present invention provides cadherin-related materials and methods that are relevant to cell-cell adhesion. in one of its aspects, the present invention provides purified and isolated polynucleotides (e.g., DNA and RNA, both sense and antisense strands) encoding the novel cell adhesion molecules designated herein as protocadherins, including protocadherin-42, protocadherin-43, protocadherin pc3, protocadherin pc4 and protocadherin pc5. Preferred polynucleotide sequences of the invention include genomic and cDNA sequences as well as wholly or partially synthesized DNA sequences, and biological replicas thereof (i.e., copies of the sequences made in vitro). Biologically active vectors comprising the polynucleotide sequences are also contemplated.

Specifically illustrating protocadherin polynucleotide sequences of the present invention are the inserts in the plasmids pRC/RSV-pc42 and pRC/RSV-pc43 which were deposited with the American Type Culture Collection (ATCC), 12301 Parklawn Drive, Rockville, Md. 20852 on Dec. 16, 1992 and were assigned ATCC Accession Nos. 69162 and 69163, respectively.

The scientific value of the information contributed through the disclosures of the DNA and amino acid sequences of the present invention is manifest. For example, knowledge of the sequence of a partial or complete DNA encoding a protocadherin makes possible the isolation by standard DNA/DNA hybridization or PCR techniques of full length cDNA or genomic DNA sequences that encode the protein (or variants thereof) and, in the case of genomic DNA sequences, that specify protocadherin-specific regulatory sequences such as promoters, enhancers and the like. Alternatively, DNA sequences of the present invention may be chemically synthesized by conventional techniques. Hybridization and PCR techiques also allow the isolation of DNAs encoding heterologous species proteins homologous to the protocadherins specifically illustrated herein.

According to another aspect of the invention, host cells, especially eucaryotic and procaryotic cells, are stably transformed or transfected with the polynucleotide sequences of the invention in a manner allowing the expression of ptotocadherin polypeptides in the cells. Host cells expressing protocadherin polypeptide products, when grown in a suitable culture medium, are particularly useful for the large scale production of protocadherin polypeptides, fragments and variants thereby enabling the isolation of the desired polypeptide products from the cells or from the medium in which the cells are grown.

The novel protocadherin protein products of the invention may be obtained as isolates from natural tissue sources, but are preferably produced by recombinant procedures involving the host cells of the invention. The products may be obtained in fully or partially glycosylated, partially or wholly de-glycosylated, or non-glycosylated forms depending on the host cell selected or recombinant production and/or post-isolation processing.

Protocadherin variants according to the invention may comprise polypeptide analogs wherein one or more of the specified amino acids is deleted or replaced or wherein one or more non-naturally encoded amino acids are added: (1) without loss, and preferably with enhancement, of one or more of the biological activities or immunological characteristics specific for a protocadherin; or (2) with specific disablement of a particular ligand/antiligand binding function. Also contemplated by the present invention are antibody substances (e.g., monoclonal and polyclonal antibodies, chimeric and humanized antibodies, antibody domains including Fab, Fab', F(ab')$_2$, Fv or single variable domains, and single chain antibodies) which are specific for the protocadherins of the invention. Antibody substances can be developed using isolated natural, recombinant or synthetic protocadherin polypeptide products or host cells expressing such products on their surfaces. The antibody substances may be utilized for purifying protocadherin polypeptides of the invention, for determining tissue expression of polypeptides and as antagonists of the ligand/antiligand binding activities of the protocadherins. Specifically illustrating monoclonal antibodies of the present invention are the protocadherin-43 specific monoclonal antibodies produced by the hybridoma cell line designated 38I2C which was deposited with the ATCC on Dec. 2, 1992 and was assigned ATCC Accession No. HB 11207.

Numerous other aspects and advantages of the present invention will be apparent upon consideration of the following detailed description, reference being made to the drawing wherein FIGS. 1A–C is an alignment of protocadherin amino acid sequences of the invention with the amino acid sequences of N-cadherin and of the Drosophila fat tumor suppressor.

BRIEF DESCRIPTION OF THE DRAWINGS

FIGS. 1A–1C presents an alignment of the deduced amino acid sequences of the extracellular subdomains of pc42 (EC-1 through EC-7), pc43 (EC-1 through EC-6), mouse N-Cadherin (EC-1 through EC-5) and Drosophila fat EC-18. A sequence on a line in FIG. 1A continues on the same line in FIGS. 1B and 1C.

DETAILED DESCRIPTION

The present invention is illustrated by the following examples wherein Examples 1, 2 and 3 describe the isolation by PCR of protocadherin polynucleotide sequences. Example 3 also describes the chromosome localization of several protocadherin genes of the invention. Example 4 describes the isolation by DNA/DNA hybridization of additional protocadherin polynucleotide sequences of the present invention. Example 5 presents the construction of expression plasmids including polynucleotides encoding protocadherin-42 or protocadherin-43 and the transfection of L cells with the plasmids. The generation of antibodies to protocadherin-42 and protocadherin-43 is described in Example 6. Example 7 presents the results of immunoassays of transfected L cells for the expression of protocadherin-42 or protocadherin-43. Example 8 describes the cell aggregation properties of L cells transfected with protocadherin-42, protocadherin-43 or a chimeric protoeadherin43/E-cadherin molecule. The calcium-binding properties of pc43 are described in Example 9. The results of assays of various tissues and cell lines for the expression of protocadherin-42 and protocadherin-43 by Northern blot, Western blot and in situ hybridization are respectively presented in Examples 10, 11 and 12. Example 13 describes immunoprecipitation experiments identifying a 120 kDa protein that coprecipitates with protocadherin-43.

EXAMPLE 1

The polymerase chain reaction (PCR) was used to isolate novel rat cDNA fragments encoding cadherin-related polypeptides.

Design of PCR Primers

Two regions of conserved amino acid sequence, one from the middle of the third cadherin extracellular subdomain (EC-3) and the other from the C-terminus of the fourth extracellular subdomain (EC-4), were identified by comparison of the published amino acid sequences for L-CAM (Gallin et al., supra), E-cadherin (Nagafuchi et al., supra), mouse P-cadherin (Nose et al., supra), uvomorulin (Ringwald et al., supra), chicken N-cadherin (Hatta et al., supra), mouse N-cadherin [Miyatani et al., Science, 245:631–635 (1989)] and human P-cadherin [Shimoyama et al., J. Cell. Biol., 109:1787–1794 (1989)], and the corresponding degenerate oligonucleotides respectively set out below in IUPAC-IUB Biochemical nomenclature were designed for use as PCR primers.

Primer 1 (SEQ ID NO: 1)

5' AARSSNNTNGAYTRYGA 3'

Primer 2 (SEQ ID NO: 2)

3' TTRCTRTTRCGNGGNNN 5'

The degenerate oligonucleotides were synthesized using an Applied Biosystems model 380B DNA synthesizer (Foster City, Calif.).

Cloning of cDNA Sequences by PCR

PCR was carried out in a manner similar to that described in Suzuki et al., Cell Regulation, 2: 261–270 (1991) on a rat brain cDNA preparation. Total RNA was prepared from rat brain by the guanidium isothiocyanate/cesium chloride method described in Maniatis et al., pp. 196 in Molecular Cloning: A Laboratory Manual, Cold Spring Harbor, N.Y.: Cold Spring Harbor Laboratory (1982). Brain poly(A)$^+$ RNAs were then isolated using a FastTrack® kit (Invitrogen, San Diego, Calif.) and cDNA was prepared using a cDNA synthesis kit (Boehringer Mannheim Biochemicals, Indianapolis, Ind.). The PCR reaction was initiated by adding 2.5 units of Taq DNA polymerase (Boehringer Mannheim Biochemicals) to 100 ng template cDNA and 10 µg of each primer, after which 35 reaction cycles of denaturation at 94° C. for 1.5 minutes, annealing at 45° C. for 2 minutes, and polymerization at 72° C. for 3 minutes were carried out. Two major bands of about 450 base pairs (bp) and 130 bp in size were found when the products of the PCR reaction were subjected to agarose gel electrophoresis. The 450 bp band corresponded to the expected length between the two primer sites corresponding to the middle of the third cadherin extracellular subdomain (EC-3) and the carboxyl terminus of the fourth cadherin extracellular subdomain (EC-4), but the 130 bp band could not be predicted from any of the previously identified cadherin sequences. The 450 bp and 130 bp bands were extracted by a freezing and thawing method. The resulting fragments were phosphorylated at the 5' end with T4 polynucleotide kinase and subcloned by a blunt-end ligation into the Sma I site of M13mp18 (Boehringer Mannheim Biochemicals) in a blunt end ligation for sequence analysis. Sequencing of the fragments was carried out by the dideoxynucleotide chain termination method using a Sequenase kit (United States Biochemicals, Cleveland, Ohio). DNA and amino acid sequence were analyzed using the Beckman Microgenic program (Fullerton, Calif.).

Analysis of cDNA Sequences

Nineteen novel partial cDNA clones were isolated. The DNA and deduced amino acid sequences of the clones (including sequences corresponding to the PCR primers) are set out as follows: RAT-123 (SEQ ID NOs: 3 and 4, respectively), RAT-212 (SEQ ID NOs: 5 and 6), RAT-214 (SEQ ID NOs: 7 and 8), RAT-216 (SEQ ID NOs: 9 and 10), RAT-218 (SEQ ID NOs: 11 and 12), RAT-224 (SEQ ID NOs: 13 and 14), RAT-312 (SEQ ID NOs: 15 and 16), RAT-313 (SEQ ID NOs: 17 and 18), RAT-314 (SEQ ID NOs: 19 and 20), RAT-315 (SEQ ID NOs: 21 and 22), RAT-316 (SEQ ID NOs: 23 and 24), RAT-317 (SEQ ID NOs: 25 and 26), RAT-321 (SEQ ID NOs: 27 and 28), RAT-323 (SEQ ID NOs: 29 and 30), RAT-336 (SEQ ID NOs: 31 and 32), RAT-352 (SEQ ID NOs: 33 and 34), RAT-411 (SEQ ID NOs: 35 and 36), RAT-413 (SEQ ID NOs: 37 and 38), and RAT-551 (SEQ ID NOs: 39 and 40).

The deduced amino acid sequences of the cDNA clones are homologous to, but distinct from the known cadherins. The cadherins described thus far have highly conserved, short amino acid sequences in the third extracellular subdomain (EC-3) including the consensus sequence D-Y-E or D-F-E located at the middle region of the subdomain and the consensus sequence D-X-N-E-X-P-X-F (SEQ ID NO: 41) or D-X-D-E-X-P-X-F (SEQ ID NO: 42) at its end (Hatta et al., supra), while the corresponding sequences of other subdomains, except for the fifth extracellular subdomain (EC-5), are D-R-E and D-X-N-D-N-X-P-X-F (SEQ ID NO: 43), respectively. In contrast, the deduced amino acid sequences of the new clones that correspond to cadherin extracellular subdomains include the sequence D-Y-E or D-F-E at one end, but have the sequence D-X-N-D-N-X-P-X-F instead of D-X-N-E-X-P-X-F or D-X-D-E-X-P-X-F, at the other end. The polypeptides encoded by the partial clones are homologous to previously identified cadherins but did not show significant homology to any other sequences in Genbank. Therefore, the partial cDNAs appear to comprise a new subclass of cadherin-related molecules.

EXAMPLE 2

Various cDNA fragments structurally similar to the rat cDNAs described in Example 1 were isolated from human, mouse, and Xenopus brain cDNA preparations and from Drosophila and C. elegans whole body cDNA preparations by PCR using Primers 1 and 2 as described in Example 1. The DNA and deduced amino acid sequences of the resulting PCR fragments (including sequences corresponding to the PCR primers) are set out as follows: MOUSE-321 (SEQ ID NOs: 44 and 45), MOUSE-322 (SEQ ID NOs: 46 and 47), MOUSE-324 (SEQ ID NOs: 48 and 49), MOUSE-326 (SEQ ID NOs: 50 and 51), HUMAN-11 (SEQ ID NOs: 52 and 53), HUMAN-13 (SEQ ID NOs: 54 and 55), HUMAN-21 (SEQ ID NOs: 56 and 57), HUMAN-24 (SEQ ID NOs: 58 and 59), HUMAN-32 (SEQ ID NOs: 60 and 61), HUMAN-42 (SEQ ID NOs: 62 and 63), HUMAN-43 (SEQ ID NOs: 64 and 65), HUMAN-212 (SEQ ID NOs: 66 and 67), HUMAN-213 (SEQ ID NOs: 68 and 69), HUMAN-215 (SEQ ID NOs: 70 and 71), HUMAN-223 (SEQ ID NOs: 72 and 73), HUMAN-410 (SEQ ID NOs: 74 and 75), HUMAN-443 (SEQ ID NOs: 76 and 77), XENOPUS-21 (SEQ ID NOs: 78 and 79), XENOPUS-23 (SEQ ID NOs: 80 and 81), XENOPUS-25 (SEQ ID NOs: 82 and 83), XENOPUS-31 (SEQ ID NOs: 84 and 85), DROSOPHILA-12 (SEQ ID NOs: 86 and 87), DROSOPHILA-13 (SEQ ID NOs: 88 and 89), DROSOPHILA-14 (SEQ ID NOs: 90 and 91) and C.ELEGANS-41 (SEQ ID NOs: 92 and 93). Comparison of the deduced amino acid sequences indicates significant similarity between sets of these clones. In particular, there are three sets of clones that appear to be cross-species homologues: RAT-218, MOUSE-322 and HUMAN-43; RAT-314, MOUSE-321 and HUMAN-11; and MOUSE-326 and HUMAN-42.

EXAMPLE 3

To ascertain the complete structure of the new proteins defined by the PCR products, two full length human cDNAs corresponding to the partial cDNAs HUMAN-42 and HUMAN-43 were isolated.

Isolation of Full-length Human cDNAs

A human fetal brain cDNA library (Stratagene, La Jolla, Calif.) in the λZapII vector was screened by the plaque hybridization method [described in Ausubel et al, Eds., *Current Protocols in Molecular Biology*, Sections 6.1.1 to 6.1.4 and 6.2.1 to 6.2.3, John Wiley & Sons, New York (1987)] with $^{32}$P-labelled HUMAN-42 and HUMAN-43 DNA fragments. The positive clones were plaque-purified and, using a helper virus, the inserts were cut out by an in vivo excision method in the form of a Bluescript SK(+) plasmid. The insert sequences were then subcloned into the M13 vector (Boehringer Mannheim, Biochemicals) for sequencing. Several overlapping cDNA clones were isolated with each probe including two cDNAs which contained the putative entire coding sequences of two novel proteins designated protocadherin-42 (pc42) and protocadherin-43 (pc43). The DNA and deduced amino acid sequences of pc42 are set out in SEQ ID NOs: 94 and 95, respectively, while the DNA and deduced amino acid sequences of pc43 are set out in SEQ ID NOs: 96 and 97, respectively.

A description of the cloning of protocadherin sequences of the invention was published in Sano et al., *The EMBO Journal*, 12(6): 2249–2256 (1993) after filing of the priority application hereto. The deduced amino acid sequence of pc43 was previously presented at the Dec. 9, 1991 meeting of the American Society for Cell Biology. An abstract of the presentation is published as Suzuki et al., *J. Cell. Biol.*, 115: 72a (Abstract 416) (Dec. 9, 1991).

Analysis of Full-length Human Clones

Comparison of the full length cDNA sequences of pc42 and pc43 to the sequences of the various DNA fragments originally obtained by PCR reveals that MOUSE-326 and HUMAN-42 correspond to a potion of the fourth extracellular subdomain (EC-4) of pc42, and RAT-314, MOUSE-321, and HUMAN-11 correspond to a portion of the third extracellular subdomain (EC-3) of pc43 and RAT-218, MOUSE-322 and HUMAN-43 correspond to a portion of the fifth extracellular domain (EC-5) of pc43.

The overall structures of pc42 and pc43 are similar to that of typical cadherins but the new molecules also have distinct features. Both protocadherin cDNA sequences contain putative translation initiation sites and translated amino acid sequences start with typical signal sequences, but the clones lack the prosequences that are present in all known cadherin precursors. The cDNAs encode proteins having a large N-terminal extracellular domain and a relatively short C-terminal cytoplasmic domain connected by a transmembrane sequence. The extracellular domains of pc42 and pc43 are different in length and pc42 contains seven subdomains that closely resemble the typical cadherin extracellular subdomain while pc43 has six such subdomains. The sizes of the protocadherin cytoplasmic domains are similar to those of typical cadherins, but the sequences do not show any significant homology with those of known cadherins or cadherin-related proteins.

Amino acid identity determinations between extracellular subdomains of human pc42 and pc43, and of mouse N-cadherin (SEQ ID NO: 98) (presented as an example of a "typical" cadherin) and the eighteenth extracellular subdomain of Drosophila fat tumor suppressor (EC-18, SEQ ID NO: 99) (the eighteenth extracellular subdomain of fat is a prototypical fat subdomain) are presented in Table 1 below, wherein, for example, "N-EC-1×pc42" indicates that the first extracellular subdomain of N-cadherin was compared to the extracellular subdomain of pc42 indicated on the horizonal axis.

TABLE 1

|  | EC-1 | EC-2 | EC-3 | EC-4 | EC-5 | EC-6 | EC-7 |
|---|---|---|---|---|---|---|---|
| N-EC-1 × pc42 | 20 | 27 | 26 | 26 | 31 | 29 | 17 |
| N-EC-1 × pc43 | 31 | 23 | 23 | 26 | 31 | 24 |  |
| N-EC-2 × pc42 | 28 | 30 | 32 | 30 | 37 | 31 | 19 |
| N-EC-2 × pc43 | 30 | 28 | 30 | 36 | 29 | 30 |  |
| N-EC-3 × pc42 | 21 | 26 | 30 | 29 | 31 | 30 | 22 |
| N-EC-3 × pc43 | 25 | 18 | 26 | 28 | 28 | 25 |  |
| N-EC-4 × pc42 | 28 | 28 | 26 | 25 | 29 | 27 | 17 |
| N-EC-4 × pc43 | 21 | 25 | 28 | 28 | 29 | 24 |  |
| N-EC-5 × pc42 | 24 | 21 | 25 | 24 | 24 | 19 | 12 |
| N-EC-5 × pc43 | 15 | 21 | 20 | 20 | 25 | 16 |  |
| fat EC-18 × pc42 | 22 | 35 | 32 | 34 | 42 | 35 | 19 |
| fat EC-18 × pc43 | 32 | 30 | 36 | 36 | 33 | 29 |  |

The amino acid identity values between the extracellular subdomains of pc42 and pc43, and N-cadherin EC-1 through EC-5 and Drosophila fat EC-18 are mostly less than 40%. These identity values are comparable to the values between the subdomains of other cadherin subclasses. However, higher identity values indicate that pc42 and pc43 are more closely related to fat than to N-cadherin.

Amino acid identity determinations between extracellular subdomains of human pc42 and pc43 are presented in Table 2 below.

TABLE 2

| | pc42 | | | | | | |
|---|---|---|---|---|---|---|---|
| pc43 | EC-1 | EC-2 | EC-3 | EC-4 | EC-5 | EC-6 | EC-7 |
| EC-1 | 33 | 27 | 29 | 26 | 25 | 26 | 25 |
| EC-2 | 26 | 38 | 29 | 33 | 34 | 28 | 21 |
| EC-3 | 26 | 32 | 41 | 30 | 32 | 31 | 22 |
| EC-4 | 25 | 34 | 30 | 41 | 39 | 31 | 18 |

TABLE 2-continued

| | | | pc42 | | | | |
|---|---|---|---|---|---|---|---|
| pc43 | EC-1 | EC-2 | EC-3 | EC-4 | EC-5 | EC-6 | EC-7 |
| EC-5 | 23 | 32 | 29 | 27 | 36 | 34 | 16 |
| EC-6 | 25 | 25 | 26 | 25 | 28 | 23 | 26 |

The identity values between respective EC-1, EC-2, EC-3, EC-4, EC-5 subdomains and the last subdomains of pc42 and pc43 are generally higher values than values obtained for comparisons of the protocadherins to N-cadherin. These results suggest that pc42 and pc43 are more closely related to one another than they are to classic cadherins.

FIGS. 1A–C presents an alignment of the deduced amino acid sequences of the extracellular subdomains of pc42 (EC-1 through EC-7) (amino acids 42–818 of SEQ ID NO: 95), pc43 (EC-1 through EC-6) (amino acids 29–688 of SEQ ID NO: 97), mouse N-cadherin (EC-1 through EC-5) (amino acids 1–557 of SEQ ID NO: 98) and Drosophila fat EC-18 (SEQ ID NO: 99). A sequence on a line in FIG. 1A continues on the same line in FIGS. 1B and 1C. Gaps were introduced to maximize homology. In FIGS. 1A–1C, the position at which an amino acid appears in a SEQ ID NO is indicated in parenthesis. For example, in FIG. 1A the first amino acid of EC1 of protocadherin-43 is an alanine which appears at position 29 in SEQ ID NO: 97 and the last amino acid of the protocadherin-43 EC1 appearing in FIG. 1A is an alanine which appears at position 63 in SEQ ID NO: 97. The amino acid residues described by capital letters in the "motif" line are present in more than half of the subdomains of N-cadherin, pc42, pc43 and Drosophila fat. The amino acid residues described by small letters in the motif line are less well conserved in human pc42, pc43, and Drosophila fat. FIGS. 1A–C shows that many amino acids characteristic of other cadherin extracellular domain repeats are conserved in the pc42 and pc43 sequences, including the cadherin sequence motifs DXD, DRE and DXNDNXPXF (SEQ ID NO: 43), two glycine residues, and one glutamic acid residue. Additionally, pc42 and pc43 share unique futures in comparison to N-cadherin. More amino acids at specific sites are conserved between pc42 and pc43, such as the DXDXGXN (SEQ ID NO: 100) protocadherin sequence motif near the amino terminus of the pc42 and pc43 subdomains and the AXDXGXP (SEQ ID NO: 101) sequence motif near the carboxyl terminus of the subdomains. Additionally, both protocadherins share regions that do not show significant homology with the typical cadherin motif (of N-cadherin) near the carboxyl terminus of EC-1, in the middle of EC-2 and EC-4, and at the carboxyl terminus of the last repeat. A cysteine residue is located at a similar position in the middle of EC-4 of pc42 and pc43. In general, the extracellular subdomains of pc42 and pc43 are more similar to EC-18 of fat than the extracellular subdomains of N-cadherin.

Possible Alternative Splicing

Sequence analysis of various overlapping protocadherin cDNA clones revealed that some clones contained unique sequences at the 3' end, although the 5' end sequences were identical to other clones. The sequences forming the boundaries of the 3' end regions are consistent with the consensus sequence of mRNA splicing, suggesting that these clones may correspond to alternatively spliced mRNAs. The DNA and deduced amino acid sequences of one possible product of alternative splicing of pc42 mRNA are set out in SEQ ID NOs: 102 and 103. The DNA and deduced amino acid sequences of two possible products of alternative splicing of pc43 mRNA are respectively presented in SEQ ID NO: 104 and 105, and SEQ ID NOs: 106 and 107.

Chromosome Localization

The chromosomal location of the protocadherin 413 gene (SEQ ID NO: 37) and of the pc42 and pc43 genes was determined by conventional methods.

Briefly, C3H/HeJ-gld and Mus spretus (Spain) mice and [(C3H/HeJ-gld×Mus spretus) $F_1$×C3H/HeJ-gld] interspecies backcross mice were bred and maintained as previously described in Seldin, et al., *J. Exp. Med.*, 167: 688–693 (1988). *Mus spretus* was chosen as the second parent in the cross because of the relative ease of detection of informative restriction fragment length variants (RFLVs) in comparison with crosses using conventional inbred laboratory strains. Gene linkage was determined by segregation analysis.

Genomic DNA isolated from mouse organs by standard techniques was digested with restriction endonucleases and 10 μg samples were electrophoresed in 0.9% agarose gels. DNA was transferred to Nytran membranes (Schleicher & Schull, Inc., Keene, N.H.), hybridized with the appropriate probe at 65° C. and washed under stringent conditions, all as previously described in Maniatis et al., supra). To localize the pc42 gene, a mouse sequence probe corresponding to nucleotides 1419 to 1906 of SEQ ID NO: 94 was used and for pc43 a rat sequence probe corresponding to nucleotides 1060 to 1811 of SEQ ID NO: 96 was used. To localize the procadherin 413 gene, a probe including the sequence set out in SEQ ID NO: 37 was used. Other clones used as probes in the current study and RFLVs used to detect anonymous DNA loci were all previously described [Chromosome 7, DNA segment, Washington 12 (D7Was12); the parathyroid hormone (Pth); calcitonin (Calc); hemoglobin, β chain (Hbb); metallothionein-I (Mt-1); adenine phosphoribosyl-transferase (Aprt); growth hormone receptor (Ghr); prostaglandin E receptor EP2 subtype (Ptgerep2); dihydrofolate reductase-2 (Dhfr2); fibroblast growth factor a (Fgfa); and ghcocorticoid receptor-1 (Grl-1)].

Comparison of the haplotype distribution of protocadherin genes with those determined for loci throughout the mouse genome allowed each to be mapped to specific regions of mouse chromosomes. The probability for linkage was >99% and indicated assignment of both the pc42 gene and the pc43 gene was chromosome 18. The assignment of the protocadherin 413 gene was chromosome 7. The region of chromosome 18 to which the pc42 and pc43 genes were mapped corresponds to the ataxia (ax) loci [Burt, *Anat. Rec.*, 196: 61–69 (1980) and Lyon, *J. Hered.*, 46: 77–80 (1955)] and twirler (Tw) loci [Lyon, *J. Embryol. Exp. Morphol.*, 6: 105–116 (1958)], while the region of chromosome 7 to which the protocadherin 413 gene was mapped corresponds to the shaker (sh-1) locus [Kikuchi et al., *Acta Oto-Laryngol.*, 60 : 287–303 (1965) and Lord et al., *Am. Nat.*, 63: 453–442 (1929)]. These loci have been implicated as involved in hereditary neural disease in the mouse. This result is consistent with in situ hybridization results (see Example 12) showing that pc42 and pc43 are strongly expressed in the brain and particularly in the cerebellum.

EXAMPLE 4

Two additional novel human protocadherin cDNAs and one additional novel rat protocadherin cDNA were isolated using rat protocadherin fragments described in Example 1 as probes.

Initially, the rat clone RAT-214 (SEQ ID NO: 7) was used as a probe to screen a rat brain cDNA library (Stratagene, La Jolla, Calif.). The final washing step was performed twice at 50° C. in 0.1× SSC with 0.1% SDS for 15 minutes. Various clones were identified which contained partial cDNA inserts encoding related protocadherin amino acid sequences. The nucleotide sequence of one novel rat clone designated #6-2 is set out in SEQ ID NO: 108. The first fifteen nucleotides of SEQ ID NO: 108 are the sequence of a linker and are not part of the rat #6-2 clone.

A human fetal brain cDNA library obtained from Stratagene was screened with the 0.7 kbp PstI fragment of clone #6-2. The fragment appears to encode the EC-2 and EC-3 of the rat protocadherin. After screening about $2 \times 10^6$ phages, eleven positive clones were isolated. Sequencing of the clones identified a novel full length human protocadherin cDNA designated human pc3. The nucleotide and deduced amino acid sequence of human pc3 are set out in SEQ ID NOs: 109 and 110.

The 0.7 kbp PstI fragment of rat clone #6-2 was also used to rescreen the Stratagene rat brain cDNA library for full length rat cDNA clones. A clone containing an insert encoding a full length novel protocadherin cDNA was isolated. The DNA and deduced amino acid sequence of the insert are set out in SEQ ID NO: 111 and 112. The full length rat cDNA was named pc5 because it does not appear to be the homolog of the human pc3 clone based upon a comparison of the sequences.

Concurrently, the 0.8 kbp Eco RI-Pst I fragment of partial rat cDNA designated #43 (SEQ ID NO: 113), which was obtained by screening the Stratagene rat brain cDNA library with a probe corresponding to the human pc43 cytoplasmic domain, was used to probe the Stratagene human cDNA library for full length human protocadherin cDNAs. The fragment appears to encode EC-3 through the beginning of EC-6 of clone #43. One partial clone identified encodes a novel human protocadherin named human pc4. The nucleotide sequence and deduced amino acid sequences of the human pc4 clone are set out in SEQ ID NOs: 114 and 115. The amino acid sequence encoded by the pc4 clone appears to begin in the middle of EC-2 of pc4 and continues through the cytoplasmic tail of the protocadherin.

EXAMPLE 5

The full length human cDNAs encoding pc42 and pc43 were expressed in L cells (ATCC CCL 1) using the pRC/RSV expression vector (Invitrogen, San Diego, Calif.). The cDNAs were isolated from the Bluescript SK(+) clones described in Example 2 by digestion with SspI followed by blunt-ending with DNA polymerase and digestion with XbaI (for pc42), or by double digestion with SpeI and EcoRV (for pc43). The pRC/RSV expression vector was digested with HindIII, followed by blunt-ending and re-digestion with XbaI for insertion of pc42 sequences, or by digested with XbaI followed by blunt-ending and re-digestion with SpeI for insertion of pc43 sequences. The isolated protocadherin DNAs were ligated into the linearized pRC/RSV vector. The resulting pc42 expression plasmid designated pRC/RSV-pc42 (ATCC 69162) and pe43 expression plasmid designated pRC/RSV-pc43 (ATCC 69163) were purified by CsCl gradient centrifugation and transfected into L cells by a Ca-phosphate method.

The pc42 and pc43 transfectants were morphologically similar to the parental cells. Northern blot analysis of L cells transfected with pc42 or pc43 DNA sequences showed that the transfected cells expressed mRNAs of a size expected to encode the particular protocadherin.

EXAMPLE 6

Rabbit polyclonal antibodies specific for pc42 and pc43 were generated as well as a mouse monoclonal antibody specific for pc43.

Preparation of Polyclonal Antibodies Specific for pc42 and pc43

DNA sequences encoding portions of the extracellular domain of pc42 and pc43 were each fused to a maltose binding protein-encoding sequence and expressed in bacteria. Specifically, DNAs corresponding to EC-4 through EC-7 of pc42 and EC-3 through EC-5 of pc43 were prepared by PCR and subcloned in the correct reading frame into the multicloning site of the pMAL expression vector (New England Biolabs, Beverly, Mass.) which contains sequences encoding maltose binding protein immediately upstream of the multicloning site. The resulting plasmids were then introduced into *E. coli* NM522 cells (Invitrogen, San Diego, Calif.) by a single step transformation method. Expression of the fusion proteins was induced by the addition of IPTG and the fusion proteins were purified from cell extracts by amylose resin affinity chromatography (New England Biolabs) as described by the manufacturer. The fusion proteins were used for the immunization of rabbits without further purification.

Polyclonal antibodies were prepared in rabbits by immunization at four subcutaneous sites with 500 µg of purified fusion protein in Freund's complete adjuvant. Subsequent immunizations with 100 µg of the fusion protein were in Freund's incomplete adjuvant. Immune sera was passed through sepharose coupled to maltose binding protein (New England Biolabs) and polyclonal antibodies were purified from immune sera using Sepharose affinity columns prepared by reaction of the purified fusion protein with CNBr Sepharose (Pharmacia). Reactivity of the polyclonal sera with purified pc42 fusion protein and pc42 transfected cell extracts (described in Example 5) was confirmed.

Preparation of Monoclonal Antibodies Specific for pc43

The pc43 fusion protein (containing the EC-3 through EC-5 subdomains of pc43) was used to generate monoclonal antibodies in mice according to the method of Kennett, *Methods in Enzymol.*, 58:345–359 (1978). Briefly, mice were immunized with the pc43 fusion protein (100 µg) at two subcutaneous sites. The spleen from the highest titer mouse was fused to the NS1 myeloma cell line. The resulting hybridoma supernatants were screened in a ELISA assay for reactivity with the pc43 fusion protein and with maltose binding protein. The fusion wells with the highest reactivity to the pc43 extracellular domains were subcloned. The hybridoma cell line designated 38I2C (ATCC HB 11207) produced a $IgG_1$ subtype monoclonal antibody specific for pc43. Reactivity of the monoclonal antibody produced by hybridoma cell line 38I2C to pc43 was confirmed by immunoblotting the pc43 L cell transfectants described in Example 5. The 38I2C monoclonal antibody is specific for human pc43.

EXAMPLE 7

L cells transfected with DNA sequences encoding pc42 and pc43 as prepared in Example 5 were assayed for expression of the protocadherins by immunoblot and by immunofluorescence microscopy.

Immunoblot Analysis

Cell extracts of pc42 and pc43 transfectants were subjected to SDS-PAGE and then blotted electrophoretically onto a PVDF membrane (Millipore, Bedford, Mass.). The membranes were incubated with 5% skim milk in Tris-buffered saline (TBS) for two hours and then respectively with either pc42 polyclonal sera or pc43 monoclonal antibody for one hour. The membranes were washed three times (for 5 minutes each wash) with TBS containing 0.05% Tween 20 and respectively incubated with alkaline phosphatase-conjugated anti-rabbit IgG antibody or anti-mouse IgG antibody (Promega, Madison, Wis.) in the same buffer for one hour. After washing the membranes with TBS containing 0.05% Tween 20, reactive bands were visualized by using Western Blue solution (Promega).

Anti-pc42 polyclonal antibodies stained a band of about 170 kDa molecular weight in pc42 transfected cells, but not parental L cells. The pc43-specific monoclonal antibody (38I2C) and polyclonal antibodies stained two adjacent bands of about 150 kDa molecular weight in pc43 transfected cells. The pc43 antibodies did not stain bands in parental L-cells. The molecular weights indicated by the staining of bands by the pc42 and pc43 antibodies are significantly larger than the molecular weights predicted from the deduced amino acid sequences. This discrepancy in molecular weight is common among various cadherin-related proteins and may be attributable to the glycosylation and/or cadherin specific structural properties. The pc42 antibody also stained smaller bands, which may be proteolytic degradation products.

When transfected cells were trypsinized and cell extracts were prepared, run on SDS/PAGE and immunoblotted with the appropriate antibody, the pc42 and pc43 polypeptides expressed by the transfected cells were found to be highly sensitive to proteolysis and were easily digested by 0.01% trypsin treatment. In contrast to the classic cadherins, however, these proteins were not protected from the digestion in the presence of 1–5 mM $Ca^{2+}$.

Immunofluorescence Microscopy

Transfected cells were grown on a cover slip precoated with fibronectin and were fixed with 4% paraformaldehyde for 5 minutes at room temperature or with cold methanol on ice for 10 minutes followed by 4% paraformaldehyde fixation. After washing with TBS, the cells were incubated with TBS containing 1% BSA for 30 minutes and then with anti-pc42 polyclonal antibody or anti-pc43 monoclonal antibody in TBS containing 1% BSA for 1 hour at room temperature. Cover slips were then washed with TBS containing 0.01% BSA and respectively incubated with FITC-conjugated anti-rabbit antibody or anti-mouse antibody (Cappel, Durham, N.C.) for 60 minutes at room temperature. The cells were washed again with TBS containing 0.01% BSA and subjected to fluorescence microscopy. Both pc42-specific and pc43-specific polyclonal antibodies stained the cell periphery of transfected cells expressing the protoeadherin proteins, mainly at the cell-cell contact sites. The antibodies did not stain the parent L cells, nor did rabbit preimmune sera stain the pc42 and pc43 transfectants.

EXAMPLE 8

The cell aggregation properties of the transfected L cells expressing protocadherin proteins were examined. Transfected L cells were cultured in Dulbecco's Modified Eagles Medium (DMEM) (Gibco, Grand Island N.Y. supplemented with 10% fetal bovine serum at 37° C. in 5% $CO_2$. Cells grown near confluence were treated with 0.01% trypsin in the presence of 1 mM EGTA for 25 minutes on a rotary shaker at 37° C. and collected by centrifugation. The cells were washed three times with $Ca^{2+}$ free HEPES-buffered saline (HBS) after adding soybean trypsin inhibitor, and were resuspended in HBS containing 1% BSA. The cell aggregation assay [Urushihara et al., *Dev. Biol.*, 70: 206–216 (1979)] was performed by incubating the resuspended cells in a 1:1 mixture of DMEM and HBS containing 1% BSA, 2 mM $CaCl_2$ and 20 µg/ml of deoxyribonucelease on a rotary shaker at 37° C. for 30 minutes to 6 hours.

The pc42 and pc43 transfectants did not show any significant cell aggregation activity during periods of incubation less than 1 hour. This is in contrast to the cell aggregation that occurs with classic cadherins in similar experiments (Nagafuchi et al., supra, and Hatta et al., supra). However, prolonged incubation of transfected cells (more than 1–2 hours) resulted in gradual re-aggregation of the cells into small aggregates. Similar results were obtained when single cell suspensions of transfected cells were prepared by trypsin treatment in the presence of $Ca^{2+}$. No re-aggregation was observed under the same conditions when untransfected L cells or L cells transfected with pRC/RSV vector alone were tested. When pc43 transfectants labelled with DiO (Molecular Probes, Eugene, Oreg.) were incubated with unlabelled pc42 transfectants in the cell aggregation assay, aggregation of labelled and unlabelled cells was almost mutually exclusive indicating that protocadherin binding is homophilic.

In view of the fact that the protocadherin cytoplasmic domains exhibit no apparent homology to cadherin domains, experiments were performed to determine if the difference in cytoplasmic domains could account for the difference in cell aggregation activity observed in cadherin and protocadherin transfectants. The cytoplasmic domain of pc43 was replaced with the cytoplasmic domain of E-cadherin and aggregation of cells transfected with the chimeric construct was analyzed.

The Bluescript SK(+) clone described in Example 2 which contained the entire coding sequence for pc43 was digested with EcoRV and then partially digested with XbaI to remove the sequence corresponding to the cytoplasmic domain, and the plasmid DNA was purified by agarose gel electrophoresis. The cDNA corresponding to the cytoplasmic domain of mouse E-cadherin was synthesized by PCR using mouse cDNA made from mouse lung mRNA as a template and specific primers corresponding to a region near the N-terminus of the cytoplasmic domain sequence or the region containing the stop codon of mouse E-cadherin (Nagafuchi et al., supra). A XbaI sequence was included to the 5' end of the upstream primer. The E-cadherin cytoplasmic domain cDNA was then subcloned into the linearized pc43 Bluescript clone. The DNA containing the entire resulting chimeric sequence was cut out with SpeI and EcoRV and was subcloned into the SpeI-blunted XbaI site of the expression vector pRc/RSV vector. Finally, L cells were transfected with the resultant construct by a calcium phosphate method. After screening with G418 for about 10 days, the transfectants were stained with FITC-labeled 38I2C anti-pc43 antibody and subjected to FAGS analysis. A portion of highly labeled cells were isolated and cloned. Transfectants showed a morphology similar to that of parental L cells and the expressed protein was localized at the cell periphery using pc43 antibody for immunofluorescence microscopy.

Cell aggregation activity of the chimeric transfectants was analyzed as follows. The chimeric pc43 transfectants Were labeled with DiO for 20 minutes at room temperature. The resultant cells were trypsinized in the presence of 1 mM EGTA and single cell suspension was made. Then, the cells were mixed with unlabeled other type of transfectants and incubated on a rotary shaker for two hours. The results were examined with a fluorescence and a phase contrast microscope apparatus. Antibody inhibition of cell aggregation was examined by incubation of the transfectants in the presence of polyclonal anti-pc43 antibody (100 ng/ml) in the standard assay medium.

In the cell aggregation assay, the chimeric pc43 transfectants showed clear $Ca^{2+}$-dependent cell aggregation within forty minutes of incubation. Cell aggregation was inhibited by the addition of pc43-specific polyclonal antibody.

EXAMPLE 9

The procedures of Maruyama et al, *J. Biochem.*, 95: 511–519 (1984) were used to determine the calcium binding properties of pc43 by Western blot analysis in the presence or absence of calcium-45. The pc43 fusion protein described in Example 6 containing pc43 subdomains EC-3 through EC-5 was compared to the calcium binding protein calmodulin. Samples of purified pc43 fusion protein were run on SDS/PAGE and electrophoretically transferred to PVDF membrane. Binding of the $^{45}Ca^{2+}$ to the pc43 fusion protein was detected by autoradiography and was determined to be nearly as efficient as binding of $^{45}Ca^{2+}$ to calmodulin. In contrast, there was no binding of calcium to purified maltose binding protein lacking the pc43 extracellular domain. The pc43 subdomains EC-3 through EC-5 contain sequences highly homologous to the putative $Ca^{2\pm}$ binding motifs found in E-cadherin. [See, Ringwald et al., *EMBO J.*, 6: 3647–3653 (1987).]

EXAMPLE 10

The expression of mRNA encoding pc42 and pc43 was assayed in various tissues and cell lines by Northern blot.

Total RNAs were prepared by the guanidium isothiocyanate method and poly(A)+ RNAs were isolated using a FastTrack kit (Invitrogen). RNA preparations were electrophoresed in a 0.8% agarose gel under denaturing conditions and transferred onto a nitrocellulose filter using a capillary method. Northern blot analyses were performed according to the method of Thomas, *Proc. Natl. Acad. Sci. USA*, 77: 5201–5205 (1980). The final wash was in 0.2× standard saline citrate containing 0.1% sodium dodecyl sulfate at 65° C. for 10 minutes.

Protocadherin mRNA Expression in Adult Rat Tissues

Total mRNA preparations of rat tissues including brain, heart, liver, lung, skin, kidney and muscle were separated electrophoretically under denaturing conditions (10 μg mRNA/lane) and transferred onto nitrocellulose filters. The filters were hybridized with $^{32}$P-labelled cDNA fragments MOUSE-326 (which corresponds to EC-4 of human pc42) and RAT-218 (which corresponds to EC-5 of human pc43). The mRNAs of both protocadherins were highly expressed in brain. The pc42 probe detected a major band of 7 kb and a minor band of 4 kb in size, possibly representing the products of alternative splicing. The pc43 probe hybridized to a major band of 5 kb in size and with minor bands of smaller sizes.

Developmental Expression of Protocadherin mRNA in Rat Brain

To examine the developmental regulation of mRNA expression of the protocadherins, brain mRNA from rats at embryonic days 17 and 20, neonatal days 5 and 11 and from adult rats was prepared and subjected to Northern blot analysis as described above for other rat tissues. β-actin was used as an internal standard. mRNA levels for pc42 and pc43 proteins increased during embryonic development of the brain as compared with β-actin expression.

Protocadherin mRNA Expression in Human Cell Lines

Several neuronal and glial cell lines (including human SK-N-SH neuroblastoma, human U251 glioma, and mouse Neuro-2a neuroblastoma cell lines) were assayed by Northern blot using $^{32}$P-labelled for expression of pc42 and pc43 mRNA. Human cell lines were probed with HUMAN-42 (which corresponds to EC-4 of human pc42) and HUMAN-43 (which corresponds to EC-5 of human pc43) cDNA fragments while the mouse cell line was probed with MOUSE-326 (which corresponds to EC-4 of human pc42) and RAT-322 (which corresponds to EC-5 of human pc43) cDNA fragments. SK-N-SH human neuroblastoma cells and U251 human glioma cells were found to express pc43 mRNA and Neuro-2a mouse neuroblastoma cells were found to express pc42 mRNA.

EXAMPLE 11

Expression of pc43 protein in various tissues, extracts and cells was assayed by Western blot and immunofluorescence microscopy.

Expression in Rat Cardiac Muscle Extracts

A rat heart non-ionic detergent extract was prepared by freezing a heart in liquid nitrogen after removal, powdering in a mortar and pestle, grinding briefly in a polytron in 0.5% Nonidet P40 in [10 mM PIPES (pH 6.8), 50 mM NaCl, 250 mM $NH_4SO_4$, 300 mM sucrose, 3 mM $MgCl_1$] and microfuging for 15 minutes. Samples were separated by SDS/PAGE and electrophoretically transferred to nitrocellulose (Towbin et al., *PNAS* 76:4350–4354, 1979). Two pc43 protein bands with molecular weights of 150 KDa and 140 KDa were detected with rabbit polyclonal antibodies to pc43 by the immunoblot method described in Example 7.

Expression in Tissue Sections and Cells

To determine the localization of the protocadherins in various tissues, human and rat adult tissues were removed, incubated in 30% sucrose in PBS for 30 minutes at 4° C., embedded in OCT compound (Tissue-Tek, Elkhart, Ind.) in cryomolds and quickly frozen. Six micron sections were cut and placed on glass slides. The slides were washed with PBS and fixed in 3% p-formaldehyde for 5 minutes. To permeablize the tissue sections, the slides were immersed in −20° C. acetone for 10 minutes and air dried. The sections were blocked with 2% goat serum and 1% BSA in PBS for 30 minutes and then incubated with the rabbit anti-pc43 polyclonal antisera for 1 hour at room temperature. The sections were rinsed 3 times in PBS containing 0.1% BSA and incubated with a biotinylated anti-rabbit (Vector Laboratories, Burlingame, Calif.) in 1% BSA in PBS for 30 minutes. After rinsing 3 times, strepavidin-conjugated with FITC (Vector Laboratories) was added for 30 minutes and again washed 3 times. For co-localization studies, an appropriate primary antibody was used with a TRITC-conjugated secondary antibody.

A. Muscle

Immunolocalization of pc43 in rat cardiac muscle shows that pc43 is localized in a repeating pattern which is consistent with pc43 being associated with the sarcomeres. Sarcomeres are repetitive contractile units between the *fascia adherens* in skeletal and cardiac muscle. Co-localization with cytoskeletal proteins shows that pc43 is present at the ends of the sarcomeres in the Z lines which are associated with desmin and the actin-binding protein vinculin, and alpha-actinin. The thin microfilaments of F-actin are associated with the thick myosin filaments between the Z lines. In contrast, N-cadherin is localized at the ends of cardiac myocytes at the *fascia adherens* junctions at sites of myocyte:myocyte contact. The localization of pc43 in cardiac muscle suggests that pc43 may play a role in muscle contraction in the anchoring of the contractile apparatus to the plasma membrane.

Similar localization for pc43 was observed in rat skeletal muscle. Ultrastructural studies have shown that dystrophin, the gene product lacking in Duchenne muscular dystrophy, is a component of the sarcolemma [Porter et al., *J. Cell. Biol.*, 117:997–1005 (1992)]. The sarcolemma is connected to the contractile apparatus at the M and Z lines where pc43 is localized.

B. Brain

Reactivity of anti-pc43 polyclonal antibody and monoclonal antibody 3812C on frozen sections of rat and human cerebellum, respectively, shows that the major sites of pc43 expression are located in Purkinje cells and the granule cell layer which contains numerous small neurons.

C. Placenta

Strong reactivity of monoclonal antibody 3812C with human syncytiotrophoblasts was also observed in development of the placenta at an early state (5–7 weeks of gestation). Expression appeared to gradually decrease as the stage progressed indicating that pc43 may be involved in the implantation of fertilized eggs into the placenta.

D. Neuroblastoma and Astrocytoma Cells

Immunocytochemical localization of pc43 in Sk-N-SH neuroblastoma cells and UW28 astrocytoma cells using anti-pc43 antibodies reveals a punctate cell surface distribution of pc43 and in some cells there is a localization at the tips of extensions of neuronal foot processes. At sites of cell-cell contact of UW28 astrocytoma cells, pc43 is organized in a series of parallel lines. The lines start at the contact site and extend approximately 5 micron. F-actin microfilaments were identified with rhodamine-phalloidin (Molecular Probes, Eugene, Oreg., as described by the manufacturer) showing that the microfilaments in the cell appear to end in the pc43 linear structures which extend from the edge of the cell at sites of cell contact.

Immunoblotting studies with pc43 specific antibodies show that a protein with a molecular weight of 140 kDa is recognized in human Sk-N-SH neuroblastoma cells and in UW28 astrocytoma cells.

E. Osteoblasts

Immunocytochemical localization of pc43 using monoclonal antibody 3812C in tow human ostogenic sarcoma cell lines [SaOS (ATCC HTB 85) and MG-63 (ATCC CRL 1427)] and in cultures of normal human trabecular osteoblasts [culture system described in Civitelli et al., *J. Clin. Invest.*, 91: 1888–1896 (1993)] showed that pc43 is expressed in osteoblasts in a pattern similar to that seen in UW28 astrocytoma cells. At sites of cell-cell contact, pc43 is organized in a series of parallel lines that appear to correspond to the actin stress fibers. In addition, in some cells, pc43 appears to localize at the tips of contacting cell processes. Northern blot analysis provides additional evidence that pc43 is expressed in normal human trabecular osteoblasts. A pc43 specific DNA probe hybridized to a major band of 5 kb in samples of poly-A mRNA isolated from normal human trabecular osteoblasts.

EXAMPLE 12

In situ hybridization experiments using protocadherin specific RNA probes were performed on cryosections of rat tissue.

Sense and antisense $^{35}$S-riboprobes were made using the standard procedure described by Promega (Madison, Wis.). An approximately 400 bp EcoRI-XbaI fragment of the MOUSE-326 cDNA clone was used as a pc42 specific probe. This fragment encodes the middle of EC-3 to the end of EC-4 of pc42. An approximately 700 bp SmaI fragment of the RAT-218 cDNA clone was used as a pc43 specific probe. The fragment encodes the end of EC-3 to the end of EC-5 of pc43.

Rat adult tissues were harvested and immediately embedded with OCT Compound Crissue-Tek) in cryomolds and quickly frozen in a bath of 95% ethanol/dry ice. The frozen blocks were stored at −80° C. until cut. Six micron tissue sections were cut using a cryostat (Reichert-Jung, Model #2800 Frigocut N, Leiea, Inc., Gilroy, Calif.). Cut tissue sections were stored at −80° C.

The in situ protocol used was a variation of that described by Angerer et al., *Methods in Enzymology*, 152: 649–660, (1987). All solutions were treated with diethylpyrocarbonate (DEPC, Sigma, St. Louis, Mo.) to remove RNase contamination. The tissue sections were first fixed in 4% parsformaldehyde at 4° C. for 20 minutes. To remove excess panformaldehyde and stop the tissue fixation, the slides were washed in PBS (phosphate buffered saline), denatured in a graded series of alcohols (70, 95, 100%) and then dried. To prevent the tissue from detaching from the glass slide during the in situ procedure, the tissue sections were treated in a poly-L-lysine solution (Sigma) at room temperature for 10 minutes. To denature all RNA in the tissue, the sections were placed in a solution of 70% formamide/2× SSC (0.15M NaCl/0.3M Na citrate, pH 7.0) at 70° C. for 2 minutes after which they were rinsed in chilled 2× SSC, dehydrated in a graded series of alcohols and then dried. Once dried, the sections were prehybridized in hybridization buffer [50% formamide/50 mM DTT (dithiothrietol)/0.3M NaCl/20 mM Tris, pH 8.0/5 mM EDTA/1× Denhardt's (0.02% Ficoll Type 400/0.02% polyvinylpyrrolidone/0.02% BSA)/10% Dextran Sulfate] at the final hybridization temperature for approximately 4 hours. After prehybridization, approximately 1×10$^6$ cpm of the appropriate riboprobe was added to each section. The sections were generally hybridized at 45° C. overnight (12–16 hours). To insure that the hybridization seen was specific, in some experiments the hybridization stringency was increased by raising the hybridization temperature to 50° C. As both the 45° C. and 50° C. experiments gave comparable results, the standard hybridization temperature used was 45° C.

To remove excess, nonhybridized probe, the sections were put through a series of washes. The sections were first rinsed in 4× SSC to remove the bulk of the hybridization solution and probe. Next a 15 minute wash in 4× SSC/50 mM DTT was carried out at room temperature. Washes at increased stringencies were also utilized. A 40 minute wash in 50% formamide/2× SSC/50 mM DTT was performed at 60° C. Four final room temperature washes were carried out for 10 minutes each: two in 2× SSC and two in 0.1× SSC. The washed slides were dehydrated in a graded series of alcohols and dried.

To visualize the hybridized probe, the slides were dipped in Kodak NTB2 nuclear emulsion (International Biotechnology, New Haven, Conn.) which had been diluted 1:1 in dH$_2$O. Once dry, the slides were stored at 4° C. in light-tight boxes for the appropriate exposure time. The in situ slides were independently viewed by two persons and scored positive or negative for hybridization signal.

All in situ hybridization studies were performed on rat tissue. Because results from Northern blot experiments (see Example 9) indicated that both pc42 and pc43 are expressed in adult brain, in situ hybridization studies were carried out to localize the expression of these molecules to specific brain cell types. Hybridization seen in the normal adult rat brian was specific (no background hybridization was seen with the sense probes) and was localized to specific regions in the brain. The overall pattern of expression seen for pc42 and pc43 was very similar, with the major difference being in the level of expression. pc43 appears to be expressed at a lower level than pc42. Both molecules are expressed in the germinal and pyramidal cells of the hippocampus, Purkinje cells of the cerebellum and neurons in grey matter. In addition, pc42 is expressed in glial cells in the white matter but, in contrast to the expression of pc43 in glioma cell lines (as described in Example 9), expression of pc43 in normal glial cells was not observed. In the spinal chord, both protocadherins are expressed in the motor neurons in the gray matter and pc42 is expressed in the glial cells in the white matter.

When expression of both protocadherin molecules was analyzed in brains and spinal chords from rats having EAE (experimental allergic encephalomyelitis) [Vandenbark et al., Cell. Immunol., 12: 85–93 (1974)], the same structures as described above were found to be positive. In addition, expression of pc42 was observed in the leukocytic inffitrates in the EAE tissues. Expression of pc42 in leukocytes was confirmed by in situ hybridization analysis of two leukocytic cell lines, RBL-1 and y3.

Expression of both protocadherin-42 and -43 was observed in the developing brain of rat embryos at all embryological days tested (E15-E19). In addition protocadherin-43 was observed in the developing rat heart at all embryological days tested (E13-E19). This finding is consistent with the immunohistochemistry results showing protocadherin-43 expression in adult heart.

To determine possible roles of protocadherins in the development of the nervous system, expression profiles of protocadherin members in developing rat brain and adult rat brain were also examined by in situ hybridization. A series of coronal, sagittal and horizontal sections of rat brains at postnatal days 0, 6, 14, 30 (P0 through P30) and at 3 months (young adult) were hybridized with labelled cRNA probes corresponding to various protocadherins of the invention including pc42, pc43, RAT-212, RAT-411, and RAT-418. In developing brain, RAT-411 was expressed at high levels in neurons of the olfactory bulb, i.e., mitral cells and periglomerular cells. The expression of RAT-411 mRNA was transient; expression appeared at P0, peaked at P6, diminished by P14, and was undetectable at P30 and in adult brain. In the adult, pc43 mRNA was found to be expressed predominantly in Purkinje cells in the cerebellum. The expression of pc43 mRNA in Purkinje cells was observed from the beginning of Purkinje cell differentiation at around P6. Other protocadherin members were expressed at very low levels in various areas of developing and adult brains. These results indicate that protocadherin members are differentially expressed during the development of the central nervous system, and suggest that RAT-411 and pc43 have specific roles during the development of olfactory bulb neurons and Purkinje cells, respectively.

EXAMPLE 13

Conventional immunoprecipitations using pc43-specific polyclonal antibodies and monoclonal antibody 38I2C were performed to identify proteins that interacted with pc43 in L cell transfectants.

The pc43 and chimeric pc43 transfectants were metabolically labeled by incubating the cells in Dulbecco's modified Eagle's medium containing [$^{35}$S] methionine (50 uCi/ml) overnight. After washing, the transfectants were lysed with PBS containing Triton X 100 and incubated with anti-pc43 antibody. The immunocomplexes were then collected using protein A-Sepharose beads. The resulting beads were washed five times with a washing buffer (50 mM Tris-HCl, pH 8.0, containing 0.5M NACl, 0.1% ovalbumin, 0.5% NP-40, 0.5% Triton×100 and 1 mM EDTA) at room temperature. Protein was separated by SDS-PAGE and subjected to autoradiography.

The chimeric pc43 co-precipitated with 105 kDa and a 95 kDa bands that are likely to correspond to α- and β-catenins, respectively, because anti-α-catenin and anti-β-catenin antibodies stained comparable bands. Pc43, on the other hand, co-precipitated with a 120 kDa band.

While the present invention has been described in terms of specific methods and compositions, it is understood that variations and modifications will occur to those skilled in the art. Therefore, only such limitations as appear in the claims should be placed on the invention.

What is claimed is:

1. Purified and isolated human protocadherin pc3 polypeptide comprising the amino acid sequence of SEQ ID NO: 110.

2. Purified and isolated rat protocadherin pc5 polypeptide comprising the amino acid sequence of SEQ ID NO: 112.

* * * * *

UNITED STATES PATENT AND TRADEMARK OFFICE
CERTIFICATE OF CORRECTION

PATENT NO. : 5,708,143
DATED : January 13, 1998
INVENTOR(S) : Shintaro Suzuki

It is certified that error appears in the above-identified patent and that said Letters Patent is hereby corrected as shown below:

Column 1, line 43 replace "carenins" with --catenins--;

Column 1, line 49 replace "an" with --a--;

Column 1, line 57 replace "arian" with --avian--;

Column 3, line 35 replace "in" with --In--;

Column 4, line 7 replace "ptotocadherin" with --protocadherin--;

Column 7, line 22 replace "them" with --there--;

Column 7, line 65 replace "potion" with --portion--:

Column 9, line 41 replace "futures" with --features--;

Column 10, line 23 replace "supra)." with --*supra*.--;

Column 10, line 38 replace "ghcocorticoid" with --glucocorticoid--;

Column 11, line 49 replace "digested" with --digestion--;

Column 11, line 54 replace "pe43" with --pc43--.

Column 13, line 53 replace "N.Y." with --N.Y.)--

Column 14, line 42 replace "pRc" with --pRC--;

Column 14, line 46 replace "FAGS" with --FACS--;

UNITED STATES PATENT AND TRADEMARK OFFICE
CERTIFICATE OF CORRECTION

PATENT NO. : 5,708,143
DATED : January 13, 1998
INVENTOR(S) : Shintaro Suzuki

It is certified that error appears in the above-identified patent and that said Letters Patent is hereby corrected as shown below:

Column 14, line 53 replace "were" with --were--;

Column 17, line 34 replace "tow" with --two--;

Column 17, line 64 replace "Crissue-Tek)" with --(Tissue-Tek)--;

Column 18, line 7 replace "parsform-" with --paraform---;

Column 18, line 8 replace "panformaldehyde" with --paraformaldehyde--.

Signed and Sealed this

Twenty-first Day of December, 1999

Attest:

Q. TODD DICKINSON

*Attesting Officer*   *Acting Commissioner of Patents and Trademarks*